US010842838B2

(12) United States Patent
Langland et al.

(10) Patent No.: US 10,842,838 B2
(45) Date of Patent: Nov. 24, 2020

(54) METHOD FOR THE USE OF BOTANICAL EXTRACTS IN THE TREATMENT OF VIRAL INFECTIONS

(71) Applicant: Aviratek Biomedical Solutions, LLC, Phoenix, AZ (US)

(72) Inventors: Jeffrey Langland, Chandler, AZ (US); Karen Denzler, Phoenix, AZ (US); Robert Waters, Mesa, AZ (US); Bertram Jacobs, Tempe, AZ (US)

(73) Assignee: Aviratek Biomedical Solutions, LLC, Phoenix, AZ (US)

( * ) Notice: Subject to any disclaimer, the term of this patent is extended or adjusted under 35 U.S.C. 154(b) by 0 days.

(21) Appl. No.: 16/261,816

(22) Filed: Jan. 30, 2019

(65) Prior Publication Data

US 2019/0231836 A1    Aug. 1, 2019

Related U.S. Application Data

(62) Division of application No. 14/443,767, filed as application No. PCT/US2013/071332 on Nov. 21, 2013, now abandoned.

(60) Provisional application No. 61/778,074, filed on Mar. 12, 2013, provisional application No. 61/729,204, filed on Nov. 21, 2012.

(51) Int. Cl.

| | |
|---|---|
| *A61K 36/28* | (2006.01) |
| *A61K 36/53* | (2006.01) |
| *A61K 36/88* | (2006.01) |
| *A61K 36/185* | (2006.01) |
| *A61K 36/254* | (2006.01) |
| *A61K 36/38* | (2006.01) |
| *A61K 36/484* | (2006.01) |
| *A61K 36/68* | (2006.01) |
| *A61P 31/20* | (2006.01) |
| *A61P 25/00* | (2006.01) |
| *A61P 35/00* | (2006.01) |
| *A61K 9/00* | (2006.01) |

(52) U.S. Cl.
CPC ............ *A61K 36/53* (2013.01); *A61K 9/0034* (2013.01); *A61K 36/185* (2013.01); *A61K 36/254* (2013.01); *A61K 36/38* (2013.01); *A61K 36/484* (2013.01); *A61K 36/68* (2013.01); *A61K 36/88* (2013.01); *A61P 25/00* (2018.01); *A61P 31/20* (2018.01); *A61P 35/00* (2018.01); *A61K 2236/13* (2013.01); *A61K 2236/333* (2013.01); *A61K 2236/37* (2013.01)

(58) Field of Classification Search
None
See application file for complete search history.

(56) References Cited

U.S. PATENT DOCUMENTS

| | | | |
|---|---|---|---|
| 2005/0095260 A1 | 5/2005 | Pardoe | |
| 2007/0122492 A1* | 5/2007 | Behr | C12Q 1/37 424/725 |
| 2012/0141610 A1* | 6/2012 | Gowey | A61K 31/519 424/725 |
| 2018/0200320 A1 | 7/2018 | Langland et al. | |
| 2019/0008825 A1* | 1/2019 | Murphy | A61K 31/203 |

FOREIGN PATENT DOCUMENTS

| | | |
|---|---|---|
| EP | 0249165 A2 * | 12/1987 |
| WO | 2009/013757 A1 | 1/2009 |
| WO | 2009/048595 A2 | 4/2009 |

OTHER PUBLICATIONS

Fiore C. et al. Antiviral Effects of Glycyrrhiza Species. Phytotherapy Research 22(2)141-148, Feb. 2008. (Year: 2008).*
Martin K. et al. Antiviral Agents from Plants and Herbs: A Systematic Review. Antiviral Therapy 8(2)77-90, 2003. (Year: 2003).*
Ruiz G. et al. A Lack of Bioactive Predictability for Marker Compounds Commonly Used for Herbal Medicine Standardization. PLoS One 11(7)1-10, 2016. (Year: 2016).*
Arndt W. et al. In vitro Characterization of a Nineteenth Century Therapy for Smallpox. PLoS One 7(3)1-9, Mar. 2012. (Year: 2012).*
Ardnt et al., In vitro characterization of a nineteenth-century therapy for smallpox. PLoS One. 2012;7(3):e32610. 9 pages.
Astani et al., Melissa officinalis extract inhibits attachment of herpes simplex virus in vitro. Chemotherapy. 2012;58 (1):70-7.
Chattopadhyay et al., Ethnomedicines and ethnomedicinal phytophores against herpesviruses. Biotechnol Annu Rev. 2008;14:297-348.
Cheng et al., Recent Advances in the Discovery of Novel Anti-Herpetic Agents from Chinese Herbal Medicines. Current Organic Chemistry. 2010;14(16):1714-1726.
Downing, Inter and Intra-Specific Differences in Medicinal Plant Use for the Treatment of Type II Diabetes Symptoms by the Cree Elders of Eeyou Istchee (QC). Thesis. 117 pages, May 2010.
Harris et al., Characterizing the cytoprotective activity of *Sarracenia purpurea* L., a medicinal plant that inhibits glucotoxicity in PC12 cells. BMC Complementary and Alternative Medicine. 2012;12;245, pp. 1-10.
Krauze-Baranowska et al., HPLC of flavanones and chalcones in different species and clones of Salix. Acta Pol Pharm. Jan.-Feb. 2013;70(1):27-34.
Perfect et al., Use of complementary and alternative medicine for the treatment of genital herpes. Herpes. Oct. 2005;12(2):38-41.
Wang et al., High genetic diversity in *Sarracenia leucophylla*(Sarraceniaceae), a carnivorous wetland herb. J Hered. May-Jun. 2004;95(3):234-43.
International Search Report and Written Opinion for Application No. PCT/US2013/071332, dated Apr. 30, 2014, 17 pages.

(Continued)

*Primary Examiner* — Ralph J Gitomer

(74) *Attorney, Agent, or Firm* — IPath, PLC; Steven J. Miller

(57) ABSTRACT

The present disclosure relates generally methods of preparation and use of certain botanical extracts for the treatment of viral infections.

5 Claims, 73 Drawing Sheets

(56) References Cited

OTHER PUBLICATIONS

U.S. Appl. No. 14/443,767, filed May 19, 2015, Publication No. 2018-0200320, Abandoned.

* cited by examiner

| Treatment began | | | 0 min | | 15 min | |
|---|---|---|---|---|---|---|
| S. purpurea | − | − | + | − | + | − |
| Ethanol | − | − | − | + | − | + |
| MPXV | − | + | + | + | + | + |

| µl/ml media | | | 5 | | 10 | | 15 | | 20 | |
|---|---|---|---|---|---|---|---|---|---|---|
| S. purpurea | − | − | − | + | − | + | − | + | − | + |
| Ethanol | − | − | + | − | + | − | + | − | + | − |
| VARV | − | + | + | + | + | + | + | + | + | + |

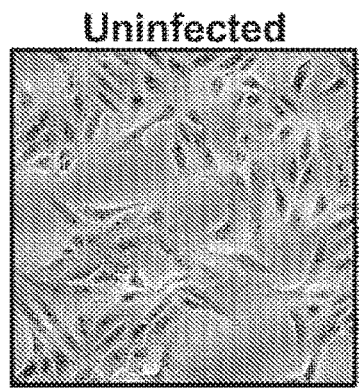
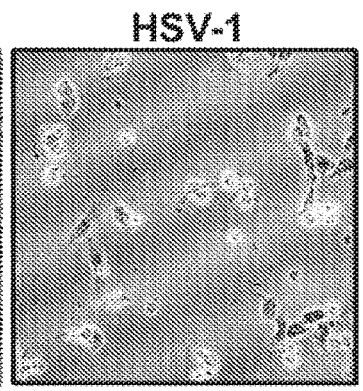
FIG. 6A         FIG. 6B
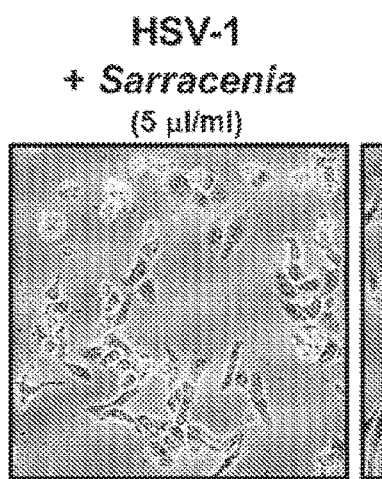
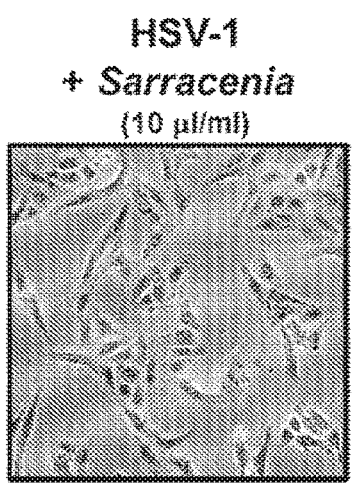
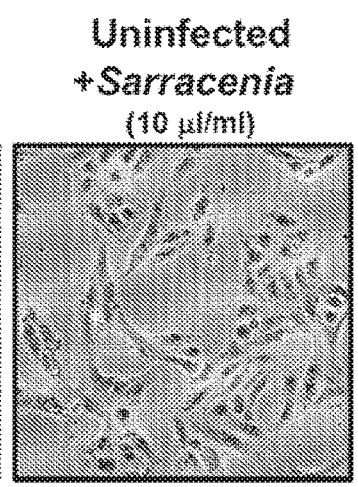
FIG. 6C         FIG. 6D         FIG. 6E

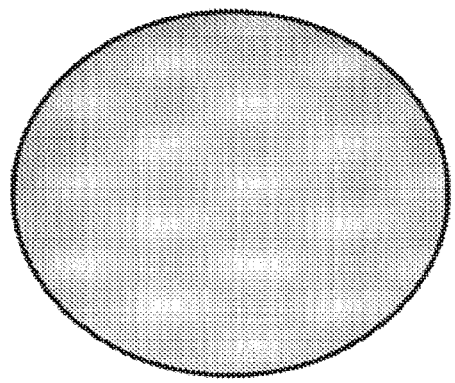
FIG. 10A — Uninfected
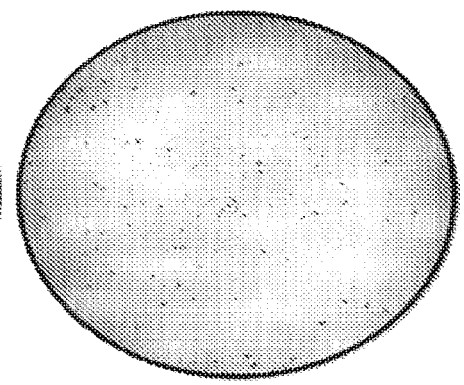
FIG. 10B — Virus
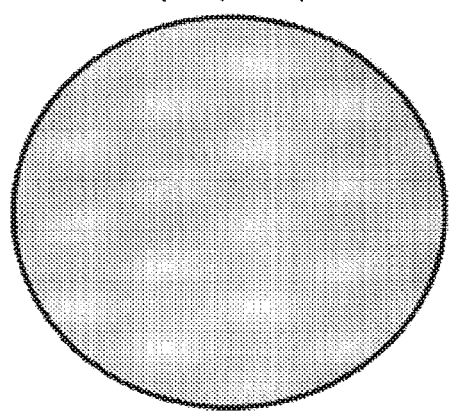
FIG. 10C — Virus + *Sarracenia* (10 µl/ml)
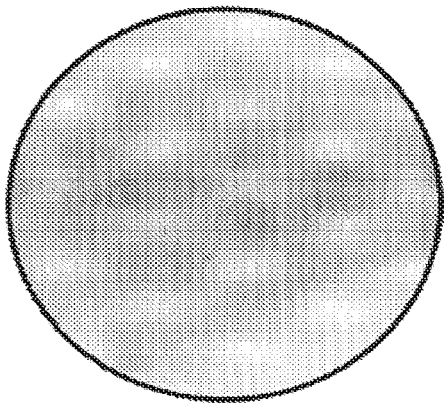
FIG. 10D — Virus + *Sarracenia* (20 µl/ml)

Uninfected

SV40

SV40
+ *Sarracenia*
(5 µl/ml)

SV40
+ *Sarracenia*
(10 µl/ml)

Uninfected
+*Sarracenia*
(10 µl/ml)

METHOD FOR THE USE OF BOTANICAL EXTRACTS IN THE TREATMENT OF VIRAL INFECTIONS

CROSS REFERENCE TO RELATED APPLICATIONS

This is a divisional application that claims priority from U.S. non-provisional application Ser. No. 14/443,767 filed on May 19, 2015, which is the U.S. national stage of PCT Application No. PCT/US2013/071332 filed on Nov. 21, 2013, which claims priority from U.S. Provisional Application No. 61/778,074 filed Mar. 12, 2013 and U.S. Provisional Application No. 61/729,204 filed Nov. 21, 2012. All applications noted hereinabove are hereby incorporated by reference in their entirety.

FIELD OF TECHNOLOGY

The present disclosure generally relates to antiviral compositions, and more specifically to the preparation of botanical extracts and their use in the treatment of viral infections, cancer, pain associated conditions.

BACKGROUND

Poxviruses: Poxviruses are the largest known animal viruses with approximately 200 distinct genes (Moss, in: Fields Virology, ed. by Knipe and Howley, Philadelphia: Lippincott Williams & Wilkins, 2001, pp. 2849-2883). They are DNA viruses that replicate entirely in the cytoplasm. These viruses infect most vertebrates and invertebrates causing a variety of diseases of veterinary and medical importance. The Poxviridae family has two main subfamilies, the chordopoxyirinae, which infect vertebrates, and the entomopoxyirinae, which infect insects. The chordopoxviruses include the genera Orthopoxvirus, Parapoxvirus, Avipoxvirus, Capripoxvirus, Leporipoxvirus, Suipoxvirus, Molluscipoxvirus, and Yatapoxvirus. Each of the chordopoxviruses has a restricted and specific host array. Humans are the sole hosts of two poxviruses, variola virus (smallpox virus) and molluscum contagiosum virus: however many members of Orthopoxvirus, Parapoxvirus, and Yatapoxvirus are zoonotic, i.e., can infect both animals and humans. Monkeypox virus, an Orthopoxvirus, is a significant zoonotic threat to humans. Vaccinia virus is the virus used in the variola virus vaccine, and it is widely used as a model poxvirus in the laboratory. Variola virus, monkeypox virus and vaccinia virus are members of the Orthopoxvirus genus.

In humans, smallpox is a serious, highly contagious, and frequently fatal infectious disease for which there is no specific treatment, and for which the only prevention is vaccination. Two clinical forms of smallpox have been described variola minor and variola major, with the variola major form of smallpox being the more common and severe. There are four types of variola major smallpox: ordinary (the most frequent); modified (mild and occurring in previously vaccinated persons); flat; and hemorrhagic. Overall, variola major has a case-fatality rate of about 30%.

The most virulent form of smallpox, hemorrhagic smallpox, destroys the linings of the throat, stomach, intestines, rectum, and vagina and causes black, unclotted blood to ooze from the mouth and other body orifices. Because hemorrhagic smallpox has a much shorter incubation period than other forms of smallpox, it is likely not to be initially recognized as smallpox when first presented to medical care. As such, most victims die prior to a correct diagnosis, often before they are quarantined. Smallpox vaccination also does not provide much protection, if any, against hemorrhagic smallpox since hemorrhagic smallpox causes death of 94% of vaccinated patients. Hemorrhagic smallpox causes death in 99% of unvaccinated patients.

Herpes simplex virus 1 (HSV-1) infection occurs in nearly 58 percent of the United States population and from 60-95 percent of adults worldwide. Approximately 100 million episodes of recurrent cold sores occur yearly in the US alone, and studies have shown that HSV-1 infection increases in prevalence with age. HSV-1 infection is transmitted primarily through mucocutaneous sites via saliva, respiratory droplets, or secretions. HSV-1 infection occurs predominantly at oral sites and has shown an increased prevalence in infection at genital sites. It can cause rash, papules, or vesicles following primary infection, and is known to reside permanently in the nervous system of the infected host. During latency, the viral genomes persist as circular, extrachromosomal episomes and the viral lytic genes are repressed. Periodically, the viral genomes in some of the neurons reactivate and the virus travels down the axon to the original site of infection, where it can cause recurrent disease resulting in skin ulcerations, neuralgia, and pain. It is the ability to cause an acute infection as well as to repeatedly reactivate and cause disease that is responsible for significant morbidity in humans. In addition to causing cold sores (herpes labialis) and more severe oral disease (herpes gingivitis), HSV-1 also causes herpes stromal keratitis, which is the leading cause of infectious blindness in the US, encephalitis in normal patients, and disseminated infections in immune compromised individuals.

Although anti-herpes virus therapies are available, their effectiveness is limited and variable. Clearly development of novel and more effective therapies for treating herpes associated infections would have a major health impact in the US and worldwide. In addition, it is leasable that new therapeutic approaches developed for HSV-1 could translate to treatment of other herpes family members including HSV-2, which can cause severe morbidity and neonatal mortality. There is no available vaccine for protection against herpes-virus infection, and current treatments include nucleoside analogs which target DNA replication or docosonal which is thought to affect viral membrane fusion. Antiviral drugs can reduce the severity and duration of lesions, but these do not prevent reactivation and do not lead to the elimination of latent viral genomes. Typical infections associated with HSV1 have an average duration from prodrome or erythema stage to healing of 6.1 to 7.9 days. For nucleoside analogs such as acyclovir or valacyclovir, clinical studies suggest that these treatments reduce the duration of lesion healing by 0.5-1.1 days. For docosonal, studies suggest an average 18 hour reduction in healing time. Moreover, drag-resistance is common and renders the current antivirals ineffective.

Another herpes virus member is Varicella Zoster Vims (VZV), the causative agent of shingles. Due to a worldwide increase in elderly and immunocompromised individuals, VZV is seen as a "re-emerging" infection of the twenty-first century. Development of a novel therapeutic is of medical importance because VZV is a major cause of morbidity, specifically postherpetic neuralgia, in the aging and immunocompromised population worldwide. Acyclovir and derivatives (fameyclovir, valacyclovir) which inhibit viral genome replication, are commonly used prescription drugs in the treatment of herpes virus infections but treatments produce a moderate reduction in postherpetic neuralgia at best. In addition, the potential for the development of drug resistance can render these medications ineffective.

Additional herpes virus members pose significant threats to the human population including Epstein Barr virus, human herpes 8 (the causative agent of Kaposi's sarcoma) and cytomegalovirus. Epstein Barr virus in particular is often associated with the development of jaw and neck cancers.

Several hundred species of human papillomavirus (HPV) have been identified. Specific species tend to be associated with human disease including HPV 16, 18, 31, and 45 as causative agents for cervical, anal, vulvar, vaginal, penile and head/neck cancer; and HPV 1 and 2. as common causative agents of warts on the hands and feet. Polyomaviruses are related to papillomaviruses and include species such as SV40, JC and BK virus.

Genital human papillomavirus is the most common sexually transmitted infection. There are more than 40 HPV types that can infect the genital areas of males and females. These HPV types can also infect the mouth and throat. Most people who become infected with HPV do not even know they have it. Certain strains of HPV can cause precancerous changes in cells in the area where the infection occurs. The infection can lead to different types of cancers, including cervical cancer in women. About 1% of sexually active adults in the U.S. have genital warts at any given time. Each year, about 12,000 women get cervical cancer in the U.S. Almost all of these cancers are HPV-associated. Other cancers that can be caused by HPV are less common than cervical cancer, but are increasing. Each year in the U.S., there are about: 1,500 women who get HPV-associated vulvar cancer, 500 women who get HPV-associated vaginal cancer, 400 men who get HPV-associated penile cancer, 2,700 women and 1,500 men who get HPV-associated anal cancer, 1,500 women and 5,600 men who get HPV-associated oropharyngeal cancers (cancers of the back of throat including base of tongue and tonsils).

Inflammatory responses may also result from various viral infections, inflammation is part of a complex biological response of vascular tissues directed against harmful stimuli, such as pathogens, damaged cells, or irritants. The classical signs of acute inflammation are pain, heat, redness, swelling, and loss of function Inflammation is a protective attempt by the body to remove the injurious stimuli and to initiate the healing process, inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process. Cytokines are several different types of substances that are produced by cells within the immune system that relay signals between the immune system cells. Pro-inflammatory cytokines are created primarily by immune cells that are engaged in the process of amplifying inflammatory reactions as a means of dealing with a health threat to the body. By relaying messages between the cells, these cytokines help to trigger the immune system's rate of response to the threat. There is abundant evidence that certain pro-inflammatory cytokines such as IL-1 $\beta$, IL-6, and TNF-$\alpha$ are involved in the process of pathological pain.

Based on the prevalence of these and other diseases and infections, there is a continuing need for new anti-viral, anti-cancer, anti-pruritic (anti-itch) analgesic (anti-pain), and anti-inflammatory treatments.

SUMMARY

The present disclosure relates generally to the preparation and use of certain botanical extracts and therapeutic compositions comprising the same, in the treatment of viral infections such as poxvirus infections, including, but not limited to, variola virus, vaccinia virus, Monkeypox virus, Cowpox virus, Ectromelia virus, Orf virus, Canarypox virus, Myxoma virus, and Moiluscum contagiosum; herpesvirus infections, including, but not limited to herpes simplex virus-1 (HSV1), herpes simplex virus-2 (HSV2), Human herpes 8 and Equine herpes virus (EHV); Varicella-Zoster virus (VZV), Cytomegalovirus, Epstein-Barr virus, Kaposi's Sarcoma Associated herpesvirus (HHV8), Human papillomavirus (including various serotypes of HPV) and polyomavirus infections (including JC and BK viruses); cancerous and pre-cancerous lesions (including, but not limited to cervical cancer, squamous cell carcinoma and actinic keratosis); cancer associated with a papilloma virus or Epstein Barr virus infection, including actinic keratosis, squamous cell carcinoma, cervical cancer jaw, neck, throat, penile and anal cancer; and, pain and itch associated with diseases in general.

Botanical extracts, in accordance with the present disclosure, comprise extracts of one or more plant tissues. In various embodiments, botanical extracts include at least one extract of a carnivorous plant species, in various embodiments of the present disclosure, botanical extracts include at least one extract of the *Sarracenia, Nepenthes, Melissa, Lavandula, Glycyrrhiza, Eleutherococcus, Hypericum, Darlingtonia, Heliamphora, Roridula, Drosera, Dionaea, Aldrovanda, Drosophyllum, Triphyophyllum, Catopsis, Brocchinia, Paepalanthus, Utricularia, Genlisea, Pinguicula, Ibicella, Byblis, Philcoxia, Stylidium* and/or *Cephalotus* genera. Such botanical extracts will be referred to herein as "Genus Extracts."

In various embodiments of the present disclosure, botanical extracts comprise extracts from plant species including, but not limited to, *S. purpurea, S. alata, S. flava, S. leucophylla, S. rubra, S. alabamensis, S. jonesii, S. minor, S. oreophila, S. psittacina, N. Judith Finn, N. speciabilis* x *N. ventricosa* (hybrid), *N. veitchii, N. eymae, N. fusca, K chaniana, N. macrophylla, M. officinalis, L. officinalis, G. glabra, E, senticosus, H, perforatum, D. californicum, R. gorgonias, D. intermedia, D. cuneifolia, D. muscipula, A. vesiculosa, N. rafflesiana, D. lusitanicum, T. peltatum, C. berteroniana, B. hechtiodes, B. tatei, P. celsus, P. acantholimon, U. gibba, U. geminiscapa, G. repens, P. potosiensis, I. lutea, B. liniflora* and *C. follicularis*. Such botanical extracts will be referred to herein as "Species Extracts."

In various aspects, the present disclosure provides methods of making botanical extracts. The extracts of the present disclosure may be combined and/or formulated with any food-grade or pharmaceutically acceptable excipient, such as to provide various therapeutic compositions or pharmaceutical formulations, as further described herein. As used herein, a therapeutic composition includes any composition or formulation intended for pharmaceutical, over-the-counter, direct-to-consumer, and all other appropriate retail and wholesale markets for human or animal consumption.

The present disclosure further provides methods of inhibiting viral replication using various botanical extracts. In various embodiments, the present disclosure provides methods of treating virus infections such as a poxvirus infection, (e.g., a vaccinia virus or a variola virus infection); and methods of reducing viral load, or reducing the time to viral clearance, or reducing morbidity or mortality in the clinical outcomes, in patients suffering from a pox viral infection. The present disclosure further provides methods of reducing the risk that an individual will develop a pathological poxvirus infection, such as a vaccinia virus infection or a variola virus infection, which has clinical sequelae. The methods generally involve administering a therapeutically effective amount of at least one botanical extract and/or botanical extract composition, either alone or in combination with other therapeutic compositions, for the treatment of a viral infection, particularly a pox viral infection.

As used herein, the term "poxvirus" includes any member of the family Poxyiridae, including, but not limited to, any member of the Orthopoxvirus genus, including variola (smallpox) virus, vaccinia virus, camelpox, cowpox, ectromelia, monkeypox, racoonpox, skunkpox, taterapox, Uasin Gishu, and volepox; any member of the Parapoxvirus genus; any member of the Avipoxvirus genus; any member of the Capripoxyinus genus; any member of the Leporipoxvirus genus; any member of the Suipoxvirus genus; any member of the Molluscipoxvirus genus; any member of the Yatapoxvirus genus; and any member of the Entomopoxvirus A, B, or C genus.

The term "poxvirus" further includes naturally-occurring (e.g., wild-type) poxvirus; naturally-occurring poxvirus variants; and poxvirus variants generated in the laboratory, including variants generated by selection, variants generated by chemical modification, and genetically modified variants (e.g., poxvirus modified in a laboratory by recombinant DNA methods).

In various aspects, the present disclosure comprises the use of a botanical extract composition comprising at least one botanical extract of *Sarracenia, Nepenthes, Melissa, Lavandula, Glycyrrhiza, Eleutherococcus, Hypericum, Darlingtonia, Heliamphora, Roridula, Drosera, Dionaea, Aldrovanda, Drosophyllum, Triphyophyllum, Catopsis, Brocchinia, Paepalanthus, Utricularia, Genlisea, Pinguicula, Ibicella, Byblis, Philcoxia, Stylidium* or *Cephalotus* genera in the treatment of viruses including, but not limited to, variola virus, vaccinia virus, Monkeypox virus, Cowpox virus, Ectromelia virus, Orf virus, Canarypox virus, Myxoma virus, and Molluscum contagiosum.; herpesvirus infections, including, but not limited to herpes simplex virus-1 (HSV1), herpes simplex virus-2 (HSV2), Human herpes 8 and Equine herpes virus (EHV); Varicella-Zoster virus (VZV), Cytomegalovirus, Epstein-Barr virus, Kaposi's Sarcoma Associated herpesvirus (HHV8), Human papillomavirus (including various serotypes of HPV), polyomavirus (including JC and BK viruses), and in the treatment of any associated herpes virus induced cancers.

In various embodiments, certain botanical extracts including extracts from one or more of the genera *Nepenthes, Drosera, Dionaea, Darlingtonia* and *Pinguicula*, demonstrate antiviral activity. Such botanical extracts will be referred to herein as "Genus II Extracts." In various embodiments, *S. purpurea* exhibited antipoxvirus activity. However, various combinations of two or more botanical extracts showed antiviral activity that was: (1) less than the predicted additive activity (i.e., a "negative" effect); (2) equal to the predicted additive activity (i.e., an "additive" effect); or, (3) unexpectedly greater than the predicted additive activity (i.e., a "synergistic" effect), demonstrating unpredicted synergistic combinations of botanical extracts not heretofore known or expected in the art.

In various embodiments, the present disclosure comprises a therapeutic composition comprising a botanical extract and at least one pharmaceutically acceptable excipient.

In certain embodiments, the present disclosure provides a method for treating or preventing a viral infection in an animal or human comprising administering a botanical extract of one or more of the genera *Sarracenia* and *Nepenthes* botanical extracts (referred to herein as "Genus III Extracts"), formulated in a pharmaceutically acceptable transdermal driving carrier/gel, to an animal or human.

In various embodiments, botanical extracts provided herein, may have utility in the treatment, prevention, and/or other effect in relation to poxvirus infections, including, but not limited to, variola virus, vaccinia virus, Monkeypox virus. Cowpox virus, Ectromelia virus, Orf virus, Canarypox virus, Myxoma virus, and Molluscum contagiosum.; herpesvirus infections, including, but not limited to herpes simplex virus-1 (HSV1), herpes simplex virus-2 (HSV2), Human herpes 8 and Equine herpes virus (EHV); Varicella-Zoster virus (VZV), Cytomegalovirus, Epstein-Barr virus, Kaposi's Sarcoma Associated herpesvirus (HHV8), Human papillomavirus (including various serotypes of HPV) and polyomavirus infections (including JC and BK viruses) (collectively, the "Target Viruses"). Accordingly, the present disclosure provides methods of treating virus infections, such as a poxvirus infection, and methods of reducing viral load, or reducing the time to viral clearance, or reducing morbidity or mortality in the clinical outcomes, in patients suffering from a viral infection. In various embodiments, the present disclosure provides methods for treating and/or preventing an infection of the Target Viruses in an animal or human comprising administering a botanical composition described herein as a liquid, or formulated in a pharmaceutically acceptable transdermal driving carrier/gel, to the animal or human.

In various embodiments, the present disclosure provides a method for prophylactic or therapeutic treatment of cancer in an animal or human comprising administering one or more botanical extracts in a pharmaceutically acceptable transdermal driving carrier/gel to an animal or human.

In various embodiments, a method for prophylactic or therapeutic treatment of cancer in an animal or human comprises administering a therapeutically effective amount of one or more Genus III Extracts.

In certain embodiments, the present disclosure provides a method for prophylactic or therapeutic treatment of cervical dysplasia in a patient in need thereof, comprising administering a therapeutically effective amount of one or more botanical extracts, either alone or with a pharmaceutically acceptable transdermal driving carrier/gel. In various embodiments, a method for prophylactic or therapeutic treatment of cervical dysplasia in a patient in need thereof comprises administering a therapeutically effective amount of one or more Genus III Extracts, either alone or with a pharmaceutically acceptable transdermal driving carrier/gel.

In various embodiments, the present disclosure provides a method of therapeutic treatment of itching (anti-pruritic) in a patient in need thereof, comprising administering a therapeutically effective amount of one or more Genus III Extracts, either alone or with a pharmaceutically acceptable transdermal driving carrier/gel. In certain embodiments, a method of therapeutic treatment of itching (anti-pruritic) in a patient in need thereof comprises administering a therapeutically effective amount of one or more Genus III Extracts, either alone or with a pharmaceutically acceptable transdermal driving carrier/gel.

In various embodiments, the present disclosure provides a method of therapeutic treatment of pain (analgesic) in a patient in need thereof, comprising administering a therapeutically effective amount of one or more Genus III Extracts, either alone or with a pharmaceutically acceptable transdermal driving carrier/gel. In various embodiments, a method of therapeutic treatment of pain (analgesic) in a patient in need thereof comprises administering a therapeutically effective amount of one or more Genus III Extracts, either alone or with a pharmaceutically acceptable transdermal driving carrier/gel.

In various embodiments, the present disclosure provides a method for the prophylactic or therapeutic treatment of precancerous lesions or cancer, including actinic keratosis, squamous cell carcinoma, cervical dysplasia, cervical cancer, jaw/neck/throat cancer, anal cancer and penile cancer, comprising the administration of one or more botanical extracts, either alone or with a pharmaceutically acceptable transdermal driving carrier/gel. In various embodiments, a composition comprising a Genus III Extract and/or a botanical formulation as described herein, alone or with a pharmaceutic ally acceptable transdermal driving carrier/gel, is used for the prophylactic or therapeutic treatment of precancerous lesions or cancer including actinic keratosis, squamous cell carcinoma, cervical dysplasia, cervical cancer, jaw/neck/throat cancer, anal cancer and penile cancer.

In various embodiments, the present disclosure includes methods comprising administering one or more botanical extracts and/or pharmaceutical formulation thereof, to a patient in need of treatment, for example, a patient infected with a virus, or to inhibit virus replication or infection of a cell in a patient, or to treat a disease or condition associated with such virus replication or infection of a cell. Although not wishing to be bound to any theories of action, botanical extracts of the present disclosure are believed to block viral replication. For example, *Sarracenia* spp. is believed to block viral RNA synthesis. *Melissa* spp. is believed to block viral attachment to the cell.

In various embodiments, a botanical extract composition comprises one or more botanical extracts. For example, in certain embodiments, a botanical extract composition comprises at least one of *Sarracenia purpurea, Melissa officinalis, Lavandula officinalis, Glycyrrhiza glabra, Eleutherococcus senticosus* and/or *Hypericum perforatum*. Such botanical extracts will be referred to herein as "Species II Extracts."

In various embodiments, botanical extract compositions comprising one or more of Species II Extracts provide additive or synergistic antiviral activity.

In various aspects, a method for preparing a liquid extract from a plant material chosen from *Sarracenia*, Nepenthes, *Melissa, Lavandula, Glycyrrhiza, Eleutherococcus, Hypericum, Darlingtonia, Heliamphora, Roridula, Drosera, Dionaea, Aldrovanda, Drosophyllum, Triphyophyllum, Catopsis, Brocchinia, Paepalanthus, Utricularia, Genlisea, Pinguicula, Ibicella, Byblis, Philcoxia, Stylidium* and *Cephalotus*, said method comprising, obtaining fresh plant material; washing and air drying said plant material: combining said plant material with a liquid comprising at least one of water, ethanol and glycerol; allowing said liquid to extract said plant material at from about room temperature to simmering temperatures to form said liquid extract; and separating said liquid extract from said plant material, is provided.

In various aspects, a method for extracting the roots or leaves from the botanical *Sarracenia purpurea* comprising, obtaining fresh plant material; washing and air drying said plant material; combining said plant material with a liquid comprising at least one of ethanol, water and glycerol, wherein the combination of plant material to liquid is from about 1:2. up to about 1:5 grams of plant material to milliliters of liquid, and wherein said ethanol is from about 45% to about 70% of said liquid and said glycerol is from about 0% to about 10% in said liquid; allowing said liquid to extract said plant material at room temperature for 2-60 days, or for 1-3 hours in simmering conditions when said liquid is only water; separating said liquid from said plant material; and optionally filtering said liquid to remove large particulates, is provided. In various embodiments, said liquid comprises 63% 190 proof ethanol, 32% water and 5% glycerol. In various embodiments, said liquid comprises from about 50% to about 80% of glycerol, with the remainder being water and no ethanol. In some embodiments, said liquid consists of only water. In various embodiments, said liquid comprises 25% water and 75% glycerol.

In various aspects, a method of extracting the aerial portions of the botanical *Melissa officinalis* comprising, removing leaves from stems; washing and air drying said leaves; blending said leaves at a ratio of 1:2-1:5 grams of plant material to milliliters of liquid, said liquid comprising distilled water and glycerol, said glycerol present at from about 50% to about 80% in said liquid; allowing said liquid to extract said leaves for 2 to 40 days at room temperature; separating said liquid from said plant material; and optionally filtering said liquid to remove large particulates, is provided.

In various aspects, a method for extracting the flowering stems of the botanical *Lavandula officinalis* comprising, obtaining fresh *Lavandula officinalis* plants; removing flowers from stems; blending said flowers at a ratio of 1:2-1:5 grams of plant material to milliliters of liquid, said liquid comprising distilled water and glycerol, said glycerol present at from about 50% to about 80% in said liquid; allowing said liquid to extract said leaves for 2 to 40 days at room temperature; separating said liquid from said plant material; and optionally filtering said liquid to remove large particulates, is provided.

In various aspects, a method for extracting the flowering stems of the botanical *Hypericum perforatum* comprising, obtaining fresh *Hypericum perforatum* plants; removing flowers and leaves from stems; blending said flowers and leaves at a ratio of 1:2-1:5 grams of plant material to milliliters of liquid, said liquid comprising 190-proof ethanol, distilled water and glycerol, said ethanol present at from 40% to 70% and said glycerol present at 0% to 5%; allowing said liquid to extract said leaves for 2 to 40 days at room temperature; separating said liquid from said plant material; and optionally filtering said liquid to remove large particulates, is provided.

In various aspects, a method for extracting the botanical *Eleutherococcus senticosus* comprising, obtaining fresh *Eleutherococcus senticosus* plants; blending said plants at a ratio of 1:2-1:5 grams of plant material to milliliters of liquid, said liquid comprising 190-proof ethanol, distilled water and glycerol, said ethanol present at from 25% to 60% and said glycerol present at 0% to 5%; allowing said liquid to extract said leaves for 2 to 40 days at room temperature; separating said liquid from said plant material; and optionally filtering said liquid to remove large particulates, is provided.

In various aspects, a method for extracting the botanical *Eleutherococcus senticosus* comprising, obtaining a powdered extract of *Eleutherococcus senticosus* obtained from a 10:1 ethanol/water extraction; combining said powdered extract at a ratio of 1:10 grams of powdered extract to milliliters of liquid, said liquid comprising 25% to 60% ethanol and 0% to 5% glycerol; mixing for 14 days at room temperature; and filtering said powder from said liquid, is provided.

In various aspects, a method for extracting the botanical *Glycyrrhiza glabra* comprising, obtaining fresh *Glycyrrhiza glabra* plants: blending said plants at a ratio of 1:2-1:5 grams of plant material to milliliters of liquid, said liquid comprising 190-proof ethanol, distilled water and glycerol, said ethanol present at from 10% to 50% and said glycerol present at 0% to 5%; allowing said liquid to extract said leaves for 2 to 40 days at room temperature; separating said liquid from said plant material; and optionally filtering said liquid to remove large particulates, is provided.

In various aspects, a method for extracting the botanical *Glycyrrhiza glabra* comprising, obtaining a powdered extract of *Glycyrrhiza glabra* obtained from a 8:1 ethanol/water extraction; combining said powdered extract at a ratio of 1:10 grams of powdered extract to milliliters of liquid, said liquid comprising 10% to 50% ethanol and 0% to 5% glycerol; mixing for 14 days at room temperature; and filtering said powder from said liquid, is provided.

In various embodiments, a therapeutic composition comprises at least one liquid extract from any of claims 1-13.

In various embodiments, an aqueous botanical extract mixture comprises: 50% extract of *Sarracenia purpurea* (equating to 50 viral inhibitory units (VIU)/ml); 12% *Melissa officinalis* (equating to 80 viral inhibitory units (VIU)./ml); 20% *Lavandula officinalis* (equating to 20 viral inhibitory units (VIU)/ml); 5% *Glycyrrhiza glabra* (equating to 40 viral inhibitory units (VIU)/ml): 5% *Eleutherococcus senticosus* (equating to 40 viral inhibitory units (VIU)/ml); and optionally, 8% *Hypericum* perforatum (equating to 30 viral inhibitory units (VIU)/ml), wherein each of said extracts are prepared by the methods of claims 1-13. In various aspects, an aqueous botanical extract mixture comprises: 40-100% extract of *Sarracenia purpurea*, 5-30% *Melissa* officinalis, 5-35% *Lavandula officinalis*, 2-30% *Glycyrrhiza glabra*, 2-20% *Eleutherococcus senticosus* and/or 5-20% *Hypericum perforatum*.

In various aspects, a synergistic botanical extract mixture comprises *Sarracenia purpurea, Melissa officinalis, Lavandula officinalis, Glycyrrhiza glabra, Eleutherococcus senticosus* and/or *Hypericum perforatum*.

In various embodiments, the use of a therapeutic composition for dermal or epithelial topical therapy, wherein said formulation comprises at least one extract of any one of claims 1-18 for a suspension in a transdermal base, is provided. In some embodiments, said transdermal base is chosen from the group consisting of VERSABASE, LIPODERM, PENTRAVAN, Pluronic Lecithin Organogel (PLO), and mixtures thereof. In further embodiments, the use of a therapeutic composition of claim 19 for transdermal drug delivery on the cervix or vaginal tract of a patient in need of therapy, is provided.

In embodiments, a therapeutic composition comprises, at least one extract in accordance with any one of claims 1-13; and at least one pharmaceutically acceptable excipient. In some embodiments, said at least one extract and said at least one pharmaceutically acceptable excipient are in a ratio of 50/50, In further embodiments, said at least one extract and said at least one pharmaceutically acceptable excipient are in a ratio of 75/25. In some embodiments, said pharmaceutically acceptable excipient is chosen from the group consisting of ammonium acryloyldimethyltaurate/VP Copolymer, aloe vera, allantoin, fatty acids, fatty alcohols, fatty acid esters, monoglycerides, diglycerides, triglycerides, glycerin, lecithin, gums, polymers, sorbitan fatty acid esters, alkoxylated fatty acids, alkoxylated fatty acid esters, and mixtures thereof.

In various aspects, a therapeutic composition comprises an extract of at least one of *Sarracenia, Nepenthes, Melissa, Lavandula, Glycyrrhiza, Eleutherococcus, Hypericum, Darlingtonia, Heliamphora, Roridula, Drosera, Dionaea, Aldrovanda, Drosophyllum, Triphyophyllum, Catopsis, Brocchinia, Paepalanthus, Utricularia, Genlisea, Pinguicula, Ibicella, Byblis* and *Cephalotus* genera plant; and a fatty acid component. In various embodiments, the therapeutic composition of claim 26 comprises a pitcher plant extract and a fatty acid component, In various embodiments, a method for inhibiting the replication of a poxvirus comprises exposing said poxvirus to at least one extract of any one of claims 1-18. In some embodiments, said poxvirus is chosen from the group consisting of orthopoxvirus, parpoxvirus, avipoxvirus, capripoxvirus, leporipoxvtrus, suipoxvirus, molluscipoxvirus and yatapoxvirus.

In various embodiments, a method for inhibiting the replication of human poxvirus pathogens comprises exposing said poxvirus pathogen to at least one extract from any one of claims 1-18. In some embodiments, said poxvirus pathogen is chosen from the group consisting of vaccinia virus, monkeypox virus, variola virus, and molluscum contagiosum virus.

In various embodiments, a method of inhibiting the replication of animal poxvirus pathogens comprises exposing said animal poxvirus pathogen to at least one extract of any one of claims 1-18.

In various embodiments, a method of inhibiting the replication of herpes virus family members comprises exposing said herpes virus to at least one extract of any one of claims 1-18. In some embodiments, said herpes viruses is selected from the group consisting of herpes simplex 1, herpes simplex 2, varicella-zoster virus, Epstein-Barr virus, cytomegalovirus and human herpes 8. In further embodiments, said herpes virus is an animal herpes virus. In yet further embodiments, said animal herpes virus is equine herpes virus-1.

In various embodiments, a method of inhibiting the replication of papilloma and polyomavirus family members comprises exposing said papilloma or polyomavirus family member to at least one extract of any one of claims 1-18.

In various embodiments, a method of inhibiting the replication of human papillomavirus pathogens comprises exposing said human papillomavirus pathogen to at least one extract of any one of claims 1-18. In some embodiments, said human papillomavirus pathogen is any one of HPV 2, 6, 7, 11, 14, 16, 18, 31, 32, 33, 35, 39, 45, 51, 52, 53, 56, 58, 59 and 63.

In various embodiments, a method of inhibiting the replication of human polyomavirus pathogens comprises exposing said polyomavirus pathogen to at least one extract of any one of claims 1-18. In some embodiments, said pathogen is any one of JC and BK viruses.

In various embodiments, a method for inducing cellular senescence and apoptosis in human papillomavirus-induced cancer cells comprises exposing said cancer cells to at least one extract of any one of claims 1-18, In various embodiments, a method for prophylactic or therapeutic treatment of human poxvirus infections comprises exposing said human poxvirus to any therapeutic composition of any one of claims 19, and 22-27. In some embodiments, the viral infection is selected from the group consisting of vaccinia virus, monkeypox virus, variola virus and molluscum contagiosum virus.

In various embodiments, a method for prophylactic or therapeutic treatment of animal poxvirus infections comprises exposing said animal poxvirus to any extract of claims 1-18.

In various embodiments, a method for prophylactic or therapeutic treatment of animal poxvirus infections comprises exposing said animal poxvirus to any therapeutic composition of claims 19, and 22-27.

In various embodiments, a method for prophylactic or therapeutic treatment of human herpes virus infections comprises exposing said human herpes virus to any extract of claims 1-18 or any therapeutic composition of claims 19, and 22-27. In some embodiments, the viral infection is selected from the group consisting of herpes simplex virus-1 (HSV1), herpes simplex virus-2 (HSV2), herpes varicella-zoster, Epstein-Barr virus, cytomegalovirus and human herpes 8.

In various embodiments, a method for prophylactic or therapeutic treatment of animal herpes virus infections comprises exposing said animal herpes virus to any extract of claims 1-18 or any therapeutic composition of claims 19, and 22-2.7. In some embodiments, the viral infection is equine herpes virus-1.

In various embodiments, a method for prophylactic or therapeutic treatment of human papillomavirus infections comprises exposing said human papillomavirus to any extract of claims 1-18 or any therapeutic composition of claims 19, and 22-27, In some embodiments, the viral infection is at least one of human papillomaviruses HPV 2, 6, 7, 11, 14, 16, 18, 31, 32, 33, 35, 39, 45, 51, 52, 53, 56, 58, 59 and 63.

In various embodiments, a method for prophylactic or therapeutic treatment of human polyomavirus infections comprises exposing said human polyomavirus to any extract of claims 1-18 or any therapeutic composition of claims 19, and 22-27. In some embodiments, the viral infection is one of human J C and BK viruses.

In various embodiments, a method for prophylactic or therapeutic treatment of pre-cancer or cancer, wherein the pre-cancer or cancer is actinic keratosis or squamous cell carcinoma, comprises exposing said pre-cancer or cancer to any extract of claims 1-18 or any therapeutic composition of claims 19, and 22-27.

In various embodiments, a method for prophylactic or therapeutic treatment of pre-cancer or cancer, wherein the pre-cancer or cancer is cervical dysplasia or cervical cancer, comprises exposing said pre-cancer or cancer to any extract of claims 1-18 or any therapeutic composition of claims 19, and 22-27.

In various embodiments, a method for prophylactic or therapeutic treatment of cancer, wherein the cancer is anal cancer, comprises exposing said cancer to any extract of claims 1-18 or any therapeutic composition of claims 19, and 22-27.

In various embodiments, a method for prophylactic or therapeutic treatment of cancer, wherein the cancer is oropharyngeal cancer, laryngeal papillomas, or oral papillomas, comprises exposing said cancer to any extract of claims 1-18 or any therapeutic composition of claims 19, and 22-27.

In various embodiments, a method for prophylactic or therapeutic treatment of warts, wherein the warts include plantar warts, common warts and anogenital warts, comprises exposing said warts to any extract of claims 1-18 or any therapeutic composition of claims 19, and 22-27.

In various embodiments, a method for prophylactic or therapeutic treatment of cancer, wherein the cancer is Kaposi's Sarcoma, comprises exposing said cancer to any extract of claims 1-18 or any therapeutic composition of claims 19, and 22-27.

In various embodiments, a method for prophylactic or therapeutic treatment of pre-cancer or cancer associated with herpes virus infections, comprises exposing said pre-cancer any extract of claims 1-18 or any therapeutic composition of claims 19, and 22-27. In some embodiments, the viral-induced cancer is one of Epstein-Barr virus and Human herpes 8 virus.

In various embodiments, a method for prophylactic or therapeutic treatment of pre-cancer or cancer associated with papillomavirus infections comprises exposing said pre-cancer or cancer to any extract of claims 1-18 or any therapeutic composition of claims 19, and 22-27. In some embodiments, the viral-induced cancer is associated with any one of human papilloma viruses HPV 16, 18, 31 and 45.

In various embodiments, a method for therapeutic treatment of itching (anti-pruritic) in a patient in need thereof, comprises administering to said patient a therapeutically effective amount of a botanical extract of any one of claims 1-18.

In various embodiments, a method for therapeutic treatment of pain (analgesic) in a patient in need thereof, comprises administering to said patient a therapeutically effective amount of a botanical extract of any one of claims 1-18.

In various embodiments, said plant is selected from the group consisting of *S. elata, S. flava, S. leucophylla* and *S. rubra*. In some embodiments, said plant is selected from the group consisting of *N. veitchii, N. spectrabilis* x *ventricosa, N. eymae, N. Judith Finn, N. chaniana, N. fusca* and *N. macrophylla*. In further embodiments, said plant is selected from the group consisting of *Drosera* spp., *Dionaea* spp., *Darlingtonia* spp., and *Pinguicula* spp.

In various embodiments, a topical therapeutic composition comprises an extract of claims 1-18 or a therapeutic composition of claims 19, and 22-21.

In various embodiments, an oral formulation comprises an extract of claims 1-18 or a therapeutic composition of claims 19, and 22-27.

In various embodiments, a suppository comprises an extract of claims 1-18 or a therapeutic composition of claims 19, and 22-27.

In various embodiments, a method for administering an extract of claims 1-18 or a therapeutic composition of claims 19, and 22-27 consisting of administering said extract or therapeutic composition through at least one of oral, buccal, rectal, intranasal, parenteral, intraperitoneal, intradermal, subcutaneous, intramuscular, transdermal, inhalation and intratracheal routes, is provided.

In various aspects, a method for the standardization of botanical extracts for antiviral activity and therapeutic value comprising, a determination and measurement of the antiviral units per milliliter, is provided.

In various aspects, an aqueous mixture comprising, 50% extract of *Sarracenia purpurea* (equating to 50 viral inhibitory units (VIU)/ml); 12% *Melissa officinalis* (equating to 80 viral inhibitory units (VIU)/ml); 20% *Lavandula officinalis* (equating to 20 viral inhibitory units (VIU)/ml); 5% *Glycyrrhiza glabra* (equating to 40 viral inhibitory units (VTU)/ml); 5% *Eleutherococcus senticosus* (equating to 40 viral inhibitory units (VIU)/ml); and optionally, 8% *Hypericum perforatum* (equating to 30 viral inhibitory units (VIU)/ml), is provided.

In various aspects, a composition comprising at least one of a Genus Extract, is provided.

In various aspects, a composition comprising at least one of a Genus II Extract, is provided.

In various aspects, a composition comprising at least one of a Species Extracts, is provided.

In various aspects, a composition comprising at least one of a Species II Extract, is provided.

In various embodiments, the composition of claim 78, further comprises a pharmaceutically acceptable excipient. In some embodiments, the composition of claim 78, further comprises a gel carrier. In further embodiments, the composition of claim 78 is aqueous.

In various aspects, a composition comprising at least one of the following botanical extract pairs, Melissa and Sarracena; Melissa and Glycyrrhiza: Melissa and Eleutherococcus; Sarracenia and Eleutherococcus; Sarracenia and Glycyrrhiza; Sarracenia and Hypericum; Sarracenia and Lavandula; Eleutherococcus and Glycyrriza; Glycyrhizza and Lavandula; Eleutherococcus and Hypericum; and Eleutherococcus and Lavandula, is provided. In various embodiments, the composition of claim 83 further comprises a pharmaceutically acceptable excipient In some embodiments, the composition of claim 83, further comprises a gel carrier. In further embodiments, the composition of claim 83 is aqueous.

In various aspects, a composition comprising at least one of a Genus III Extract, is provided.

BRIEF DESCRIPTION OF THE DRAWINGS

FIGS. 5A and 5B illustrate a specificity of a *S. purpurea* extract on Orthopoxvirus;

FIGS. 6A-6E illustrates an effect of a *S. purpurea* extract on HSV1 induced CPE;

FIGS. 10A-10D illustrate an effect of a *S. purpurea* extract on VZV plaque formation;

DETAILED DESCRIPTION

Figure 1A:
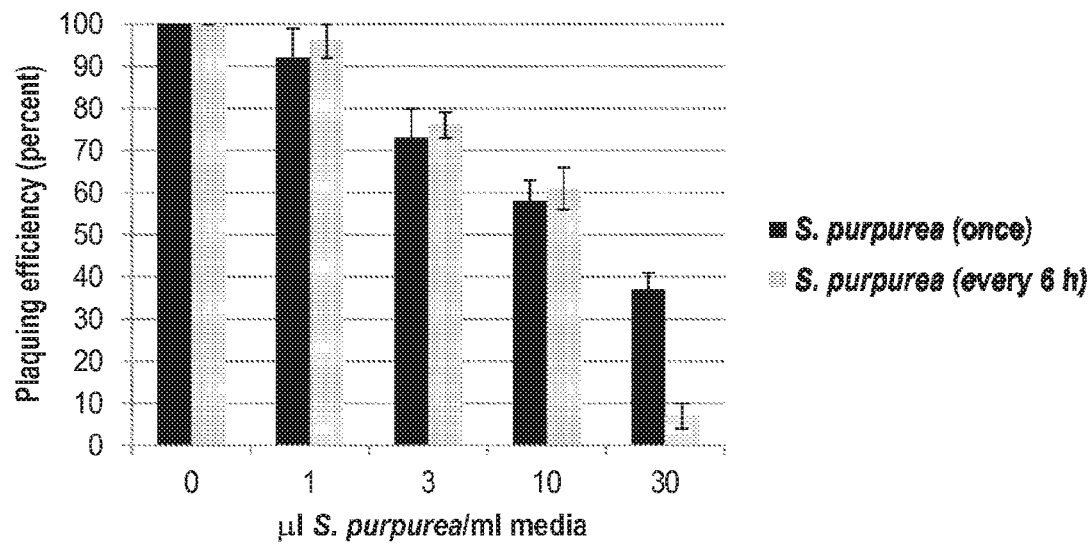
FIGS. 1A-1C illustrate the effect of a *S. purpurea* extract on VACV replication.

In accordance with the present disclosure, methods making botanical extracts are disclosed, in addition to various methods of blending certain botanical extracts, compounding of various botanical extracts into therapeutic compositions, and various methods of use of both botanical extracts and therapeutic compositions for the treatment and prophylaxis of infections, diseases and symptoms thereof. In various embodiments, tissue from a plant of a genus and/or species identified in the present disclosure is used in the preparation of a botanical extract. In certain embodiments of the present disclosure, one or more of Species II Extracts, amongst others, can be used in the preparation of a botanical extract.

Botanical extracts in accordance with the present disclosure, function therapeutically in an antiviral capacity either individually or in specific combinations. Select combinations of botanical extracts provide unexpected synergistic antiviral activity. In various embodiments, the viral infection is associated with poxvirus infections, including, but not limited to, the Target Viruses. As such, the present disclosure provides methods of treating infections of the Target Viruses and methods of reducing viral load, or reducing the time to viral clearance, or reducing morbidity or mortality in the clinical outcomes, in patients suffering from a viral infection.

The present disclosure contemplates the use of one or more of Genus Extracts, Genus II Extracts, Genus III Extracts, Species Extracts and Species II Extracts in various embodiments.

In various aspects, botanical extract preparations may undergo quality control and/or standardization wherein the antiviral activity of each extract is measured and/or adjusted prior to and after preparation of the aqueous blend. As used herein, 1 VIU is defined as a viral inhibitory unit and is the quantity of an extract, composition, or formulation required to inhibit viral replication by 50%. In various aspects, the antiviral activity of a botanical extract, botanical extract composition, or therapeutic composition is measured using a plaque reduction technique in a cell culture system and titration of the extract, composition, or formulation, as described elsewhere herein. In various embodiments, the antiviral activity of an extract, composition, or formulation may be expressed in any suitable manner, such as VIU/ml.

As used herein, the term "percent plaque formation" and variations thereof refers to the proportion of expected plaque formation in an in vitro biological activity assay to assess the antiviral effects of a compound, extract, composition, formulation, or the like. In various embodiments, an in vitro antiviral activity assay may comprise exposing and infecting a cell culture with a known number of infectious viral particles, for example 200 plaque forming units (pfu). In such an example, observation of 200 viral plaques following a suitable period of incubation would be scored as 100% plaque formation. Similarly, observation of 144 viral plaques would be scored as 72% plaque formation.

In various aspects, a botanical extract or composition may be subsequently combined with an excipient or agent to prepare a therapeutic composition. For example, in various embodiments, a 50:50 ratio (vol:wt) of botanical extract composition to VERSABASE gel may be formulated to provide a therapeutic composition. The use of VERSABASE gel in a therapeutic composition of a botanical extract may provide the following benefits: The ammonium acryloyldimethyltaurate/VP Copolymer may act as a gelling agent for the aqueous solution to allow for topical application without dripping or drying out. The aloe vera may enhance skin penetration of the active botanical constituents allowing for transdermal uptake. The allantoin may act as a keratolytic agent to improve moisture binding capacity of the epidermis to also improve drug penetration into the skin. Other base gels with these activities may be used may be used, but these application-associated activities (including transdermal absorption and surface adhesion) are necessary for the efficacy and therapeutic value of the botanical antivirals. Such alternative gels include: LIPODERM® (Professional Compounding Centers of America, Inc., Houston, Tex.), PENTRAVAN® (Fargon, Inc., St. Paul, Minn.), and Plutonic Lecithin Organogel. LIPODERM reportedly comprises ethoxydiglycol, water, glycerin, $C_{12}$-$C_{15}$ alkyl benzoate, glyceryl stearate, dimethicone, cetearyl alcohol, cetearyl glucoside, polyacrylamide, cetyl alcohol, magnesium aluminum silicate, xanthan gum, aloe vera, tocopheryl acetate, bitter almond kernel oil, grape seed extract, wheat germ oil, vitamin-A palmitate, vitamin-C palmitate, ProLipo mutli-emulsion liposomic system, tetrasodium EDTA, phenoxyethanol and sodium hydroxymethyl glycinate. Rather than using commercially available bases such as these, ingredients similar to those found in these bases may be used to form new bases that can be used in the therapeutic compositions herein. For example, other fatty alcohols, oils, lipids, gums, polymers, and the like, may be compounded with the botanical extracts discussed to produce therapeutic compositions within the scope of the present disclosure.

In various aspects, the proportion of a botanical extract within a composition can be adjusted to increase synergistic activity and efficacy.

Methods of Making a Botanical Extract

In accordance with the present disclosure, methods of making a liquid botanical extract are provided, comprising:
  obtaining plant material from any species within *Sarracenia, Nepenthes, Melissa, Lavandula, Glycyrrhiza, Eleutherococcus, Hypericum, Darlingtonia, Heliamphora, Roridula, Drosera, Dionaea, Aldrovanda, Drosophyllum, Triphyophyllum, Catopsis, Brocchinia, Paepalanthus, Utricularia, Genlisea, Pinguicula, Ibicella, Byblis, Philcoxia, Stylidium* or *Cephalotus* genera;
  mixing an extraction solution with the plant material to form a plant material/extraction solution mixture;
  storing the mixture for up to about 60-days at room temperature in amber or clear glass jars or other suitable receptacle, and/or heating the mixture for up to about 1 day in any suitable reaction vessel to produce a botanical extract with plant material suspended therein;
  removing the plant material from the botanical extract by any suitable means; and optionally filtering the resulting botanical extract to remove any remaining particulates.

Fresh plant material may be used for the preparation of liquid botanical extracts. As used herein, "fresh plant material," means plants that are subject to an extraction process less than about 10 days following harvest. The plant material may comprise any combination of flowers, leaves, stems, shoots, roots, tubers, twigs, buds, and the like, from any of *Sarracenia, Nepenthes, Melissa, Lavandula, Glycyrrhiza, Eleutherococcus, Hypericum, Darlingtonia, Heliamphora, Roridula, Drosera, Dionaea, Aldrovanda, Drosophyllum, Triphyophyllum, Catopsis, Brocchinia, Paepalanthus, Utricularia, Genlisea, Pinguicula, Ibicella, Byblis, Philcoxia, Stylidium* or *Cephalotus* genera.

In accordance with the present disclosure, the extraction solution comprises at least one of an alcohol, water, a diol and a polyol. As used herein, the term "distilled water" may mean water that is purified by distillation, including double distillation, and may also be used to refer to water that is purified by other methods, such as reverse osmosis, carbon filtration, micro filtration, ultrafiltration, ultraviolatet oxidation, or electrodialysis. "Alcohol" as used herein means any lower molecular weight $C_1$-$C_{10}$ alkanol, such as methanol, ethanol, n-propanol, i-propanol, n-butanol, t-butanol, and the like. In various embodiments, 190-proof ethanol is used as the alcohol. Other forms of ethanol, such as 200-proof ethanol, or any other dilution of ethanol or any alcohol may also be used. "Diol" as used herein means any hydrocarbon substituted with exactly two-OH (hydroxyl) groups, including any ether or ester derivative thereof, such as ethylene glycol, propylene glycol, MP diol, ethylene glycol monomethyl ether, propylene glycol monomethyl ether, and the like. "Polyol" as used herein means any hydrocarbon substituted with three or more-OH (hydroxyl) groups, including any ether or ester derivative thereof, such as glycerin (glycerol), various sugar alcohols, fatty monoglycerides, fatty diglycerides, fatty triglycerides, and the like. In various embodiments, the extraction solution comprises, for example: ethyl alcohol; water; glycerin; ethyl alcohol, water and glycerin; ethyl alcohol and water; water and glycerin; ethyl alcohol and glycerin; methanol, water and glycerin; methanol and i-propanol; or isopropyl alcohol, water and propylene glycol monomethyl ether.

In various embodiments, the plant material/extraction solution mixture may be stored at room temperature for 2-60 days. In further embodiments, the plant material/extraction solution mixture may be boiled/simmered for less than one day, such as, for example 30 minutes to 3 or 4 hours.

In various embodiments, the plant material may be removed from the botanical extract by straining, pressing, and/or by centrifugation. Pressing may be performed using any type of press. The botanical extract may be optionally filtered through any suitable filtration means to remove various sized particulates remaining after the bulk plant material is removed.

In various embodiments, root, stem and/or leaf material may be used. For example, leaves may be separated from plant stems, and then only the leaves used. In other embodiments, entire plants may be used, or only the stem material. In further embodiments, roots may be separated from plants and only the roots used. The plant may be chosen from the group consisting of *Sarracenia, Nepenthes, Melissa, Lavandula, Glycyrrhiza, Eleutherococcus, Hypericum, Darlingtonia, Heliamphora, Roridula, Drosera, Dionaea, Aldrovanda, Drosophyllum, Triphyophyllum, Catopsis, Brocchinia, Paepalanthus, Utricularia, Genlisea, Pinguicula, Ibicella, Byblis, Philcoxia, Stylidium* and *Cephalotus* genera.

Botanical Extracts

*S. purpurea.*

In various embodiments, root and/or leaf material may be used to produce a *Sarracenia* botanical extract. For *S. purpurea*, leaves may be harvested, split longitudinally and any detritus removed. Leaves may then be subsequently washed and air dried before blending with extraction solution in a blender at a ratio of from about 1:10 to about 1:30 grams of plant material:milliliter extraction solution. For example, a ratio of about 1:15 grams of plant material: milliliter extraction solution may be used for extraction. In various embodiments, an extraction solution may comprise, for example 190-proof ethanol/distilled water/glycerol (63%/32%/5%) or distilled water/glycerol (25%/75%). In various embodiments, the ethanol may vary from about 45% to about 70% and the glycerol may vary from about 0% to about 10%. In various embodiments, the extraction solution may comprise from about 50% to about 80% glycerol, with the remainder being water and no ethanol. The plant material/extraction solution mixture may be incubated at room temperature in amber glass jars for up to about 60 days, such as, for example, 7 days. If the extraction solution comprises only distilled water, the plant material/extraction solution mixture may be simmered for about 1-3 hours to perform extraction rather than incubation at room temperature. Any suitable combination of extraction solution and incubation condition such as temperature, time, agitation, light protection, and duration may be used in accordance with various embodiments of the present disclosure.

*M. officinalis.*

In various embodiments, leaf material from *Melissa officinalis* may be used to produce a botanical extraction. For example, twelve inch aerial portions of *M. officinalis* may be harvested, and the leaves may be removed from stems and the stems discarded. The leaves may be subsequently washed and air dried before blending with extraction solution at a ratio of from about 1:6 to about 1:20, for example, about 1:8, grams plant material milliliter extraction solution, in a blender in the presence of any suitable extraction solution, such as distilled water/glycerol (25%/75%). In various embodiments, the percentage of glycerol in an extraction solution may vary from about 50% to about 80%. The plant material/extraction solution mixture may be incubated at room temperature in amber glass jars for from 2-40 days, such as, for example, 7 days. In accordance with various embodiments, any suitable combination of extraction solution and incubation condition such as temperature, time, agitation, light protection, and duration may be used to perform extraction.

*L. officinalis.*

In various embodiments, leaf material from *Lavandula officinalis* may be used to produce a botanical extract. For example, six inch flowering stems of *Lavandula officinalis* may be harvested, and the flowers may be removed from the stems and the stems discarded. Flowers may be blended with extraction solution in a blender at a ratio of from about 1:2 to about 1:20, for example, about 1:8, grams plant material: miliiliter extraction solution. In various embodiments, extraction solution may comprise distilled water and glycerol, for example, distilled water/glycerol (25%/75%). The plant material/extraction solution mixture may be incubated at room temperature in amber glass jars for from 2-40 days, such as, for example, 7 days. Any suitable combination of extraction solution and incubation condition such as temperature, time, agitation, light protection, and duration may be used in accordance with various embodiments of the present disclosure.

*H. perforatum.*

In various embodiments, leaf and flower material from *Hypericum* perforatum may be used to produce a botanical extract. For example, six inch flowering stems of *H. perforatum* may be harvested, and the flowers and leaves may be removed from stems and stems may be discarded. Flowers/leaves may be blended with extraction solution in a blender at a ratio of from about 1:2. to about 1:10, for example, about 1:4, grams plant material milliliter extraction solution. In various embodiments, extraction solution used for extraction of *H. perforatum* may comprise ethanol, distilled water, and glycerol. For example, 190-proof ethanol/distilled water/glycerol (58%/32.%/10%) may be used. In various embodiments, the percentage of ethanol in an extraction solution used to extract *H. perforatum* can range from about 40-70%, and the glycerol can range from about 0% to about 5%. The plant material/extraction solution mixture may be incubated at room temperature in amber glass jars for from 2-40 days, such as, for example, 7 days. Any suitable combination of extraction solution and incubation condition such as temperature, time, agitation, fight protection, and duration may be used in accordance with various embodiments of the present disclosure.

*E. senticosus.*

In various embodiments, fresh plant material or a previously extracted and dried powdered extract of *Eleutherococcus senticosus* may be used to prepare a botanical extract. In various embodiments, fresh *E. senticosus* root material (less than 10 days post harvest) may be blended with extraction solution in a blender at a ratio of from about 1:2 to about 1:10 grams plant material:milliliters extraction solution. For example, a ratio of about 1:6 grams plant material:milliliters extraction solution may be used. In various embodiments, comprising at least one of 190 proof ethanol, distilled water and glycerol. For example, *E. senticosus* root material may be extracted with a mixture of ethanol, distilled water, and glycerol, such as, for example, 42%/53%/5% ethanol-water-glycerol. In various embodiments, the ethanol may comprise from about 25% to about 60% of the extraction solution, and the glycerol may comprise from about 0% to about 5% of the extraction solution. The liquid/plant mixture may be left at room temperature for 2-40 days, such as for example for 21 days. For a preparation from a powdered extract, *Eleutherococcus senticosus* powdered extract (10:1, originally extracted in ethanol and water) may be mixed at a 1:10 ratio with 190-proof ethanol/distilled water/glycerol (42%/53%/5%) and agitated daily for 14 days. In this case, the ethanol may be present from 25% to about 60% and the glycerol present at from about 0% to about 5%.

*G. glabra.*

Either fresh plant material or a previously extracted and dried powdered extract may be used to prepare a liquid extract. Fresh plant material (less than 10 days following harvest) is mixed at a ratio of from 1:2 to 1:5 grams plant material to milliliters liquid, with the liquid comprising at least one of 190 proof ethanol, distilled water and glycerol. F or example, a mixture of 26%/64%/10% ethanol-water-glycerol may be used as the liquid for extraction. In various embodiments, the ethanol may be present from 10% to 50% and the glycerol may be present from about 0% to about 5%. The liquid/plant mixture may be left at room temperature for 2-40 days, such as for example for 21 days. For a preparation from a powdered extract, *Glycyrrhiza glabra* powdered extract (8:1, originally extracted in ethanol and water) may be mixed at a 1:8 to 1:10 ratio with a liquid comprising at least one of 190 proof ethanol, distilled water and glycerol. For example, a liquid comprising 190-proof ethanol/distilled water/glycerol (26%/64%/10%) may be used. The mixture is agitated daily for 2-20 days, such as for example 14 days. Any suitable combination of extraction solution and incubation condition such as temperature, time, agitation, light protection, and duration may be used in accordance with various embodiments of the present disclosure.

Other Genera in General:

Other species from each of the six (6) genera represented above (*Sarracenia, Melissa, Lavandula, Glycyrrhiza, Eleutherococcus* and *Hypericum*) may be used in similar extraction procedures to obtain botanical extracts. Various other plants may be also be extracted in accordance with these methods, adapted as necessary for the different genera and species therein, including for example, *Nepenthes, Darlingtonia, Heliamphora, Roridula, Drosera, Dionaea, Aldrovanda, Drosophyllum, Triphyophyllum, Catopsis, Brocchinia, Paepalanthus, Utricularia, Genlisea, Pinguicula, Ibicella, Byblis, Philcoxia, Stylidium* and *Cephalotus* genera.

Following extraction, a botanical extract, such as any of the botanical extracts described above or elsewhere herein, may be separated from the plant material used to create the extract, in various embodiments, a tincture press may be used to filter the botanical extract using an unbleached paper filter. In various embodiments, a centrifuge may be used to remove the solid debris from an extract. Any suitable means of separating liquid extract from solid debris may be used in accordance with various embodiments of the present disclosure.

Botanical Extract Standardization.

In various aspects, a botanical extract used in botanical extract composition may be standardized according to a biological activity, In various embodiments, a botanical extract may be standardized with reference to the ability of the extract to inhibit replication of a particular virus. For example, a botanical extract may be standardized based on in vitro antiviral activity against a virus such as such as HSV1, HSV2, VZV, SV-40, or the like. Any suitable target virus against which a formulation comprising a botanical extract of the present disclosure may be used can be used in an in vitro antiviral activity assay. Likewise, any suitable in vitro assay that may be used to evaluate the ability of a virus to infect, replicate, or otherwise demonstrate aspects of a viral disease process may be used for botanical extract standardization in accordance with the present disclosure.

Standardization of extracts may be performed, for example, on individual lots of plant material, extraction batches, or the like. Such standardization may facilitate production of botanical extract compositions having consistent efficacy or biological activity despite variations in factors such as the concentration or quantity of a biologically active constituent in plant biomass obtained from different sources or extraction process efficiency. In various embodiments, standardization of each botanical extract in a composition comprising multiple extracts facilitates the manufacture of a multi-extract compositions with consistent antiviral activity against a target virus or viruses.

Figure 22:
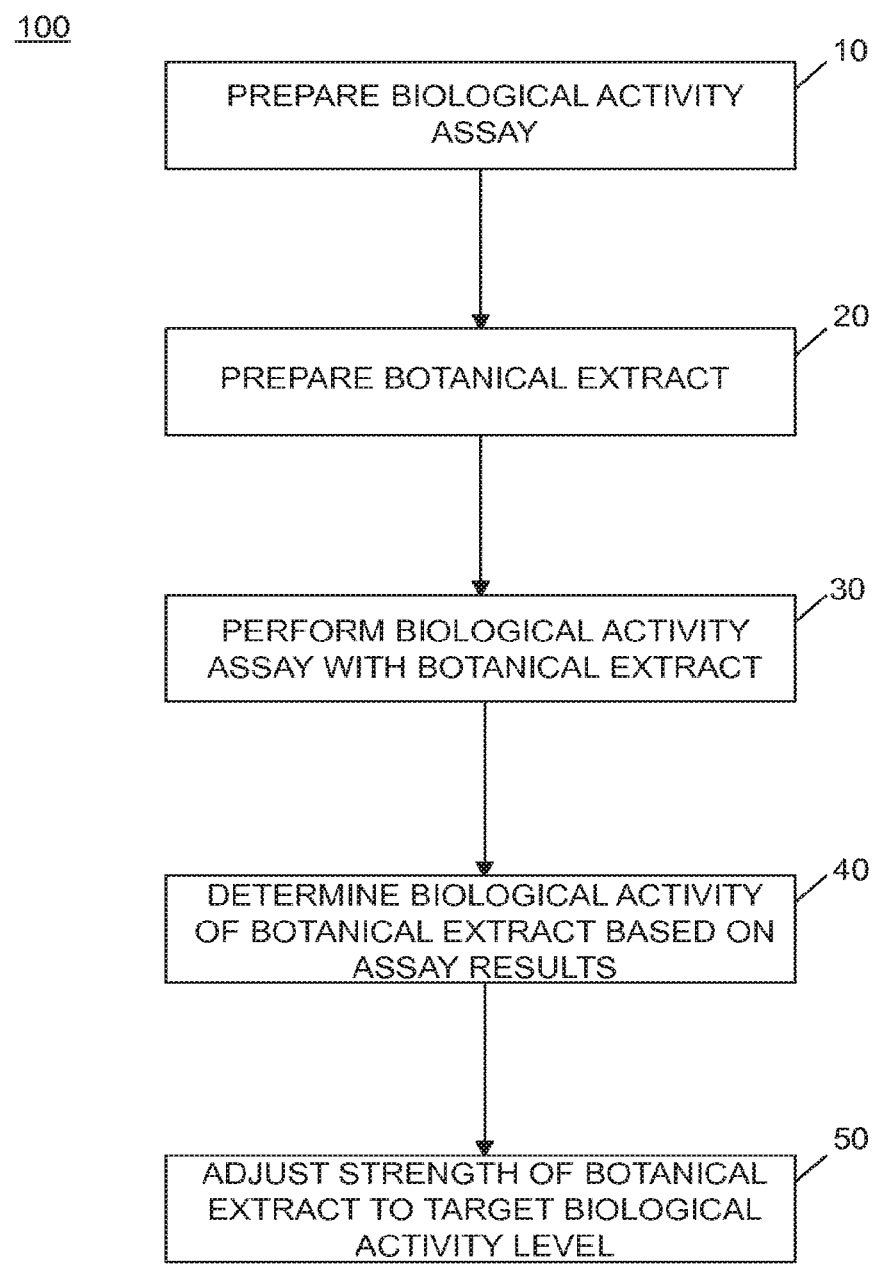
FIG. 22 illustrates a process for standardization of a botanical extract.

Referring now to FIG. 22, a process 100 for standardizing the biological activity of a botanical extract is provided. In various aspects, a biological activity assay may be prepared 10. Preparation of a biological activity assay 10 may comprise, for example, growing a cell culture to a target cell density and/or preparing a dilution of a viral stock to a target infectious viral partical density. In further aspects, a botanical extract may be prepared 20. Preparation of a botanical extract 20 may comprise, for example, preparation of an extract from a plant tissue, as described elsewhere herein. Preparation of a botanical extract may further comprise preparing various concentrations of a botanical extract, such as, for example, a dilution series. In further aspects, a process 100 may comprise performing a biological activity assay with the botanical extract 30. In step 30, the various concentrations of a botanical extract prepared in step 20 may be used to perform a biological activity assay to assess the activity of the extract. The biological activity of a botanical extract is determined based on assay results 40. Following determination of the biological activity of the botanical extract based on the results of a biological activity assay in step 40, the strength of the botanical extract may be adjusted to a target biological activity level in step 50, such as by dilution or concentration of the botanical extract.

In various embodiments, a process 100 for standardizing the biological activity of a botanical extract may comprise a process for standardizing the antiviral activity of a botanical extract, including one or more of the steps of:

Growing cell cultures to a target cell density for viral infection;

Preparing a dilution of a viral stock to a known plaque forming unit (pfu) concentration;

Preparing a botanical extract;
Preparing a serial dilution of the botanical extract to produce botanical extract treatment concentrations;
Treating aliquots of the viral stock with each concentration of the serial dilution of the botanical extract, along with a control (no extract) treatment;
Adding the treated aliquots of the viral stock to the cultured cells to produce infected cell cultures,
Adding fresh media containing an equivalent botanical extract concentration to each infected cell culture.
Incubating infected/treated cell cultures for an incubation period.
Measuring and recording viral plaque formation.
Adjusting the concentration of the botanical extract based on the determined biological activity.

In various embodiments, preparing a dilution of a viral stock to a known plaque forming unit concentration involved titrating the viral stock to, for example, 200 pfu per viral stock aliquot. The viral stock aliquot may then be treated and/or used to infect a cell monoculture. Measuring and recording viral plaque formation may comprise counting the number of viral plaques and reporting the viral plaque formation as a percentage of plaque formation, wherein the percentage of plaque formation is the observed number of plaques divided by the expected number of plaques based on the titrated viral concentration of the viral stock aliquot.

In various aspects, a botanical extract, botanical extract composition, or a therapeutic composition comprising a botanical extract may be standardized according to any suitable criteria. For example, in various embodiments, a botanical extract or a composition thereof may be standardized based on anti-inflammatory activity. Any suitable biological activity, quantitative or qualitative chemical marker, or the like may be used for standardization of a botanical extract or a composition comprising a botanical extract in accordance with the present disclosure.

Botanical Extract Compositions

In various aspects, suitable botanical extracts are provided having anti-HSV1 activity, including extracts of *Sarracenia purpurea, Melissa officinalis, Lavandula officinalis, Glycyrrhiza glabra, Eleutherococcus senticosus* and *Hypericum perforatum*. These botanical extracts demonstrate antiviral activity towards HSV1 at comparably low cell cytotoxicity. In further aspects, one or more of these botanical extracts are combined (e.g., by blending two or more botanical extracts, or compounding them together in a therapeutic composition, etc.) to form botanical extract compositions.

In various embodiments, botanical extract compositions may comprises two or more botanical extracts in combination. The combinations may be formulated by various proportions of botanical extracts, such as by various volume ratios or by biological activity proportions. For example, a botanical extract composition may comprise 50% botanical extract of *Sarracenia purpurea,* 15% botanical extract of Melissa officinalis, 15% botanical extract of *Lavandula officinalis,* 10% botanical extract of *Glycyrrhiza glabra,* 5% botanical extract of *Eleutherococcus senticosus* and 5% botanical extract of *Hypericum perforatum*. In various embodiments, such as for therapeutic compositions that may be used for topical application for herpes virus family infections, the botanical extract composition can comprise 50% extract of *Sarracenia purpurea,* 12% *Melissa* officinalis, 20% *Lavandula officinalis,* 5% *Glycyrrhiza glabra,* 8% *Eleutherococcus senticosus* and 5% *Hypericum perforatum,* Each botanical extract may be prepared by methods described in greater detail herein. Any suitable combination of botanical extracts in any suitable proportion may be combined to produce a botanical extract composition in accordance with various aspects and embodiments.

In various embodiments, botanical extract compositions are set for according to standardized anti-HSV1 activity and may comprise any one or more of:
a *Sarracenia purpurea* extract having a standardized anti-HSV1 activity of about 60-300 VIU/ml;
a *Melissa officinalis* extract having a standardized anti-HSV1 activity of about 1000-4000 VIU/ml;
a *Lavandula officinalis* extract having a standardized anti-HSV1 activity of about 75-300 VIU/ml;
a *Glycyrrhiza glabra* extract having a standardized anti-HSV1 activity of about 50-500 VIU/ml;
an *Eleutherococcus senticosus* extract having a standardized anti-HSV1 activity of about 100-2000 VIU/ml); and
a *Hypericum perforatum* extract having a standardized anti-HSV1 activity adjusted of about 1000-4000 VIU/mL in various further embodiments, botanical extract compositions are set forth by volume and optionally according to standardized anti-HSV1 activity, and may comprise any one or more of:
about 25-50% v/v *Sarracenia purpurea*, optionally with a standardized anti-HSV1 activity adjusted to be from about 60-300 VIU/ml;
about 6-12% v/v *Melissa officinalis*, optionally with a standardized anti-HSV1 activity adjusted to be from about 1000-4000 VIU/ml;
about 10-20% v/v *Lavandula officinalis*, optionally with a standardized anti-HSV1 activity adjusted to be from about 75-300 VIU/ml;
about 2.5-5% v/v *Glycyrrhiza glabra*, optionally with a standardized anti-HSV1 activity adjusted to be from about 50-500 VIU/ml;
about 2.5-8% v/v *Eleutherococcus senticosus*, optionally with a standardized anti-HSV1 activity adjusted to be from about 100-2000 VIU/ml); and
about 4-10% v/v *Hypericum perforatum*, optionally with a standardized anti-HSV1 activity adjusted to be from about 1000-4000 VIU/ml In various further embodiments, botanical extract compositions are set forth according to volume and according to standardized anti-HSV1 activity, and may comprise any one or more of:
about 50% v/v *Sarracenia purpurea*, optionally with a standardized anti-HSV1 activity adjusted to about 125 viral inhibitory units (VIU)/ml;
about 12% v/v *Melissa officinalis*, optionally with a standardized anti-HSV1 activity adjusted to about 2000 VIU/ml;
about 20% v/v *Lavandula officinalis*, optionally with a standardized anti-HSV1 activity adjusted to about 150 VIU/ml;
about 5% v/v *Glycyrrhiza glabra*, optionally with a standardized anti-HSV1 activity adjusted to about 100 VIU/ml;
about 8% v/v *Eleutherococcus senticosus*, optionally with a standardized anti-HSV1 activity adjusted to about 500 VIU/ml; and
about 10% v/v *Hypericum perforatum*, optionally with a standardized anti-HSV1 activity adjusted to about 2000 VIU/ml.

In various further embodiments, botanical extract compositions are set forth according to anti-HSV1 activity and optionally according to volume.

Human infection with alpha viruses (HSV1, HSV2 and varicella-zoster virus) typically present with lesions on the epidermis. In various embodiments, a botanical extract composition may be further combined with a base gel product to produce a therapeutic composition. Accordingly, in various embodiments, therapeutic compositions are provided as a suspension of the aqueous extract in a gel to provide topical application and suitable transdermal 'driving' capabilities. In further embodiments, a gel suspension is prepared using a botanical extract composition combined with a gel (e.g., VERSABASE). Various other excipients may be optionally added, including ammonium acryloyldimethyltaurate/VP Copolymer, aloe vera, edetate di sodium, allantoin, and methylchloroisothiazolinone/methylisothiazolmone. In various embodiments, a botanical extract composition is blended with a gel in a proportion suitable for various therapeutic applications. For example, in various embodiments, a 50:50 ratio (vol:wt) of a botanical extract composition to gel (e.g., VERABASE Gel) may be used to produce a therapeutic composition.

In another aspect, a blend for the treatment of cervical dysplasia associated with HPV infection is provided. In various embodiments, such as for therapeutic compositions that may be used for cervical dysplasia, the botanical extract composition can comprise 83.5% extract of *Sarracenia purpurea,* 7% *Melissa* officinalis, 1.5% *Lavandula officinalis,* 1.5% *Glycyrrhiza glabra,* 1.5% *Eleutherococcus senticosus* and 5% *Hypericum perforatum.*

In various embodiments, botanical extract compositions are set for according to standardized anti-HPV activity and may comprise any one or more of:

- a *Sarracenia purpurea* extract having a standardized anti-HPV activity of about 60-300 VIU/ml;
- a *Melissa officinalis* extract having a standardized anti-HPV activity of about 1000-4000 VIU/ml;
- a *Lavendula officinalis* extract having a standardized anti-HPV activity of about 75-300 VIU/ml;
- a *Glycyrrhiza glabra* extract having a standardized anti-HPV activity of about 50-500 VIU/ml;
- an *Eleutherococcus senticosus* extract having a standardized anti-HPV activity of about 100-2000 VIU/ml; and
- a *Hypericum perforatium* extract having a standardized anti-HPV activity of about 2000 VIU/ml; ranging from 1000-4000 VIU/ml In various further embodiments, botanical extract compositions are set forth by volume and optionally according to standardized anti-HPV activity, and may comprise any one or more of:

- about 40-99% v/v *Sarracenia*, optionally with a standardized anti-HPV activity adjusted to be from about 60-300 VIU/ml;
- about 3-14% v/v *Melissa officinalis*, optionally with a standardized anti-HPV activity adjusted to be from about 1000-4000 VIU/ml;
- about 1-4% v/v *Lavendula officinalis*, optionally with a standardized anti-HPV activity adjusted to be from about 75-300 VIU/ml;
- about 1-4% v/v *Glycyrrhiza glabra*, optionally with a standardized anti-HPV activity adjusted to be from about 50-500 VIU/ml;
- about 1-4% v/v *Eleutherococcus senticosus*, optionally with a standardized anti-HPV activity adjusted to be from about 100-2000 VIU/ml; and
- about 2-8% v/v *Hypericum* perforatium, optionally with a standardized anti-HPV activity adjusted to be from about 1000-4000 VIU/ml.

In various further embodiments, botanical extract compositions are set forth according to volume and according to standardized anti-HP V activity, and may comprise any one or more of:

- about 83% v/v *Sarracenia*, optionally with a standardized anti-HPV activity adjusted to about 125 VIU/ml;
- about 7% v/v *Melissa officinalis*, optionally with a standardized anti-HPV activity adjusted to about 2000 VIU/ml;
- about 2% v/v *Lavendula officinalis*, optionally with a standardized anti-HPV activity adjusted to about 150 VIU/ml;
- about 2% v/v *Glycyrrhiza glabra*, optionally with a standardized anti-HPV activity adjusted to be from about 100 VIU/ml;
- about 2% v/v *Eleutherococcus senticosus*, optionally with a standardized anti-HPV activity adjusted to be from about 500 VIU/ml; and
- about 4% v/v *Hypericum perforatum*, optionally with a standardized anti-HPV activity adjusted to be from about 2000 VIU/ml.

In various further embodiments, botanical extract compositions are set forth according to anti-HPV activity and optionally according to volume.

Botanical extract compositions wherein one or more botanical extracts are added, substituted, or deleted may be produced and/or formulated into a therapeutic composition in accordance with various embodiments of the present disclosure. Such modifications of the botanical extract compositions of the present disclosure may be produced for any suitable purpose, such as, for example, to modulate a synergistic activity or efficacy of a composition.

In various embodiments, a botanical extract composition can be comprised entirely of an extract of *Sarracenia purpurea.*

In accordance with various embodiments, the relative proportions of each botanical extract in a mixture can vary. In various embodiments, a botanical extract composition can comprise 40-99% extract of *Sarracenia purpurea,* 1-30% *Melissa* officinalis, 1-30% *Lavandula officinalis,* 1-30% *Glycyrrhiza glabra,* 1-20% *Eleutherococcus senticosus* and 1-20% *Hypericum perforatum.*

In various embodiments, the botanical extracts from species including *Sarracenia purpurea, Melissa officinalis, Lavandula officinalis, Glycyrrhiza glabra, Eleutherococcus senticosus* and/or *Hypericum perforatum* are formulated into a blend to provide optimal activity.

In various embodiments, a botanical extract composition may comprise any suitable combination of botanical extracts at any individual volume proportion relative to the total volume of the composition. Likewise, a botanical extract having have any suitable standardized antiviral activity level (expressed in VIU), determined for any viral agent, may be used to produce a botanical extract composition. In various embodiments, the volume proportion of a botanical extract in a composition may be adjusted based on a measured antiviral activity level of the extract. Similarly, the antiviral activity of an extract per unit volume may be adjusted, for example, by dilution or concentration, to provide a standardized antiviral activity level suitable for adding the extract to a botanical extract composition at a volume proportion compatible with the volumes or activities of other botanical extracts that may be present in the composition. The foregoing embodiments are presented by way of example, and not by way of limitation. Any suitable proportion of an individual botanical extract in a botanical extract composition, with the individual botanical extract having any suitable range of antiviral or other standardized biological activity, is within the scope of the present disclosure. In various embodiments, one or more mechanisms of action may be associated with various botanical extracts or botanical extract compositions.

Figure 4:
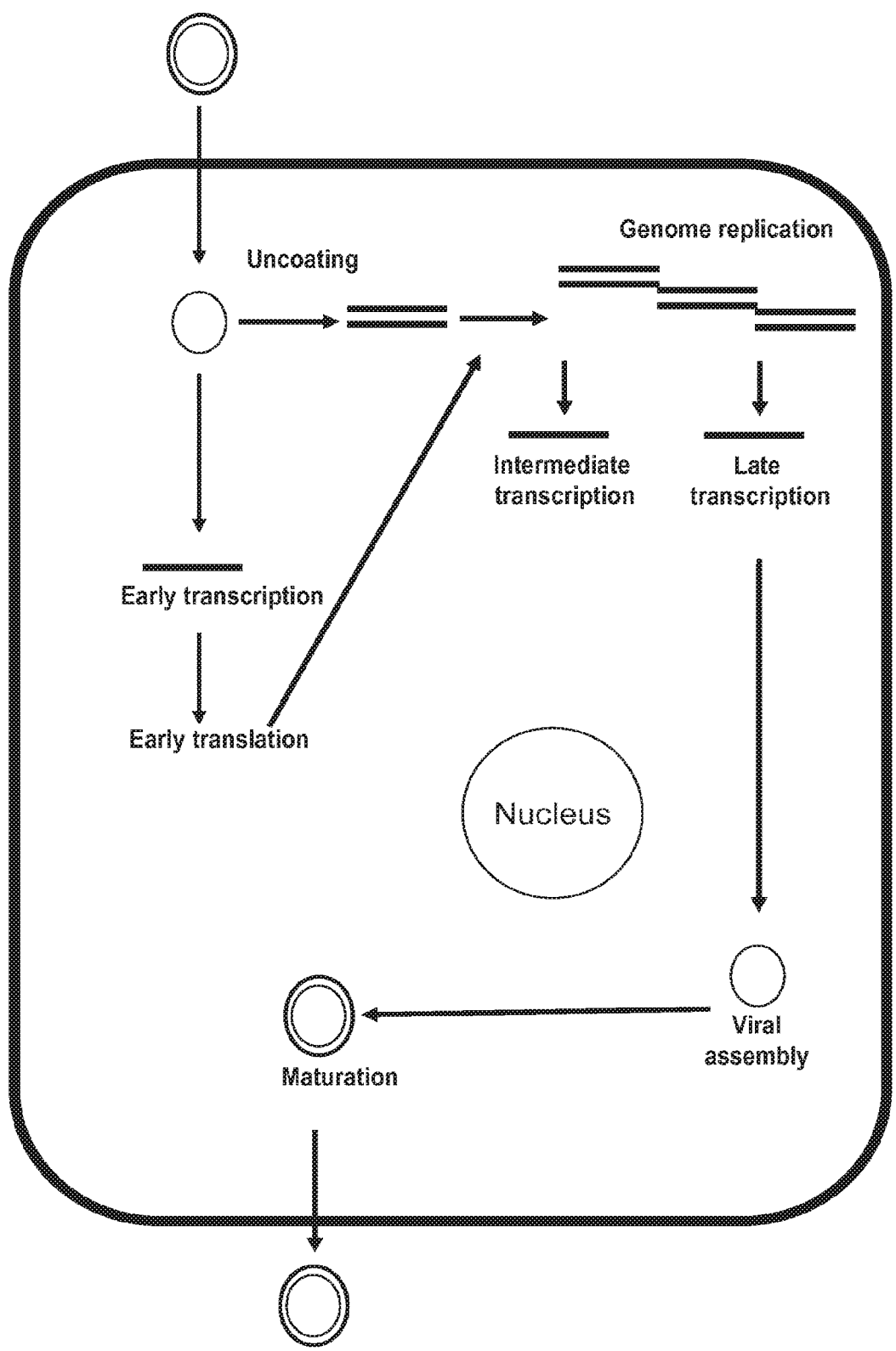
FIG. 4 illustrates a possible mechanism of action of poxvirus therapeutics.

With reference to FIG. 4, various the viral targets are shown. FIG. 4 illustrate a possible mechanism of action of a poxvirus therapeutic composition in accordance with various embodiments of the present disclosure. The illustration indicates the general replication cycle of VACV. Cidofovir (VISTIDE®, Gilead Sciences Inc., Foster City, Calif.) is known to interfere with genome replication, while ST-246 is known to interfere with the maturation step.

Figure 7:
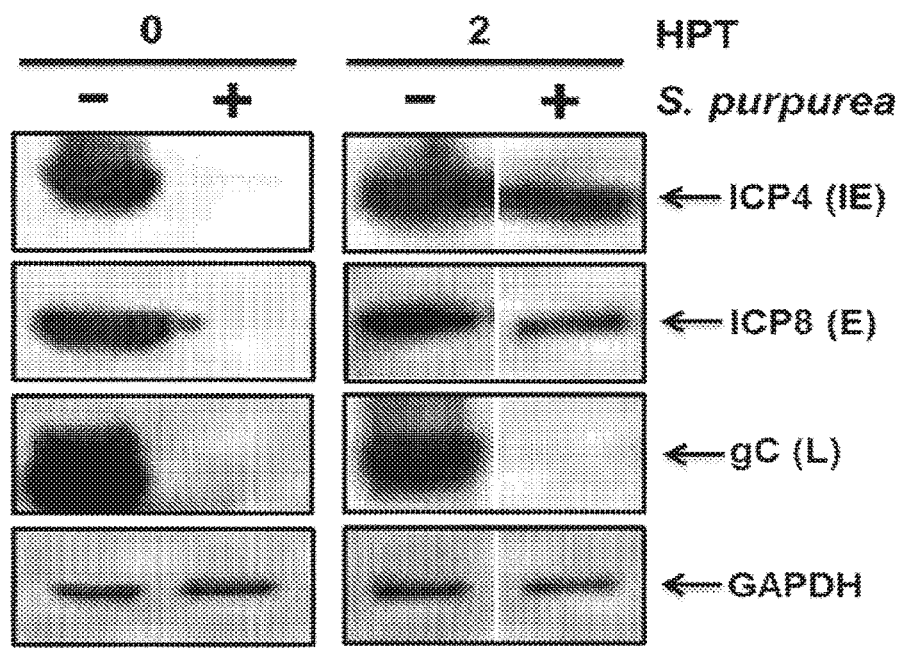
FIG. 7 illustrates an effect of a *S. purpurea* extract on HSV1 protein accumulation.

While not desiring to be bound by theory, it is believed that *S. purpurea* inhibits the replication of poxviruses (including vaccinia virus, monkeypox virus and variola virus) soon after entry of the virus into the cell by inhibiting viral mRNA synthesis, such as between the viral entry and early transcription steps illustrated in FIG. 4. Upon screening of the spectrum of antiviral activity that may be associated with *S. purpurea*, the extract was found to have antiviral activity against other non-related DNA viruses including HSV1 and SV40 (a papovavirus related to human papillomavirus), but not toward RNA viruses including mouse hepatitis virus, reovirus, vesicular stomatitis virus, and encephalomyocarditis virus. Of the botanicals included within various botanical extract compositions described herein, such as the blend of all Species II Extracts, *S. purpurea* has been one of the more well characterized. When cells are infected with HSV1 typical cytopathic effects are observed. If, following infection, the cells are treated with *S. purpurea* extract, the cytopathic effect could be virtually eliminated. In order to assess at which point in the virus replication cycle *S. purpurea* was acting on the HSV1, a Western blot was performed to detect the level of an immediate-early protein synthesized by the virus (ICP4) (FIG. 7).

Following treatment with *S. purpurea*, the accumulation of ICP4 is almost non-detectable. This suggests that the *S. purpurea* is targeting an early event in the virus replication cycle, either virus uptake into the cell, immediate-early transcription, or immediate-early protein synthesis. Given the previous results with poxviruses, it is believed the extract is likely targeting viral transcription.

As further described herein, the antipoxvirus activity associated with *S. purpurea* extracts was found not to be limited to a particular genus of carnivorous botanicals. Extracts prepared from other carnivorous genera also demonstrated antiviral activity. Such carnivorous genera included *Nepenthes, Drosera, Dionaea, Darlingtonia*, and *Pinguicula*.

A number of other plant genera were assayed for conservation of the antiviral activity associated with *S. purpurea*. Species from other genera tested, including *Sarracenia* spp., *Nepenthes* spp., *Drosera* spp., *Dionaea* spp., *Darlingtonia* spp., and *Pinguicula* spp., all have antiviral activity against vaccinia virus. The strongest antiviral activity has been associated with *Sarracenia* spp. and *Nepenthes* spp. For *Sarracenia* spp. and *Nepenthes* spp., this antiviral activity has been observed toward poxviruses, herpesviruses and papovaviruses.

The genus *Nepenthes* includes a carnivorous pitcher plant. *Nepenthes* is similar to *Sarracenia* in terms of general appearance, but is geographically distributed in very different regions of the world compared to *Sarracenia*. For other species, this conserved antiviral activity has only been tested against vaccinia virus, although it may be effective against herpes and papilloma/polyomaviruses.

Our screening of botanicals for activity against HSV1 ranked *M. officinalis* as one of the strongest anti-HSV1 extracts of the various botanical extracts disclosed herein.

Current data is limited on the mechanism of action of the various other botanical extracts within the Species II Extracts. For *Lavandula officinalis*, preliminary data suggests the anti-herpes viral target is likely an early event, possibly affecting viral entry into the cell. For *Glycyrrhiza glabra*, treatment of HSV1 infected cells results in the production of a smaller plaque phenotype. This is a very different effect compared to *Melissa* extracts, where plaque numbers are reduced while plaque size remains consistent. This may suggest that *Glycyrrhiza* extracts may be affecting a later event in the viral replication cycle or viral cell-to-cell spread or altering the phenotype of subsequently infected cells (i.e. inducing a cellular antiviral response or repressing factors/receptors required by the virus). For *Eleutherococcus senticosus*, the antiviral target appears to be an early event in the viral replication cycle, but likely unique from *Melissa* or *Lavandula* since this botanical does not affect EHV-1 replication whereas both *Lavandula* and *Melissa* can inhibit replication of EHV-1. For *Hypericum perforatum*, a mechanism of action against HSV1 has not yet been identified.

Since many of these botanicals target different points in the replication cycle, various combinations of the Species II Extracts provide synergistic activity towards the inhibition of viral replication. Blends that comprise Species II Extracts may produce multi-targeted efficacy against viral replication, wherein the different botanicals inhibit different targets in the viral replication cycle, thereby effectively inhibiting viral replication with stronger efficiency. In addition, given that these botanical extracts inhibit the virus at different sites, it is assumed that the development of potential viral resistance to such a blended therapy will be greatly reduced.

Methods of Preparing Therapeutic Compositions Comprising Botanical Extracts

Methods for the preparation of therapeutic compositions in accordance with the present disclosure comprise formulating one or more of the botanical extracts disclosed herein with one or more pharmaceutically acceptable excipients or carriers to form a solid, semi-solid or liquid. Solid compositions include, but are not limited to, powders, tablets, dispersible granules, capsules, cachets, and suppositories. Liquid formulations include solutions a botanical extract is present, such as emulsions or a solution containing liposomes, micelles, or nanoparticles comprising a botanical extract as disclosed herein. Semi-solid formulations include, but are not limited to, gels, suspensions and creams. The form of the therapeutic compositions described herein include liquid solutions or suspensions, solid forms suitable for solution or suspension in a liquid prior to use, or as emulsions. These formulations also optionally contain minor amounts of nontoxic, auxiliary substances, such as wetting or emulsifying agents, pH buffering agents, and so forth In various embodiments, a botanical extract, or a blend of botanical extracts, may be compounded into a therapeutic composition with one or more pharmaceutically acceptable excipients. For example, for dermal or epithelial topical therapeutic use of a single botanical extract or a blend of extracts, the aqueous mixture is suspended in a transdermal base or other pharmaceutical base, such as a gel, to provide such drug delivery properties as adherence and transdermal 'driving' capabilities, for example.

Pharmaceutically acceptable excipients include for example, solvents (such as water, glycols, alcohols, ethers), and solubilizers and carriers (such as fatty acids, glycerin, monoglycerides, diglycerides, triglycerides, sorbitan fatty esters, alkoxylated fatty acids, alkoxylated fatty acid esters, lecithin, and the like). Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) PI. C. Ansel et al., eds., T.sup.th ed., Lippincott, Williams, & Wilkins; and Handbook of Pharmaceutical Excipients (2.000) A. H. Kibbe et al., eds., 3.sup.rd ed. Amer. Pharmaceutical Assoc., all of which are herein incorporated by reference.

Pharmaceutically acceptable excipients, such as emulsifiers, solubilizers, emollients, vehicles, adjuvants, carriers or diluents, are commercially available. Moreover, pharmaceutically acceptable auxiliary substances, such as pH adjusting and buffering agents, tonicity adjusting agents, stabilizers, wetting agents, preservatives and the like, are commercially available.

In various embodiments, the botanical extracts of the present disclosure can be administered topically. The botanical extracts described herein can be formulated into a variety of topically administrable formulations, such as solutions, suspensions, lotions, gels, pastes, medicated sticks, balms, creams or ointments. Such therapeutic compositions optionally contain solubilizers, stabilizers, tonicity enhancing agents, buffers and preservatives. For topical administration, the present botanical extracts may be applied in liquid form. However, it will generally be desirable to administer them to the skin as formulations, in combination with a dermatologically acceptable carrier/gel, which may be a solid or a liquid. The resultant liquid or gel therapeutic compositions can be applied from absorbent pads, used to impregnate bandages and other dressings, used in transdermal patches, or sprayed onto the affected area using pump-type or aerosol sprayers.

Examples of useful dermatological formulations which can be used to deliver the botanical extracts may be found in, for example Jacquet et al. U.S. Pat. No. 4,608,392; Geria U.S. Pat. No. 4,992,478; Smith et al. U.S. Pat. No. 4,559,157 and Wortzman U.S. Pat. No. 4,820,508, each of which is incorporated in its entirety herein by reference.

Various embodiments provide a therapeutic composition comprising a botanical extract described herein and a gel, or other suitable base composition, providing adherence and transdermal driving capabilities (absorption through the skin). In various embodiments, the therapeutic composition comprises 25% of a botanical extract and 75% of at least one pharmaceutical excipient such as a base gel composition. The therapeutic composition can range from 25-70% of a botanical extract and corresponding 75-30% pharmaceutical excipient(s).

In various embodiments, such as for formulations used for topical application for herpes virus family infections, a therapeutic composition may comprise 50% of a botanical extract composition and 50% gel. In various embodiments, such as for formulations used for cervical dysplasia applications, a therapeutic composition may comprise 60% of a botanical extract composition and 40% gel. The botanical extract composition can range from 25-70% of a botanical extract described above and corresponding 75-30% gel.

In various embodiments, the compounding base is a transdermal driver gel, such as, for example, VERSABASE gel. VERSABASE gel is manufactured by Professional Compounding Center of America and reportedly contains ammonium acryloyldimethyltaurate/VP Copolymer, aloe vera, edetate disodium, allantoin, methylchloroisothiazolinone and methylisothiazolinone.

In various embodiments, it is believed the VERSABASE gel provides the following: ammonium acryloyldimethyltaurate/VP Copolymer acting as a gelling agent for the aqueous solution to allow for topical application without dripping or drying out; aloe vera acting to enhance skin penetration of the active botanical constituents allowing for transdermal uptake; allantoin acting as a keratolytic agent to improve moisture binding capacity of the epidermis to also improve drug penetration into the skin.

In certain embodiments, other commercially available compounding bases may be used. Such alternative bases include but are not limited to LIPODERM, PENTRAVAN, and Pluronic Lecithin Organogel (PLO). PLO base is a thermoreversible gel that is liquid at low temperatures (4° C.) and becomes more solid as the temperature increases (body temperature). This property makes it useful for applications, especially on the cervix or vaginal tract of patient, for transdermal drug delivery.

Alternatively, individual pharmaceutically acceptable ingredients, such as fatty acids, fatty acid esters, alkoxylated fatty acids, alkoxylated fatty acid esters, monoglycerides, diglycerides, triglycerides, sorbitan fatty acid esters, and the like, can be blended in any combination with the various botanical extracts or blends of extracts as desired to produce therapeutic compositions within the scope of the present disclosure. More particularly, the botanical extracts of the present disclosure can be compounded into therapeutic compositions by combination with appropriate, pharmaceutically acceptable carriers or diluents, and may be formulated into preparations in solid, semi-solid, liquid or gaseous forms, such as tablets, capsules, powders, granules, ointments, creams, mulls, gels, solutions, suppositories, injections, inhalants and aerosols.

In various embodiments, pharmaceutical excipients include fatty acids. Any fatty acid, or combination of fatty acids, may be blended with a botanical extract or blend of extracts herein to produce a therapeutic composition. For example, any $C_6$-$C_{24}$ fatty acid may be used in the pharmaceutical formulas of the present disclosure. Fatty acids for use herein also include $C_6$-$C_{24}$ fatty acids having any degree of unsaturation in the carbon chain. Fatty acids for use herein may be from natural oil and fat sources such as tallow, lard, coconut oil, palm oil, peanut oil, rice bran oil, olive oil, cottonseed oil, wheat germ oil, soy bean oil, corn oil, sunflower oil, and safflower oil, amongst others. Natural oils may supply a distribution of fatty acid chain lengths. For therapeutic compositions within the scope of the present disclosure, any combination of free fatty acid, natural oils, hydrogenated oils, partially hydrogenated oils, vegetable and animal fats, monoglycerides, diglycerides and triglycerides may be used, and may be combined with any other emulsifiers, emollients, carriers, solubilizers, solvents, and the like, as desired.

In various embodiments, a therapeutic composition comprises a botanical extract and a fatty acid. For example, a therapeutic composition within the scope of the present disclosure comprises a botanical extract and a fatty acid substance. For example, the plant species *Sarracenia purpurea* may be used. In various embodiments, a therapeutic composition comprises any botanical extract or blend of extracts discussed above combined with at least one fatty acid.

In various embodiments, administration of a botanical extract or therapeutic composition thereof can be achieved in various ways, including preparations for oral, buccal, rectal, parenteral, intraperitoneal, intradermal, subcutaneous, intramuscular, transdermal, intratracheal, etc., administration.

In various embodiments, botanical extracts of the present disclosure are formulated for oral administration by combining the botanical extract(s) with, e.g., pharmaceutically acceptable carriers or excipients. In various embodiments, the compounds of the present disclosure are formulated in oral dosage forms that include, for example, tablets, powders, pills, capsules, liquids, gels, syrups, elixirs, slurries, suspensions, and the like.

For oral preparations, the botanical extracts can be combined with appropriate additives to make liquids, tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

In various embodiments, therapeutic compositions for oral use are obtained by mixing one or more solid excipients with one or more of the botanical extracts described herein, optionally grinding the resulting mixture, and processing the mixture of granules, after adding suitable auxiliaries, if desired, to obtain tablets. Suitable excipients include fillers such as sugars, (e.g. lactose, sucrose, mannitol, or sorbitol); cellulosic substances: (e.g., maize starch, wheat starch, rice starch, potato starch, gelatin, gum tragacanth, methylcellulose, microcrystalline cellulose, hydroxypropylmethylcellulose, sodium carboxymethylcellulose); or other materials such as, for example, polyvinylpyrrolidone (PVP or "povidone") or calcium phosphate. In specific embodiments, disintegrants can be added. Disintegrants include, for example, cross-linked croscarmellose sodium, polyvinylpyrrolidone, agar, or alginic acid and sodium alginate.

In various embodiments, tablets can be provided with one or more suitable coatings. In specific embodiments, concentrated sugar solutions are used for coating the dosage form. Sugar solutions can optionally contain additional components, such as for example, gum arable, talc, polyvinylpyrrolidone, carbopol polyacrylate gels, polyethylene glycol, titanium dioxide, lacquer solutions, organic solvents or solvent mixtures. Colorants can be added to the coatings for marketing or dose identification, or other purpose.

In various embodiments, therapeutically effective amounts of at least one of the botanical extracts of the present disclosure are formulated into other oral dosage forms. Oral dosage forms include push-fit capsules made of gelatin, as well as soft sealed capsules made of gelatin and a plasticizer, such as glycerol or sorbitol. In various embodiments, push-fit capsules contain the botanical extract(s) mixed with one or more fillers. Fillers include, for example, lactose, binders such as starches, and/or lubricants such as talc or magnesium stearate and, optionally, stabilizers. In various other embodiments, soft capsules can contain one or more botanical extracts dissolved or suspended in a suitable liquid. Suitable liquids include, for example, one or more fatty oils, glycerin, glycerides, liquid paraffin, or various polyethylene glycols.

In various embodiments, therapeutically effective amounts of at least one of the botanical extracts of the present disclosure are formulated for buccal or sublingual administration. Formulations suitable for buccal or sublingual administration include, for example, tablets, lozenges, or gels. In still other embodiments, the botanical extracts described herein are formulated for parental injection, including formulations suitable for bolus injection or continuous infusion. In specific embodiments, formulations for injection are presented in unit dosage form (e.g., in ampoules) or in multi-dose containers.

In various embodiments, the botanical extracts can be formulated into formulations for injection by dissolving, suspending or emulsifying one or more botanical extracts or in an aqueous or nonaqueous solvent, such as vegetable or other similar oils, synthetic aliphatic acid glycerides, esters of higher aliphatic acids or propylene glycol: and if desired, with conventional additives such as solubilizers, isotonic agents, suspending agents, emulsifying agents, stabilizers and preservatives. Parenteral injection formulations optionally contain excipients such as suspending, stabilizing and/or dispersing agents. In specific embodiments, therapeutic compositions for parenteral administration include aqueous solutions of the botanical extracts in water-soluble form. In additional embodiments, suspensions of the botanical extracts herein are prepared as oily injection suspensions. Suitable lipophilic solvents or vehicles for use in the therapeutic compositions described herein include, for example, fatty acid blends such as those found in natural oils such as peanut oil, fatty acid esters, mono-, di- and triglycerides, or liposomes. In various embodiments, aqueous injection suspensions contain substances which increase the viscosity of the suspension, such as sodium CMC, sorbitol or dextran. Optionally, the suspension can include suitable stabilizers or other agents that increase the solubility of the botanical extracts to allow for highly concentrated solutions. Alternatively, the botanical extract can be dehydrated or lyophilized into a powdered form for later mixing with a suitable vehicle by the practitioner.

In various embodiments, the botanical extracts of the present disclosure can be formulated for administration by inhalation. Inhalation administration can include an intranasal spray. Various forms suitable for administration by inhalation include aerosols, mists or powders. Therapeutic composition comprising botanical extracts of the present disclosure can be conveniently delivered in the form of an aerosol spray presentation from pressurized packaging or a nebulizer, e.g. with the use of a propellant (e.g., dichlorodifluoromethane, trichlorofluoromethane, dichlorotetrafluoroethane, carbon dioxide or the like). In various embodiments, the dosage unit of a pressurized aerosol is determined by selection of a valve that can meter the dose. In certain embodiments, capsules and cartridges of the formulation can be provided for use within a pressurized delivery system. In various embodiments, the botanical extracts of the present disclosure can be formulated into liquid formulations sprayable from non-aerosol packaging.

In various embodiments, the botanical extracts of the present disclosure can be formulated into rectal compositions such as enemas, rectal gels, rectal foams, rectal aerosols, suppositories, jelly suppositories, or retention enemas, which contain suppository bases such as cocoa butter or other glycerides, in addition to synthetic polymers such as polyvinylpyrrolidone, PEG, and the like. Suppository forms can include a low-melting wax such as, but not limited to, a mixture of fatty acid glycerides. Furthermore, the botanical extracts can be formulated into suppositories by mixing with a variety of bases such as emulsifying bases or wafer-soluble bases. The suppository can include vehicles such as cocoa butter, carbowaxes and polyethylene glycols, which melt at body temperature, yet are solidified at room temperature.

One of skill in the art will readily appreciate that dose levels can vary as a function of the specific compound, the severity of the symptoms and the susceptibility of the subject to side effects. The amount of the botanical extracts required for use in treatment will vary not only with the particular botanical extracts and finished pharmaceutical formulations selected, but also with the route of administration, the nature of the condition being treated and the age and condition of the patient and will be ultimately at the discretion of the attendant physician or clinician.

In various embodiments, botanical extracts and therapeutic compositions thereof, used in the methods described herein, may be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

The dosage forms for oral or rectal administration such as syrups, elixirs, and suspensions may be provided wherein each dosage unit, for example, teaspoonful, tablespoonful, tablet or suppository, contains a predetermined amount of the botanical extract. Similarly, dosage forms for injection or intravenous administration may comprise the therapeutic composition containing a botanical extract as a solution in sterile water, normal saline or another pharmaceutically acceptable carrier.

The term "unit dosage form," as used herein, refers to physically discrete units suitable as unitary dosages for human and animal subjects, each unit containing a predetermined quantity of botanical extract of the present disclosure calculated in an amount sufficient to produce the desired effect in association with a pharmaceutically acceptable diluent, carrier or vehicle. The specifications for the novel unit dosage forms of the present disclosure depend on the particular botanical extract employed and the effect to be achieved, and the pharmacodynamics associated with each botanical extract in the host.

In various embodiments, combination therapy comprises the concurrent administration of at least one dose of a therapeutic composition comprising a botanical extract and an additional antiviral formulation effective against a virus or a cancer. As used herein, the term "concurrently" means that the two formulations are administered separately and are administered within about 5 seconds to about 15 seconds, within about 15 seconds to about 30 seconds, within about 30 seconds to about 60 seconds, within about 1 minute to about 5 minutes, within about 5 minutes to about 15 minutes, within about 15 minutes to about 30 minutes, within about 30 minutes to about 60 minutes, within about 1 hour to about 2 hours, within about 2 hours to about 6 hours, within about 6 hours to about 12 hours, within about 12 hours to about 2.4 hours, or within about 2.4 hours to about 48-hours of one another. As used herein, the term "simultaneously" means that the two formulations are administered at the same time.

Useful dosages of the botanical extracts herein can be determined by comparing their in vitro and in vivo activity in animal models. Methods for the extrapolation of effective dosages in mice, and other animals, to humans are known to the art; for example, see U.S. Pat. No. 4,938,949, incorporated in its entirety herein by reference.

Given below are the following non-limiting Examples of various embodiments:

Anti-Poxvirus Activity

Initial analysis was done to measure the ability of *S. purpurea* extract to inhibit poxvirus infections in vitro. We examined the ability of *S. purpurea* to prevent vaccinia virus (VACV) plaque formation in cells treated immediately after infection with increasing amounts of extract, administered once or every six hours, for a total of 24 hours. Referring now to FIG. 1A, a dose dependent reduction in VACV plaquing efficiency associated with increasing amounts of *S. purpurea* extract was observed. RK-13 cells were infected with 150 plaque forming units ("pfu") of VACV followed by the addition of the indicated concentration of *S. purpurea* extract to the cell culture media. Cells were treated one-time only with the extract (black bars) or every 6 hours with fresh extract (gray bars). After 48 hours, plaques were visualized and quantified. Error bars represent standard deviation (n=3). To ensure *S. purpurea* was responsible for the decrease in plaquing efficiency, cells were treated with 45%:50%:5% ethanol:distilled water:glycerol (carrier for the *S. purpurea* extract) prior to infection. This carrier treatment did not affect VACV plaquing efficiency. We subsequently assayed for the ability of VACV to replicate in cells under single-cycle conditions, treated once or every six hours, with *S. purpurea* extract. Treatment with *S. purpurea* began immediately following VACV infection and viral titers were determined every six hours. Referring now to FIG. 1 B, *S. purpurea* treatment resulted in a dramatic decrease in VACV replication, when compared to the untreated cells. RK-13 cells were infected with VACV at an multiplicity of infection ("MOI")=10 followed by addition of ethanol/glycerol carrier (closed diamonds) or the addition of 2.5 μl *S. purpurea* extract/ml media (open squares and closed triangles). Cells were treated one-time only with the extract (open squares) or every 6 hours with fresh extract (closed diamonds). Cells were harvested at the indicated times and viral titers determined. Error bars represent deviation between assays (n=2).

A single treatment of *S. purpurea*, caused a 100-1000 fold reduction in VACV replication throughout the course of the infection, however some viral replication was still observed. In cells treated with fresh extract every six hours, a 10,000-fold decrease in VACV replication was observed. Multiple treatments with *S. purpurea* completely abolished VACV replication since titers did not increase over the course of the infection. In cells treated with the carrier, VACV replicated to levels similar to that seen in untreated cells (data not shown). To further determine the efficacy of using *S. purpurea* to treat a poxvirus infection, the selectivity index (SI) associated with the extract was determined. Referring now to FIG. 1C, for viral translation levels (closed squares), HeLa cells were infected with VACV at an MOI=10 followed by the addition of the indicated concentrations of *S. purpurea* extract/ml media. At 6 hours post infection ("HPI"), cell lysates were prepared, the VACV E3L protein detected by Western blot, and quantified. For cell viability, HeLa cells were treated with the indicated concentrations of *S. purpurea* extract (closed squares) or ethanol/glycerol carrier (closed triangles) for 6 hours and the number of viable cells determined by a trypan blue exclusion assay. In *S. purpurea* treated cells, the EC50 required to inhibit VACV replication was 10-15 μL/mL, while the CC50 was 70-75 μL/mL of the extract, which results in a SI of approximately 5-7 (FIG. 1C). This SI is similar to that reported for cidofovir (CDV), an already proven treatment for poxvirus infections. Additionally, a 25 μL/mL sufficiently-inhibited viral protein translation to a level that prevented VACV replication (FIG. 1B) without inducing cellular cytotoxicity (FIG. 1C).

In various embodiments, the antipoxvirus activity associated with *S. purpurea* extracts was found not to be limited to *Sarracenia*. Extracts prepared from other genera also demonstrated antiviral activity. Such genera included *Nepenthes, Drosera, Dionaea, Darlingtonia* and *Pinguicula*.

Anti-Poxvirus Activity-Mechanism of Action

Figure 2A:
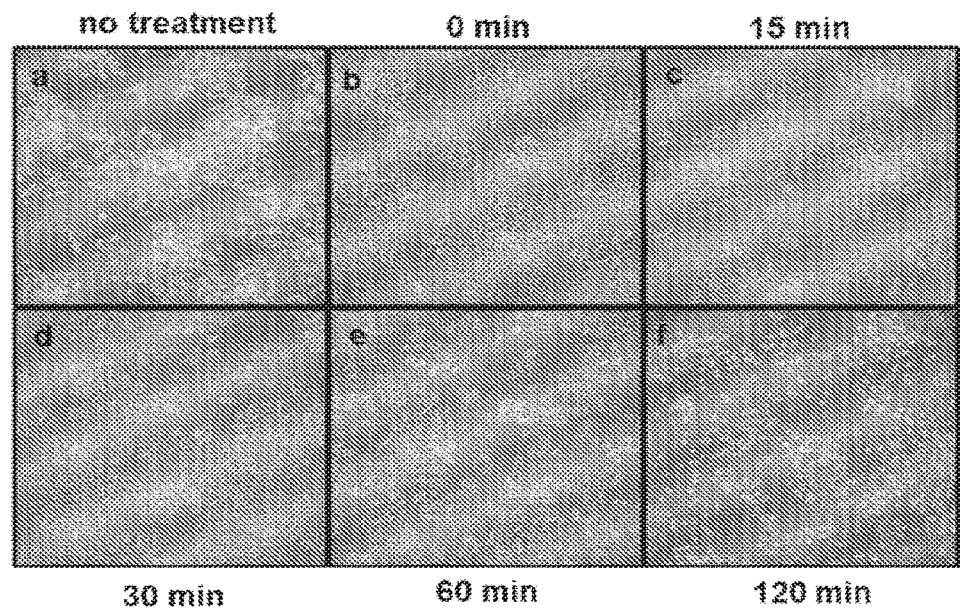
FIGS. 2A-2D illustrate the effect of a *S. purpurea* extract on VACV induced CPE and protein synthesis.
Figure 2B:
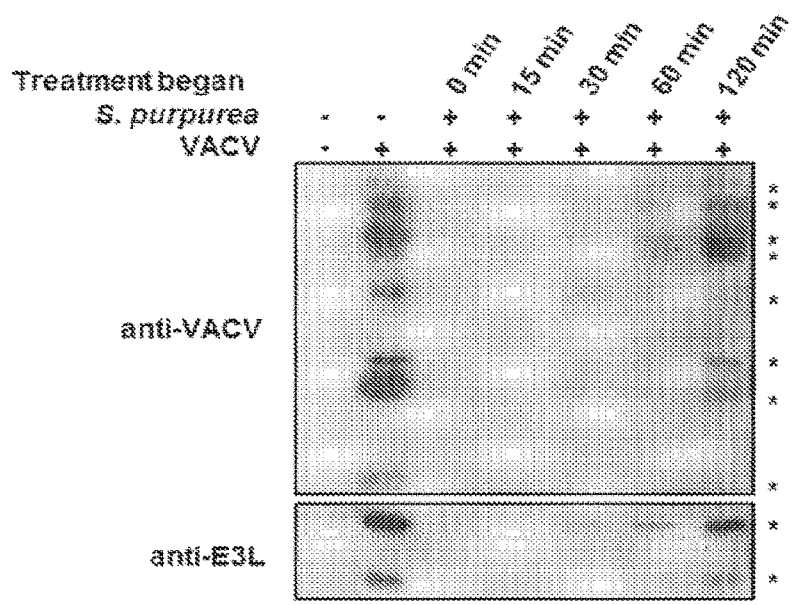
Figure 2C:
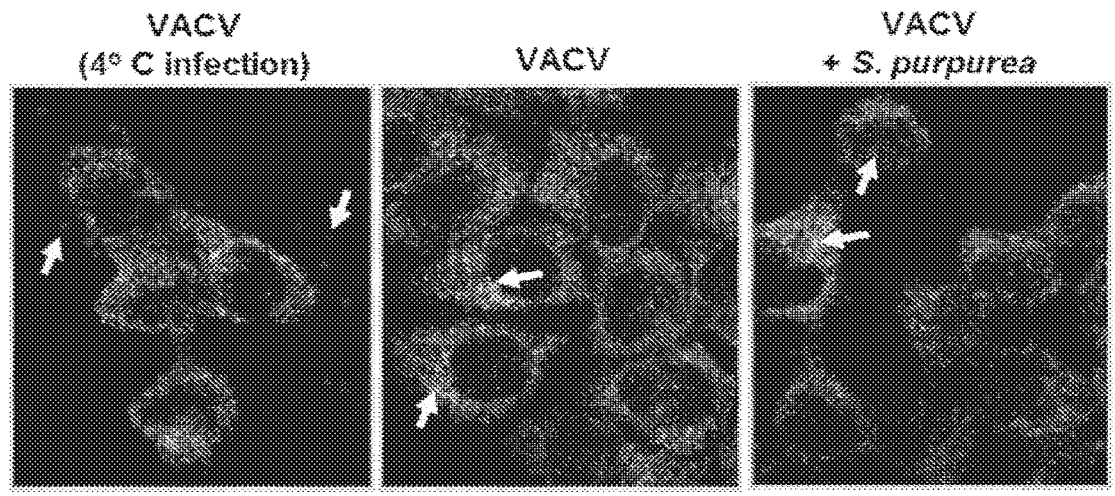
Figure 2D:
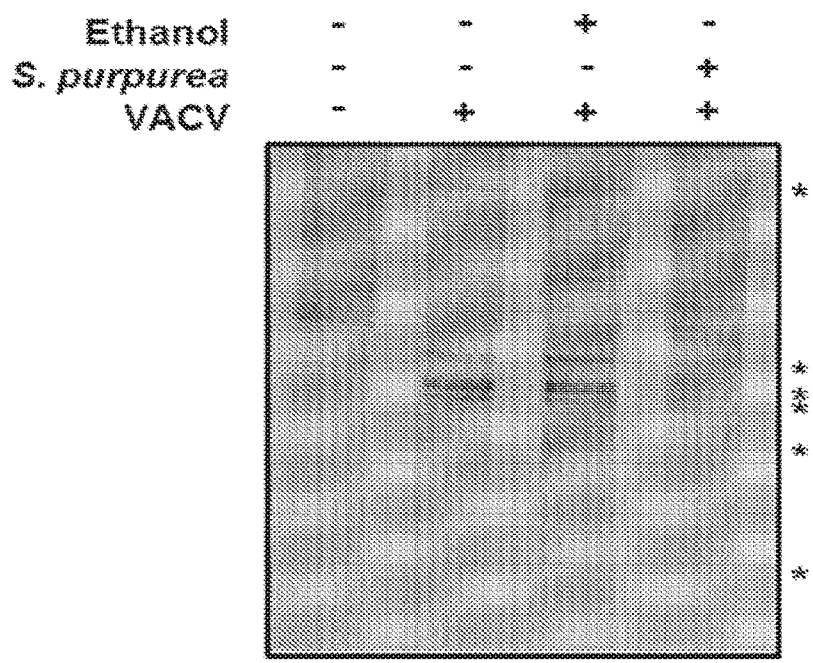

In order to understand the mechanism of action associated with *S. purpurea*, various treatment schedules were tested. Referring now to FIGS. 2A and 2B, HeLa cells were infected with VACV at an MOI=10 followed by the addition of 25 μl *S. purpurea* extract/ml media immediately (0 mm) or at 15, 30, 60 or 120 min post infection. 'No treatment' cells received ethanol/glycerol carrier only. For FIG. 2A, at 6 HPI, the cell monolayers were photographed. For FIG. 2B, at 3 HPI, cell lysates were prepared and the VACV E3L protein or total VACV proteins detected by Western blot. The asterisks (*) in the figures indicate the position of VACV proteins and the VACV-E3L protein. Duplicate experiments were performed at 6 HPI (not shown) Referring now to FIG. 2C, Hela cells were infected with a VACV construct expressing cyan fluorescent protein fused to the viral A5 core protein. In the first panel, the infection was maintained at 4° C. For the middle and last panel, the infection was done at 37° C., in the absence or presence of *S. purpurea*, respectively. With reference now to FIG. 2D, HeLa cells were mock infected or infected with VACV at an MOI=10 followed by the addition of 2.5 ul *S. purpurea* extract/ml media or ethanol/glycerol carrier. At 4 HPI, the cell monolayers were radiolabeled with [$^{35}$S]-methionine, cell lysates prepared, proteins separated by SDS-PAGE, and visualized by autoradiography. The asterisks (*) indicate the position of VACV proteins.

In cells treated with a single dose of *S. purpurea* overnight prior to infection with VACV followed by washing, no inhibition of VACV replication was observed, suggesting the extract does not induce a cellular antiviral component. Moreover, treating a purified VACV stock with *S. purpurea* did not affect replication of the virus, suggesting that the extract does not have a direct effect on free virus particles.

Figures 9A, 9B, 9C, 9D:
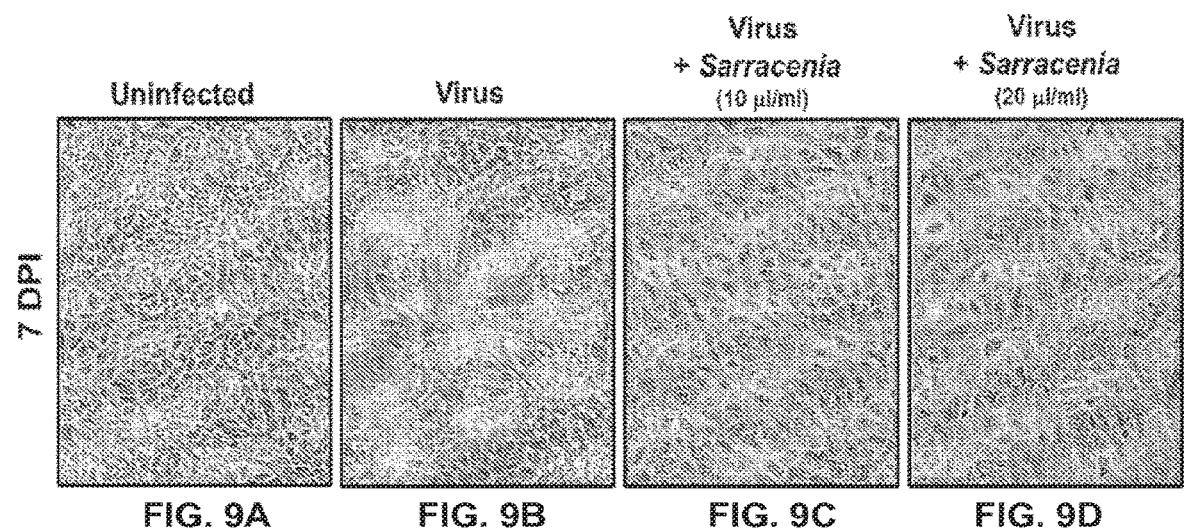
FIGS. 9A-9H illustrate an effect of a *S. purpurea* extract on VZV replication.
Figures 9E, 9F, 9G, 9H:
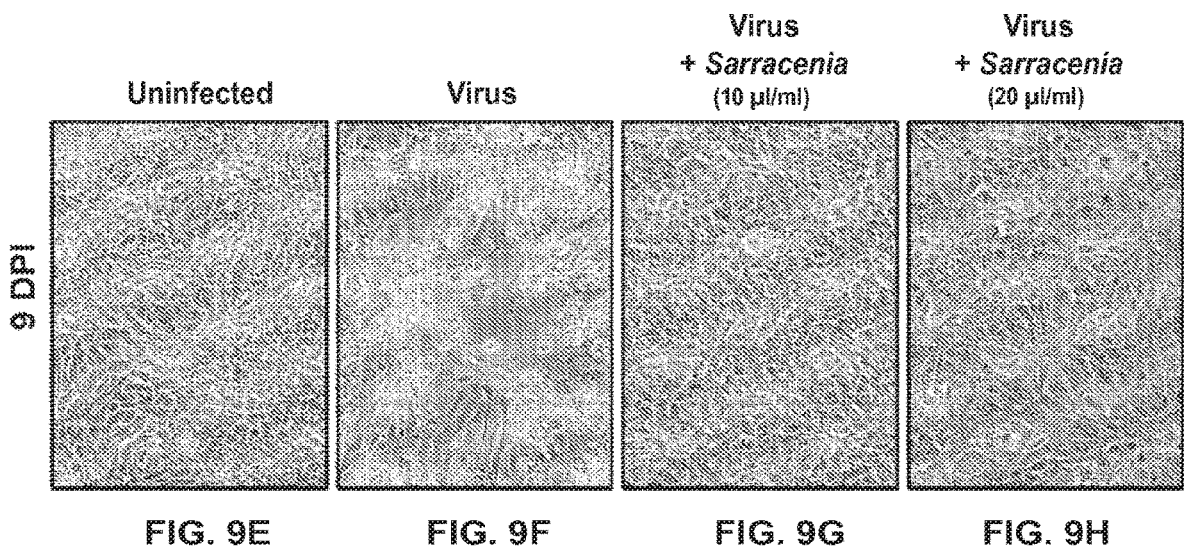

Further, activity against varicella-zoster virus (VZV) was assessed. Again, infection of cells in culture with VZV leads to a distinct cytopathic effect. Treatment of infected cells with *S. purpurea* extract immediately after infection was able to completely abolish this cytopathic effect (FIG. 9). Notably, these assays were performed with a single dose of *S. purpurea* extract (on day 1) and cytopathic effects measured on days 7 and 9. This inhibition in the replication of VZV by *S. purpurea* was confirmed by Western blot to detect the g1 protein of the virus. From this assay, this protein could not be detected in cells infected by VZV which were treated with *S. purpurea* extract. These results suggest that the *S. purpurea* extract can effectively inhibit the replication of alpha herpes virus members including HSV1, VZV, HSV2 and EHV1.

Figure 32A:
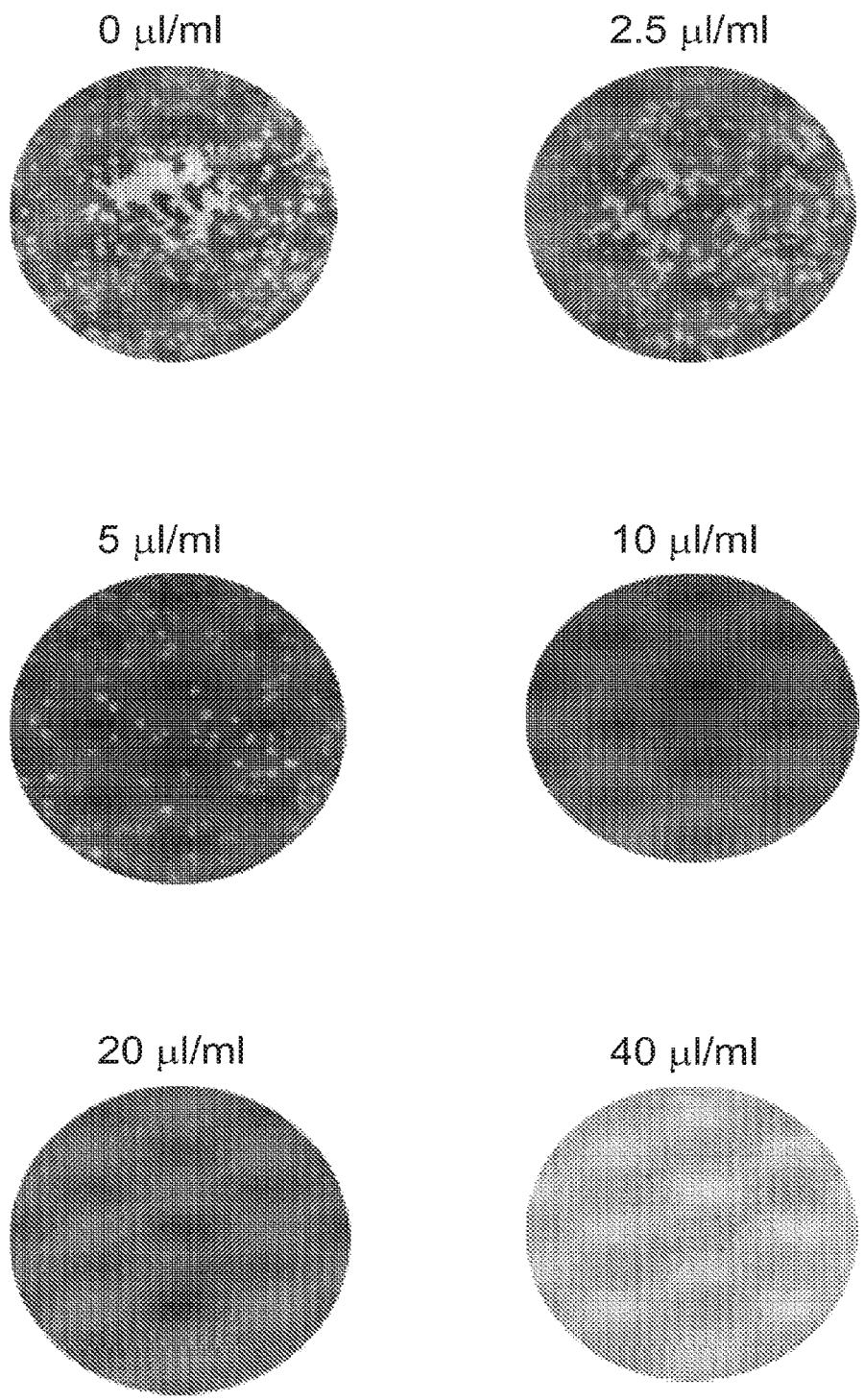
FIGS. 32A-32E illustrate antiviral activity of *Sarracenia* species.
Figure 32B:
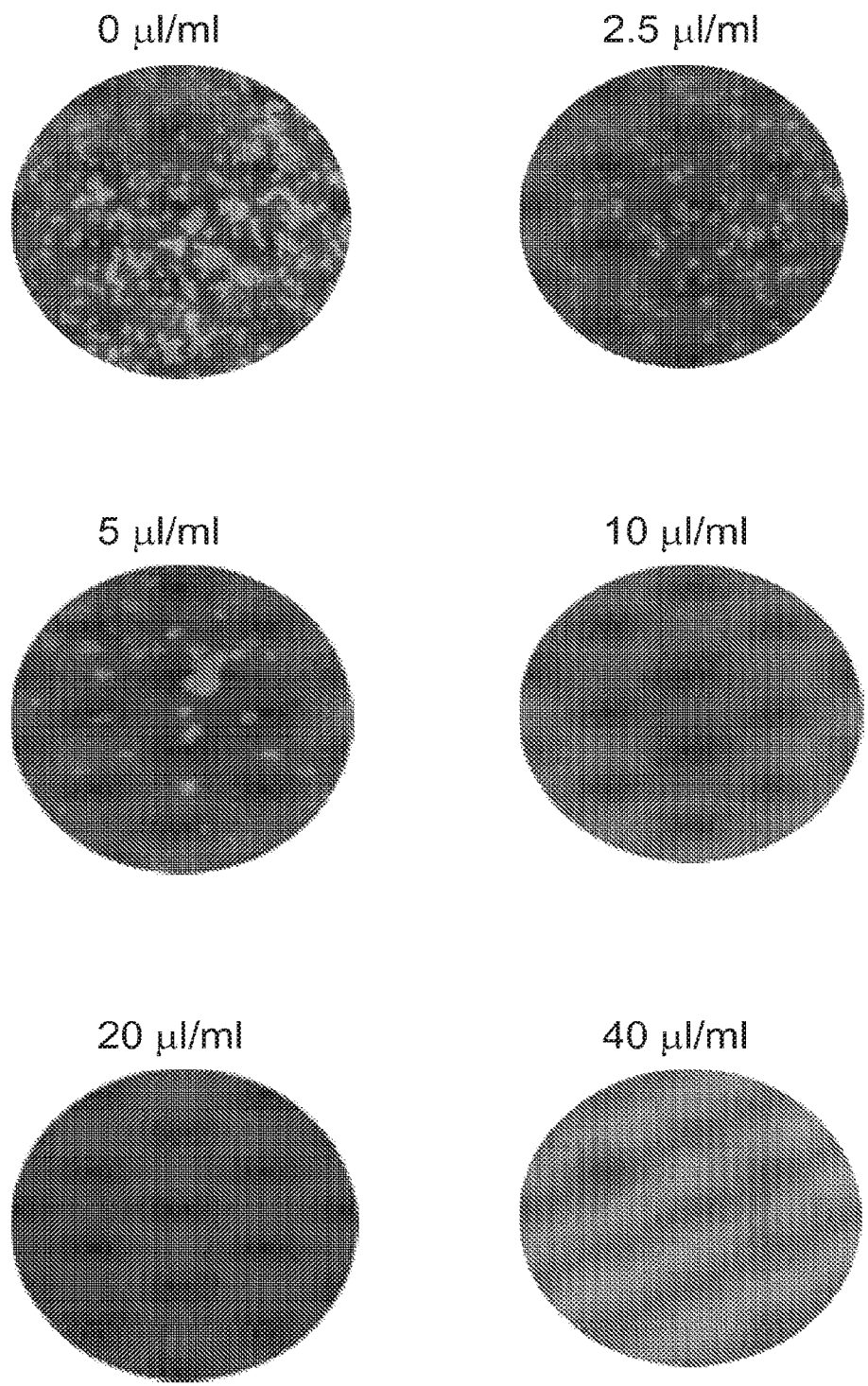
Figure 32C:
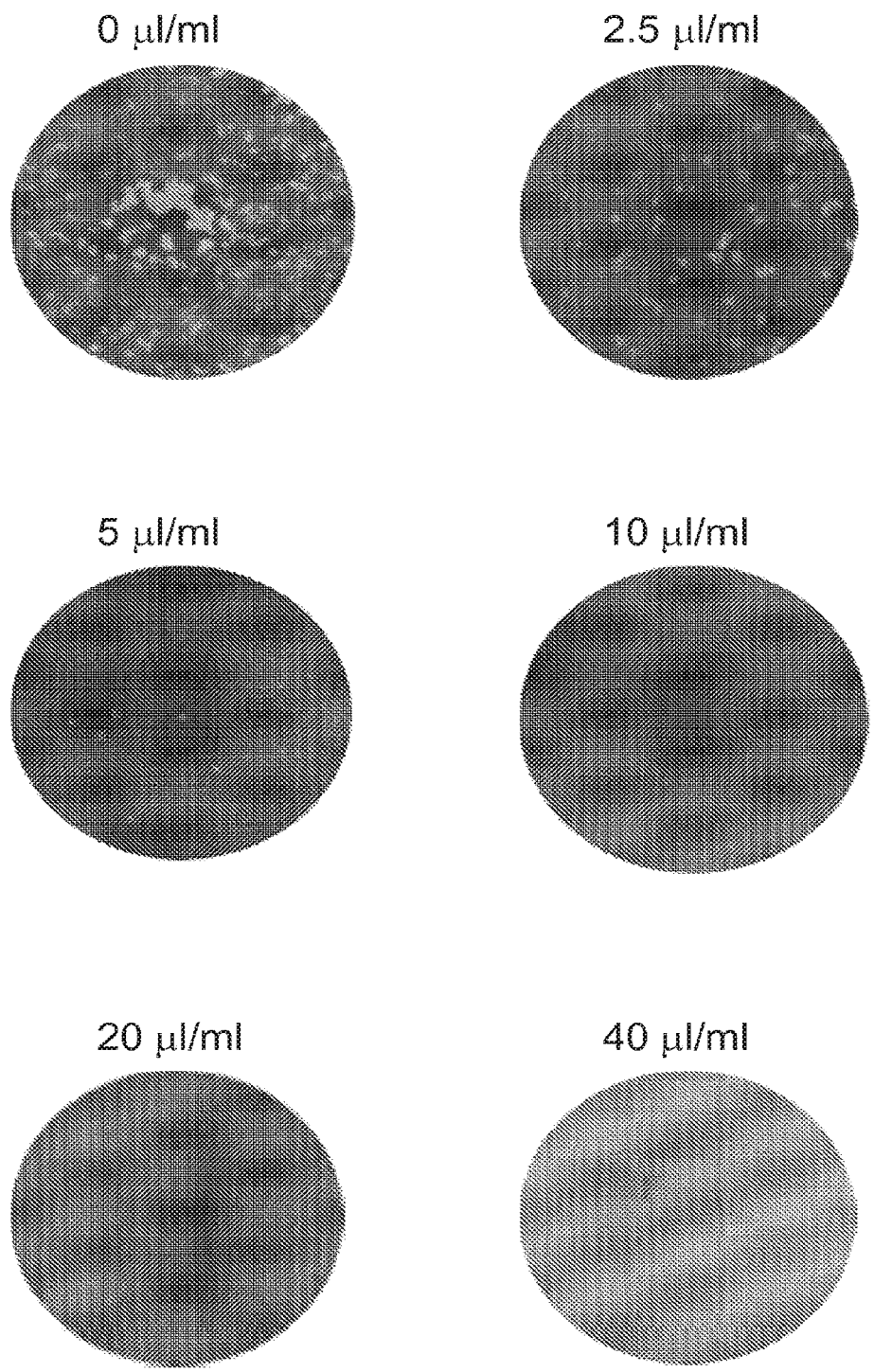
Figure 32D:
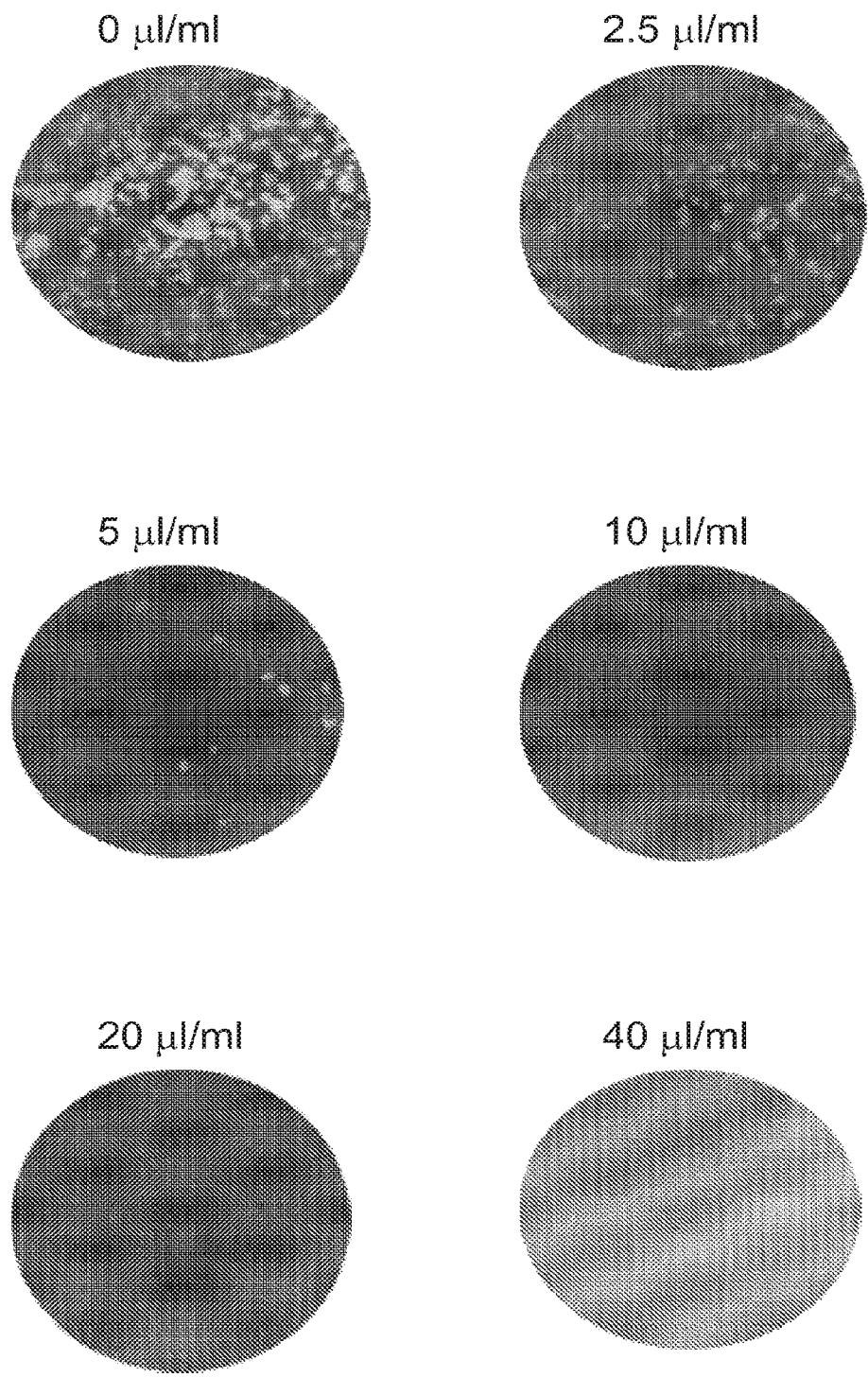
Figure 32E:
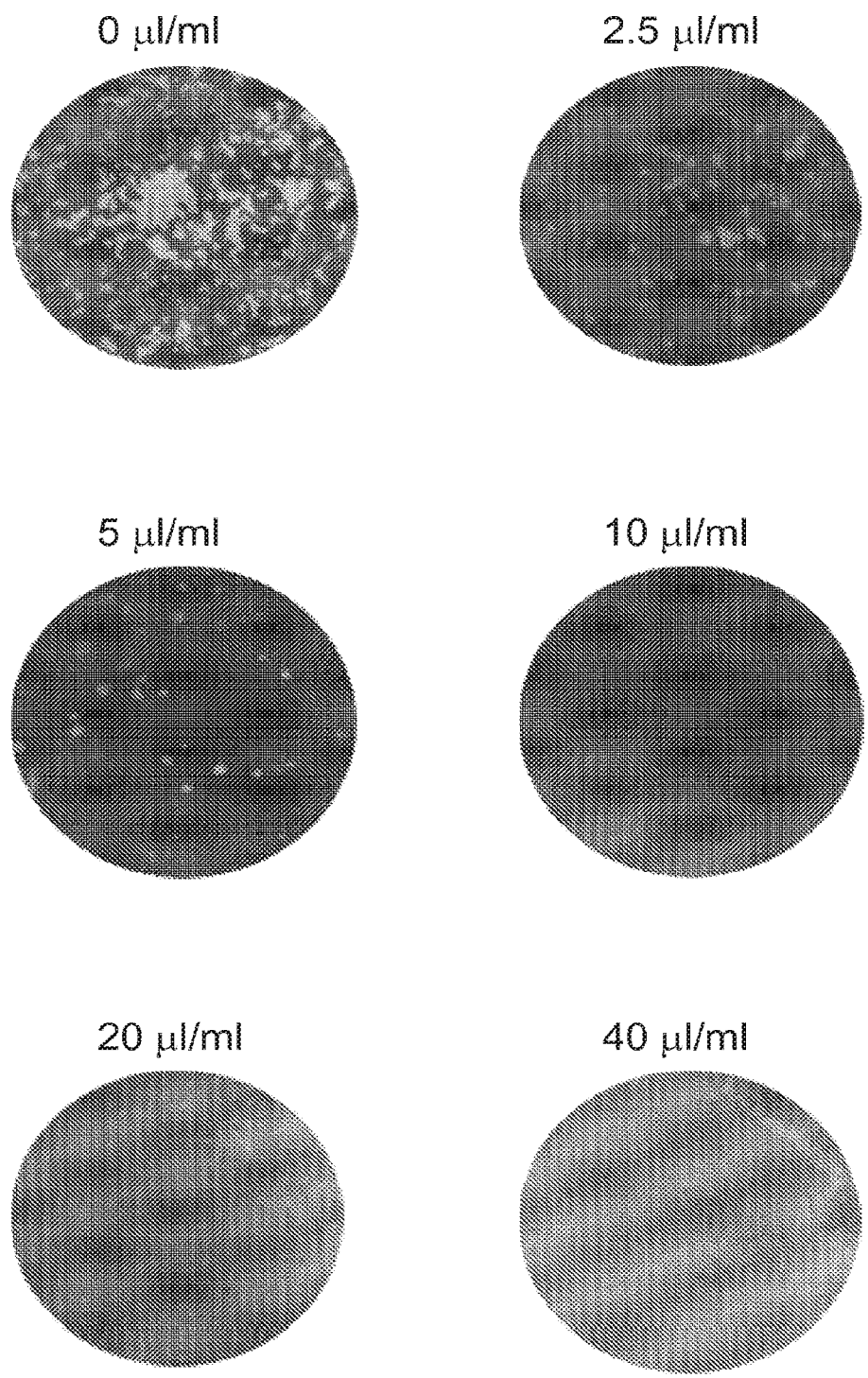
Figure 34:
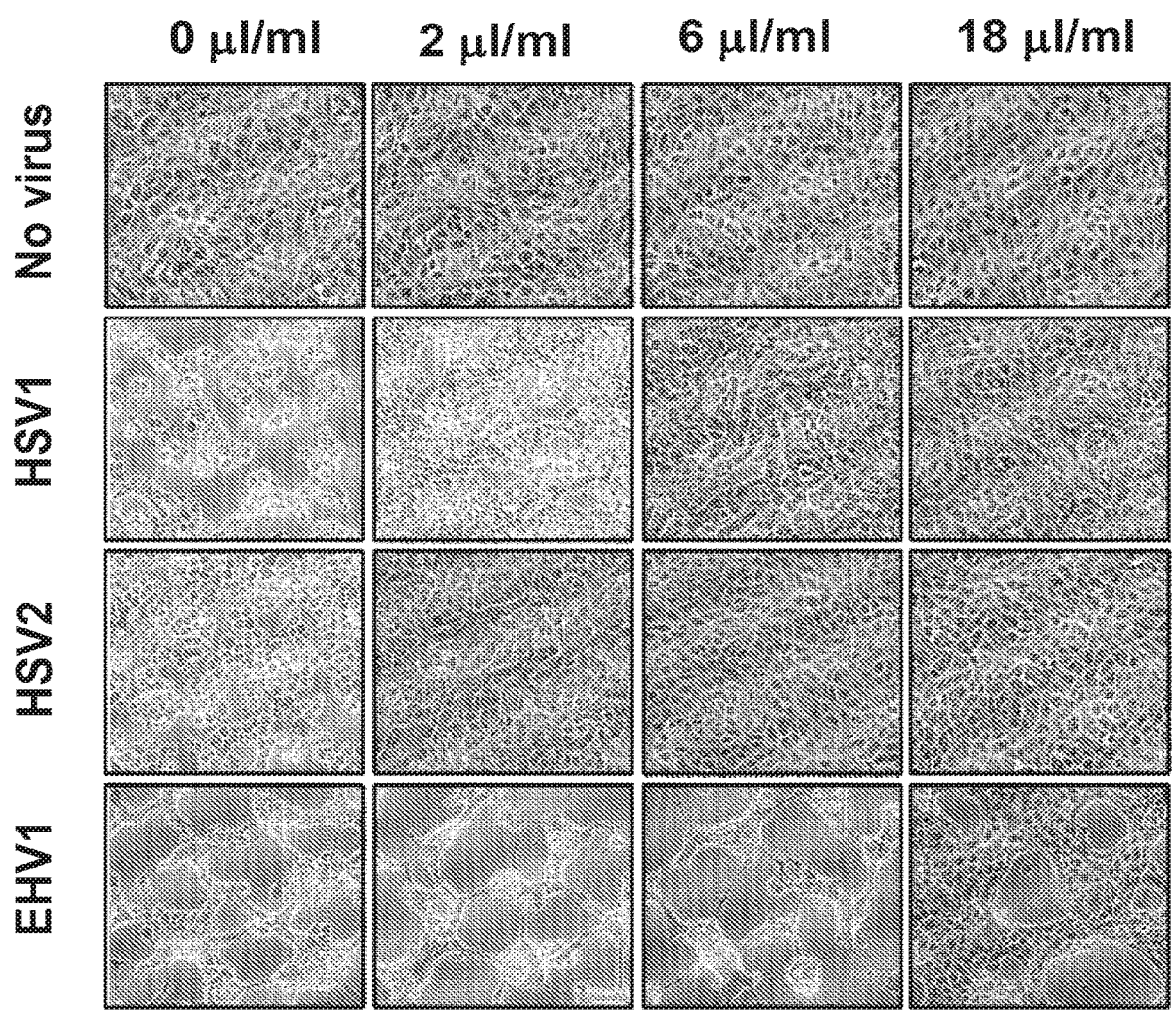
FIG. 34 illustrates inhibition of herpes virus CPE by *M. officinalis;*
Figure 35A:
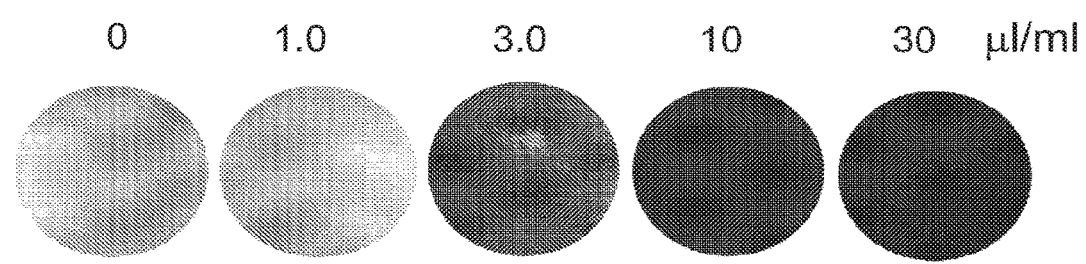
FIGS. 35A and 35B illustrate inhibition of HSV1 spread by *M. officinalis;*
Figure 35B:
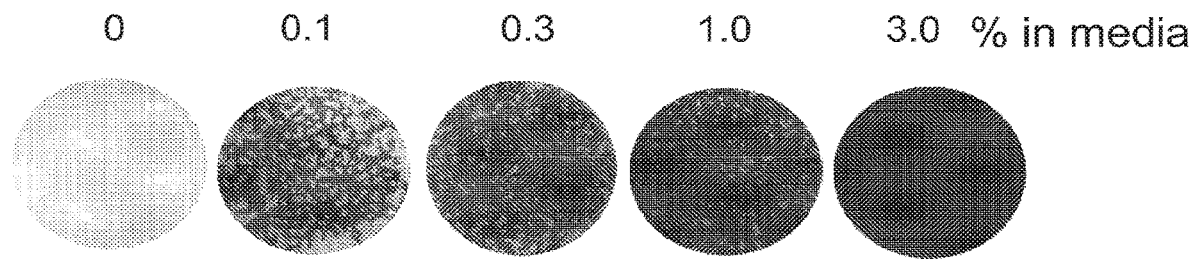

Referring now to FIGS. 32A-32E, related *Sarracenia* species were tested for similar anti-herpes virus activity. *S. elata* (FIG. 32B), *S. flava* (FIG. 32C), *S. leucophylla* (FIG. 32D) and *S. rubra* (FIG. 32E) all demonstrated similar antiviral activity against HSV 1 compared to *S. purpurea* (FIG. 32A). For this study, Vero cells were infected with 100 pfu HSV1 followed by the addition of increasing concentrations of the indicated botanical extracts prepared from various *Sarracenia* species (per ml media). At 4 days post infection ("DPI"), cells were stained with crystal violet and plaques counted. These results suggest that multiple (if not all) species of *Sarracenia* encode components to inhibit the replication of alpha herpes viruses. *M. officinalis* mechanism of action Referring now to FIG. 34, when cells were infected with HSV1, HSV2. or EHV1, typical cytopathic effects were observed. For this study, Vero cells were infected with HSV1, HSV2, or EHV1 at an MOI=10. Infected cells were treated with increasing concentrations of *M. officinalis* extract. At 3-4 DPI, viral CPE was visualized by microscopy and photographed. If following infection, the cells were treated with *M. officinalis* extract, this cytopathic effect could be inhibited in an HSV1 and HSV2 infection and reduced in an EHV1 infection. To assess whether extracts of *M. officinalis* could inhibit viral spread from cell-to-cell, Vero cell monolayers were infected with 100 plaque forming units of HSV1. Three hours later, any remaining viral inoculum was removed and the cells were treated with increasing concentrations of *M. officinalis*. Viral cytopathic effect was monitored and when full CPE was observed in the untreated dish, the cell monolayers were stained with crystal violet. As shown in FIG. 35A, *M. officinalis* was able to prevent the spread of HSV1 from infected cells to non-infected ones. For this study, Vero cells were infected with 100 pfu HSV1. At 4 HPI, the cells were treated with the indicated concentrations of *M. officinalis* extract. As a control, a comparable set of plates were treated with human immunoglobulin (FIG. 35B). The virus infection was allowed to progress until complete CPE in the untreated plate (6 days). At that time, cells were stained with crystal violet and viral plaque/CPE recorded. As a control, cells were treated with human immunoglobulin which has previously been shown to inhibit HSV1 cell-to-cell spread.

Figure 36:
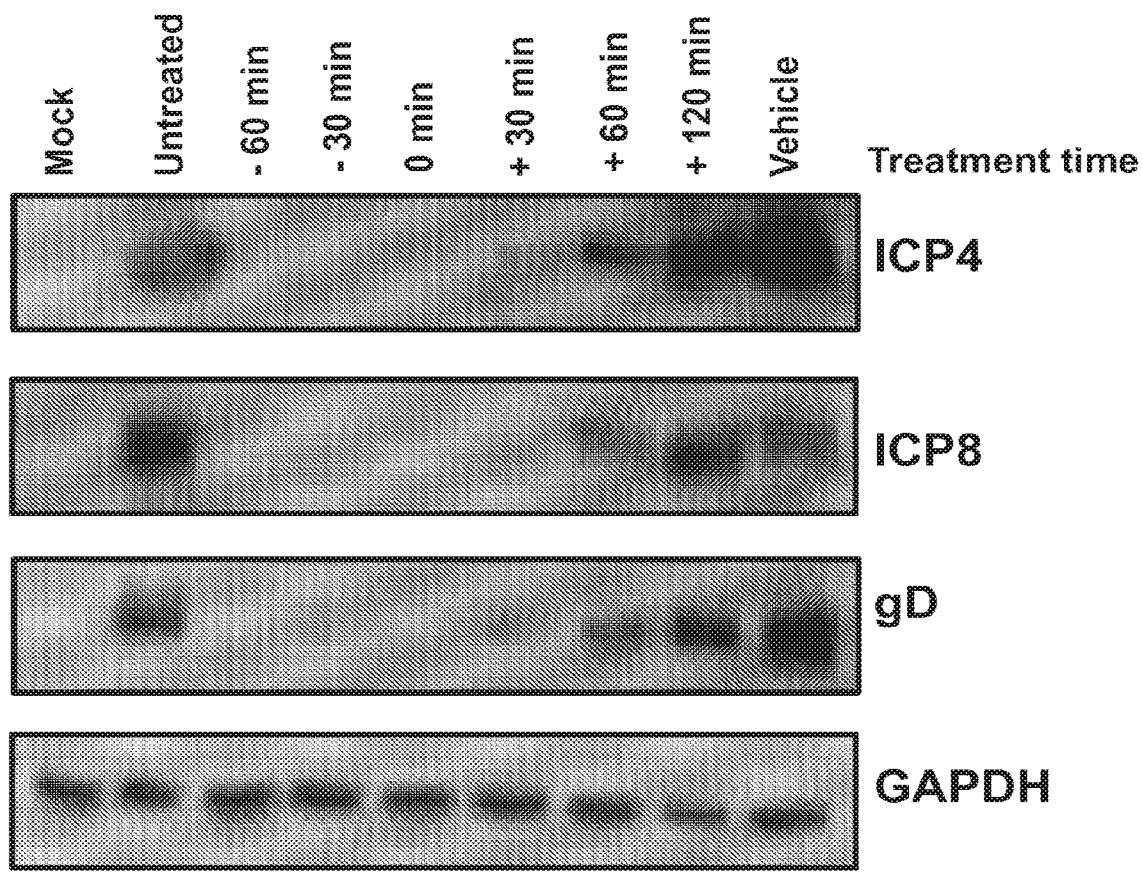
FIG. 36 illustrates inhibition of HSV 1 protein accumulation by *M. officinalis;*

Referring now to FIG. 36, in order to assess at which point in the virus replication cycle *M. officinalis* was acting on the HSV1, cells were infected with HSV1 and treated with *M. officinalis* at multiple times post infection. For this study, Vero cells were infected with HSV1 at an MOI=10. Cells were treated with *M. officinalis* extract at the indicated times post infection. At 24 HPI, cells lysates were prepared and the levels of HSV1 ICP4, ICP8 and gD determined by Western Blot analysis. Antiserum to GAPDH was used as a control. Viral replication was monitored by Western blot of an immediate-early viral protein (ICP4), an early viral protein (ICP8) and a late viral protein (gD). *M. officinalis* treatment must occur either prior to infection or during infection to inhibit HSV1 replication (FIG. 36). This suggests that the *M. officinalis* is targeting an early event in the virus replication cycle, likely either directly killing the virus, virus attachment to the cell, or virus uptake into the cell. In order to determine the exact target of anti-herpes activity associated with *M. officinalis*, multiple experiments were performed to measure the effect of the extract on the free virus (direct virucidal), viral attachment to the cell, or viral entry into the cell.

Figure 37A:
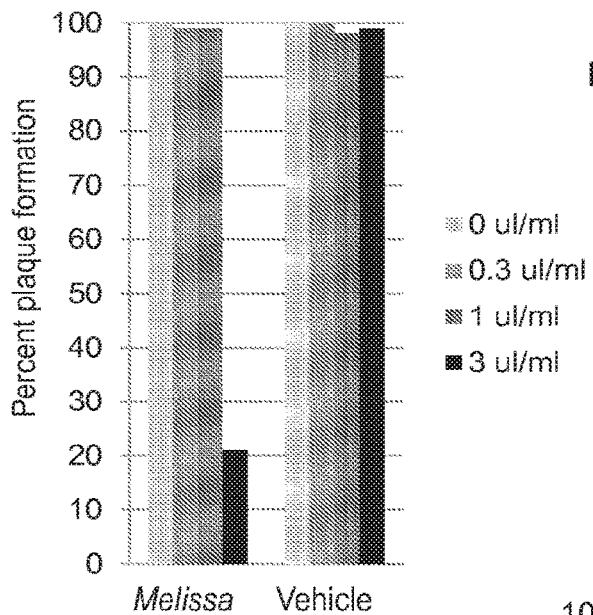
FIGS. 37A-37C illustrate activity of *M. officinalis* toward HSV1.
Figure 37B:
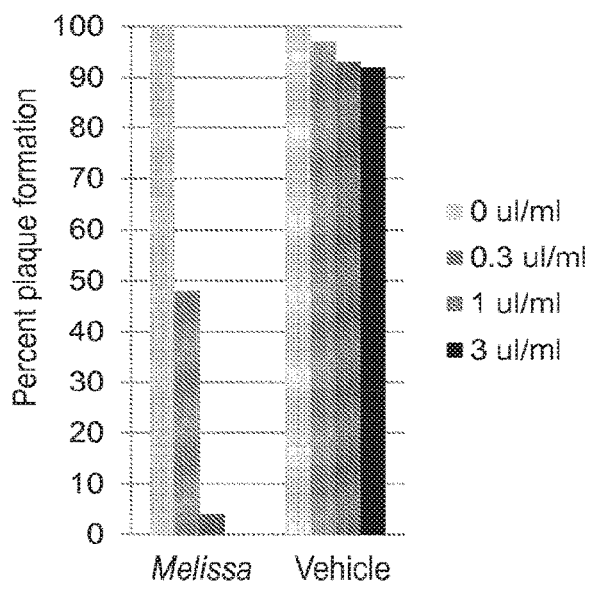
Figure 37C:
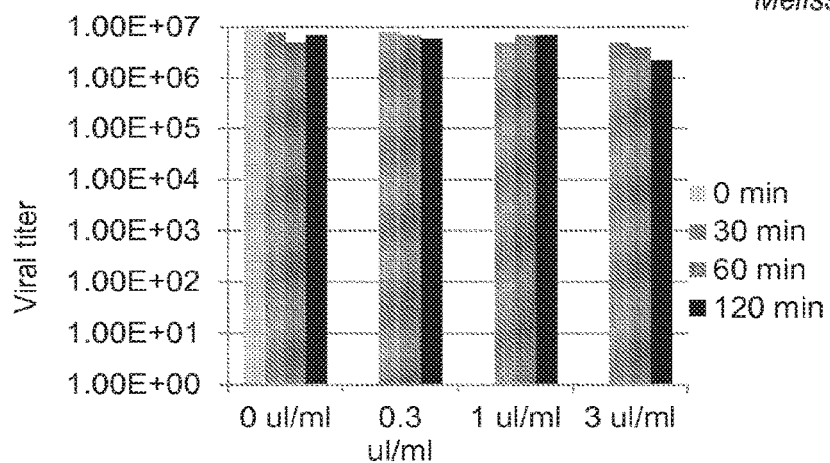

With reference now to FIGS. 37A-37C, the inhibitory effects of *M. officinalis* extract on HSV1 attachment to the cell are illustrated. For this study, standard viral entry (FIG. 37A), viral attachment (FIG. 37B) and direct virucidal assays (FIG. 37C) were performed, the results of which are illustrated. For the standard viral entry assay, virus was incubated with cells for 3 hrs at 4° C., followed by a wash. Virus exposed cells were treated with different concentrations of extract in medium for 2 hrs at 37° C. Free virus was inactivated and washed from the cells. Cells were stained at 3 DPI. For the direct virucidal assay, virus was treated with a botanical extract at the indicated concentrations for four different incubation times ranging from 0 to 120 min. The virus was then pelleted, resuspended, and viral activity titered. There was an observable effect on viral entry and a direct virucidal effect, but these required at least a 10 to 30-fold higher dose of extract, respectively. Therefore, these data support that *M. officinalis* inhibits HSV1 by blocking viral attachment to the cell. For the viral attachment assay, virus was incubated was cells as for the viral entry assay, except botanical extract was also added at the indicated concentrations during this step. Cells were washed, and stained at 3 DPI. HSV1 attachment to a cell requires binding to heparin-sulfate. An in vitro experiment was performed to determine if *M. officinalis* could block HSV1 binding to heparin attached to an agarose bead. In this assay, HSV1 was incubated with heparin-agarose in the presence or absence of *M. officinalis* or free heparin. Virus binding to the bead was detected by Western blot to the viral gD protein.

Figure 38:
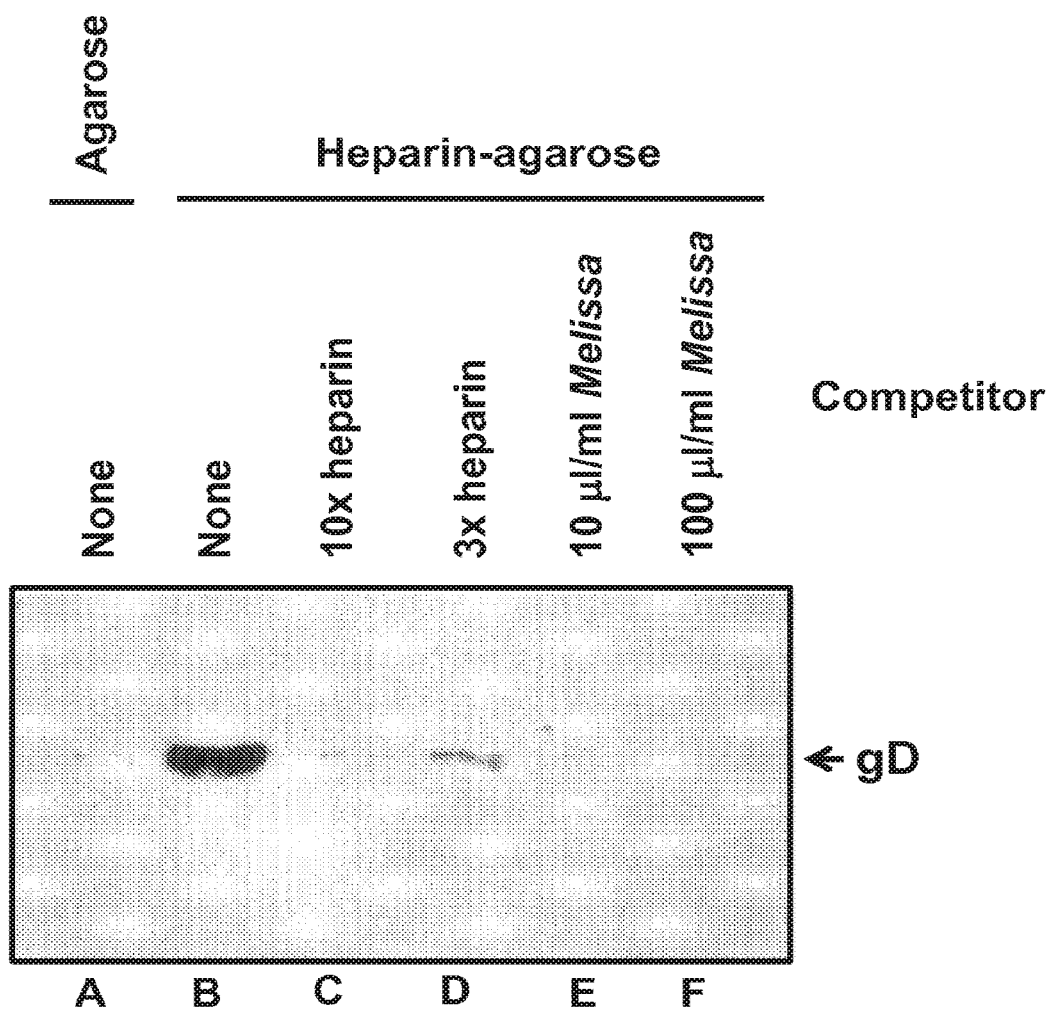
FIG. 38 illustrates *M. officinalis* extract effect on HSV1 attachment to heparin.

Referring now to FIG. 38, the *M. officinalis* extract was able to block HSV1 binding to heparin-agarose. For this study, 10 million HSV1 particles were incubated with heparin-agarose. As indicated, excess soluble heparin or *M. officinalis* extract was added during the binding assay. Following incubation for 1 hour, the agarose beads were washed repeatedly and any bound virus eluted using SDS-sample buffer. Eluted proteins were separated by SDS-PAGE and HSV1 gD detected by Western Blot analysis. This result is in agreement with previous data that *M. officinalis* targets HSV1 attachment to the cell.

Figure 39A:
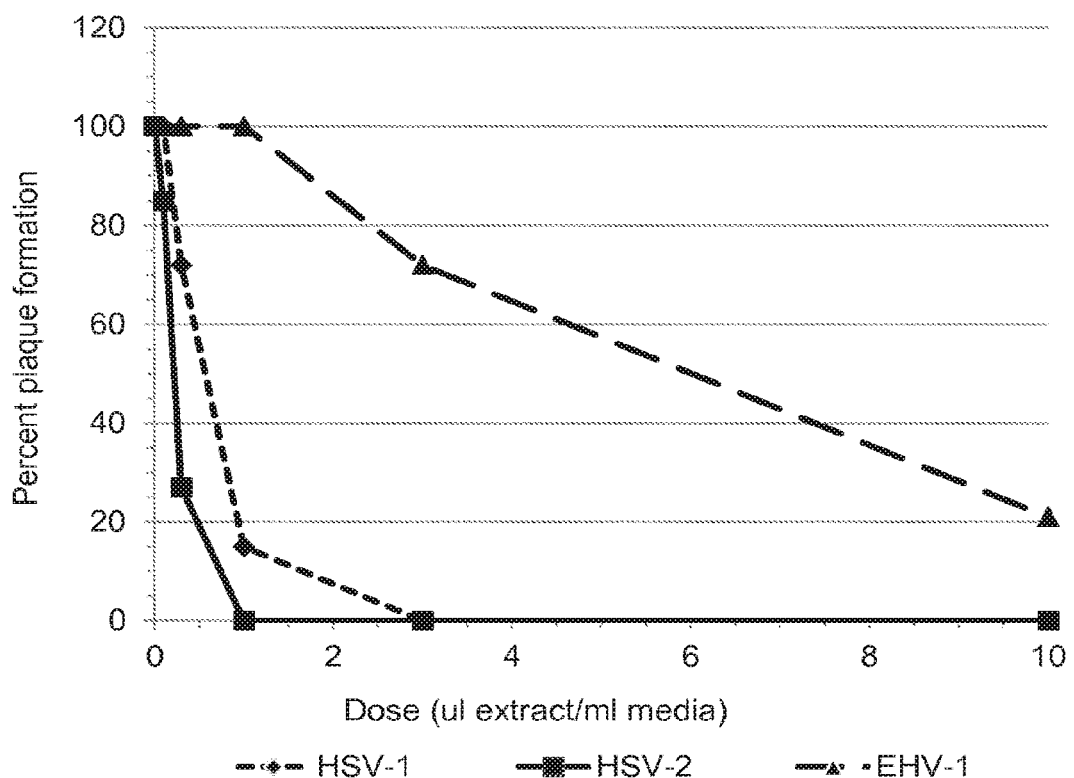
FIGS. 39A and 39B illustrate *M. officinalis* extract effect on viral families.
Figure 39B:
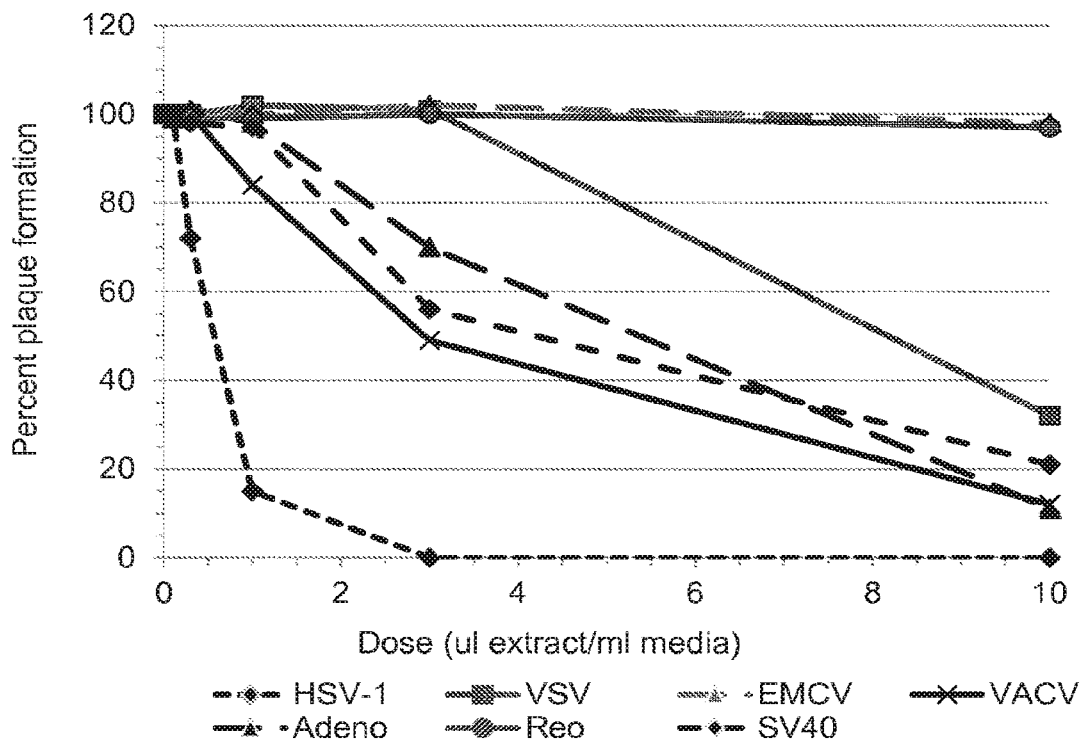

*M. officinalis* has been shown to inhibit the replication of HSV1, HSV2 and to a weaker extent, EHV1. To determine the spectrum of antiviral activity associated with *M. officinalis*, several non-herpes family viruses listed in Table 1 were tested for sensitivity to the extract. All assays were performed using standard plaque reduction procedures. As shown in FIGS. 39A and 39B, *M. officinalis* had the strongest antiviral effect toward HSV1 and HSV2. For this study, appropriate cell lines were infected with 100 pfu of the indicated virus along with treatment with increasing concentrations of *M. officinalis* extract. After the formation of plaques, cells were stained with crystal violet and plaques counted. However, a second group of viruses could be inhibited by *M. officinalis* but required doses approximately 10-fold higher than that required to inhibit HSV1 and HSV2. These moderately sensitive viruses included vesicular stomatitis virus (related to rabies virus), encephalomyocarditis virus (related to polio, hepatitis A, coxsackie and echo viruses), vaccinia virus (related to variola, the causative agent of smallpox), SV40 (related to human papillomavirus) and adenovirus. A third group of viruses were found to be insensitive to *M. officinalis* treatment and included mouse hepatitis virus (related to coronavirus) and reovirus (related to rotavirus).

infected with 100 pfu HSV1 followed by the addition of increasing concentrations of the indicated botanical extracts prepared from various *Nepenthes* species (per ml media). At 4 DPI, cells were stained with crystal violet and plaques counted *N. chaniana* and *N. fusca* had moderate levels of antiviral activity and *N. macrophylla* had minimal antiviral activity.

Figure 40:
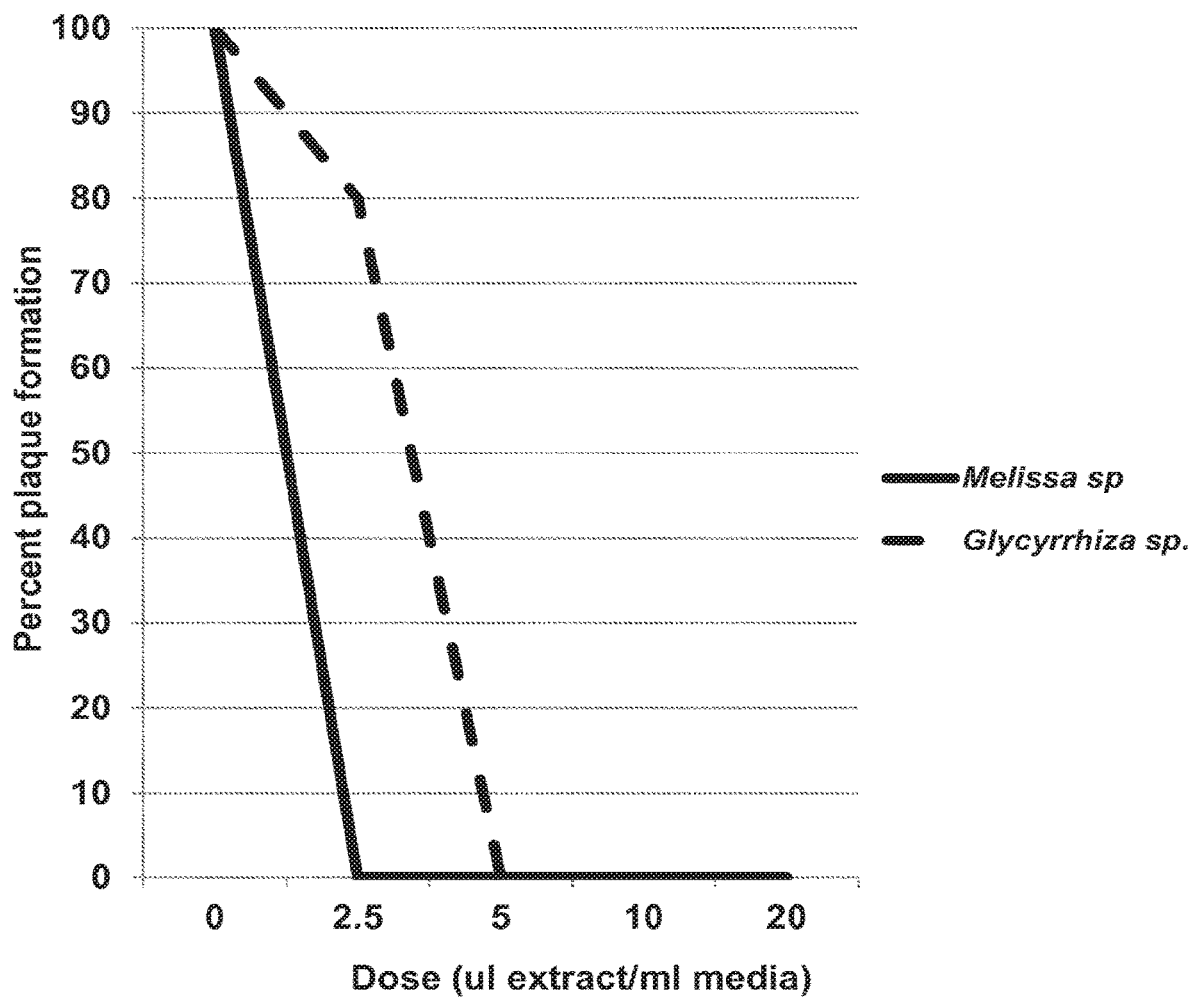
FIG. 40 illustrates effects of *M. officinalis* and *G. glabra* extracts on polyoma SV40 virus replication.

Regarding the activity of Species II Extracts to other viruses beyond the herpesvirus family, partial characterization of *Melissa* and *Glycyrrhiza* has been done towards SV40 virus, a member of the polyoma virus family and closely related to hitman papillomavirus (HPV). As shown in FIG. 40, both *Melissa* and *Glycyrrhiza* extracts were able to effectively inhibit the replication of SV40 as measured by a plaque reduction assay. In this study, Vero cells were infected with 100 pfu SV40 and treated with the indicated concentrations of *M. officinalis* or *G. glabra* extract. At 6 DPI, cells were stained with crystal violet and plaques counted. These result shown suggest that the botanical extract composition may not only be effective against members of the herpesvirus family, but will likely be a therapeutic for other viruses including human papilloma virus infections. This concept based on the idea that the botanical extract composition contains extracts from *S. purpurea, M. officinalis* and *G. glabra*, all of which demonstrate activity against both herpes and polyoma viruses.

Following treatment of patients for HSV1, HSV2, and VZV with various embodiments, it was noted that treated patients expressed a rapid decrease in pain and discomfort associated with their lesions. This activity is associated with embodiments comprising *S. purpurea* extract. The mechanism of action regarding this analgesic property is unknown, but adds to the therapeutic value of the *S. purpurea* extract by providing pain relief along with subsequent killing of the viral pathogen and/or clearance of cancerous tissue. In addition, patients have reported antipruritic (anti-itch) properties associated with *S. purpurea* following application of the extract. This has been most notable in patients treated for molluscum contagiosum.

Effect of *S. purpurea* on VACV Replication

To further determine the efficacy of *S. purpurea* treatment at preventing VACV replication, the ability of *S. purpurea* to prevent VACV induced cytopathic effect (CPE) in vitro was examined. As used herein, "HPI" refers to hours post infection, and "MPI" refers to minutes past infection. Cells were infected with VACV and then treated with *S. purpurea* at various times post-infection. At 6 HPI, the cells were examined for VACV induced CPE. In untreated cells, significant VACV induced CPE, specifically cell rounding, was observed (FIG. 2A), However, cells treated at 0, 15, and 30 MPI with *S. purpurea* showed no or low levels of CPE. In cells treated at 60 and 120 MPI, substantial CPE was

TABLE 1

Viruses tested for sensitivity to *M. officinalis* botanical extract.

| Virus | Related pathogen | Envelope | Genome | IC$_{50}$ (ml/ml) |
|---|---|---|---|---|
| Herpes family | | + | dsDNA | 0.1-0.3 (HSV) 6 (EHV) |
| VSV (Vesicular stomatitis virus | Rabies | + | ssRNA | 8.2 |
| EMCV (Encephalomyocarditis virus) | Polio | − | ssRNA | >10 |
| VACV (Vaccinia virus) | Smallpox | + | dsDNA | 3 |
| SV40 (Simian virus 40) | Papilloma | − | dsDNA | 4.5 |
| Reo (Reovirus) | Rotavirus | − | dsDNA | >10 |
| Adeno (Adenovirus) | Adenovirus | − | dsDNA | 5.4 |

Antiviral Activity of Further Botanical Extracts

Figure 33:
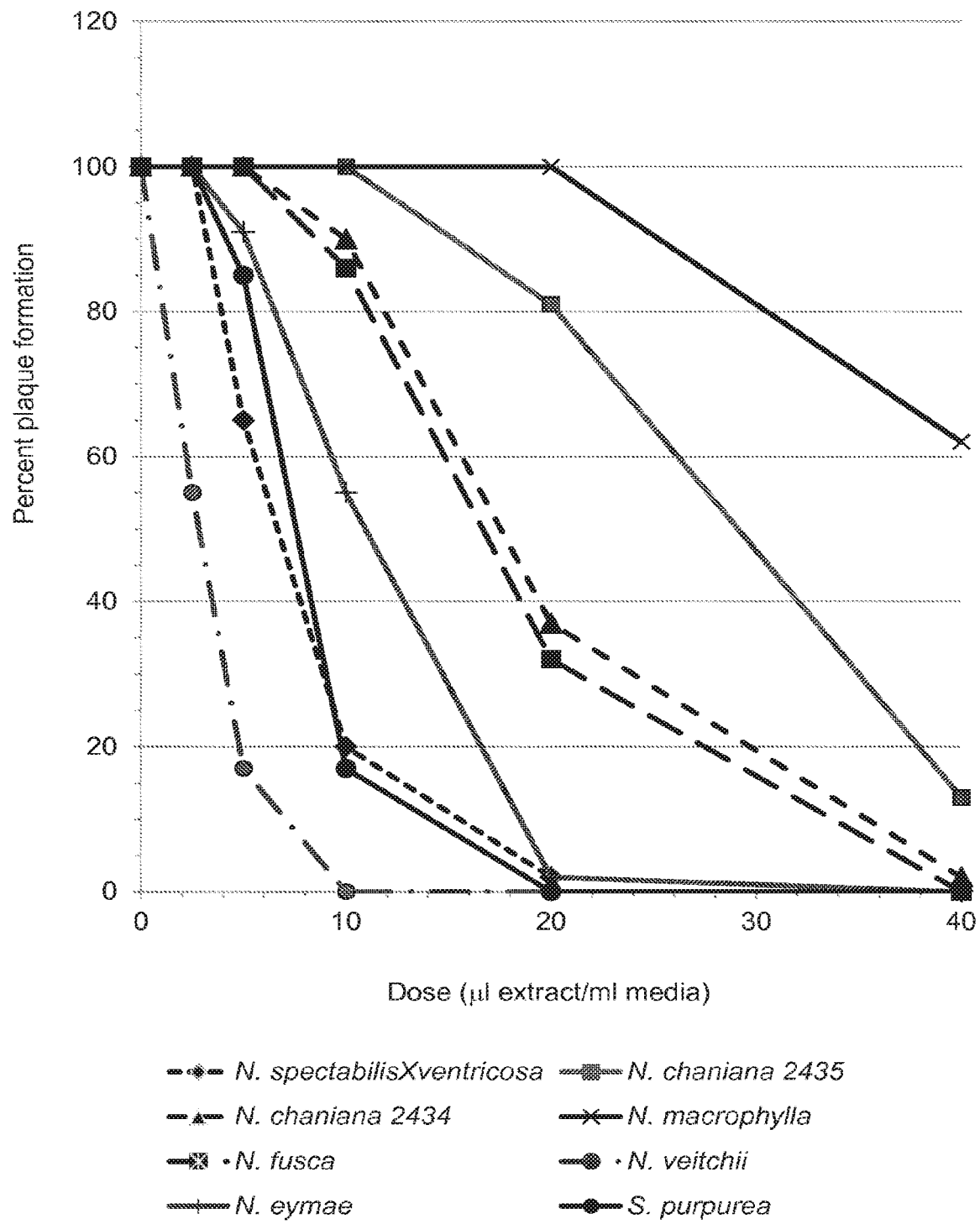
FIG. 33 illustrates antiviral activity of Nepenthes species.

Referring now to FIG. 33, anti-herpes virus activity associated with various *Nepenthes* species was examined. *N. veitchii, N, spectrabilis* x *ventricosa, N. eymae* and *N. Judith Finn* all had antiviral activity towards HSV1 (data not shown for *N. Judith Finn*). For this study, Vero cells were observed, leading us to postulate that *S. purpurea* was likely targeting an early component in VACV replication (i.e., viral uptake or early viral transcription/translation). Viral uptake was monitored using a VACV construct in which the core A5 protein was fused to cyan fluorescent protein. As shown in FIG. 2B, when the VACV infection was performed at 4° C., virus particles remained localized to the periphery of the cell. When the infection was performed at 37° C., the majority of virus particles were observed within the cytoplasm. When a similar infection at 37° C. was performed in the presence of *S. purpurea*, a similar viral localization to the cytoplasm was observed. This suggests that *S. purpurea* treatment was not inhibiting VACV uptake into the cell.

We examined if early viral protein synthesis was inhibited following *S. purpurea* treatment VACV-infected cells were treated with *S. purpurea* at various times post infection and cell lysates were assayed by Western blot using antibodies directed against total VACV proteins or the early VACV protein, E3L. VACV protein synthesis at 3 and 6 HPI in the cells treated at 0, 15, and 30 MPI with *S. purpurea*, was greatly reduced (FIG. 2C), Notably, *S. purpurea* reduced early VACV protein synthesis, as evidenced by the absence of the VACV-E3L protein. In contrast, *S. purpurea* treatment had only marginal effects on viral protein levels when added at 60 and 12.0 MPI. Ceils were also [35S]-methionine metabolically labelled to compare viral protein synthesis to cellular protein synthesis following *S. purpurea* treatment As predicted based on the cellular toxicity data (FIG. 1C), *S. purpurea* inhibited viral protein synthesis, whereas cellular protein synthesis remained unaffected (FIG. 2D). Collectively, these data indicate *S. purpurea* treatment was effective at preventing VACV early protein accumulation and acted at a point between viral uptake and early viral protein synthesis.

Figure 3A:
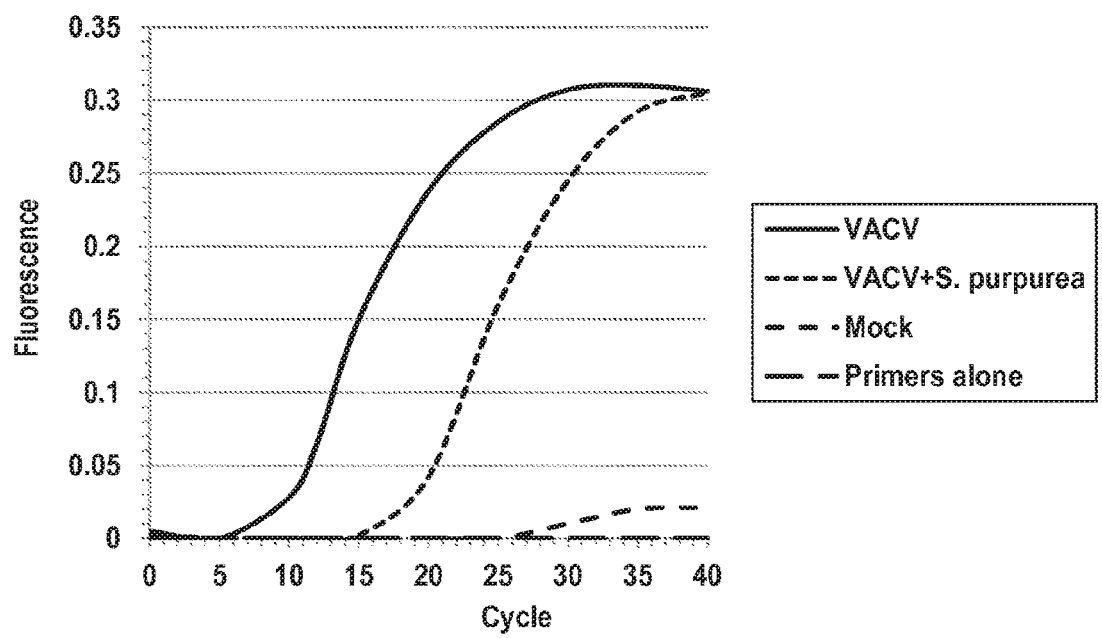
FIGS. 3A and 3B illustrate the effect of a *S. purpurea* extract on VACV transcription in vivo and in vitro.
Figure 3B:
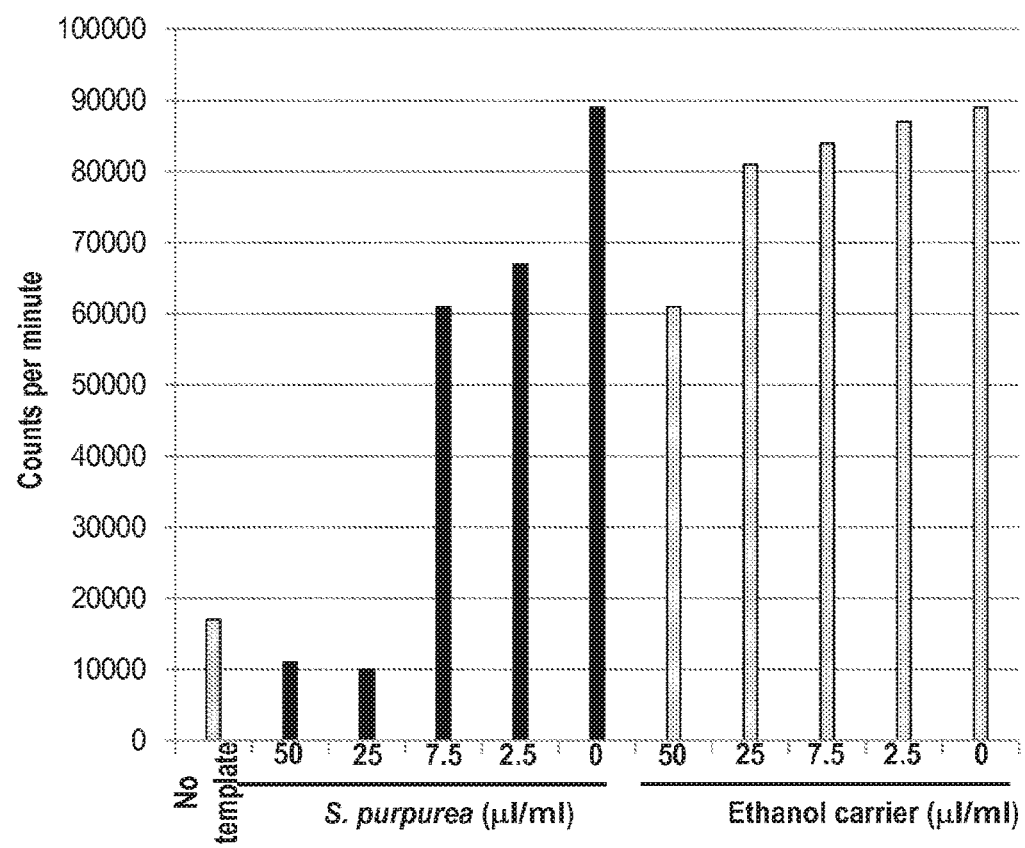

Effect of *S. purpurea* Botanical Extracts on VACV Transcription In Vivo and In Vitro Referring now to FIGS. 3A and 3B, early VACV-E3L mRNA levels were quantified in VACV-infected cells using real-time PGR to further understand the early viral stage affected following *S. purpurea* treatment. For FIG. 3A, HeLa cells were infected with VACV at an MO 1=10 followed by the addition of 25 µl *S. purpurea* extract/ml media. At 4 HPI, total RNA was isolated and VACV-E3L RNA levels determined by real-time PCR. Reactions contained total RNA from mock-infected cells, ethanol/glycerol carrier-treated VACV-infected cells, or *S. purpurea*-treated VACV-infected cells. The term "mock-infected cells" refers to cells treated similarly as virus-infected samples, but with no virus present. C(t) values were calculated using manufacturer's software. The graph illustrates data from a representative experiment. The term "C(t)" (for "cycle threshold") may be defined as the number of PCR. cycles required for a fluorescent signal to cross a threshold (i.e. exceeds background level). C(t) values and fold-change from two separate experiments are shown in Table 2.

TABLE 2

E3L gene expression in VACV-infected HeLa cells.

| Sample | C(t) | Fold-reduction |
|---|---|---|
| VAVC (exp. 1) | 13.80 | |
| VAVC (exp. 2) | 10.49 | |
| VAVC + *Sarracenia* (exp. 1) | 22.42 | 393 |
| VAVC + *Sarracenia* (exp. 2) | 19.38 | 474 |

In FIG. 3B, purified VACV virion cores were incubated in the presence of the indicated concentrations of *S. purpurea* or ethanol/glycerol carrier and [$^{35}$S]-UTP, Newly synthesized RNA products were spotted onto glass-fiber filters, washed in TCA, and quantified by scintillation counting (counts per minute). A no template reaction was performed by excluding the addition of the virion cores.

Figure 1B:
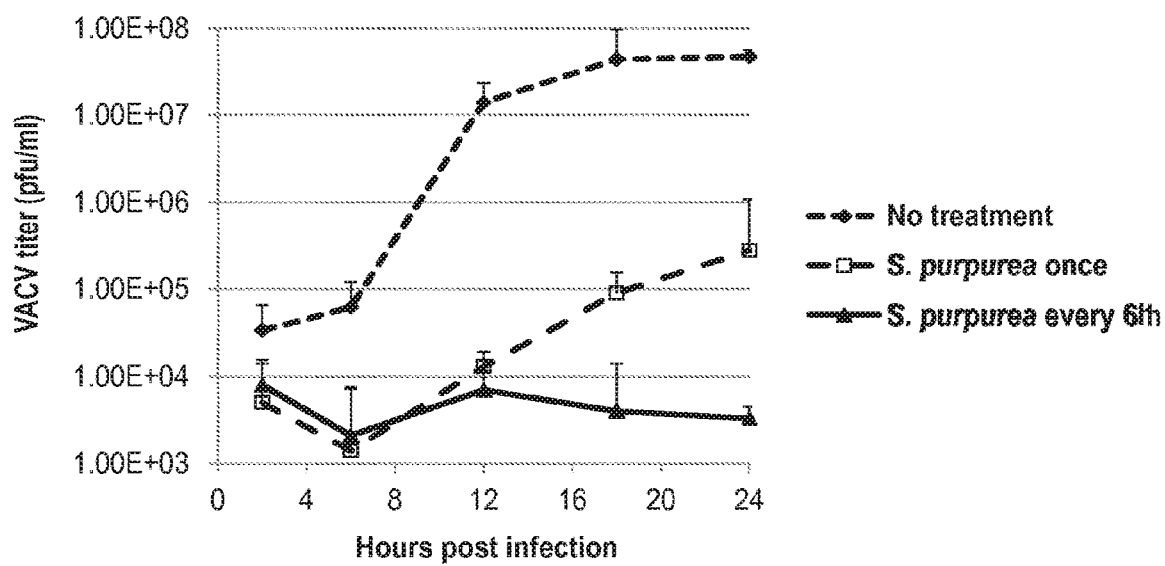
Figure 1C:
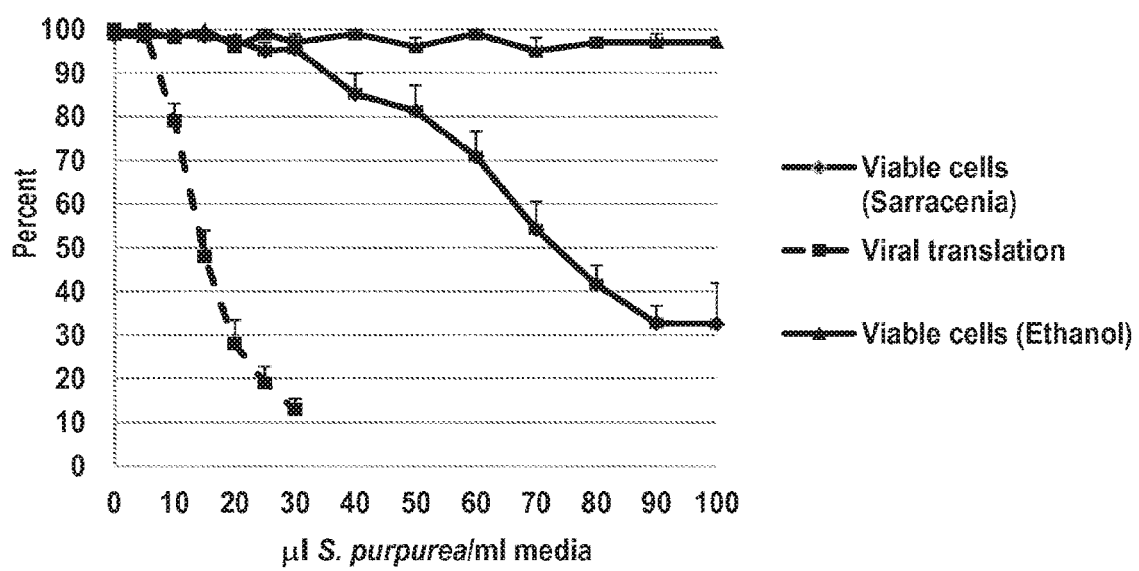

Total RNA was isolated from cells that were mock-infected, VACV-infected or VACV-infected followed by treatment with a single dose of *S. purpurea* extract. *S. purpurea* treatment resulted in a dramatic reduction of the levels VACV-E3L mRNA present within the infected cells (FIG. 3A). Based on C(t) values, the levels of early VACV mRNA were decreased by 393 to 474-fold within the treated cells. No significant change in cellular actin mRNA levels was observed following *S. purpurea* treatment. To determine if VACV replication was being blocked at the level of early viral transcription, an in vitro transcription assay using purified VACV virion cores and [$^{35}$S]-UTP was performed. The amount of VACV transcription which occurred following treatment with increasing amounts of *S. purpurea* or carrier was measured by quantifying the amount [$^{35}$S]-UTP incorporated into the newly synthesized viral mRNA. As shown, VACV transcription decreased as the amount of *S. purpurea* increased, while the levels of transcription remained relatively equal in the carrier treated cores (FIG. 38), The amount of *S. purpurea* required to completely inhibit transcription was similar to the dose that prevented VACV replication (FIG. 1B). Addition of *S. purpurea* to VACV cores which had already synthesized RNA did not reduce RNA levels suggesting that the extract did not have intrinsic RNase activity. Collectively, these data suggest that *S. purpurea* targets early viral transcription leading to an inhibition in viral replication.

Spectrum of Activity

To further ascertain the efficacy of using *S. purpurea*, Species II Extracts and botanical extracts to treat or prevent the symptoms associated with a poxvirus infection, the capability of *S. purpurea* in preventing the replication of more virulent members of the Orthopoxvirus genus, namely monkeypox virus (MPXV) and variola virus (VARV) was examined. Referring now to FIG. 5A, HeLa cells were mock-infected or infected with monkeypox virus at an MOI=10 followed by the addition of 25 µl ethanol/glycerol carrier or 25 µl *S. purpurea* extract/ml media, either 0 or 15 min after infection. At 4 HPI, cell lysates were prepared and the MPXV F3L protein detected by Western blot. Referring now to FIG. 4B, HeLa cells were mock-infected or infected with variola virus at an MOI=10 followed by the addition of the indicated concentrations of ethanol/glycerol carrier or *S. purpurea* extract to the media at 0 min after infection. At 4 HPI, cell lysates were prepared and the VARV E3L protein detected by Western blot. Cells were mock-infected or infected with MPXV and subsequently left untreated or treated with *S. purpurea* or carrier at the times indicated. Western blots for the presence of the MPXV-F3L protein, which is an ortholog of the VACV-E3L protein, were performed to determine if a successful MPXV infection had occurred. When treated with the extract at 0 or 15 MPI, *S. purpurea* treatment prevented the accumulation of the MPXV-F3L protein, whereas high levels of MPXV-F3L were detected in the both the untreated and carrier treated cells (FIG. 5A). A similar assay was performed with VARV where cells were mock-infected or infected with VARV and treated with *S. purpurea* or carrier at the dosages indicated. Western blots for the presence of the VARV E3L protein indicated a concentration dependent inhibition in the accumulation of the VARV-E3L protein in *S. purpurea* treated infections (FIG. 5B). This suggests that *S. purpurea* may effectively inhibit MPXV and VARV replication similarly to VACV. *S. purpurea* treatment also effectively inhibited rabbitpox virus early protein accumulation in other experiments that have been performed. Together, these data indicate that *S. purpurea* was effective at preventing the replication of multiple viruses within the Orthopoxvirus genus. In addition to the usefulness of *S. purpurea* as a therapeutic for these currently uncommon infections, it is believed that *S. purpurea* may also be effective against the poxvirus, molluscum contagiosum. This is a common viral disease with a higher incidence in children, sexually active adults, and those who are immunodeficient.

Clinical Studies

Limited clinical studies were conducted to test the effectiveness of *S. purpurea* in treating infected individuals infected with molluscum contagiosum. For these studies a 30% gel of *S. purpurea* was prepared using 30 ml *S. purpurea* extract combined with 70 grams VERSABASE gel. This formulation was applied topically to molluscum contagiosum-associated lesions. Application of this formulation to viral associated lesions resulted in a slow reduction in lesion size over a 3-4 week period as well as relief from itching discomfort associated with the infection (antipruritic activity). Three subjects have been treated with molluscum contagiosum associated infections with similar positive results.

(Kaposi's and molluscum): Patient diagnosed as HIV positive with AIDS. Patient has Kaposi's Sarcoma (caused by HHV 8) and molluscum contagiosum. Patient was treated with *S. purpurea* (30%) in VERSABASE gel (70%) on side of face where molluscum lesions are present and to three KS lesions. After one month, the KS lesions where were softer, flattened out and fading. Patient also got appropriate treatment for HIV. Molluscum lesions responded well to treatment with the botanical, but patient had them frozen off after a few weeks.

(HPV and molluscum): Patient was a 3 year old, male. Patient diagnosed with 30+ plantar warts, common warts, seeded warts on hands, face, knee, and elbow. Diagnosed with HPV and molluscum contagiosum by a pediatrician and dermatologist. Previous treatments were unsuccessful. Dermatologist applied salicylic acid to HPV and molluscum contagiosum once a week for 3 weeks. In addition, patient applied *S. purpurea* (30%) in VERSABASE gel (70%) nightly with bandage. After three weeks of treatment, warts and molluscum contagiosum lesions are non-visible. On subsequent follow-up examinations patient has no lesions.

(Moiluscum): Patient was a teenage male. Patient diagnosed with molluscum contagiosum on inner thigh of both legs. Patient treated with *S. purpurea* (30%) in VERSABASE gel (70%) twice daily with bandage. After two weeks of treatment, molluscum contagiosum lesions were significantly smaller. Patient also reported substantial itch relief following application of the gel. Patient subsequently moved and no follow-up diagnosis is available.

In Vitro Herpes Studies

Referring now to FIG. 6, the ability of *S. purpurea* extract to inhibit other viruses, including herpes viruses was examined. Vero cells were mock infected or infected with HSV1 at an MOI=5. Cells were treated with *S. purpurea* extract at the time of infection. At 48 HPT, cells were examined for viral induced CPE. When cells were infected with HSV1 typical cytopathic effects were observed. Following infection, if the cells were treated with *S. purpurea* extract, this cytopathic effect could be virtually eliminated.

Referring now to FIG. 7, a Western blot was performed to detect the level of an immediate-early protein synthesized by the virus (ICP4), an early viral protein (ICP8) and a late viral protein (gC) in order to assess at which point in the virus replication cycle *S. purpurea* was acting on the HSV1. Vero cells were infected with HSV1 at an MOI=5. At 0 or 2 HPI, cells were left untreated or treated with *S. purpurea* extract. At 24 HPI, cell lysates were prepared and viral protein levels measured by Western Blot analysis. Antiserum used was against HSV1 ICP4, ICP8, and gC. GAPDH antiserum was used as a control. Following treatment with *S. purpurea* during infection, the accumulation of ICP4 was almost non-detectable. This suggests that the *S. purpurea* is targeting an early event in the virus replication cycle, either virus uptake into the cell, immediate-early transcription, or immediate-early protein synthesis. If treatment with *S. purpurea* is performed 2 HPI, ICP4 is detected, but the accumulation of ICP8 is reduced and the accumulation of gC is greatly inhibited, ICP4 synthesis was detected since the treatment with *S. purpurea* was begun after ICP4 had already been synthesized within the cell. This suggests that *S. purpurea* can also inhibit the accumulation of early and late viral proteins. Given the previous results with poxviruses, it is believed the *S. purpurea* extract is likely targeting viral transcription. To confirm this inhibition of viral proteins by *S. purpurea*, single cycle growth studies were performed with *S. purpurea* extract added at various time post infection.

Figure 8:
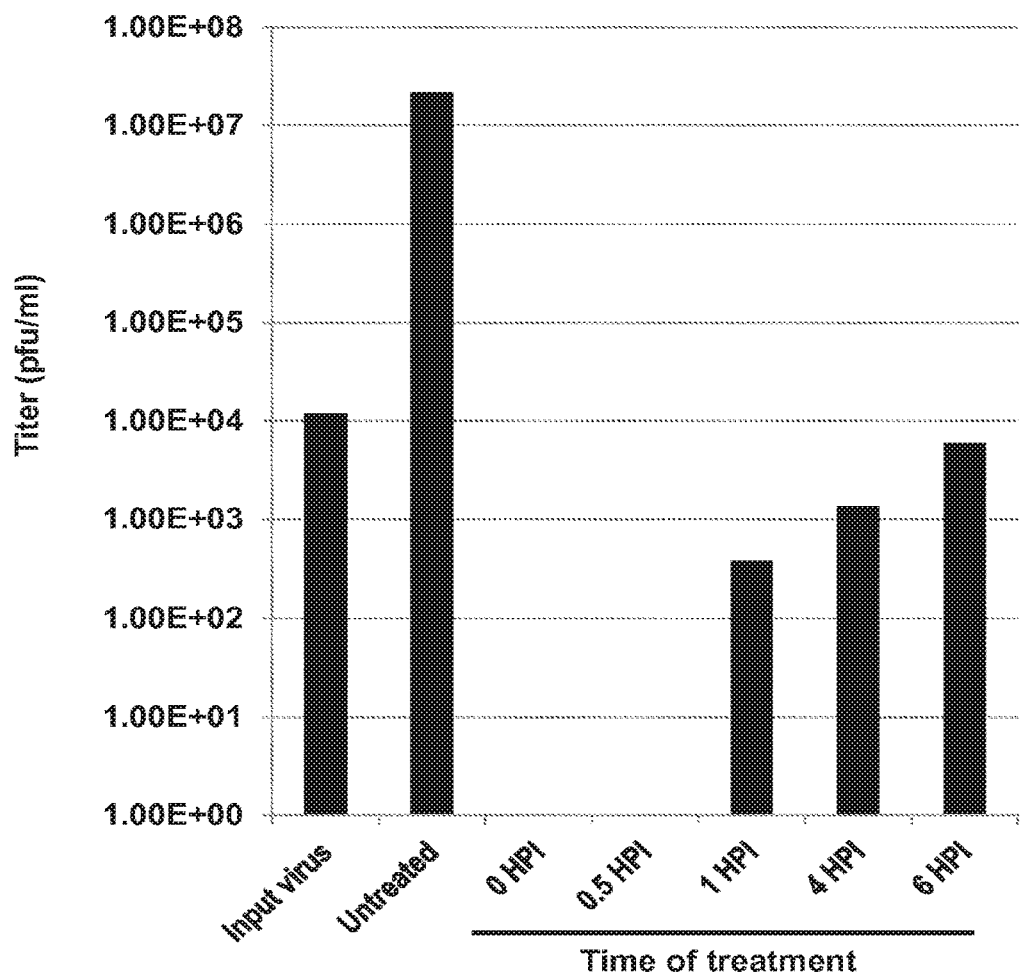
FIG. 8 illustrates an effect of a *S. purpurea* extract on HSV1 replication.

With reference now to FIG. 8, untreated HSV1 replicates efficiently and produces an approximate 3.5 log increase in viral yield above input virus. Veto cells were infected with HSV1 at an MOI=1. At the indicated times, cells were treated with *S. purpurea* extract for the remaining time of the viral replication cycle. At 24 HPI, cells were harvested and viral titers determined by standard plaque assay. Input virus titers were determined by harvesting viral infected cells at 1 hour post infection, if the virus is treated with *S. purpurea* extract at 0-0.5 HPI, a complete inhibition in viral replication was observed. If treated with *S. purpurea* between 1-6 HPI, viral yield is greatly reduced. These results agree with the protein accumulation data of FIG. 7 where early treatment with *S. purpurea* inhibits viral protein accumulation, whereas later treatment reduces the accumulation of late viral proteins, but some minor synthesis was still observed.

To ascertain if this antiviral activity was limited to HSV1, activity against Varicella-Zoster virus (VZV) was tested. Referring now to FIG. 9, BSC1 cells were infected with VZV at a low MOI. As indicated cells were left untreated or treated with *S. purpurea* extract. Viral plaque formation was monitored and shown at 7 and 9 DPI. Again, infection of cells in culture with VZV leads to a distinct cytopathic effect. Treatment of infected cells with *S. purpurea* extract immediately after infection was able to completely abolish this cytopathic effect (FIG. 9). Notably, these assays were performed with a single dose of *S. purpurea* extract (on day 1) and cytopathic effects measured on days 7 and 9.

Referring now to FIG. 10, individual plaques formed by VZV in the monolayer were observed by staining the cell monolayer to quantitate this effect. In this experiment, BSC1 cells were infected with VZV at a low MOI. As indicated, cells were left untreated or treated with 10 µl/ml or 20 µl/ml *S. purpurea* extract. At 9 and 12 DPI, cell monolayers were stained with crystal violet. The presence or absence of plaque formation is shown at 9 DPI. No plaque formation was detected for the uninfected control at either 9 or 12 DPI. At 9 DPI, the untreated virus infected cell monolayer had 288 plaques, and at 12 DPI, over 300 large plaques were present. As shown, a dramatic inhibition in plaque formation was observed following treatment with the *S. purpurea* extract. At 9 DPI, neither the 10 µl/ml or 20 µl/ml *S. purpurea* extract treated experiments had detectable plaques. At 12 DPI, about 40 small plaques were counted for the 10 µl/ml *S. purpurea* extract treatment, while the 20 µl/ml *S. purpurea* extract treatment had no detectable plaques. This inhibition in the replication of VZV by *S. purpurea* was confirmed by Western blot to detect the gI protein of the virus.

Figure 11:
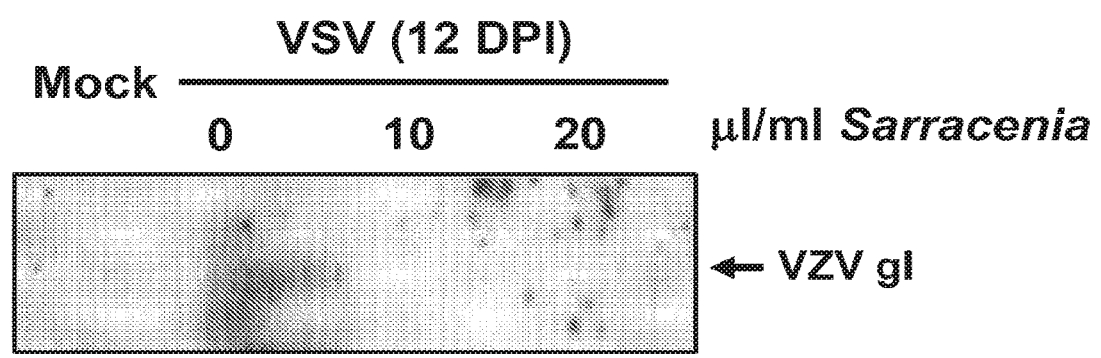
FIG. 11 illustrates an effect of a *S. purpurea* extract on VZV protein accumulation.
Figure 12:
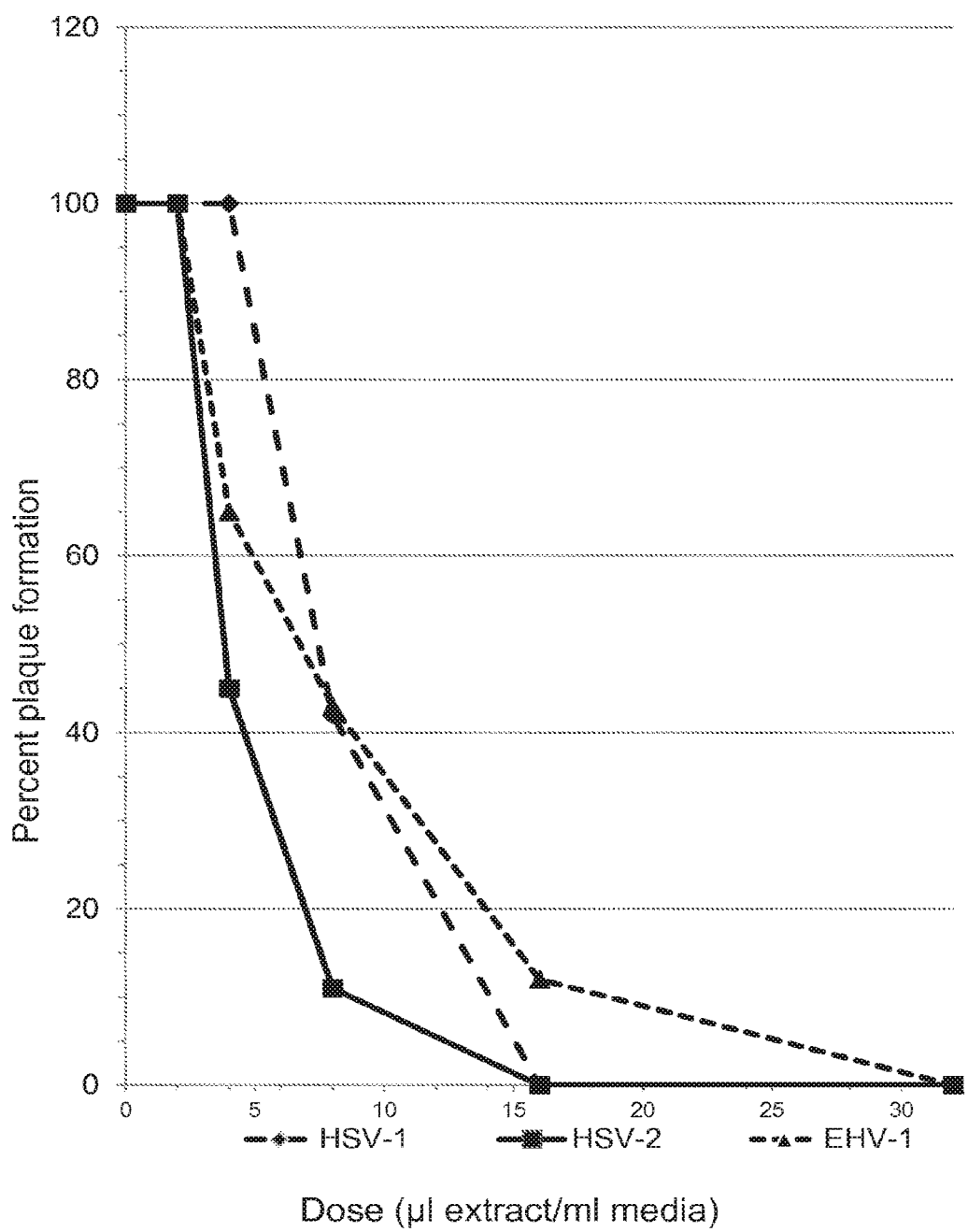
FIG. 12 illustrates an effect of a *S. purpurea* extract on the replication of herpes virus family members.
Figure 13A:
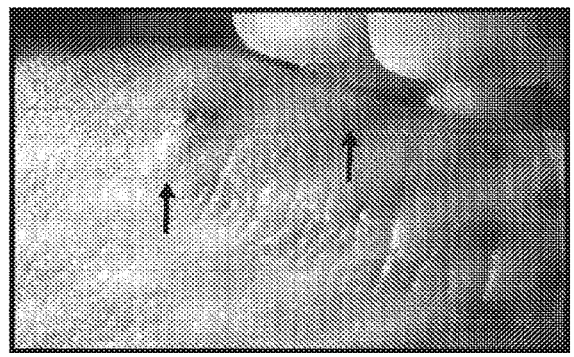
FIGS. 13A-13D illustrate an effect of a *S. purpurea* extract as a therapeutic for HSV1 infections.
Figure 13B:
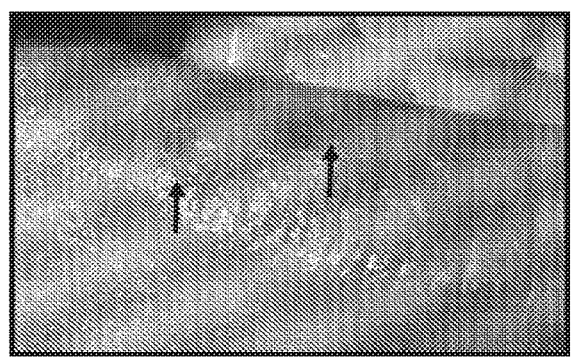
Figure 13C:
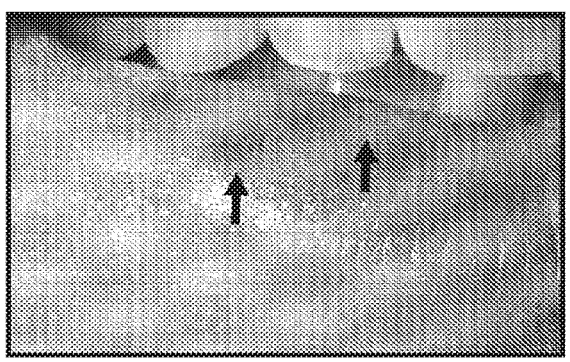
Figure 13D:
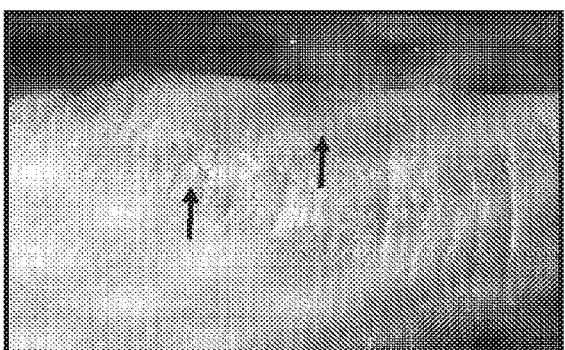
Figure 14A:
FIGS. 14A-14E illustrate an effect of a *S. purpurea* extract on polyoma virus SV40 induced CPE (cytopathic effect)
Figure 14B:
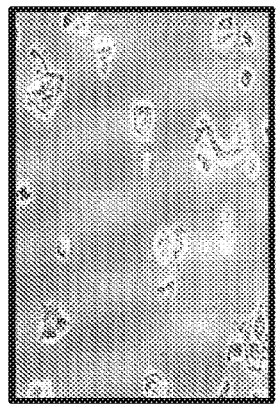
Figure 14C:
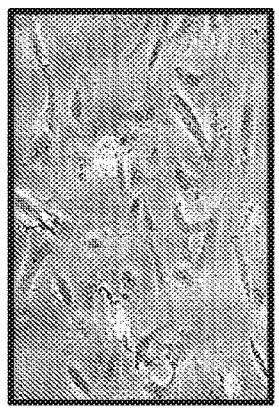
Figure 14D:
Figure 14E:
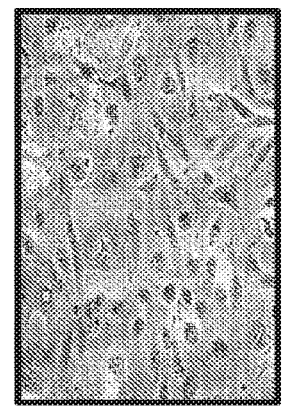

As shown in FIG. 11, this protein could not be detected in cells infected by VZV which were treated with *S. purpurea* extract. BSC 1 cells were infected with VZV at an MOI=0.01. Cells were left untreated or treated with *S. purpurea* extract. At 12 DPI, cell lysates were prepared and the level of VZV gl expression determined by Western Blot analysis. Together these results suggest that the *S. purpurea* extract can effectively inhibit the replication of HSV1 and VZV, and it is likely to inhibit other members of the herpesvirus family as well.

*S. purpurea* extract was also tested against the related herpes simplex-2 (HSV-2) and equine herpes virus-1 (EHV-1). Referring now to FIG. 12, *S. purpurea* extracts demonstrated similar antiviral activity against both HSV-2 and EHV-1 similar to that observed toward HSV-1. Vero cells were infected with HSV 1, HSV2 or EHV1 with 100 pfu/well. At the time of infection, cells were treated with various concentrations of *S. purpurea*, as indicated in the chart. At four DPI, cell monolayers were stained with crystal violet and plaque numbers counted. Plaque formation is shown as a percentage of a cell monolayer exhibiting the presence of plaques.

Clinical Herpes Studies

Clinical studies were conducted to test the effectiveness of *S. purpurea* in treating individuals with herpes virus (HSV1). For these studies a 20% gel of *S. purpurea* ("20% Gel") was prepared using 20 ml *S. purpurea* extract combined with 80 grams VERSABASE gel. Subjects diagnosed with HSV1 lesions on their lips were treated 4 times daily with 20% Gel. Lesion size and progression was monitored and photographed daily.

FIGS. 13A-13D illustrate the effects of the 20% Gel treatment for a typical subject. Viral lesions are indicated by arrows. As illustrated in FIGS. 13A-13D, over the course of the treatment period, the size and prominence of the viral lesions decreased. At the outset of treatment (Day 0, illustrated in FIG. 13 A) the lesion on the left was large and prominent. As shown in FIG. 13B (Day 1), after the first day of treatment, the lesion on the left and decreased substantially in size. On Day 2 (FIG. 13C), both lesions showed further healing, and by Day 3 of treatment (Figured 13D), the lesions were substantially healed.

Approximately 500 patients with similar HSV1 oral lesions were treated with similar results (over a 95% success rate compared to untreated HSV1 lesions). For topical therapy, 20% Gel was applied topically to viral-associated lesions. Application of 20% Gel to HSV 1 associated oral lesions ("cold-sore") every 4 hours over the course of infections led to rapid recovery of lesions FIG. Other herpes virus-associated infections were treated in patients, including infections with genital-associated HSV2 lesions and VZV-associated lesions. For the patients studied, successful effects following 20% Gel treatment were observed, suggesting an inhibition of virus replication within the tissue. For VZV patients, the formulation was applied to using an absorbent pad or impregnated bandage which could then be applied to the patient to cover afflicted areas.

In addition, some herpes virus family members are known to be associated with the development of cancers. Specifically Epstein Barr virus (EBV) and human herpes 8 (HHV8) are known to cause jaw/throat/neck cancer and Kaposi's sarcoma, respectively. A select number of subjects with such viral induced cancers were treated with success. Results of a few of these cases are shown herein.

(EBV/HHV6): Patient is a 57 year old male diagnosed with carcinoma of the pharynx. There is a right-sided posterior pharyngeal mass. Patient noticed a "bump on tongue" and was diagnosed via CT. Patient had a right-sided submandibular node palpated externally and on left pharynx on oral cavity exam in the peritonsilar region. The mass was accessible only by cotton swab. Patient reported mild discomfort in swallowing, but not enough to interfere with activities of daily living. No pain reported. Patient was diagnosed as HHV6+(IgG) and EBV+ (IgO). Patient was treated with *S. purpurea* liquid (50%) with an equal part transdermal driver gel (50%) applied directly to the peritonsilar/pharyngeal lesion. This regimen was incorporated as a part of an integrative treatment protocol. Upon administering directly to the tumor mass, patient reported that "the tumor just vanished under the swab as I was applying it." Within two days, the pharyngeal tumors were significantly smaller, and were visibly collapsing under the superficial mucosa, first in a star-like pattern. The mass became non-evident with remnants of scar tissue. At the time of discharge, patient reported that he had no trouble swallowing and was only feeling what felt to be scar tissue. No pain or bleeding rioted at the time of discharge. During treatment, PET/CT revealed interval decrease in size of tumor. For follow-up, two months after discharge patient received a clean PET/CT.

(EBV): Patient was an 8 year old male with aphthous ulcers on tongue and oral mucosa. Physical diagnosis indicates lesions likely due to EBV infection with the development of hairy leukoplakia. Symptoms appear to be stress related and the pain intensity to the level that the patient can't attend school nor eat without discomfort. Patient was treated with *S. purpurea* liquid (50%) as a gargle four times daily. With treatment patient's symptoms gradually improved. Improved symptoms were rioted within a few days with complete recovery after 2 weeks.

(Kaposi's and molluscum): Patient diagnosed as HIV positive with AIDS. Patient has Kaposi's Sarcoma (caused by HHV 8) and molluscum contagiosum. Patient was treated with *S. purpurea* (30%) in VERSABASE gel (70%) on side of face where molluscum lesions are present and to three KS lesions. After one month, the KS lesions where were softer, flattened out and fading. Patient also received appropriate treatment for HIV. Molluscum lesions responded well to treatment with the botanical.

In Vitro Polyomavirus Studies

Referring now to FIG. 14, Vero cells were infected with SV40 virus at an MOI=1. Ceils were treated with *S. purpurea* extract as indicated in the captions above the photographs. At four DPI, viral induced CPE was visualized by microscopy and photographed. After assessing the ability of *S. purpurea* extracts to inhibit poxvirus replication, the inhibitory activity against other, non-related viruses, including polyoma and papillomaviruses was also examined. Since papillomaviruses cannot be used for in vitro studies, the in vitro viral infection work was done using a related virus, simian virus 40 (SV40), which belongs to the family of polyoma viruses. When cells were infected with SV40 typical cytopathic effects were observed. In cells which were infected with SV40 followed by-treatment with the *S. purpurea* extract, the cytopathic effect was inhibited (FIG. 14).

Figure 15:
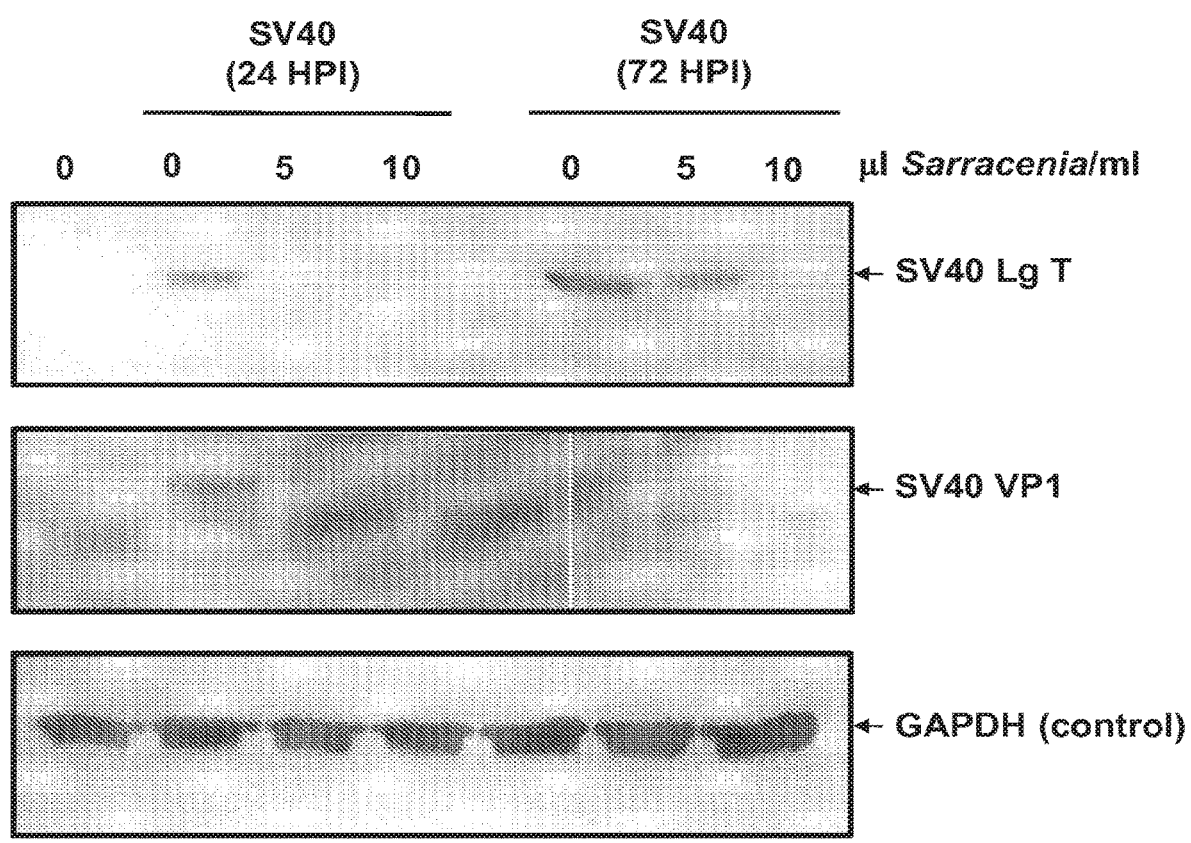
FIG. 15 illustrates an effect of a *S. purpurea* extract on polyoma virus SV40 protein accumulation.
Figure 16A:
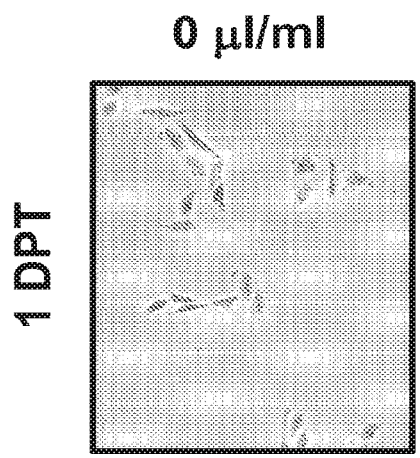
FIGS. 16A-16E illustrate an effect of a *S. purpurea* extract on cervical cancer cells.
Figure 16B:
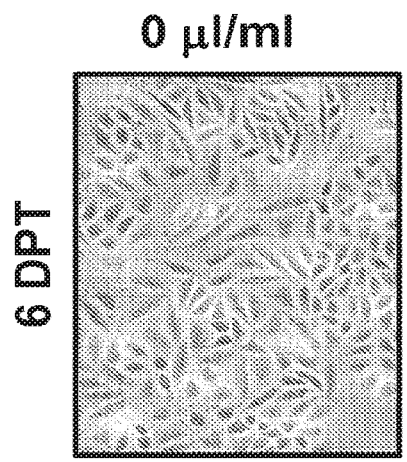
Figure 16C:
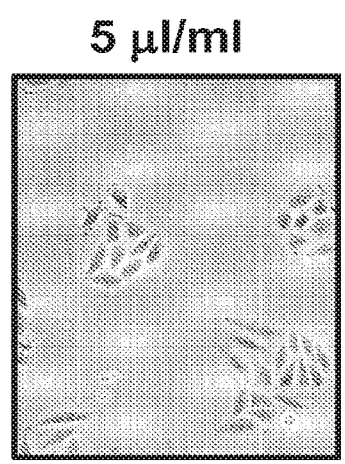
Figure 16D:
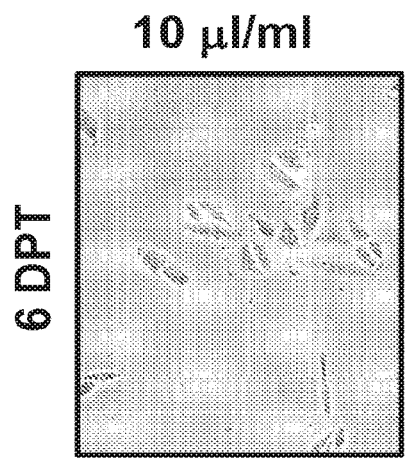
Figure 16E:
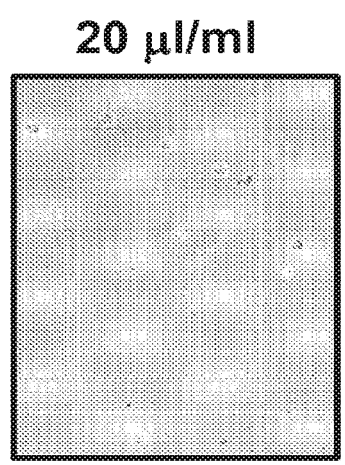
Figure 17A:
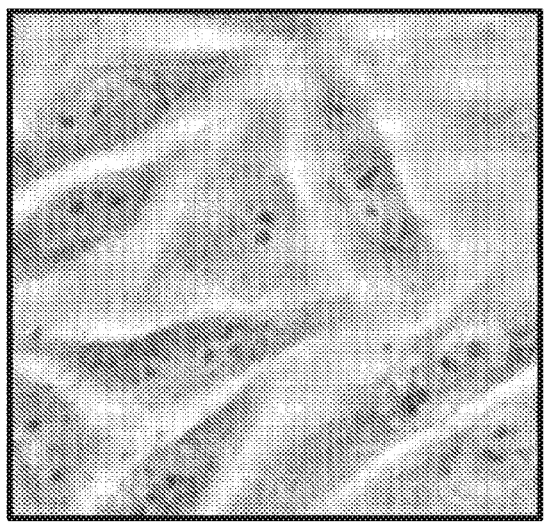
FIGS. 17A-17D illustrates an effect of a *S. purpurea* extract on cervical cancer cells at higher magnification.
Figure 17B:
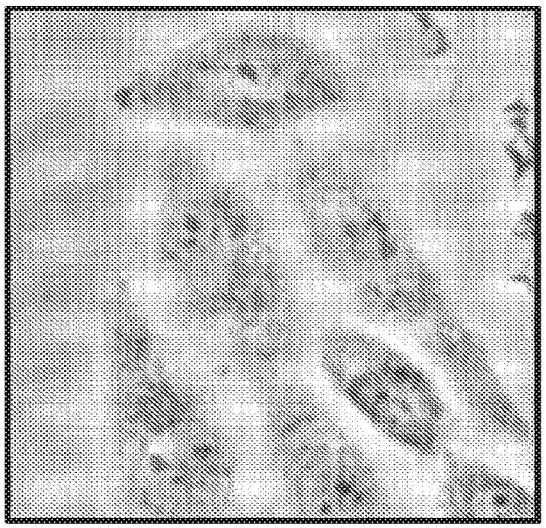
Figure 17C:
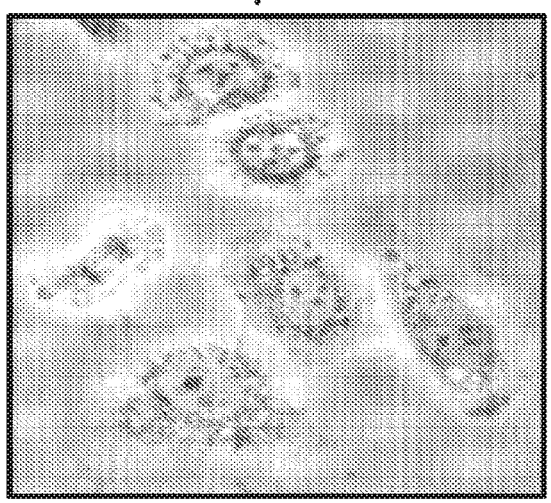
Figure 17D:
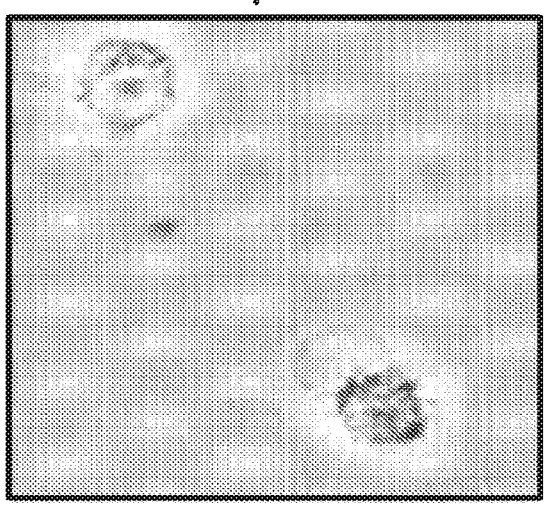
Figure 18A:
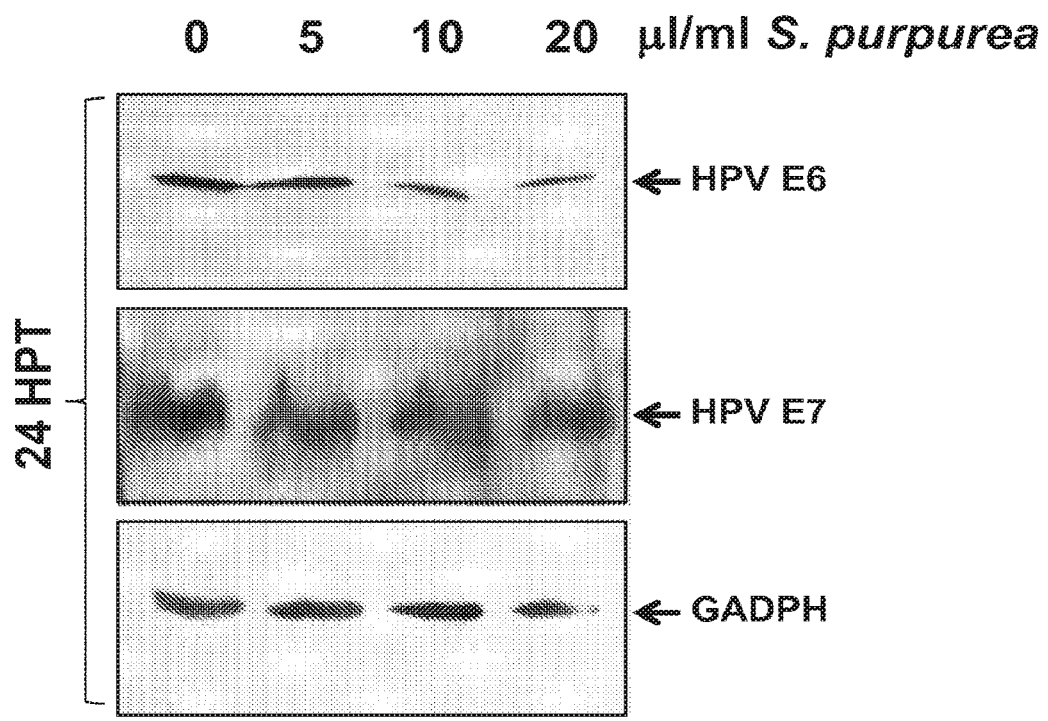
FIGS. 18A and 18B illustrate an effect of a *S. purpurea* extract on HPV protein expression in cervical cancer cells.
Figure 18B:
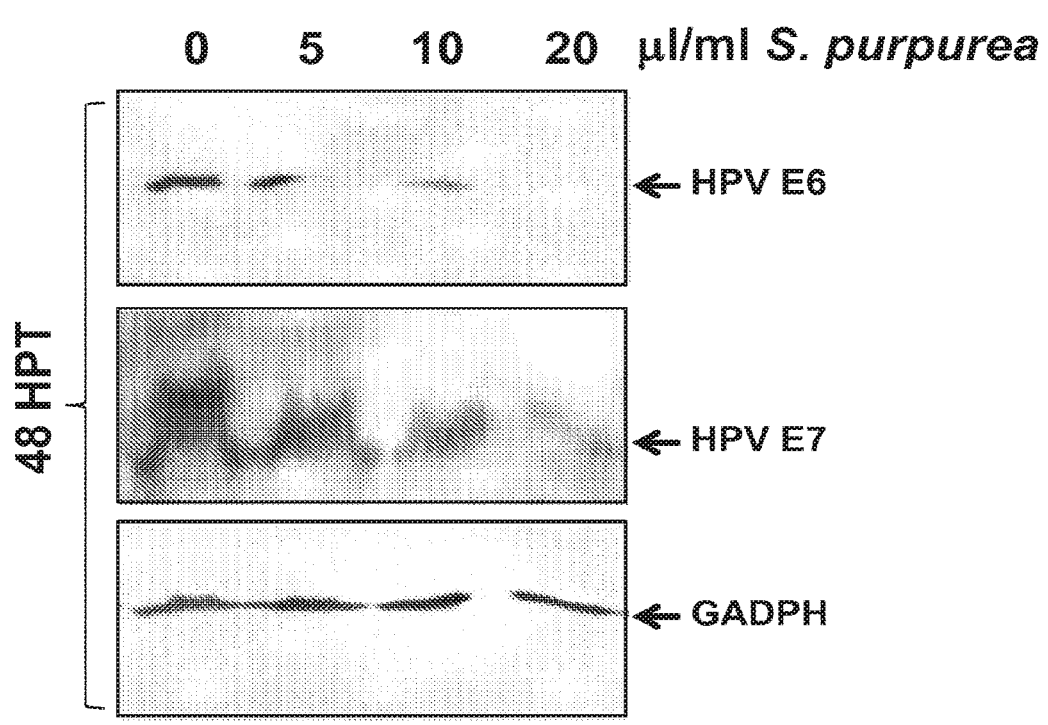
Figure 19A:
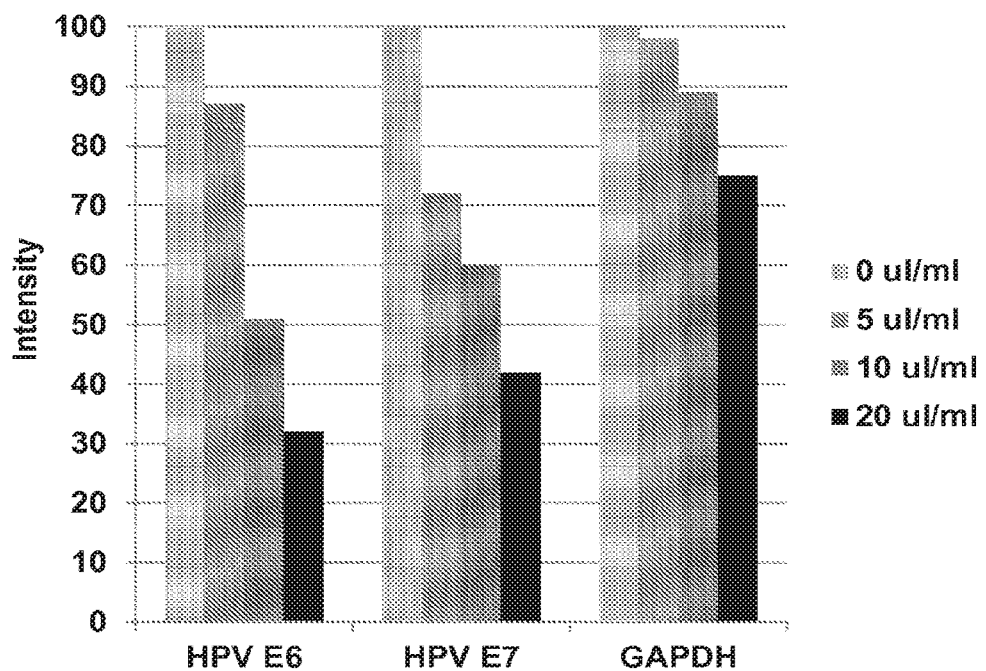
FIGS. 19A and 19B illustrate an effect of a *S. purpurea* extract on HPV protein expression in cervical cancer cells.
Figure 19B:
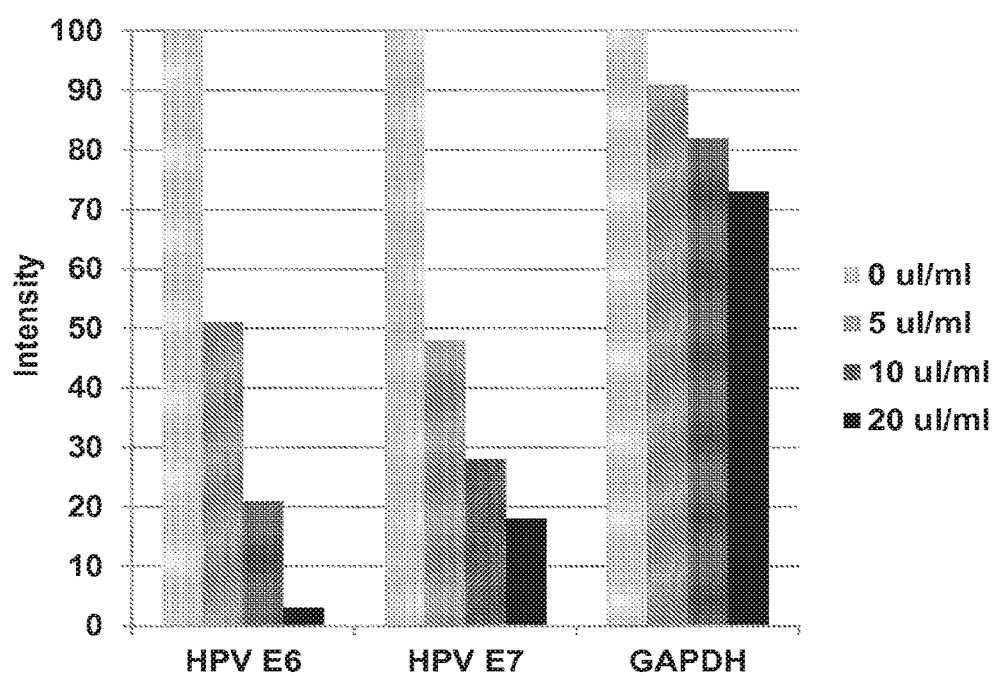

To confirm this effect as a block in virus replication, Western blot was performed to detect the synthesis of viral proteins, as shown now in FIG. 15. Vero cells were infected with SV40 at an MOI=1. Cells were treated with varying concentrations of *S. purpurea* extract as indicated. At 24 and 72 HPI, cell lysates were prepared and levels of viral protein accumulation measured by Western Blot analysis. Viral antisera included SV40 LargeT and VP1. Antiserum to GAPDH was used as a control.

The accumulation of SV40 LgT and VP1 proteins was inhibited by treatment with *S. purpurea*, Notably, since the LgT protein is an early protein made by the virus, this data again suggests that *S. purpurea* is targeting an early event in the virus replication cycle, either viral uptake, viral transcription, or viral protein synthesis. Given the results of experiments with vaccinia virus, the likely mechanism of action is proposed to be an inhibition of viral transcription. These results suggest that *S. purpurea* extract can inhibit the replication of polyoma and likely papillomaviruses. Given this, *S. purpurea* may be an effective therapeutic for infections or cancers caused by these families of viruses.

Referring now to FIGS. 16A-16E, since *S. purpurea* extracts inhibited the accumulation of early proteins during an SV40 virus infection, the effect of *S. purpurea* extracts on cervical cancer cells was determined. SiHa (cervical cancer cell line) cells were plated into 60 mm dishes at a 1:10 confluency (day 1). Duplicate plates were treated with the concentrations of *S. purpurea* extract indicated in the figures. Six days post treatment, cells were evaluated by microscopy and photographed. SiHa cells are a cervical cancer cell line which was isolated from a patient infected with Human papilloma virus (HPV 16). These cells constitutively synthesize the viral proteins E6 and E7 which are responsible for leading to cell division and cancer. When SiHa cells were treated with increasing doses of *S. purpurea* extract, an inhibition in cell division (senescence) was observed at lower doses, and cell death (likely due to apoptosis) was observed at higher doses.

Referring now to FIGS. 17A-17D, higher magnification views of cells treated with various doses of *S. purpurea* extract and demonstrating cytoplasmic vacuole formation and 'blebbing' typically indicative of apoptosis are shown.

With reference now to FIGS. 18A-19B, cells treated with *S. purpurea* demonstrated reduced levels of HPV E6 and HPV E7 protein synthesis. FIGS. 18A-19B illustrate western blot results for HPV E6 and E7 protein levels in SiHa cells treated with the indicated concentrations of *S. purpurea* extract at 24 and 48 hours post treatment. Cell lysates were prepared from the treated SiHa cells at the two time points indicated. Antiserum to GAPDH was used as a control.

HPV E6 protein induces cell division by stimulating ubiquitination of the cellular p53 protein, thereby promoting p53 degradation. Since HPV E6 levels decreased following *S. purpurea* treatment, the levels of p53 protein were assessed.

Figure 20A:
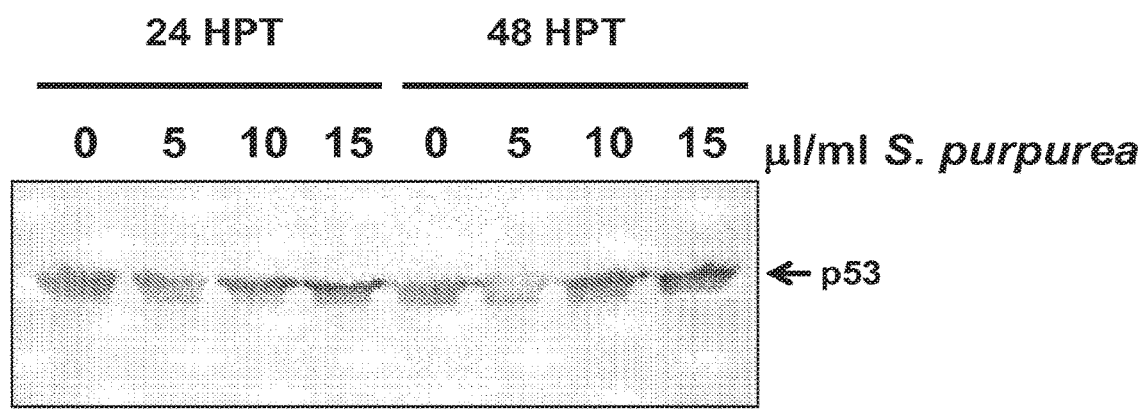
FIGS. 20A and 20B illustrate an effect of a *S. purpurea* extract on cellular p53 protein expression in cervical cancer cells.
Figure 20B:
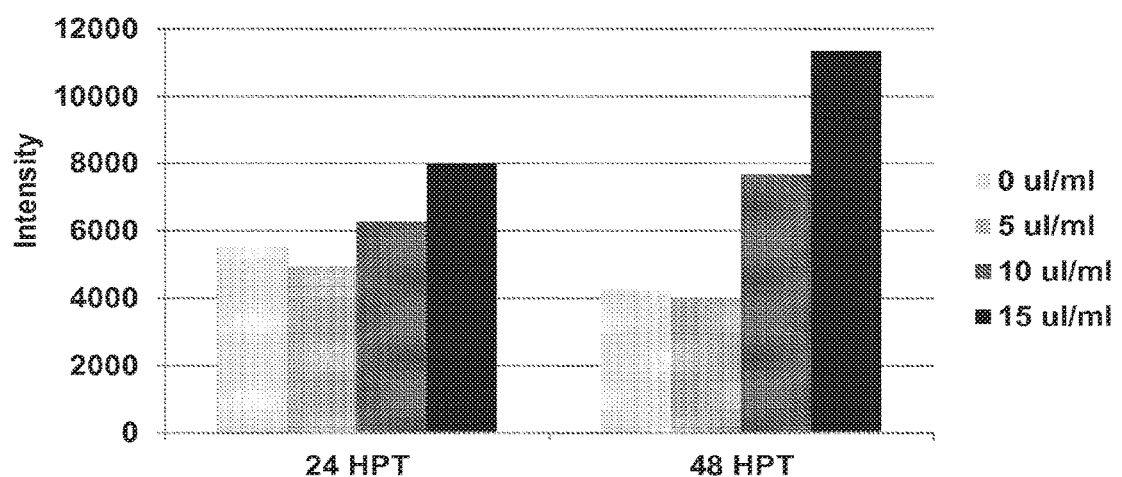

Referring now to FIGS. 20A and 20B, treatment of SiHa cells with *S. purpurea* led to increased levels of p53 protein at 24 and 48 hours post treatment SiHa cells were treated with the concentrations of *S. purpurea* extract indicated. At 24 and 48 hours post treatment, cell lysates were prepared. Cellular p53 protein levels were evaluated by western blot analysis. The results of the western blot were quantified by ImageQuant analysis (FIG. 20B) to measure the relative pixel intensity of the detected protein. These results support that *S. purpurea* may act by reducing HPV E6 (and E7) levels, leading to a recovery in cellular p53 levels and a subsequent inhibition in cell division and induction of apoptosis.

Figure 21:
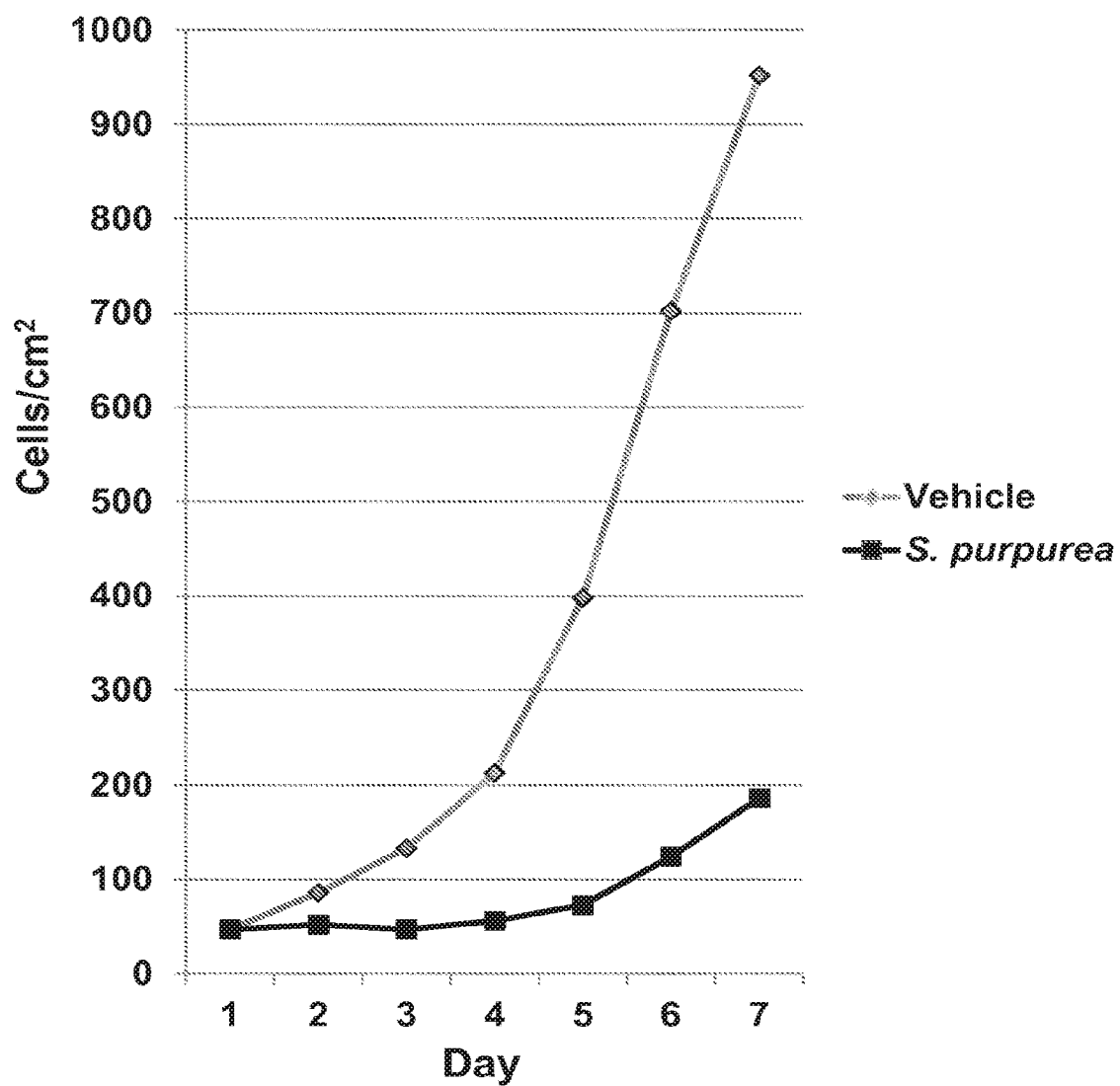
FIG. 21 illustrates an effect of a *S. purpurea* extract on cervical cancer cell replication.

With reference now to FIG. 21, in order to quantitate an effect of *S. purpurea* on cellular senescence, cell division was monitored for SiHa cell treated with a low dose of *S. purpurea* extract. SiHa cells were plated into 60 mm dishes at a 1:10 confluency. Cells were left untreated or treated with 5 µl/ml *S. purpurea* extract Medium containing 5 µl/ml *S. purpurea* extract was replaced daily for the *S. purpurea* treated cells. Every 24 hours, cells were harvested and counted using a hemocytometer. Cell numbers were monitored for a period of 7 days. As shown in FIG. 21, *S. purpurea* treatment significantly inhibited cell division compared to vehicle treated cells. These results together suggest that *S. purpurea* extract inhibits the synthesis of HPV E6 and E7 proteins which likely leads to the induction of cellular senescence and apoptosis. These results support the possible therapeutic value of *S. purpurea* extracts for treatment of HPV-induced cervical cancer.

Clinical Papillomavirus Studies

Since papillomaviruses cannot be used for in vitro studies, but represent a significant human pathogen, clinical studies were performed using a few patients infected with human papillomaviruses. To date, limited number of patients infected with genital HPV (HPV 16/18) and HPV-associated plantar warts have been treated topically with the 20% *S. purpurea* Gel. Patients treated demonstrated positive results following treatment with 20% *S. purpurea* Gel. For genital HPV infections, 20% *S. purpurea* Gel was applied topically as the aforementioned gel as well as in suppository form (containing Supposiblend® (Gallipot®), from Fagron, St. Paul, Minn., Silica Gel Micronized NF® (Letco Medical, Decatur, Ala.) and the *S. purpurea* extract). For plantar warts, success rates were improved if the outer epidermal layer was initially removed with freezing followed by application of the *S. purpurea* gel. These results together support an extract of *S. purpurea* as being a potential treatment and therapy for the infections related to papilloma and likely, polyomavirus infections.

HPV is accepted as being the causative agent for nearly all cases of cervical cancer. The development of cervical dysplasia is the development of precancerous changes to the cells lining the cervix. In addition, HPV is associated with other epithelial cancers of the anus and oral cavity. Finally, HPV has been suggested to be involved in the development of actinic keratosis and squamous cell carcinoma of the epidermis.

(HPV possible): Patient is a 62 year old male diagnosed with squamous cell carcinoma of the tongue. Patient reports having had intense jaw pain and was on multiple antibiotics. Shortly thereafter, patient found a lump in the throat. Biopsy was performed confirming squamous cell carcinoma. At that time, the physician recommended surgery but the lump was considered inoperable by the surgeon. At the time of initial intake, patient was losing weight due to not being able to eat any solid foods, and not being able to swallow due to the pain coming from the tumor. On physical examination there was a right-sided, erythematous lesion on the base of the tongue. Pain was rated at an 8/10. Patient was treated with a therapeutic composition comprising *S. purpurea* liquid (50%) with an equal part transdermal driver gel (50%). Driver was equal parts pleuronic gel and VERSABASE gel. This formulation applied directly by patient to the tumor four times daily was incorporated as a part of an integrative treatment protocol. After four days of treatment, palpable decrease in tumor diameter. After one week, patient reported no pain. After 10 days, tumor was reported to be softening up to the touch. After 1 month, tumor significantly reduced in size. After 3 months, tumor was no longer detectable and had become scar tissue.

(HPV possible): Patient is a 71 year old male diagnosed with squamous cell carcinoma of the larynx. Squamous cell carcinoma of larynx diagnosed in 2010. Patient treated with radiation therapy at that time. Patient was in remission until a year later when it returned. Patient states that he progressively lost his voice throughout this process and is now seeking integrative cancer care. Upon physical exam, larynx was visibly and palpably enlarged at time of initial examination. Patient was treated with a therapeutic composition comprising S. purpurea liquid (50%) with an equal part transdermal driver gel (50%). The driver was equal parts pleuronic gel and VERSABASE gel This formulation was applied directly by the patient to the outer surface of the neck in the region of the larynx as well as gargled four times daily. This regimen was incorporated as a part of an integrative treatment protocol. Within a few days, patient reported increased ability to talk with a more audible and discernible voice. Within 1 week, he was able to speak for most of the day without having to rest his voice as often, and reported that his voice sounded clearer and more people were able to understand him without him having to force his vocal cords. Within 3-4 weeks at the time of discharge, patient was reporting increased energy, speaking audibly and mild hoarseness. Indications of squamous cell carcinoma were non-detectable.

(HPV likely): Patient is a 61 year old female diagnosed with squamous cell carcinoma of the anus. Upon initial examination, patient reported that she noticed some growth on the outside of her anus. Upon examination, an external anal mass measuring 14.5×14.5 cm was observed. The mass was freely mobile and soft on palpation. An anal fissure was appreciated at the 12:00 position about 2-3 mm deep and 3 mm wide. Patient reported at the time of exam that the mass was previously very hard and immobile. Patient was treated with a therapeutic composition comprising S. purpurea liquid (50%) with an equal part transdermal driver gel (50%). The driver was equal parts pleuronic gel and VERSABASE gel. This formulation was applied directly by patient to the tumor via a rectal implant 2-times daily. A 60 cc TERUMO® syringe (Terumo Medical Corporation, Somerset, N.J.) with a round Robinson catheter was utilized for the application. This regimen was incorporated as a part of an integrative treatment protocol. Within one week of treatment, patient reported decreased size of the mass that was palpable by self, and also experienced decreased anal bleeding and absence of pain. Patient also reported that mucous-like stringy filaments were being released with bow el movements and during colon hydrotherapy. A sample was sent for cytology and came back as mucous only. By the time patient was discharged for part time status due to personal reasons, she reported no pain, ease of insertion of speculum during colonic irrigation, regular, w ell formed bow el movements and no pain or bleeding.

(HPV dysplasia): Patient is 34 year old white, female. She tested positive for HPV and cervical dysplasia three years prior. Colposcopy was done and patient was put on a 'watch and wait' with follow-ups scheduled. Upon re-exam, patient was positive for dysplasia (CIN1). Patient was treated with a therapeutic composition comprising S. purpurea liquid (50%) with an equal part transdermal driver gel (50%) applied once a week to the face of the cervix with the assistance of her doctor as well as self-application digitally to her vaginal wall twice daily for 4 wks. At this time, she continued with application of treatment to the face of the cervix by her doctor once a week for two more weeks and self-administration of a suppository containing the treatment daily for two additional weeks. After a period of one month, patient was re-examined. Examination results were negative for HPV and ASCUS.

(HPV warts and molluscum): Patient was a 3 year old, male diagnosed with 30+ plantar warts, common warts, seeded warts on hands, face, knee, and elbow. Patient was diagnosed with HPV and Molluscum Contagiosum by pediatrician and dermatologist. Previous treatments were unsuccessful. Dermatologist applied salicylic acid to HPV and Molluscum Contagiosum once a week for 3 weeks, in addition, patient applied a therapeutic composition comprising S. purpurea (30%) in VERSABASE gel (70%) nightly with bandage. After three weeks of treatment, warts and molluscum contagiosum lesions are non-visible. On subsequent follow-up examinations patient has no lesions.

(HPV warts): Patient was a 28 year old female diagnosed with a large (1.5 cm) Verruca plantaris (plantar wart) by a dermatologist. Surgical removal was suggested but adjunctive usage of a therapeutic composition comprising S. purpurea (30%) in VERSABASE gel (70%) was requested by the patient. Her dermatologist performed one cryogenic treatment and patient applied the therapeutic composition twice daily with a bandage. Patient reported pain relief associated with application of the therapeutic composition. After 2 months, wart completely resolved and has not returned.

(HPV genital warts): Patient diagnosed HIV disease and significant HPV warts on vaginal vulvae, especially on left side. Pap smear history was unknown. Patient was treated with a therapeutic composition comprising S. purpurea (30%) in VERSABASE gel (70%). Warts were successfully treated with botanical gel.

(HPV): Patient diagnosed with HIV. Patient had a single HPV wart on the anal verge. Patient was treated with a therapeutic composition comprising S. purpurea (30%) in VERSABASE gel (70%). Treatment successfully eradicated the wart. Post-treatment, the wart started to reappear. Treatment was restarted for the next month. Wart was eliminated and has not returned Actinic keratotis (HPV possible): Patient was a 42 year old female diagnosed with actinic keratosis lesion on left side of face. Patient scheduled for surgical removal of the lesion 10 days after diagnosis. While awaiting surgery, patient applied a therapeutic composition comprising S. purpurea (30%) in VERSABASE gel (70%) four times daily to the lesion. After seven days of treatment, lesion was non-visible. Patient subsequently cancelled surgery. initial studies have been conducted to characterize potential anti-carcinogenic activity associated with extracts of S. purpurea. In vitro data supports anticancer activity associated with S. purpurea with the SiHa cervical cancer cells. In patients with diagnosed cancerous or pre-cancerous lesions, treatment with the S. purpurea gel has demonstrated positive results. As described above, S. purpurea gel has been shown effective in the treatment of HPV associated cervical dysplasia and warts. In addition, several patients diagnosed with squamous cell carcinoma following treatment with the S. purpurea gel (applied for 1 week to 2 months depending on severity) had typical positive results included clearing of the lesions and biopsy negative diagnoses. In addition, several patients diagnosed with a pre-cancerous actinic keratosis lesion following treatment with S. purpurea gel resulted in complete clearance of the lesion typically within 1-2 weeks of application. We have also used S. purpurea gel in the treatment of HPV and Epstein-Barr associated oral-pharyngeal carcinomas. External topical or topical within the oral cavity has reduced the size of solid mass tumors present in several patients. These results suggest that an extract from S. purpurea has potential anti-carcinogenic activity.

Possible Active Constituents)

Figure 23A:
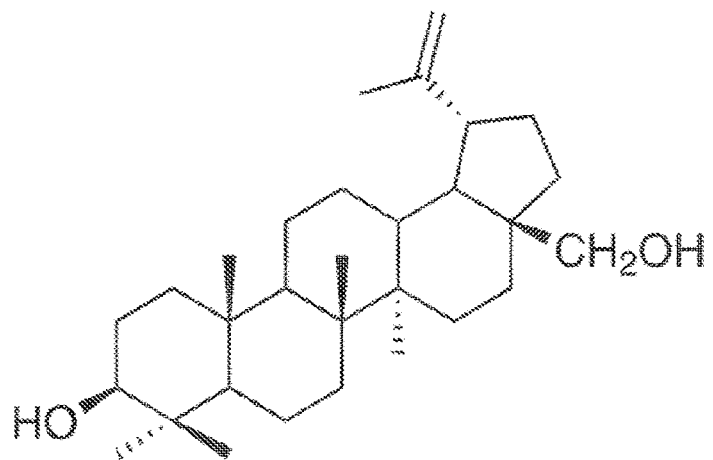
FIGS. 23A-23C illustrate structures of betulin and betulin derivatives.
Figure 23B:
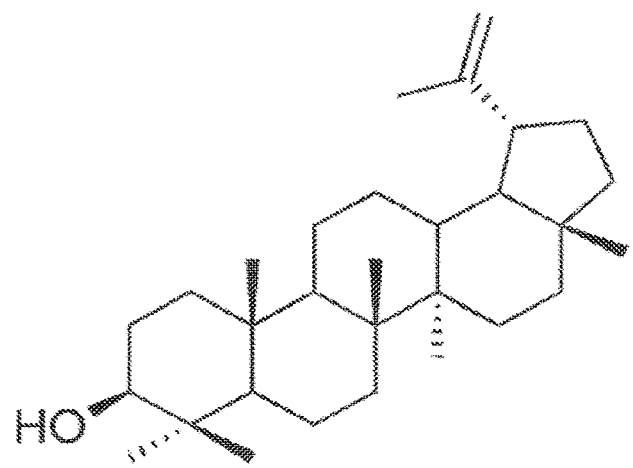
Figure 23C:
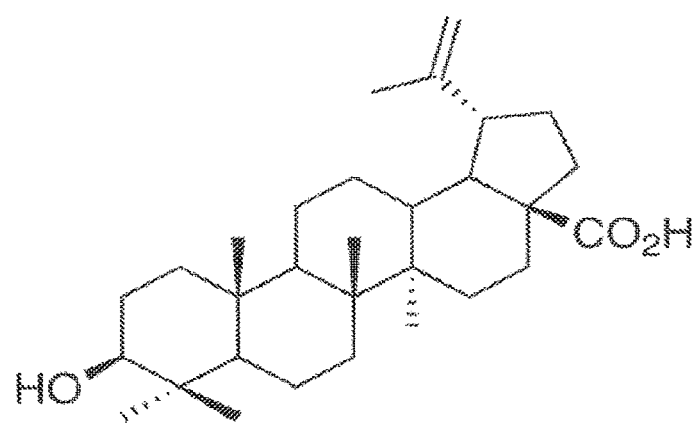
Figure 24A:
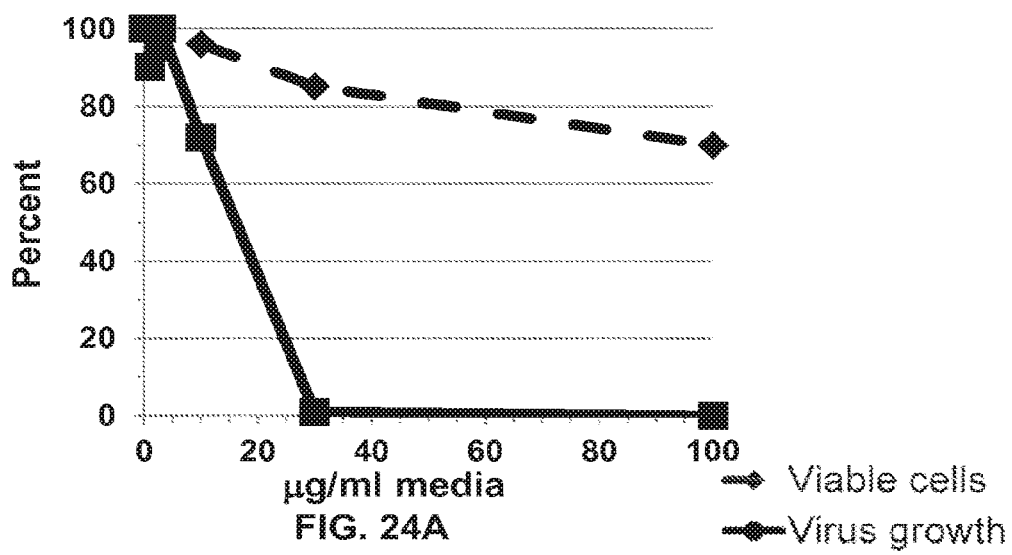
FIGS. 24A-24C illustrate antiviral activity associated with betulin and betulin derivatives.
Figure 24B:
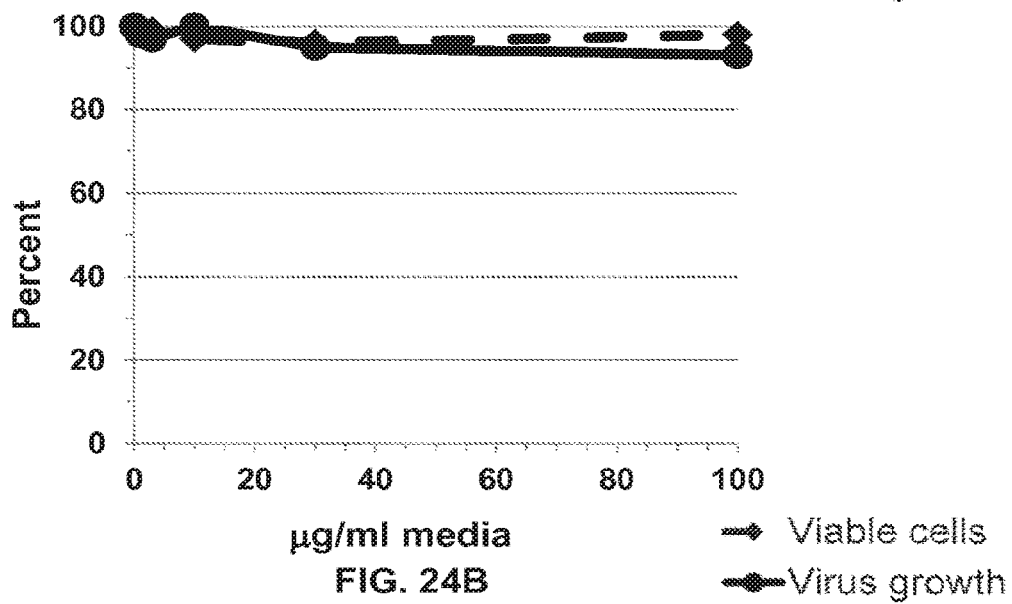
Figure 24C:
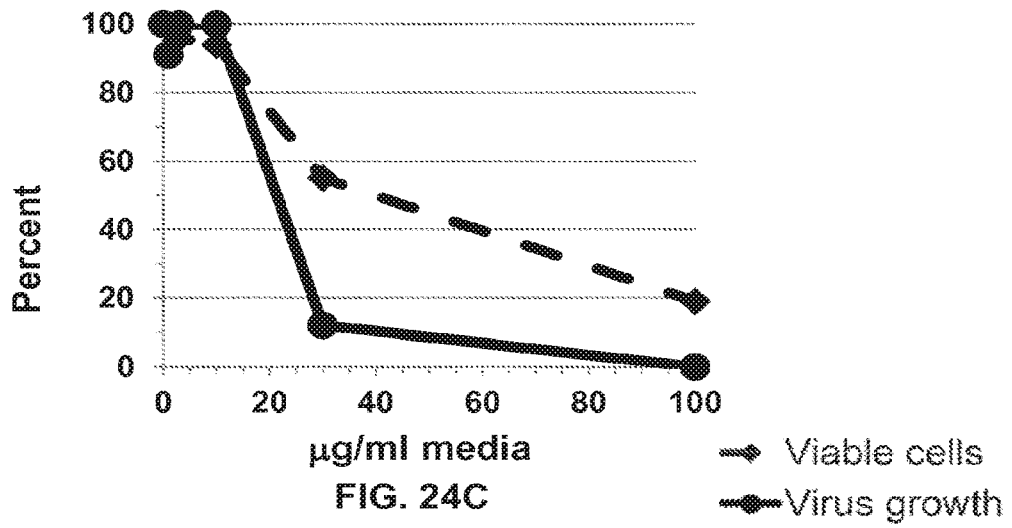

Referring now to FIGS. 23A-23C, tests with purified betulin support similar antiviral activity compared to S. purpurea extracts. Hela cells were infected with 100 pfu VACV in the presence of increasing concentrations of purified betulin, lupeol or betulinic acid. The structures of betulin, lupeol and betulinic acid are shown in FIGS. 23A, 23B, and 23C, respectively. At 48 HPI, cells were stained with crystal violet and the number of plaques formed counted. Duplicate plates were left uninfected but treated with the same concentrations of betulin, lupeol, or betulinic acid. Cell viability was evaluated 24 hours post treatment by trypan blue exclusion. Results of the antiviral activity and cell viability assays are illustrated in FIGS. 24A-24C. Related compounds, lupeol and betulinic acid did not show suitable antiviral activity. These results may suggest betulin as at least one antiviral constituent present in Sarracenia spp.

Biological Assays

Figure 25A:
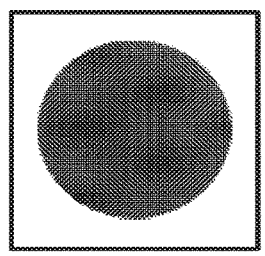
FIGS. 25A-25C illustrate antiviral activity screening results for botanical extracts.
Figure 25B:
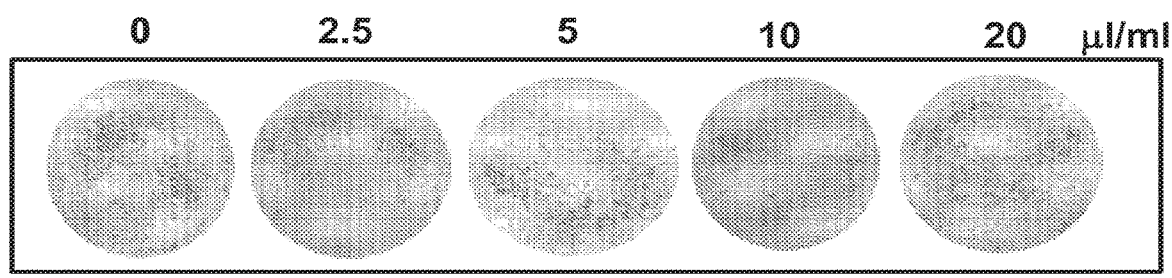
Figure 25C:
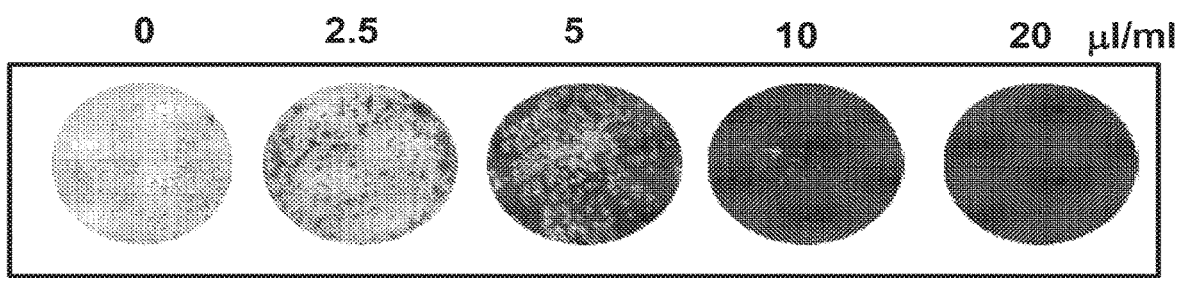
Figure 26A:
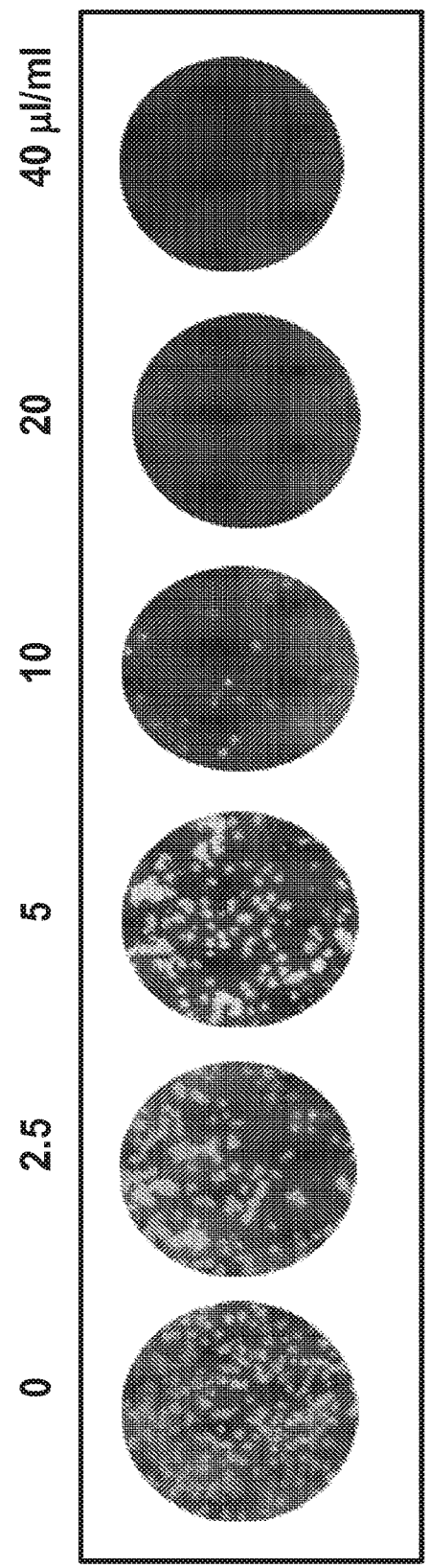
FIGS. 26A and 26B illustrate antiviral activity screening results for botanical extracts.
Figure 26B:
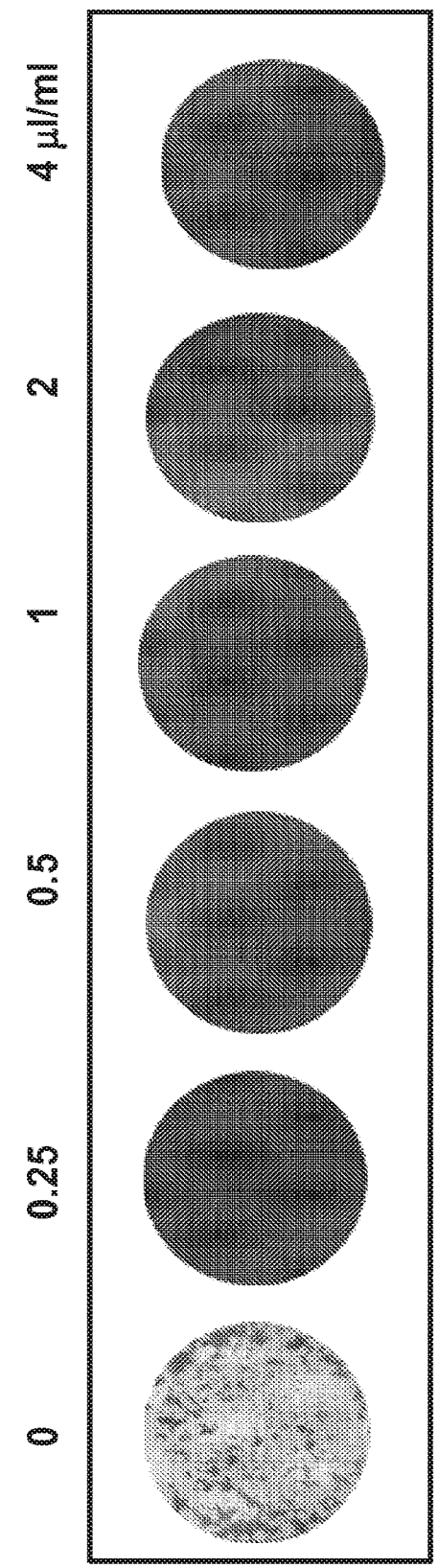

Referring now to FIGS. 25A-62B, further work was done to develop a screening methodology to identify additional botanical-based extracts with efficacy against viruses, in particular herpes viruses. FIGS. 25A-25C illustrate the results of an experiment in which Vero cells were infected with 300 pfu HSV1, followed by treatment with increasing concentrations of a botanical extract to be evaluated. At four DPI, cells were stained with crystal violet to visualize plaque/CPE. Control plates were left uninfected (FIG. 25A), while treatment plates were treated with increasing dose amounts of eithera non-effective botanical extract or an effective botanical extract. 24 hours later, cell viability determined by trypan blue exclusion (data not shown). As shown, non-effective botanical extracts (FIG. 25B) do not inhibit plaque/CPE formation by the virus. Effective botanicals (FIG. 25C) inhibit viral replication in a dose dependent manner which can be quantified and scored. Comparable effects on viability can also be scored (not shown). In FIGS. 26A and 26B, using the method described above with respect to FIG. 25, additional botanical extracts showing moderate antiviral activity (FIG. 26A) and high antiviral activity (FIG. 26B) were further evaluated quantitatively and qualitatively by measuring the effect of the botanical extract on plaque formation, plaque numbers and cell toxicity (not shown). Botanical extracts can be scored and ranked accordingly as non-effective, moderately effective, highly effective or various values in between.

These botanical screens identified five (5) additional botanical extracts with antiviral activity against HSV1. Botanical extracts from Melissa officinalis, Lavandula officinalis, Glycyrrhiza glabra, Eleutherococcus senticosus and Hypericum perforatum were blended with S. purpurea, The resulting botanical extract composition created a formulation capable of inhibiting herpes virus replication and demonstrating effective therapeutic value in the treatment of alpha herpes virus infections in patients, including HSV1 associated herpes labialis ('cold sores'), HSV2 genital infections, and varicella-zoster virus associated shingles. In addition, this composition demonstrated analgesic (anti-pain) and antipruritic (anti-itch) properties toward the relief of discomfort associated with these conditions.

Figure 27:
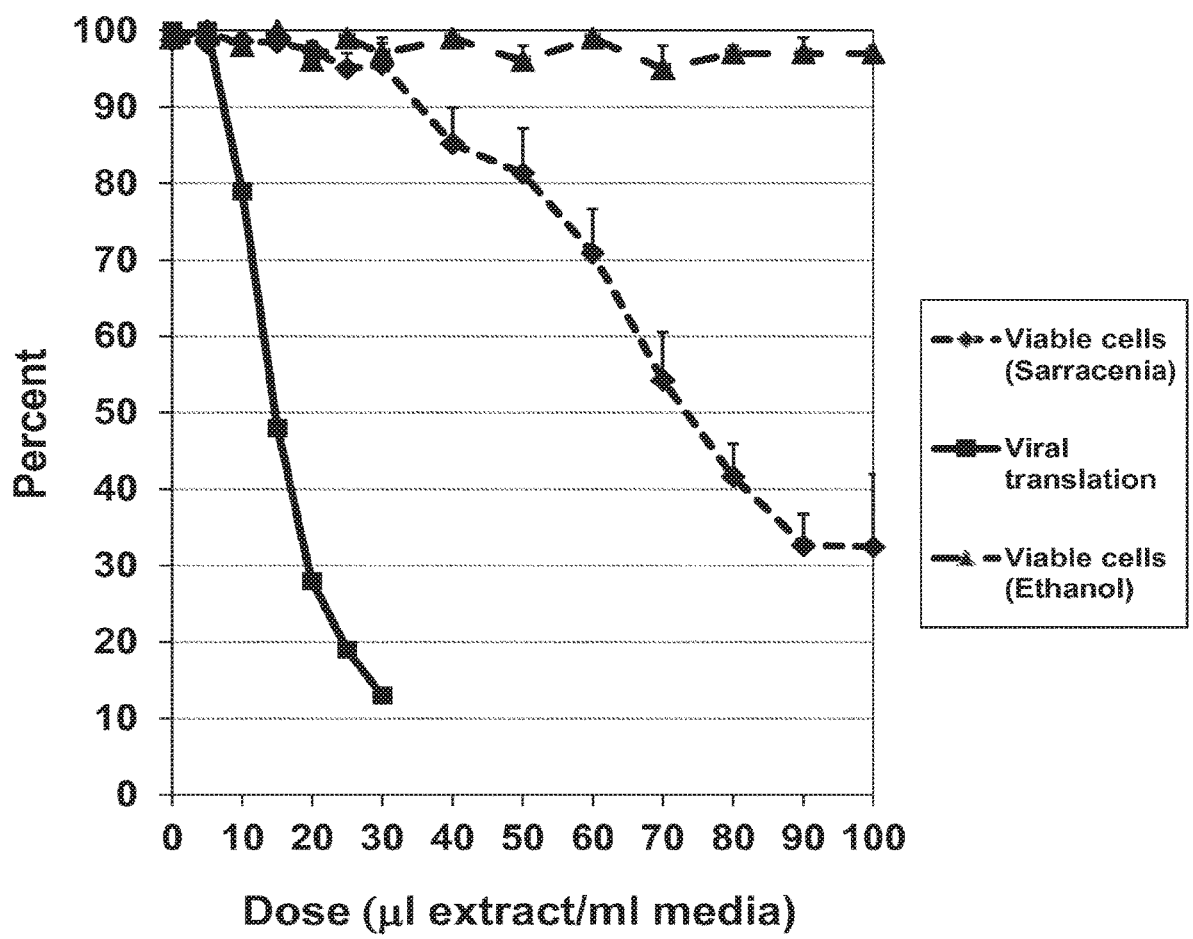
FIG. 27 illustrates a specificity of a *S. purpurea* extract antiviral activity.
Figure 28:
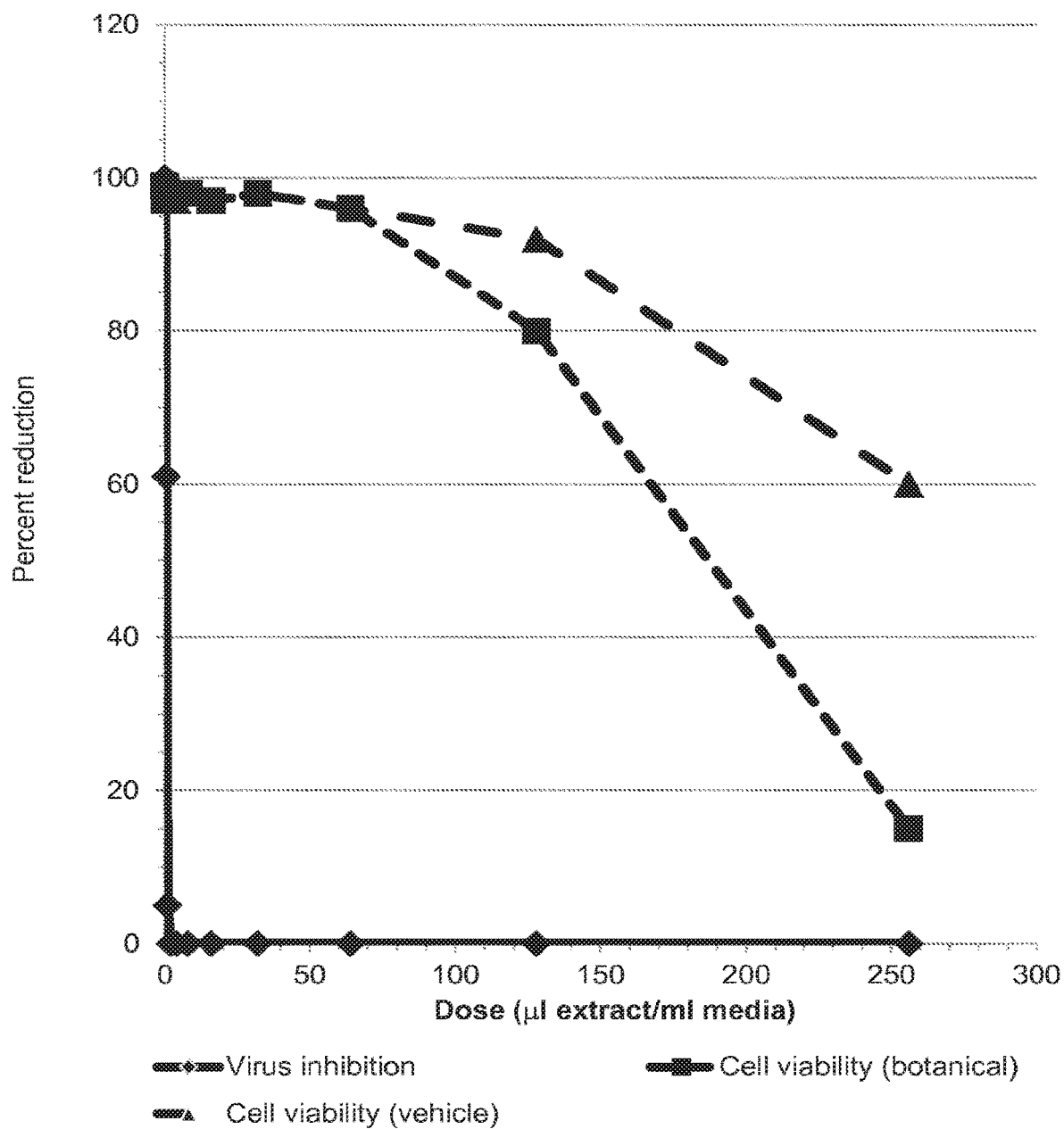
FIG. 28 illustrates a specificity of a *M. officinalis* extract antiviral activity.

Cell monolayers of Vero cells were seeded the day prior to infection to be at 90% confluency the following day. HSV1 (KOS strain) was serially diluted to a final concentration of 200 plaque forming units/100 µl. Botanical extracts to be tested for antiviral activity were filtered through a 0.2 µm syringe filter (to remove microbial contaminants), evaporated under vacuum to remove excess ethanol and the centrifuged to remove any precipitates. Viral solutions were pre-treated with increasing concentrations of the individual extracts for 20 min and then the Vero cell monolayers were infected with these treated samples for 30 min. Growth media was then added to the cell dishes and additional botanical extract added to the media at the appropriate concentration (for which the viral solutions were treated). The cells were incubated at 37° C. for 48 hours and then stained with crystal violet to visualize plaque formation. Plaques were counted and viral inhibitory units (VIU)/ml calculated (1 VIU equals the concentration of the extract required to inhibit viral replication by 50%). In parallel, Vero cell monolayers were left uninfected, but treated with increasing concentrations of the botanical extracts. Twenty-four hours later, cell viability was determined by standard trypan blue exclusion procedures. From this, the cell cytotoxic concentration could be determined (CC50 equals the concentration of the extract required to kill 50% of the cell population). Based on the VTU and CC50 values, the specificity index of each botanical extract could be determined. Botanical extracts could be identified which had no, moderate or high antiviral activity (FIGS. 27-29).

From the botanical screening procedure, six extracts with anti-HSV1 activity were identified, including Sarracenia purpurea, Melissa officinalis, Lavandula officinalis, Glycyrrhiza glabra, Eleutherococcus senticosus and Hypericum perforatum. As shown in FIGS. 27-29, these botanicals demonstrated antiviral activity towards HSV1 and comparably low cell cytotoxicity. In FIG. 2.7, the specificity of S. purpurea effect on viral replication in comparison to cell toxicity is illustrated. For viral replication, viral translation levels (closed squares) were measured. HeLa cells were infected with VACV at an MOI=10 followed by the addition of the indicated concentrations of S. purpurea extract/ml media. At 6 HPI, cell lysates were prepared, the VACV E3L protein detected by Western blot, and quantified. For cell viability, HeLa cells were treated with the indicated concentrations of S. purpurea extract (closed squares) or ethanol/glycerol carrier (closed triangles) for 6 hours and the number of viable cells determined by a trypan blue exclusion assay. In FIG. 28, the specificity of M. officinalis extract on viral replication in comparison to cell toxicity was evaluated. For viral replication, Vero cells were infected with 100 pfu HSV1 followed by the addition of the indicated concentrations of M. officinalis extract/ml media. At 4 DPI, cells were stained with crystal violet and plaques counted. For cell viability, Vero cells were treated with the indicated concentrations of M. officinalis extract or ethanol/glycerol carrier for 24 hours and the number of viable cells determined by a trypan blue exclusion assay. In FIGS. 29A-29D, the method described in FIG. 2.7 was used to evaluate the specificity of G. glabra (FIG. 29A), L. officinalis (FIG. 29B), H. performatum (FIG. 29C) and E. senticosus (FIG. 29D) extracts relative to antiviral activity and cell toxicity.

Since human infection with alpha viruses (HSV1, HSV2 and varicella-zoster virus) typically present with lesions on the epidermis, therapeutic effects of the botanical extract composition may be improved by suspension of the aqueous extract in a gel to provide topical application and transdermal 'driving' capabilities, as described herein. For this application, a gel suspension was prepared using a 50% aqueous botanical extract composition combined with 50% VERSABASE gel.

An embodiment of a therapeutic composition used for topical treatment of herpes virus infections and comprising a botanical extract composition is shown in Table 3.

TABLE 3

Therapeutic composition of botanical extracts used for topical treatment of herpes virus infections.

| Component | Percent of composition | mls/100 mls | VIU/ml |
|---|---|---|---|
| Sarracenia purpurea | 25 | 25 | 25 |
| Melissa officinalis | 6 | 6 | 40 |
| Lavendula officinalis | 10 | 10 | 10 |
| Glycyrrhiza glabra | 2.5 | 2.5 | 20 |
| Hypericum performatum | 2.5 | 2.5 | 20 |
| Eleutherococcus senticosus | 4 | 4 | 15 |
| Versabase | 50 | 50 | |

As illustrated in Table 3, in various embodiments, a botanical extract composition may comprise 25% *Sarracenia purpurea* (25 viral inhibitory units (VIU)/ml), 6% *Melissa officinalis* (40 VIU/ml), 10% *Lavandula officinalis* (10 VIU/ml), 2.5% *Glycyrrhiza glabra* (20 VIU/ml), 2.5% *Eleutherococcus senticosus* (20 VIU/ml), and 4% *Hypericum perforatum* (15 VIU/ml). The botanical extract composition thus comprises all Species II Extracts. In various embodiments, the proportions of the extracts and base gel may be modified to the adjust biological activity or the suitability of the composition for various applications.

Individual Extract Activity Toward Alpha Herpes Viruses

The antiviral activity of each of the Species II extracts was tested for efficacy against HSV1, HSV2 and EHV1. As shown in FIGS. 30A-30F, all six extracts had antiviral activity against HSV1 and HSV2. Vero cells were infected with 100 pfu HSV1, HSV2 or EHV1 followed by the addition of increasing concentrations of the indicated botanical extracts (per mi media). At 4 DPI, cells were stained with crystal violet and plaques counted.

Most botanical extracts actually demonstrated slightly stronger activity against HSV2. For EHV1, *Sarracenia purpurea* (FIG. 30A) had strong antiviral activity; *Melissa officinalis* (FIG. 30B), *Lavandula officinalis* (FIG. 30C), *Glycyrrhiza glabra* (FIG. 30D), and *Hypericum perforatum* (FIG. 30E) all had moderate antiviral activity; and *Eleutherococcus senticosus* (FIG. 30F) had no detectable activity against EHV1. These results suggest that, individually, the botanical extracts have effective antiviral activity against the human alpha herpes viruses, including HSV1 and HSV2.

Synergistic Antiviral Activity of Combined Botanical Extracts

Figure 31A:
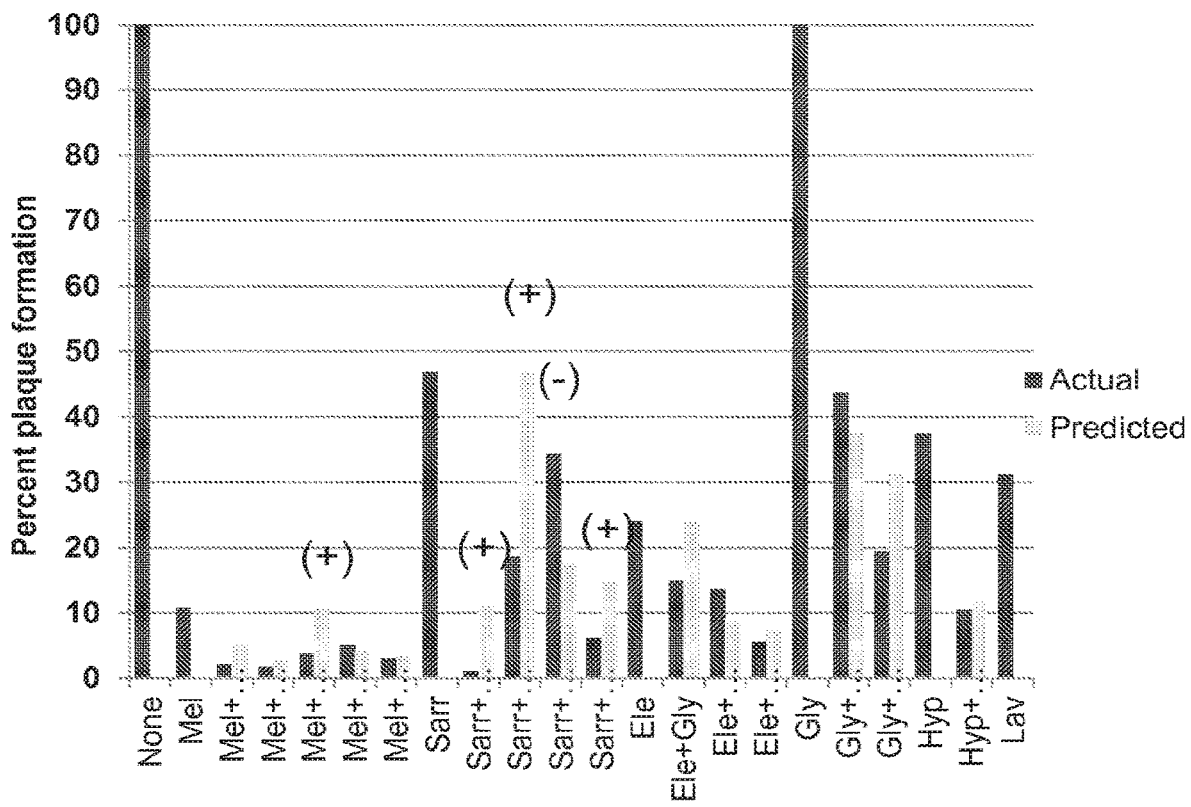
FIGS. 31A and 31B illustrate synergistic activity associated with a botanical extract.
Figure 31B:
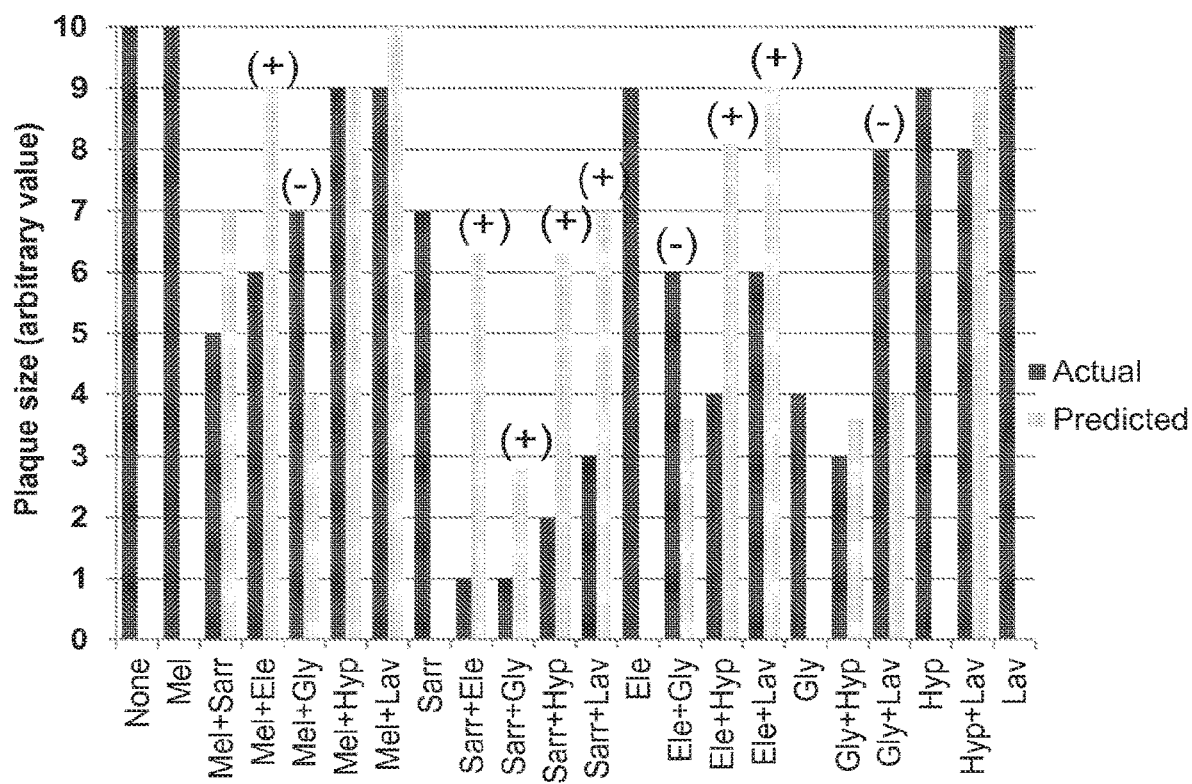

Since the Species II Extracts present in the botanical extract blend have antiviral activity in the blend as well as individually, the Species II Extracts were tested in various pairwise combinations to assess potential synergistic activity. As shown in FIGS. 31A and 31B when assessing reductions in plaque numbers by different botanical extract combinations, several combinations of botanical extracts resulted in positive synergistic antiviral effects, as shown by the (+) in the figure. For the study shown in FIGS. 31A and 31B, Vero cells were infected with 1000 pfu HSV1 followed by the addition of the indicated botanical extracts individually or various paired combinations. Doses used were at 50-75% of the 100% viral inhibitory concentration. At 4 DPI, cells were stained with crystal violet and plaques counted. FIG. 31A illustrates the data of FIG. 31B in bar graph form.

A synergistic effect exists whenever the action of a combination is greater than the sum of the activity of the individual compounds. In various embodiments, a synergistic effect exists when a combination of botanical extracts shows a greater antiviral effect than one would predict from the sum of the individual effects of the botanical extracts used in the combination. The action E to be expected for a given active ingredient combination, e.g. the combination of two botanicals, obeys the COLBY formula and can be calculated as follows (COLBY, S. R., "Calculating synergistic and antagonistic responses of herbicide combination". Weeds, Vol. 15, pages 20-22; 1967):

In the COLBY formula, X=action by active ingredient I; Y=action by active ingredient II, and E=the expected action of active ingredient I+II, and wherein $E=X+Y(XY/100)$ O is the observed action, and O/E=SF, the Synergy Factor.

If the action (O) actually observed is greater than the expected action (E), then the action of the combination is superadditive, i.e., there is a synergistic effect quantified as the Synergy Factor, SF. In this case, positive synergistic effects were observed when plaque reductions were greater then the predicted reduction values based on treatments with the individual Species II Extracts alone. As an example, if a single Species II Extract were used at a dose which inhibited viral replication by 90%, 10% of the uninhibited virus would still replicate and spread to new cells. If two Species II Extracts were combined which have additive effects and both used at a dose which inhibited 90% of viral replication, 99% of the virus would be inhibited. If however these botanicals have positive synergistic activity, inhibition is even higher. Similarly, when assessing plaque size, several botanical extract combinations provided positive synergistic effects.

As shown in FIGS. 31A and 31B, a synergistic effect was seen in particular combinations when measuring virus inhibition by plaque number. When measuring inhibition by plaque number (FIG. 31 A), 7 of the 15 pair wise botanical combinations of Species II Extracts produced additive antiviral effects. However, 7 of the 15 pairs produced synergistic effects. The pairs of botanicals showing synergistic effect included: *Melissa+Sarracena; Melissa+Glycyrrhiza; Sarracenia+Eleutherococcus; Sarracenia+Glycyrrhiza; Sarracenia+Lavandula; Eleutherococcus+Glycyrriza; Glycyrhizza+Lavandula*. As can be further seen in FIGS. 31A and 31B, when measuring virus inhibition by plaque size, 4 of the 15 Species II Extract combinations produced additive effects. However, 8 of the 15 pairs of Species II Extracts showed synergistic effect. In the plaque size experiments (FIG. 31B), the pairs showing synergistic effect included: *Melissa+Sarracenia; Melissa+Eleutherococcus; Sarracenia+Eleutherococcus; Sarracenia+Glycyrrhiza; Sarracenia+Hypericum; Sarracenia+Lavandula; Eleutherococcus+Hypericum*; and *Eleutherococcus+Lavandula*.

As shown in FIGS. 31A and 31B, a synergistic effect was seen in particular combinations when measuring virus inhibition by plaque number. When measuring inhibition by plaque number, 10 of the 15 pair wise botanical combinations of Species II Extracts produced additive antiviral effects. However, 4 of the 15 pairs produced synergistic effects. The pairs of botanicals showing synergistic effect included: *Melissa+Glycyrrhiza; Sarracenia+Eleterococ-* cus; *Sarracenia+Glycyrrhiza*; and *Sarracenia+Lavandula*. Also shown in FIGS. 31A and 31B, when measuring virus inhibition by plaque size, 5 of the 15 Species II Extract combinations produced additive effects. However, 7 of the 15 pairs of Species II Extracts showed synergistic effect. In the plaque size experiments, the pairs showing synergistic effect included: *Melissa+Eleutherococcus; Sarracenia+Eleutherococcus; Sarracenia+Glycyrrhiza; Sarracenia+Hypericum; Sarracenia+Lavandula; Eleutherococcus+Hypericum;* and *Eleutherococcus+Lavandula*.

In view of these results, other pairs of botanical extracts, and more complicated blends such as those incorporating three or more botanical extracts, may likewise show synergistic antiviral effects.

Additionally, the combination of *Sarracenia* and *Drosera* extracts was found to dramatically inhibit the replication of members of the poxvirus family. This was demonstrated in various experimental methodologies including a reduction in the viral growth level, an inhibition in the ability of the virus to form plaques, a block in viral protein synthesis, and an inhibition in viral induced cell killing. Reduction in virus yield was approximately 90% with a single treatment, Clinical Herpes Studies Limited clinical studies were conducted to test the effectiveness of a botanical extract composition as disclosed herein in treating alpha herpes virus infected individuals. Table 4 lists the number of subjects who were diagnosed with herpes family virus infections and subsequently treated with the botanical extract composition described in Table 3. Approximate success rates of therapeutic treatment are indicated.

TABLE 4

Conditions and number of patients treated

| Condition | Number of patients | Approx. success rate |
|---|---|---|
| HSV1 cold sores | >500 | 95% |
| HSV2 genital lesions | 25 | 100% |
| VZV (Shingles) | 18 | 95% |
| Epstein Barr | 2 | 100% |

For these studies, a gel-based therapeutic composition of a botanical extract composition was prepared as described herein. Since these infections presented as epidermal lesions, therapy was done topically. The gel formulation was applied directly and topically to viral-associated lesions. For HSV1, treatment was given to subjects diagnosed with herpes labialis (oral 'cold sores'). Subjects applied the Melivir gel topically every 4 hours over the course of the infection. Subjects were required to clean the lesion area prior to application of the gel and were NOT allowed to apply cosmetics or other topical gels/creams to the area. For subjects treated in the macule/erythema, vesicle or papule stage, a decrease in inflammation was typically observed within 12-18 hours and scabbing within 24-48 hours. Complete healing was observed in most subjects within 3-5 days following treatment. For subjects treated in the prodrome stage (prior to eruption of a lesion), typical results recorded an inhibition of progression of symptoms and no eruption of a visible lesion. To date, approximately 500 subjects with similar HSV1 oral lesions with similar results (over a 95% success rate compared to untreated HSV1 lesions). Notably, for most subjects that had previously reported common HSV1 outbreaks (every 1-3 months), repeated treatments with the gel formulation during subsequent outbreaks were required less frequently, with a greater time period between outbreaks.

We have also treated other herpes virus-associated infections with subjects including genital-associated HSV2 lesions (25 subjects). For genital treatment, the gel formulation was applied topically every 4 hours along with a suppository therapeutic composition comprising the same botanical extract composition. Significant healing of the infected tissue was observed within 24-48 hours with complete healing typically in 4-5 days.

Figure 41A:
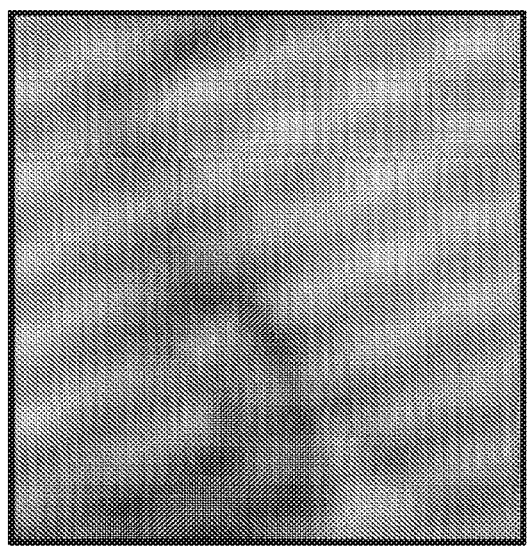
FIGS. 41A-41C illustrate effects of therapeutic treatment of VZV infected subject with a botanical extract formulation.
Figure 41B:
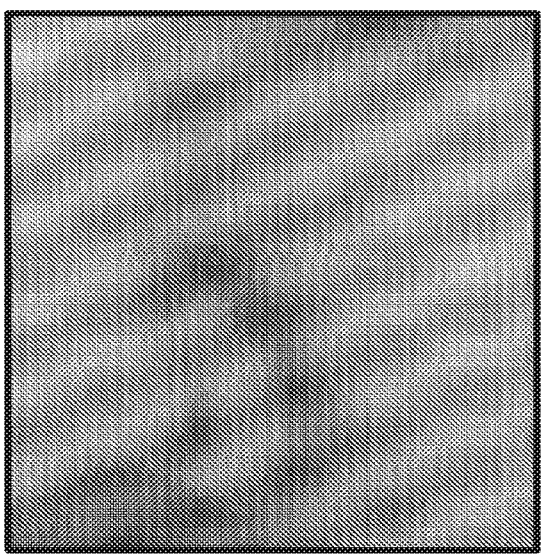
Figure 41C:
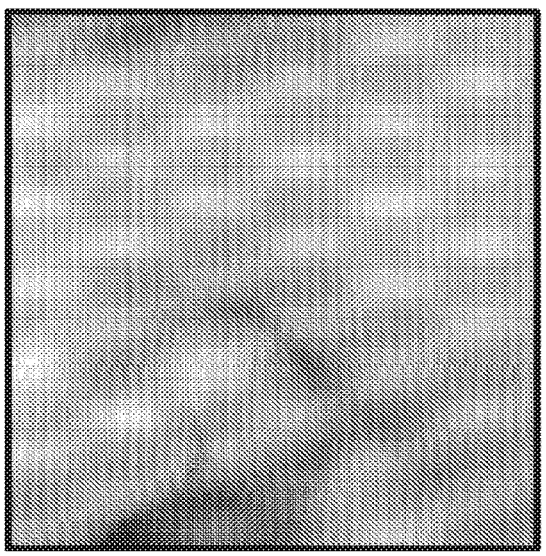

For varicella-zoster (VZV) subjects (18 subjects) presenting with shingles symptoms, the gel formulation was applied using an absorbent pad or impregnated bandage which could then be applied to the patient to cover afflicted areas. This patch allowed the gel to remain localized to the afflicted area without being removed by clothing or rubbing. Similar to HSV1 and HSV2, healing of the lesions was observed within a few days (typically 4-7 days) following application of the gel. Typical results for a VZV patient treated with the gel formulation are shown in FIGS. 41A-41C. In this study, the subject was diagnosed with a VZV lesion on the left side of nose. The subject had severe lesion with swelling, inflammation, and pain. Subject was treated with the botanical blend shown in Table 3 and monitored for healing and pain levels. The photographs illustrate the visual symptoms at days 1 (FIG. 41 A), 6 (FIG. 41B) and 9 (FIG. 41C).

Although limited to only two subjects, subjects infected with Epstein-Barr virus have also been treated. Epstein-Barr virus belongs to the herpes virus family, but is classified as a gamma herpes virus. It is the causative agent of infectious mononucleosis and other diseases. Subjects treated included a subject diagnosed with hairy leukoplakia. This presented as painful lesions along the tongue of this subject. The aqueous botanical blend (no VERSABASE gel) was administered as a mouth rinse (not to be swallowed) every 4 hours. Within 4 days of treatment, lesions had healed.

Infections with alpha herpes viruses are typically associated with pain and discomfort at the lesion sites. Following treatment of patients for HSV1, HSV2, and VZV, it was noted that virtually all patients expressed a rapid decrease in pain and discomfort associated with their lesions. This activity is likely associated with analgesic (anti-pain) and antipruritic (anti-itch) properties and component(s) present in the *S. purpurea* botanical present in the botanical extract composition. This property of *S. purpurea* has previously been reported in regards to other forms of pain. The mechanism of action regarding this analgesic property is unknown, but adds to the therapeutic value of the botanical extract composition by providing pain relief along with subsequent killing of the viral pathogen (HSV): Patient is 28 year old female whose chief complaint was herpes simplex I and/or II outbreak vaginally and orally. Patient history was positive for exposure to herpes simplex I via rape. Blood work was positive for herpes simplex I however, type II is also possible. Patient had one vaginal sore that was positive for sharp infernal pain, dull aching, and surface tenderness and complained of "tingling, burning, and itching" of labia. Patient was given a botanical extract composition (30%) in VERSABASE gel (70%) and was instructed to apply every two hours to infected areas after rinsing the area or douching with warm water. Patient reported initial "warm, tingling sensation" upon application of treatment which subsided after a "few minutes." The patient's labial symptoms subsided within one day and non-visible by the end of the third day of application.

Patient's vaginal pain subsided within two days and the sore erythema decreased each day.

(VZV): Patient was a 42 year old, male. Patient presented with lesions on left side of nose and orbital region. Patient diagnosed with herpes zoster. Patient initially prescribed acyclovir. Patient also began regime of a botanical extract composition (30%) in VERSABASE gel (70%) applied twice. Within a few hours of treatment, patient reported pain was reduced from 8/10 to 5/10. Previously patient was unable to sleep. Pain relief allowed patient to sleep. After 3 days of treatment, lesion size had reduced and pain reduced to 3/10. After 6 days, pain reduced to 1/10 and scabbing of lesions on left nostril. After nine days, lesions have completely resolved.

Results from this work clearly demonstrate that extracts from *S. purpurea* can indeed inhibit the replication of various members of the poxvirus family, including vaccinia virus, monkeypoxvirus (an emerging human pathogen), variola virus (the causative agent of smallpox) and likely molluscum contagiosum. In further characterization of the botanical extract blend, research presented herein has shown that this extract can inhibit the replication of other, non-related viruses, including members of the herpes virus family, and the papilloma and polyomavirus families. These pathogens are responsible for millions of infections every year, including cold sores, genital lesions, shingles, warts, cervical cancer, oral/throat/neck cancers, anal cancer, and may be associated with actinic keratosis and squamous cell carcinoma. In support of this, experimental results demonstrate that *S. purpurea* extracts can be used as a therapeutic for infections caused by these viruses as well as cervical dysplasia, oral, throat and neck cancers, squamous cell carcinoma and the pre-cancerous lesions associated with actinic keratosis.

Therapeutic Composition for Treatment of Cervical Dysplasia

Figure 29A:
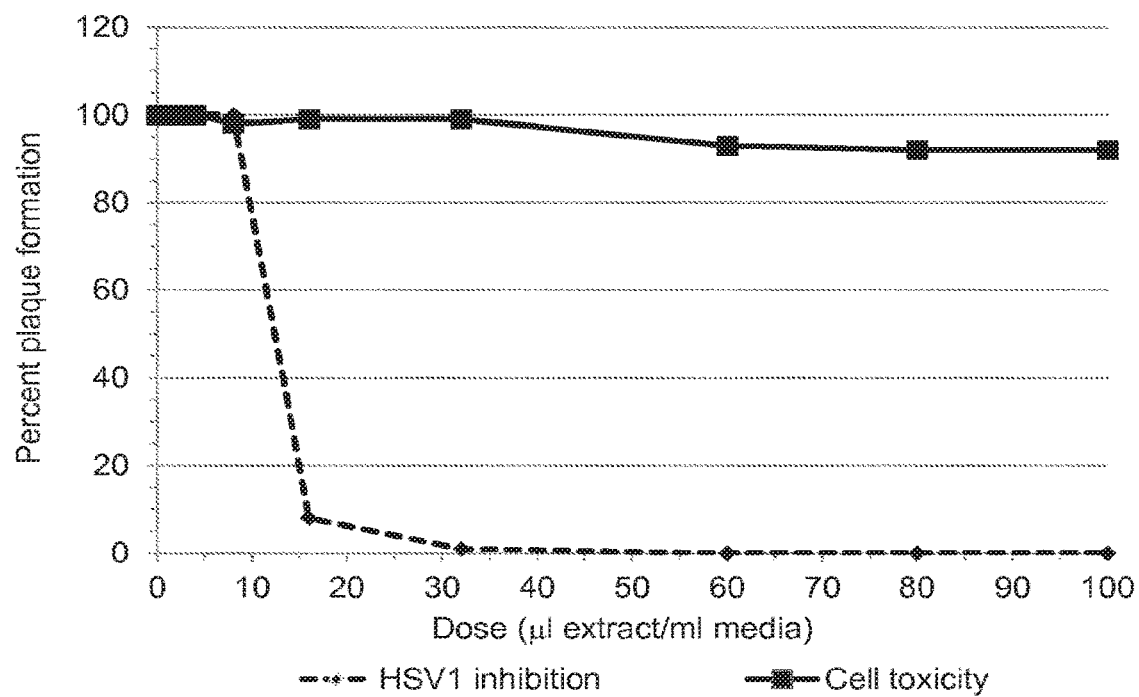
FIGS. 29A-29D illustrate a specificity of a *G. glabra, L. officinalis,* H. performatum and *E. senticosus* extract antiviral activity.
Figure 29B:
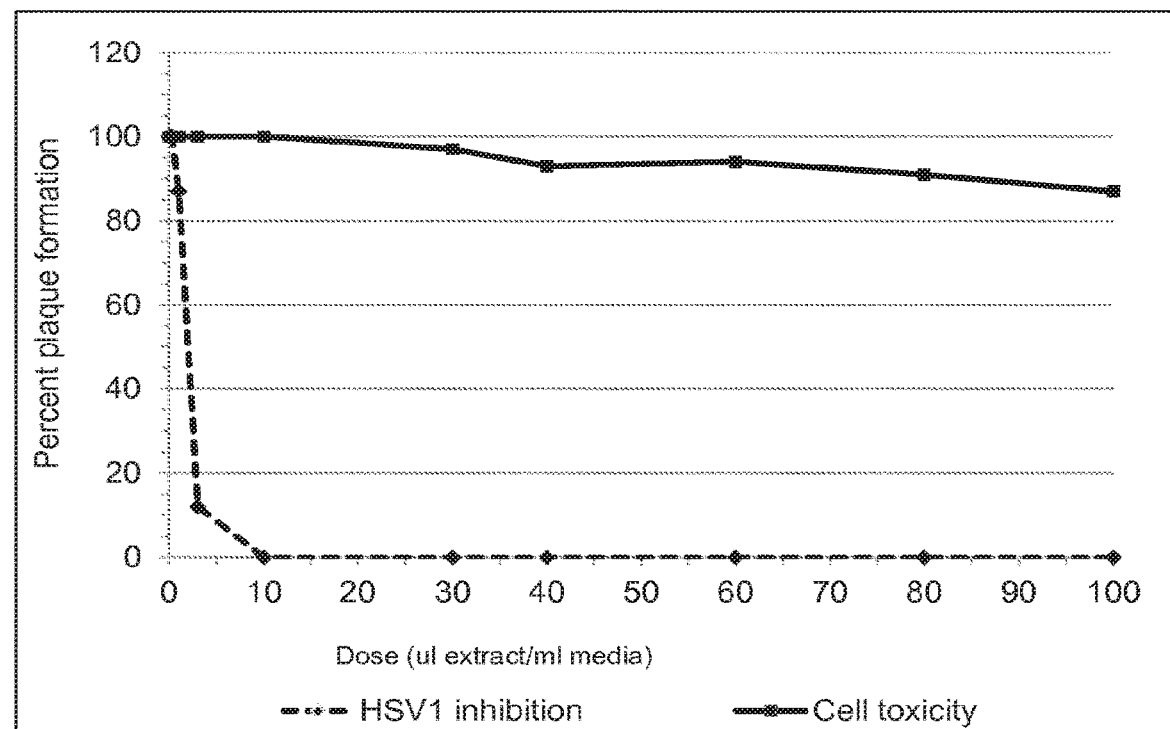
Figure 29C:
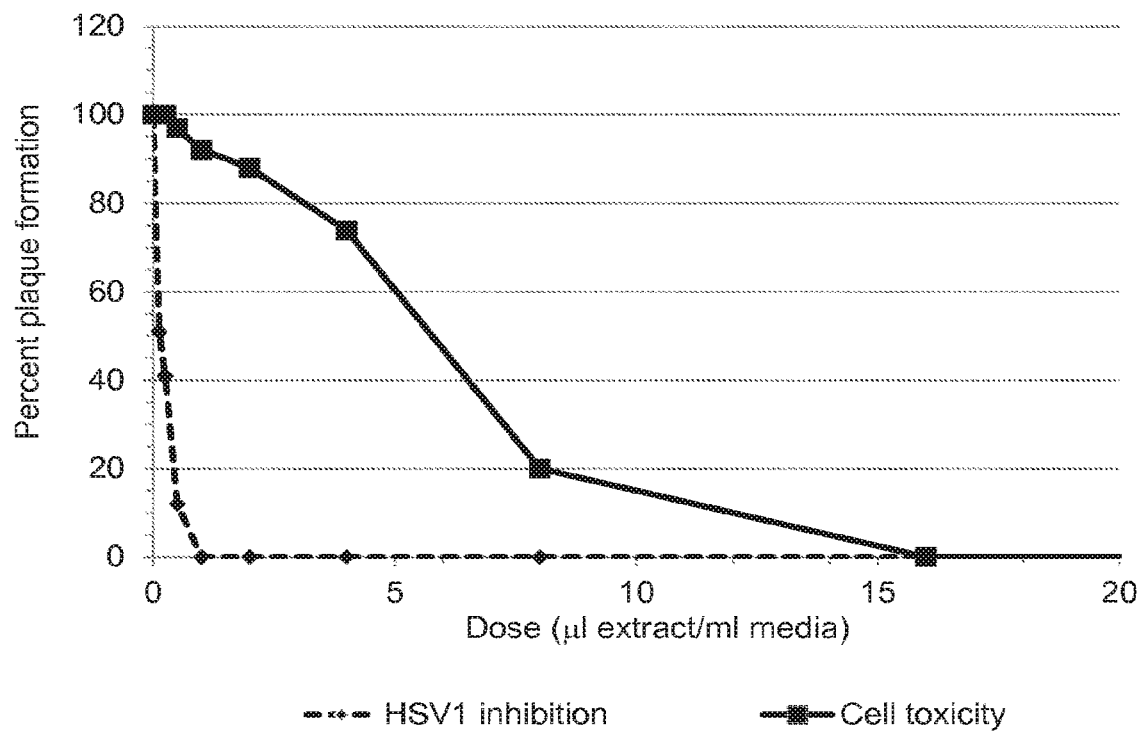
Figure 29D:
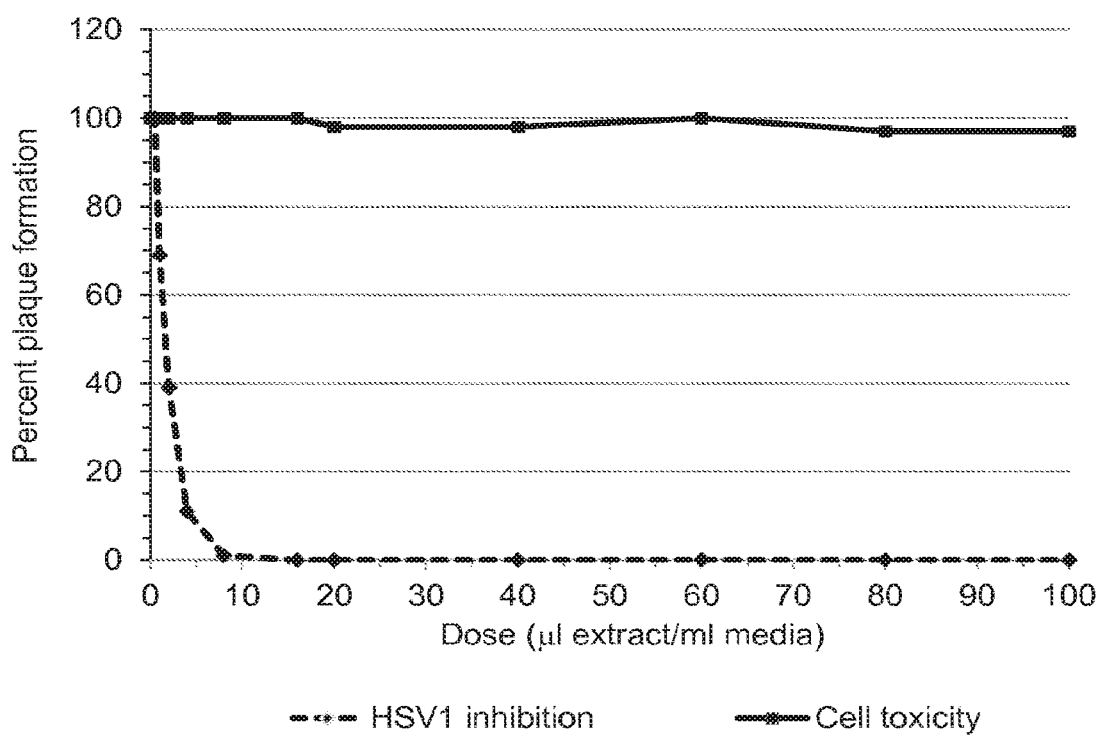
Figure 30A:
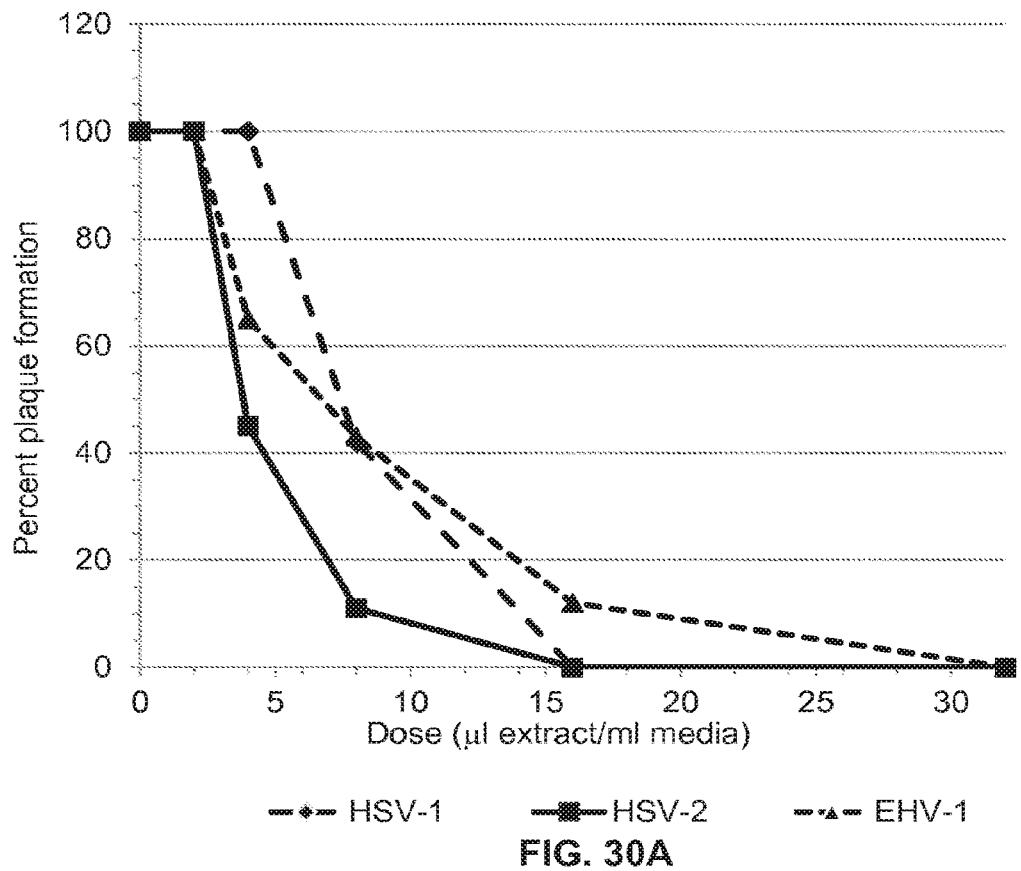
FIGS. 30A-30F illustrate anti-herpes virus activity associated with botanical extracts.
Figure 30B:
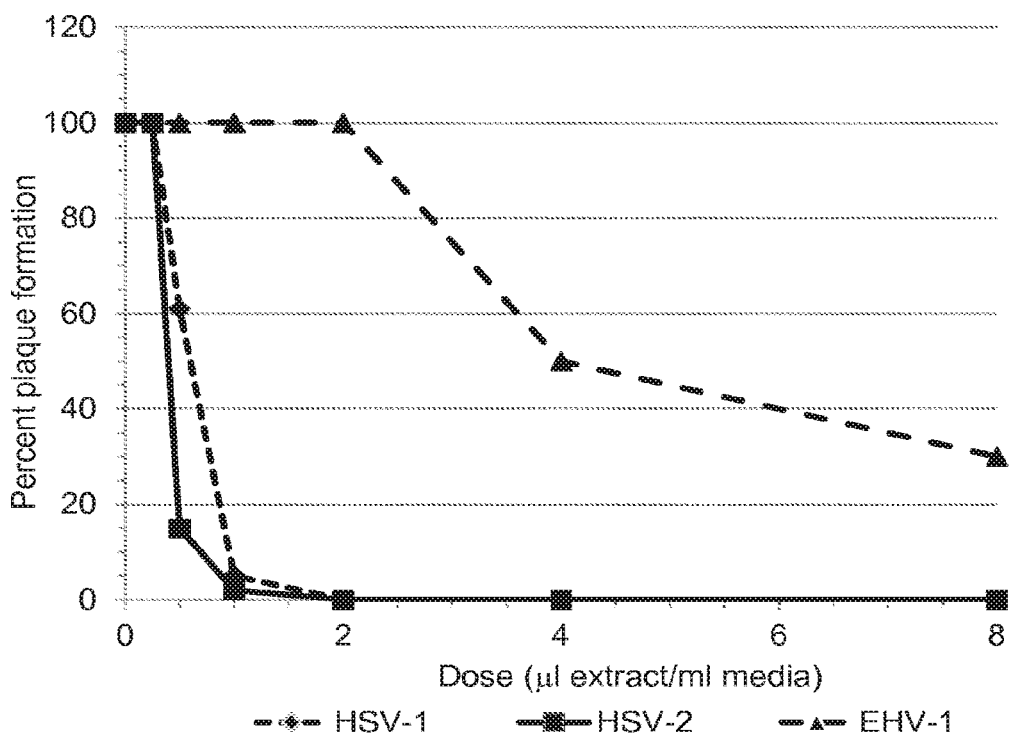
Figure 30C:
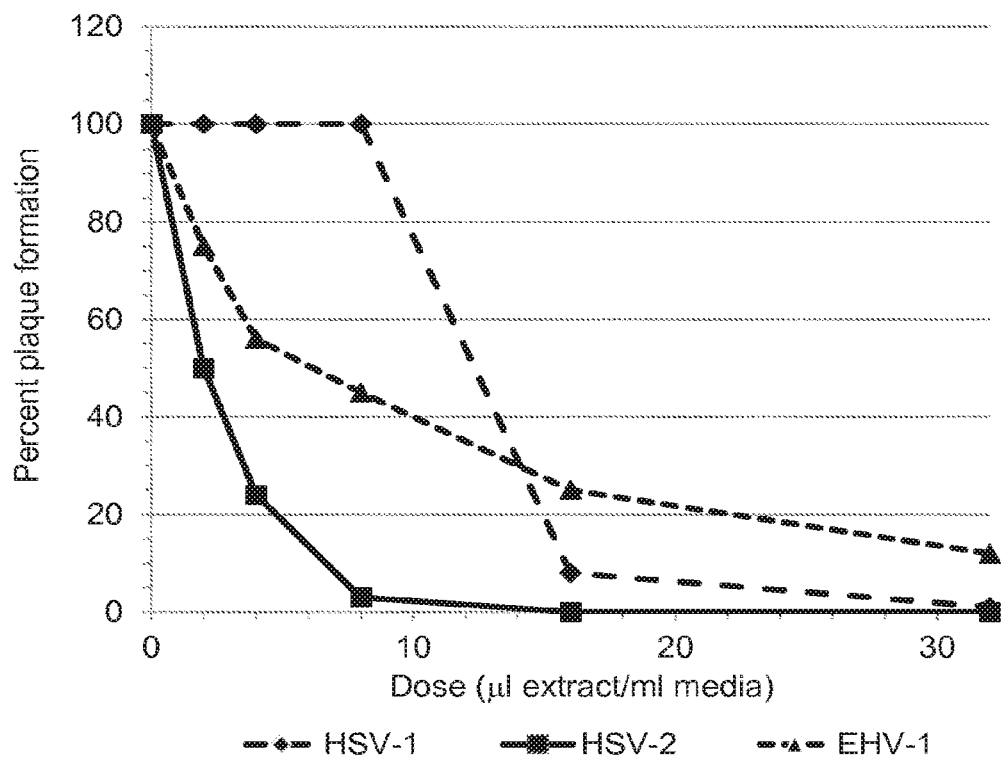
Figure 30D:
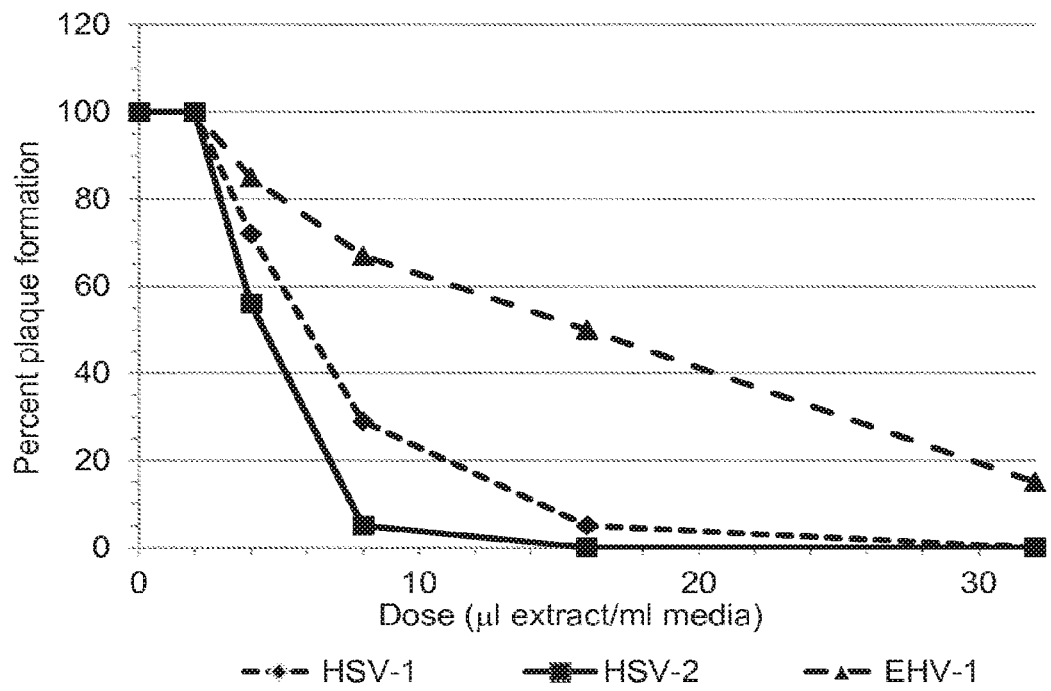
Figure 30E:
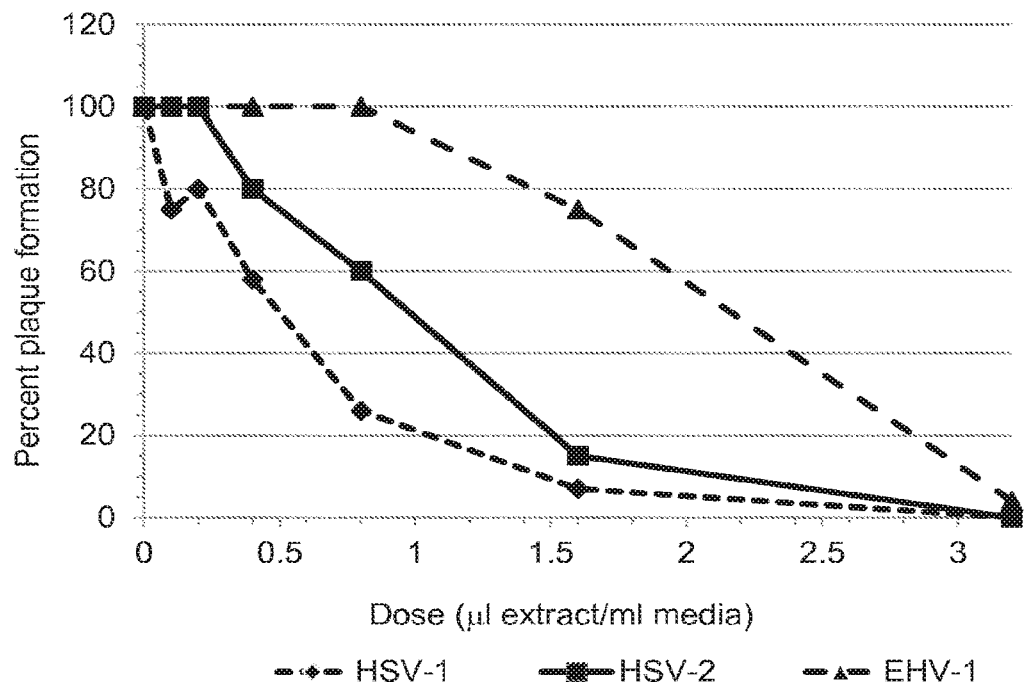
Figure 30F:
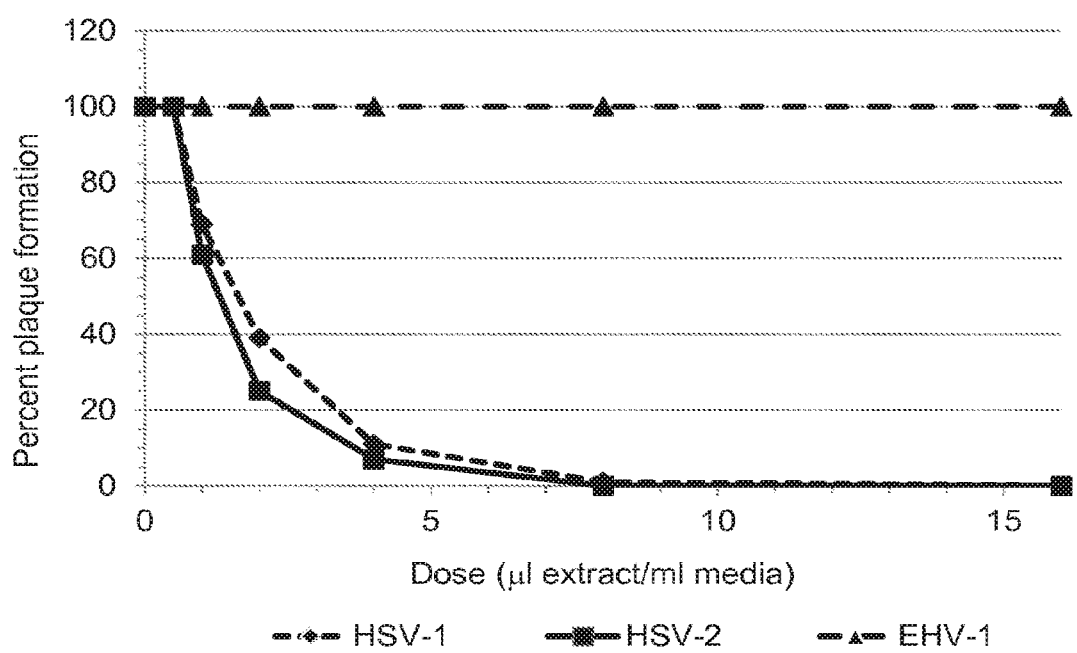

A modification of this blend has been used for the treatment of cervical dysplasia associated with HPV infection. This final blend is initially prepared as a aqueous (liquid) blend of the six botanical extracts containing 83% v/v *Sarracenia purpurea* (125 viral inhibitory units (VTU)/ml; ranging from 60-300 VIU/ml), 7% v/v *Melissa officinalis* (2000 VIU/ml; ranging from 1000-4000 VIU/ml), 2% v/v *Lavandula officinalis* (150 VIU/ml; ranging from 75-300 VIU/ml), 2% v/v *Glycyrrhiza glabra* (100 VIU/ml; ranging from 50-500 VIU/ml), 2% v/v *Eleutherococcus senticosus* (500 VTU/rat, ranging from 100-2000 VIU/ml), and 4% v/v *Hypericum perforatum* (2000 VIU/ml; ranging from 1000-4000 VTU/ml) (FIG. 29b). Following preparation of the aqueous (liquid) blend, this solution is subsequently combined in a 60:40 ratio (vol:wt) of aqueous blend to VERSABASE gel to formulate the final application product. Variations in the percentages of the botanicals within this blend can be done to increase synergistic activity and efficacy.

Methods for viral efficacy studies and botanical extract standardization to antiviral activity For standardization of antiviral activity associated with the botanical extracts, the following methodology was used for HSV1:

Vero cells were grown to 90-100% confluency in Dulbecco's MEM media containing 10% heat inactivated fetal bovine serum and anti-fungal/anti-bacterial at 37° C. in a 5% $CO_2$ growth incubator to produce cell monolayers.

Viral stocks were diluted to prepare aliquots containing 200 plaque forming units (pfu) in 100 μl media Botanical extracts were prepared as described herein and filtered through 0.2 μm syringe filters. Ethanol-based extracts were vacuum evaporated for 45 minutes at room temperature.

Serial dilutions of botanical extracts were prepared in 2-fold concentration steps ranging from 0.1 to 32 μl/ml, and each botanical extract concentration was added to a viral stock aliquot and incubated at room temperature for 20 minutes.

Treated viral samples were then added to the cell monolayers and incubated with occasional rocking for 30 minutes.

After this infection step, fresh medium containing 0.3% human gamma globulin and 0.9% agar was added to the cell monolayers containing an equivalent concentration of the botanical as that added to the viral stock aliquot tubes.

The infected/treated cell monolayers were incubated at 37° C. in a 5% $CO_2$ growth incubator.

After 3 days, the agar medium was removed and the cell monolayers stained with crystal violet to visualize plaque formation.

Plaque numbers were calculated and graphed.

For other viruses, the same protocol was followed with the following variations: For HSV2:

For Step 8, cells were grown for 2 days, rather than 3 days. For VZV:

For Step 6, fresh medium did not contain human gamma globulin.

For Step 8, crystal violet staining was done at 9 days post infection, rather than at 3 days. For SV-40:

For Step 1, BSC-1 cells were used instead of Vero cells. Medium was MEM with 10% heat inactivated fetal bovine serum with anti-fungal and anti-bacterial additives.

Following infection in Step 5, the plates were overlayed with medium containing 0.9% agar. The plates were fed with fresh medium every 3-4 days.

For Step 8, staining with crystal violet after removal of the agar medium overlay was performed 7-10 days post infection.

For poxviruses:

For Step 6, medium did not contain human gamma globulin. *S. purpurea* regulation of inflammation and pro-inflammatory cytokines In the present research, herpes virus infected subjects presented outbreak signs of infection including the afflicted area becoming reddened, itching and swollen. These symptoms are associated with the body's inflammatory response towards the virus infection. Following application of the botanical extract composition or *Sarracenia purpurea* alone, subjects typically reported a decrease in pain, redness and swelling within a few to 24 hours post application. These results suggest that *S. purpurea* components are diminishing the inflammatory response to the infection. Since inflammation is associated with an induction of pro-inflammatory cytokines, these results may suggest that *S. purpurea* is capable of decreasing the expression of these key cytokines.

To confirm *S. purpurea* was able to regulate the expression of pro-inflammatory cytokines, an in vitro assay was developed. Peripheral blood mononuclear cells (PBMCs) were isolated from two different healthy subjects. For immune stimulation, cells were treated with phorbol 12-myristate 13-acetate (PMA) plus ionomycin (50 ng/ml and 1/ml, respectively) or lipopolysaccharide (LPS) (100 ng/ml). Treatments included the following combinations PMA+ionomycin for 2 hours then washed LPS for 2 hours then washed S. purpurea extract for 4 hours followed by PMA+ionomycin for 2 hours then washed S. purpurea extract for 4 hours followed by LPS for 2 hours then washed S. purpurea extract for 4 hours then washed Untreated Following 6, 12 and 24 hours post treatment, total RNA was purified from the cells as per manufacturer's recommended protocol (Qiagen RNA isolation kit). The mRNA expression level of various cytokines was measured by Real-Time PGR analysis. Real-time PGR primers and reagents were obtained commercially and analyzed under the following PGR. conditions:

Heat to 95° C. for 10 minutes

Heat to 95° C. for 15 seconds

Heat to 40° C. for 40 seconds

Read the fluorescence level

Heat to 72° C. for 30 seconds

Repeat steps 2-5 for 44 cycles

Cytokine primers included: CCL3 (MIP-1α, Macrophage inflammatory protein-1α), TNF-α (Tumor necrosis factor-α), IL8 (Interleukin-8), IL5 (Interleukin-5), 1L1ß (Interleukin-1 ß), IL2 (Interleukin-2), IL10 (Interleukin-10), IFN-γ (interferon-γ), IL6 (Interleukin-6).

Figure 42A:
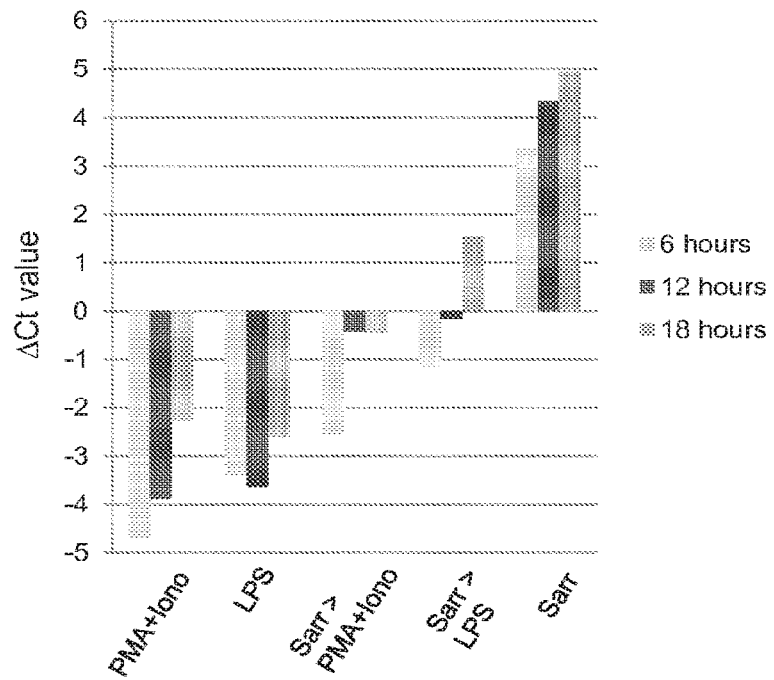
FIG. 42A-42R illustrate in vitro anti-inflammatory activity associated with *S. purpurea* extracts.
Figure 42B:
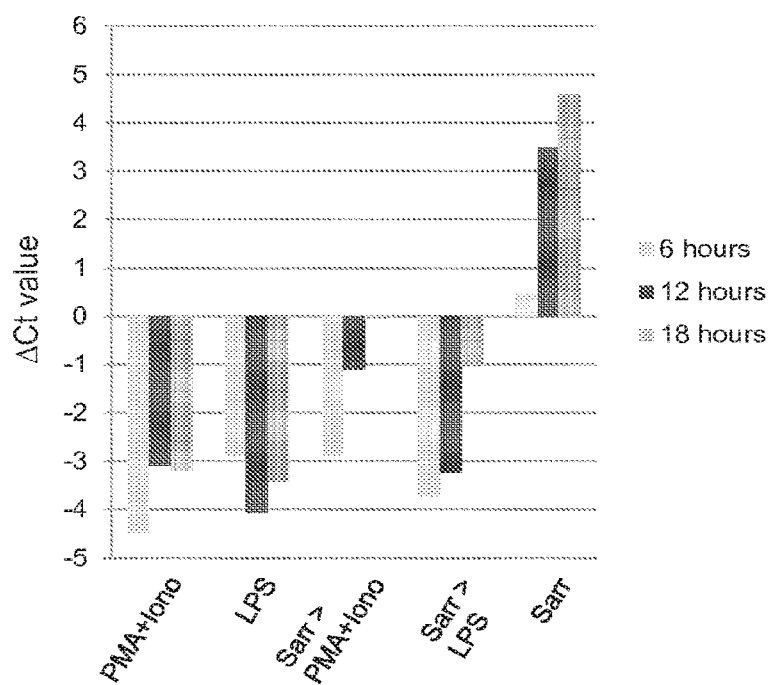
Figure 42C:
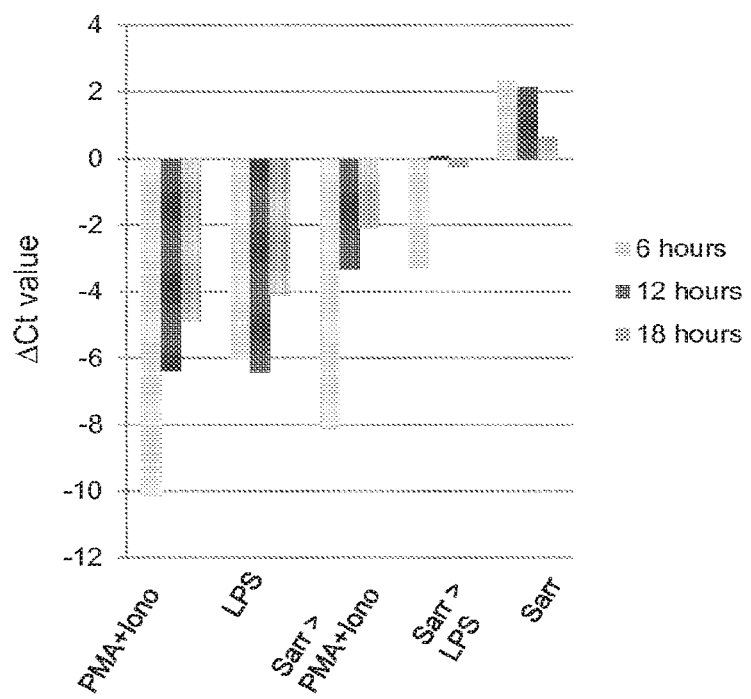
Figure 42D:
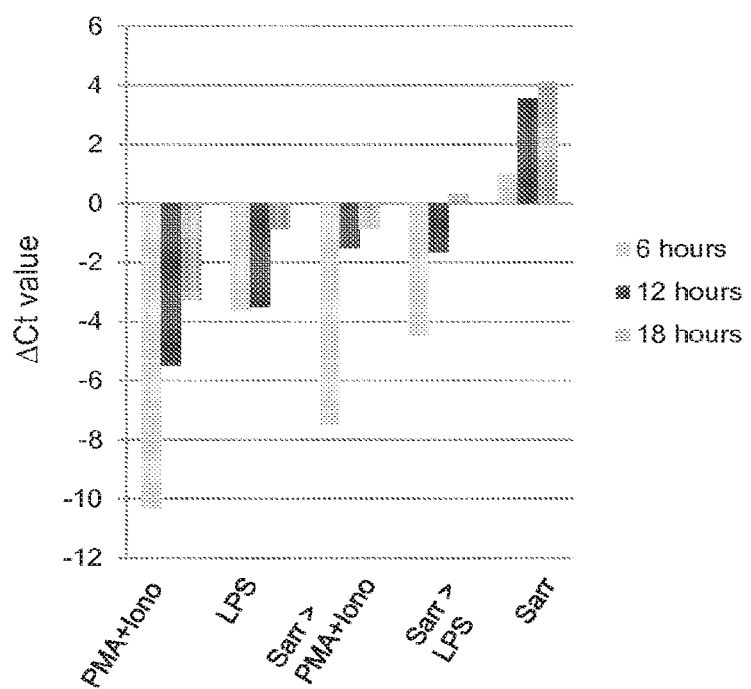
Figure 42E:
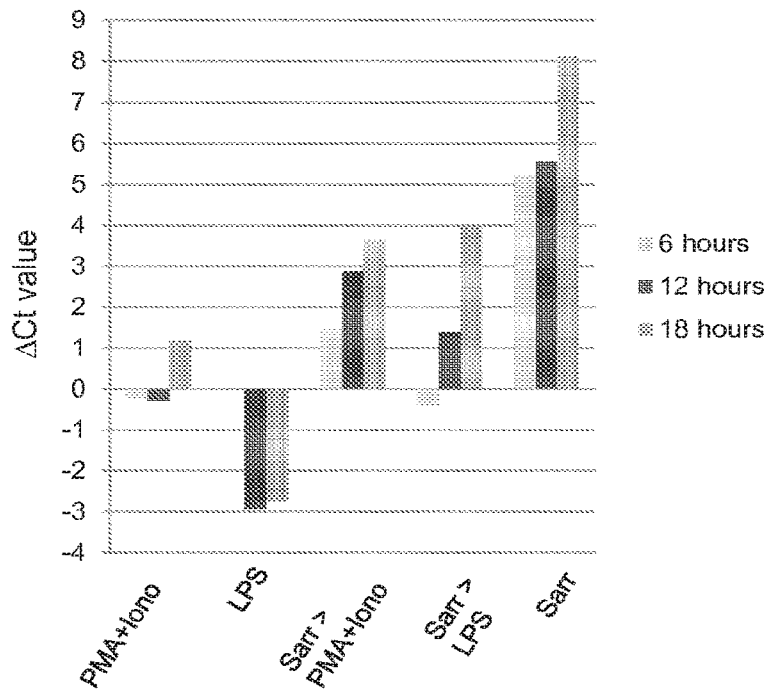
Figure 42F:
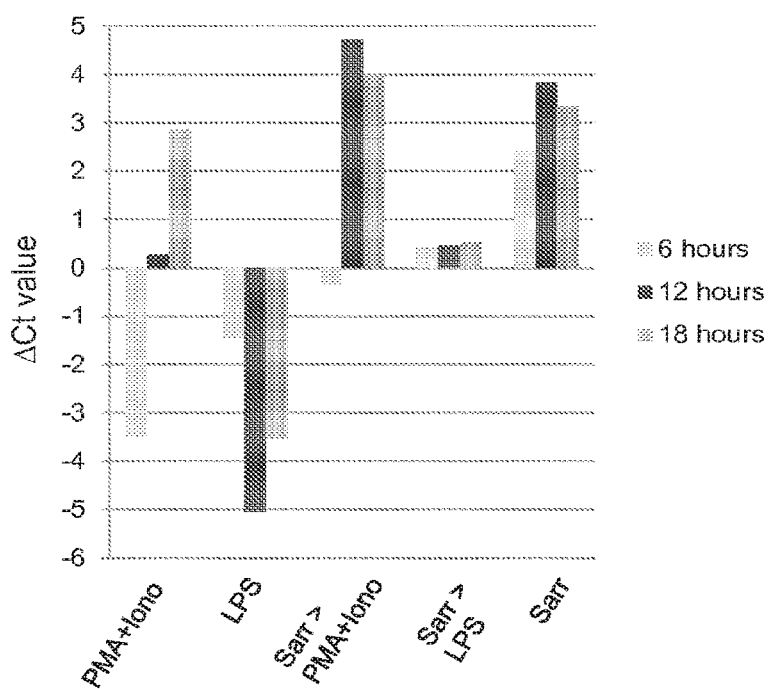
Figure 42G:
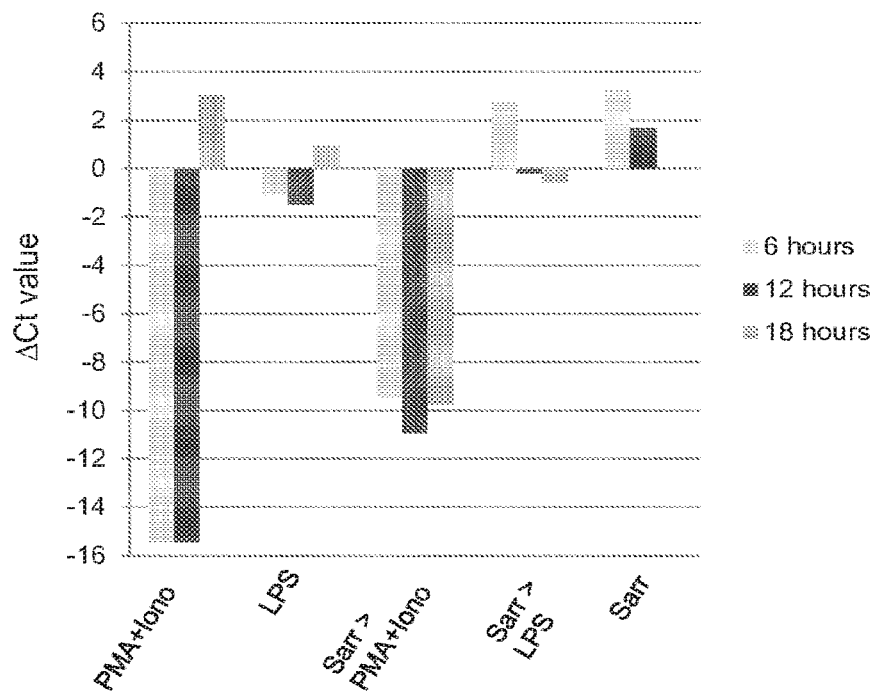
Figure 42H:
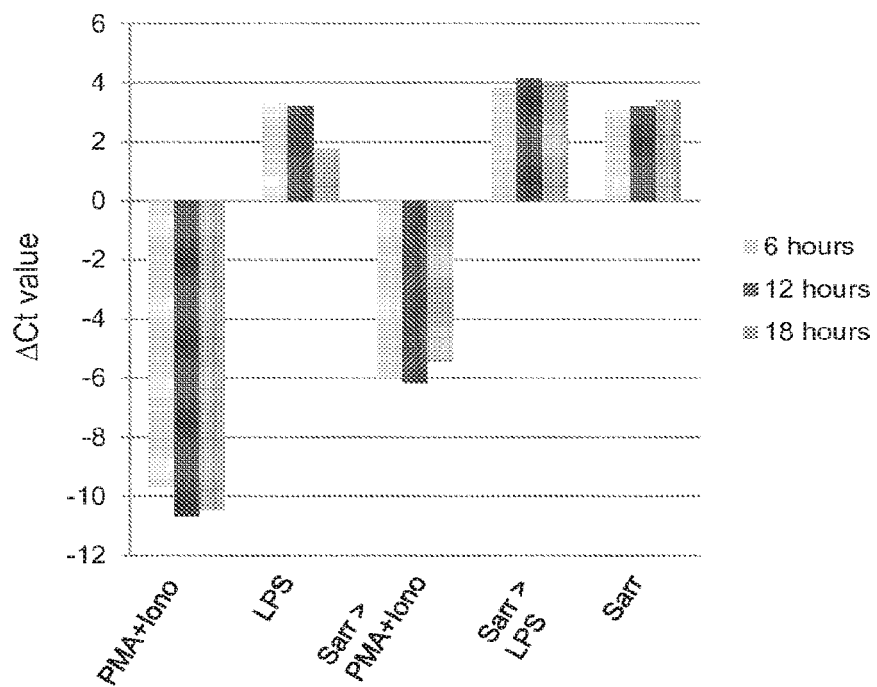
Figure 42I:
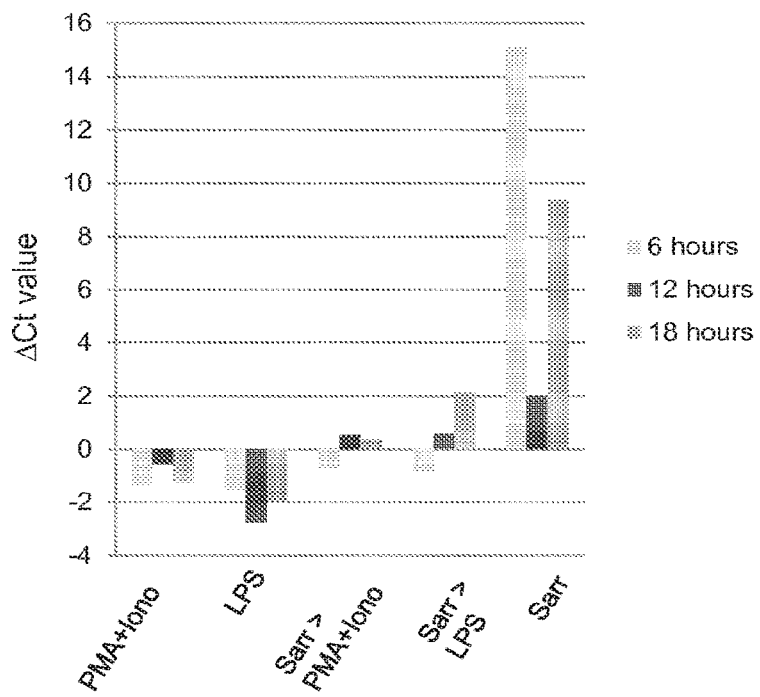
Figure 42J:
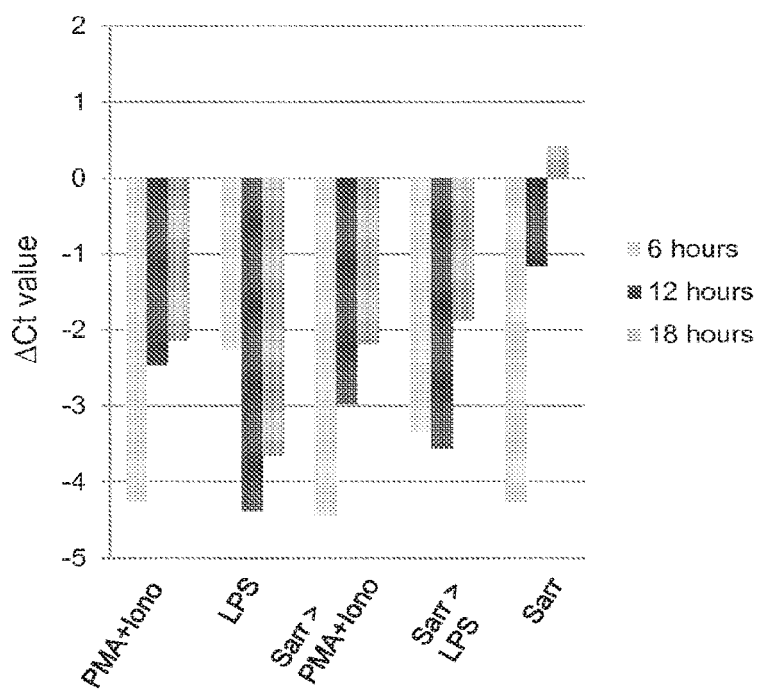
Figure 42K:
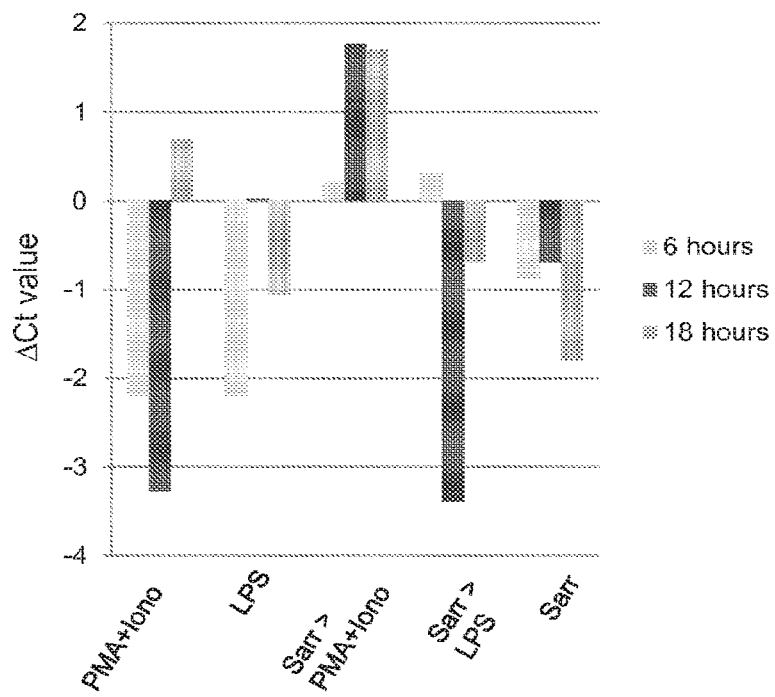
Figure 42L:
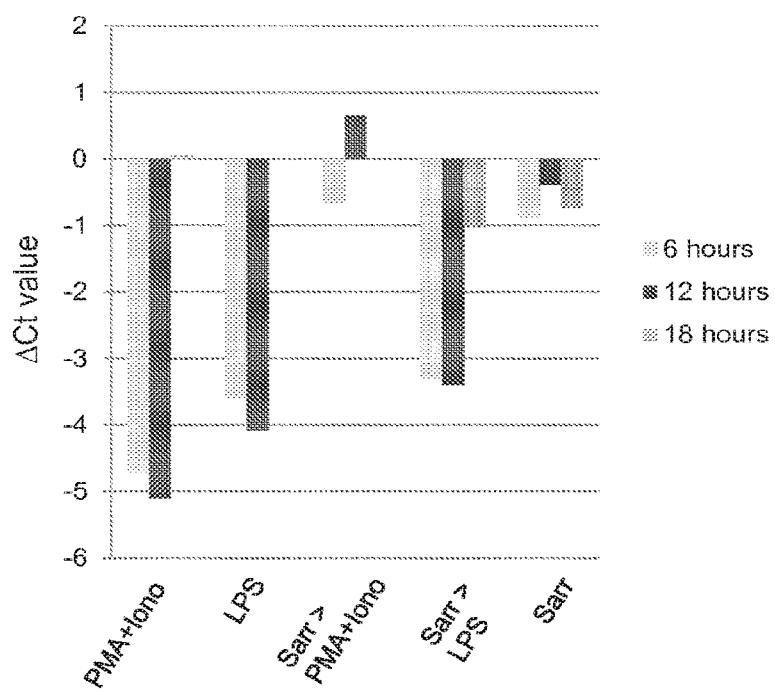
Figure 42M:
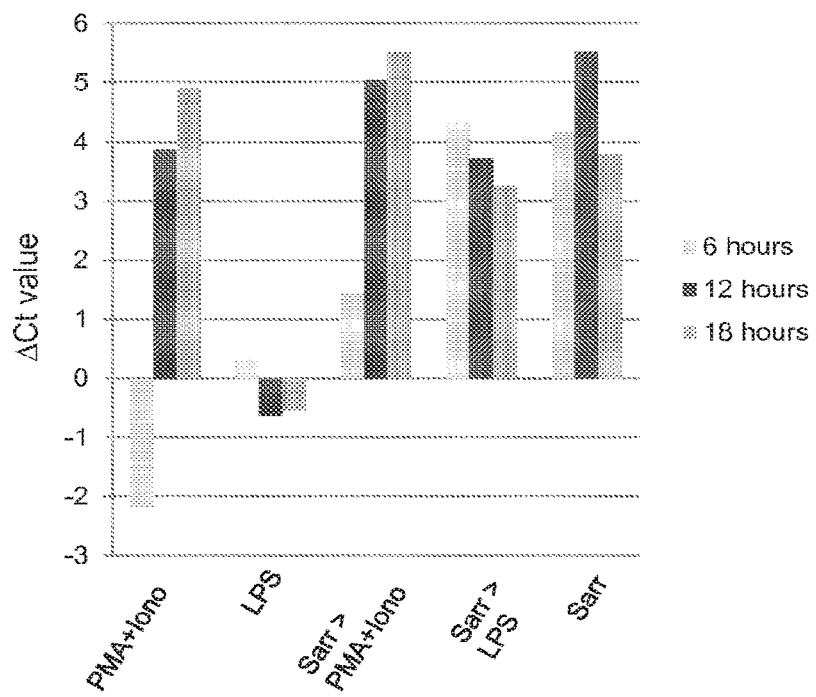
Figure 42N:
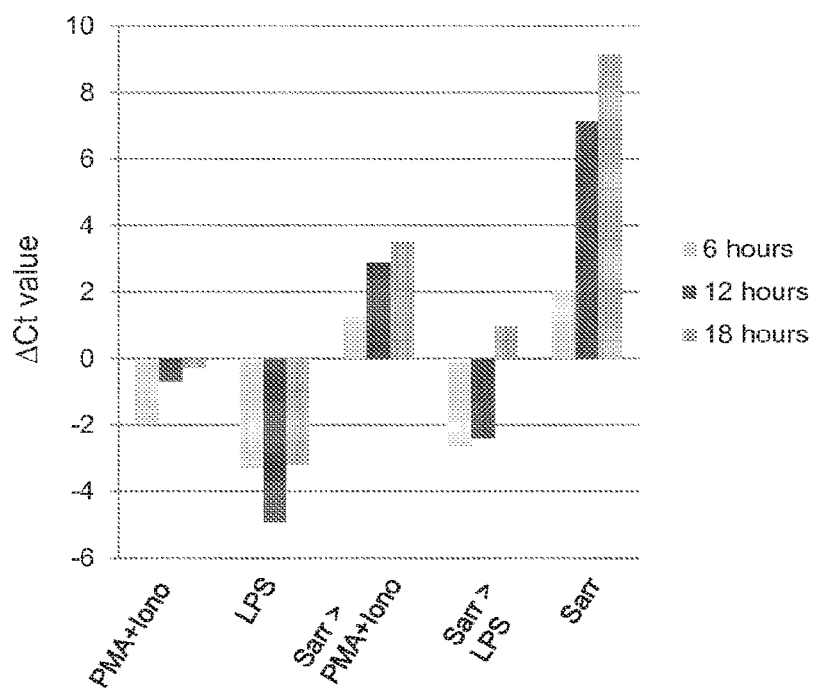
Figure 42O:
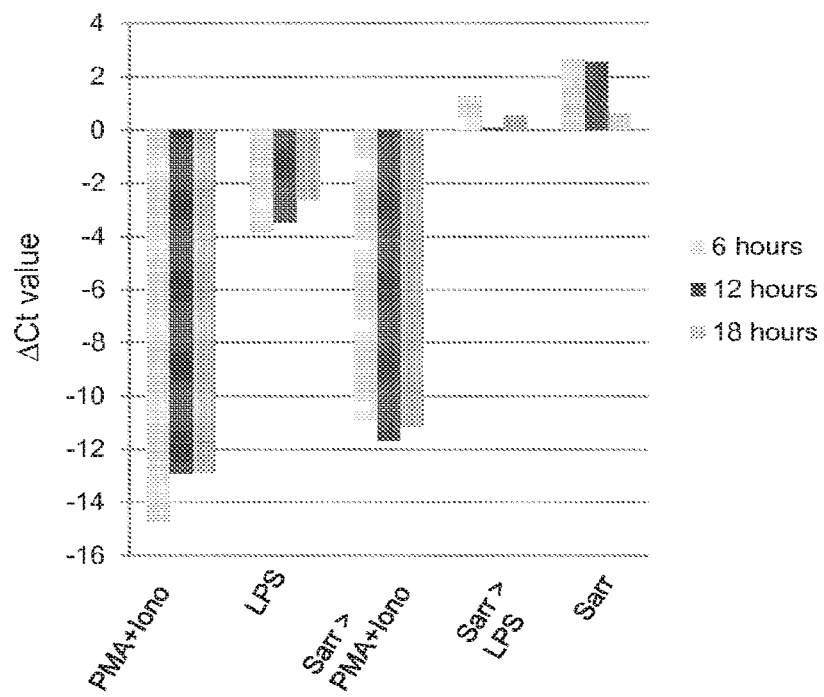
Figure 42P:
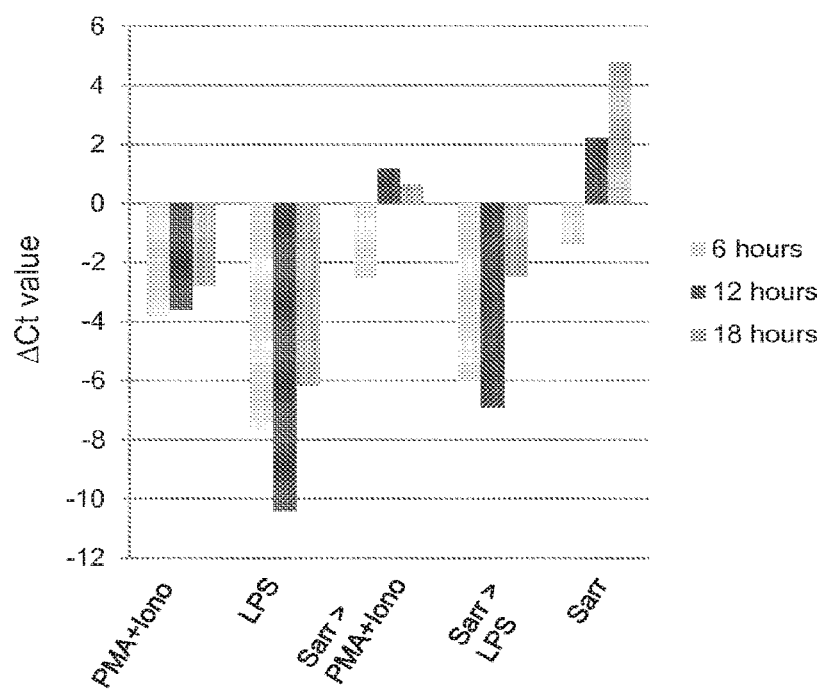
Figure 42Q:
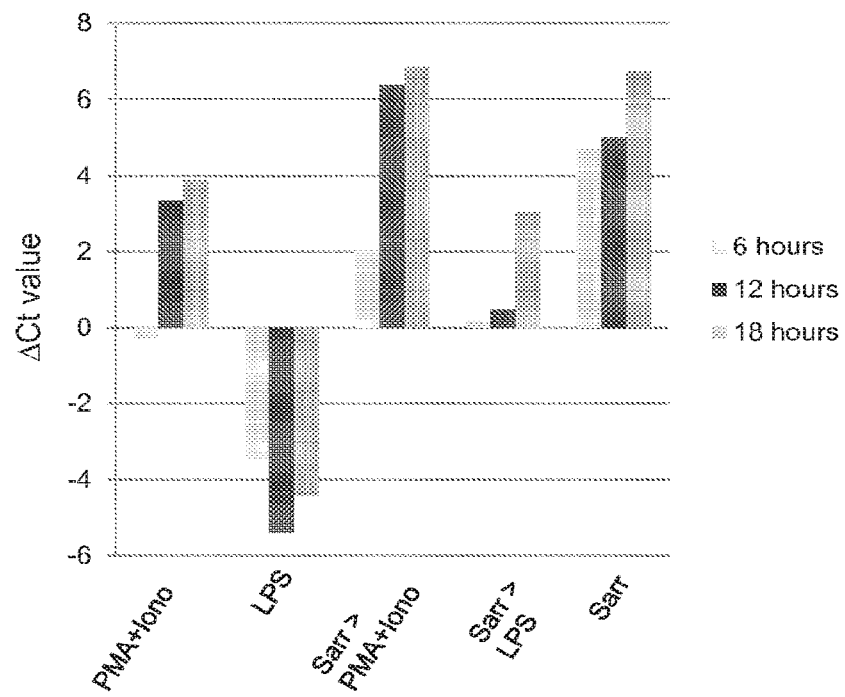
Figure 42R:
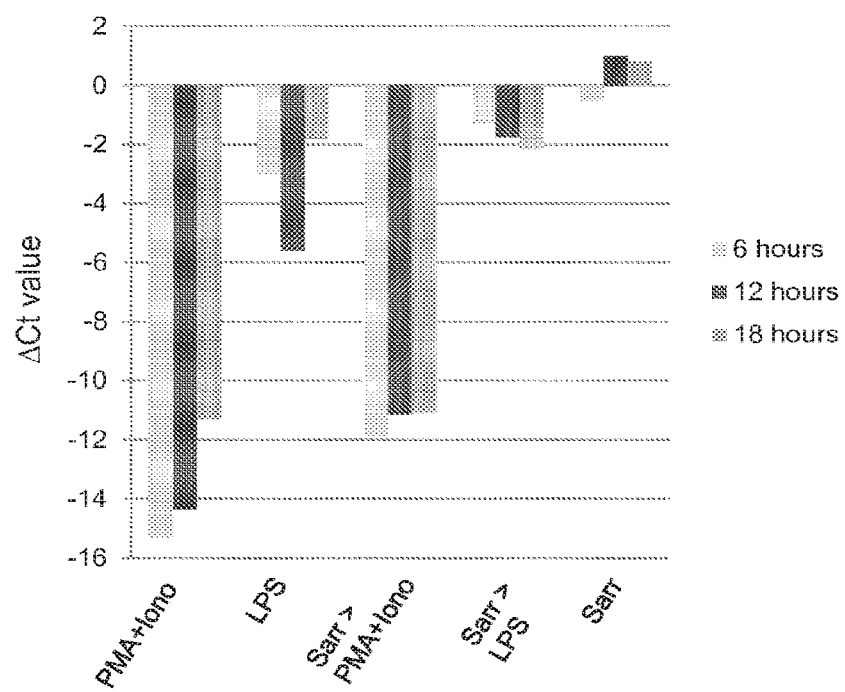
Figure 43A:
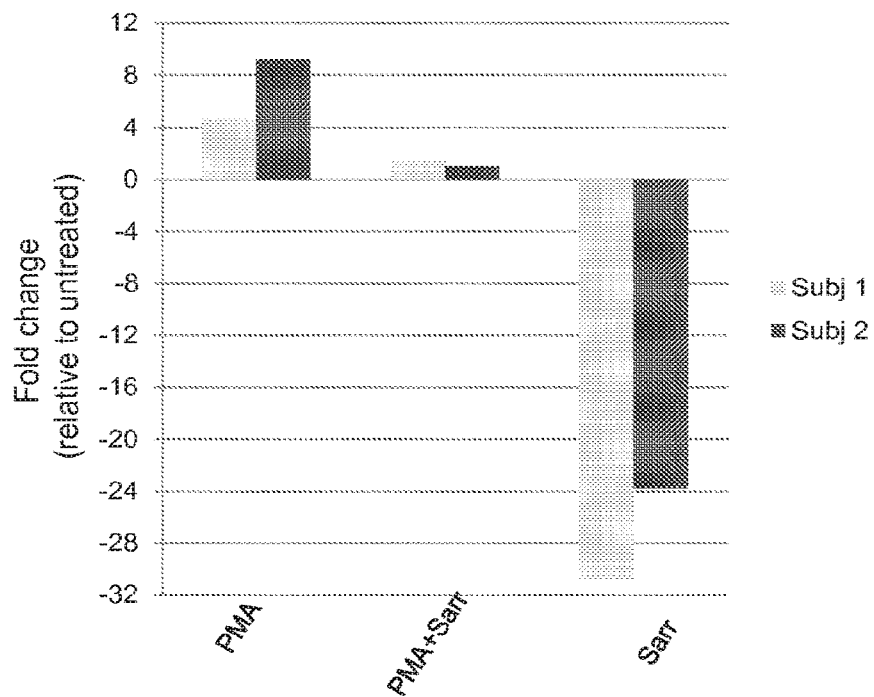
FIGS. 43A-43I illustrate cytokine response of *S. purpurea* treated PBMCs.
Figure 43B:
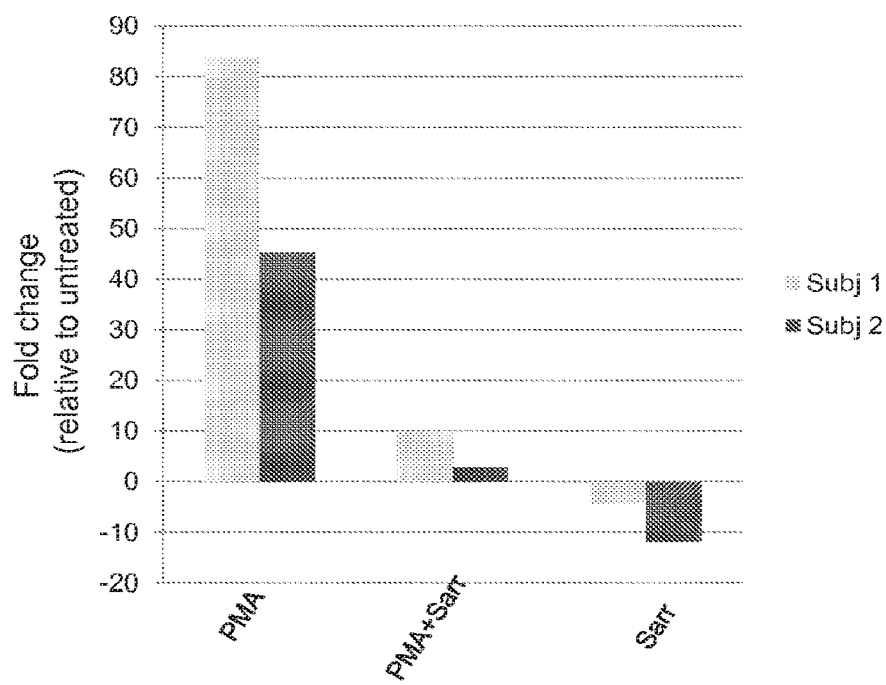
Figure 43C:
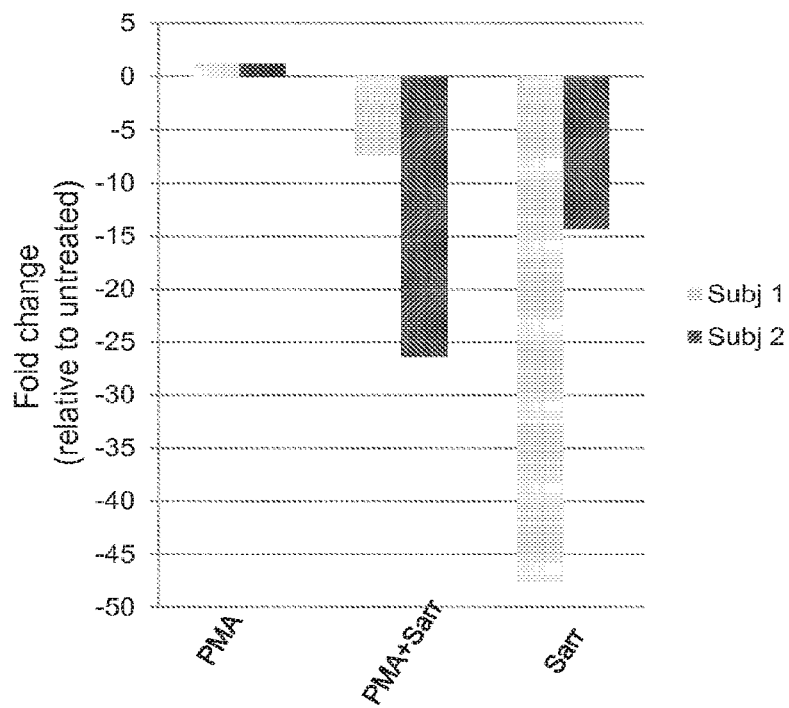
Figure 43D:
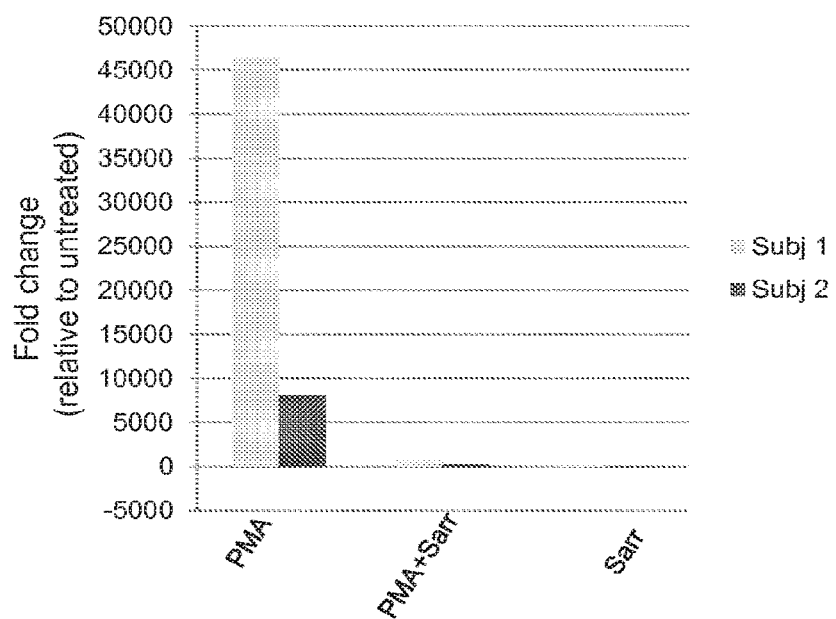
Figure 43E:
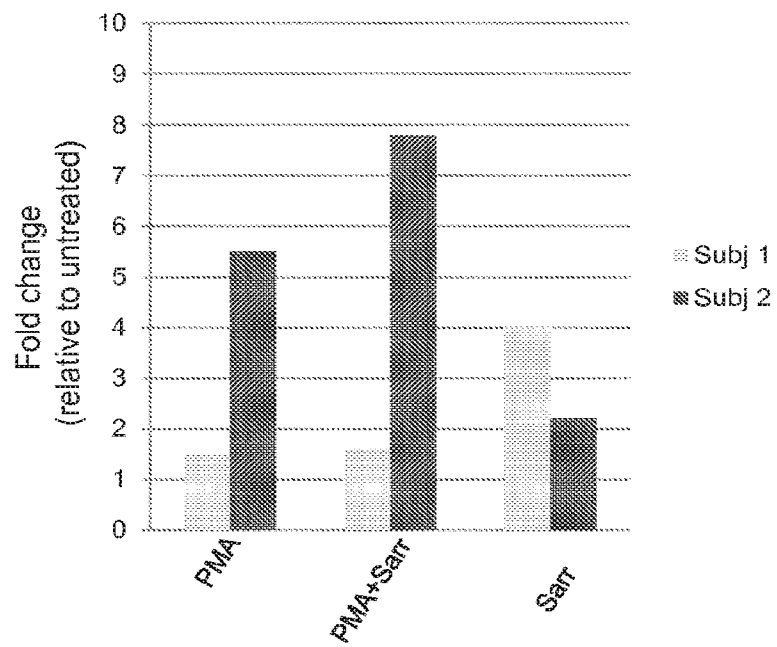
Figure 43F:
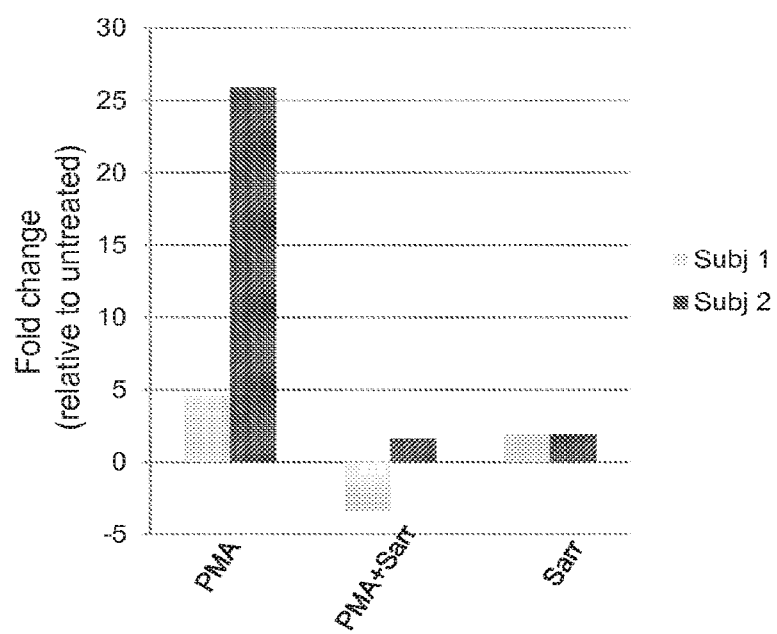
Figure 43G:
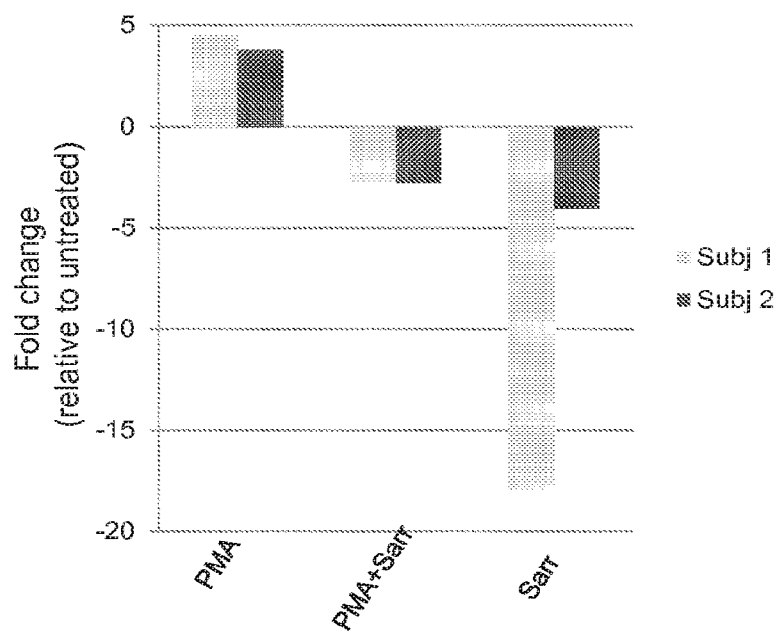
Figure 43H:
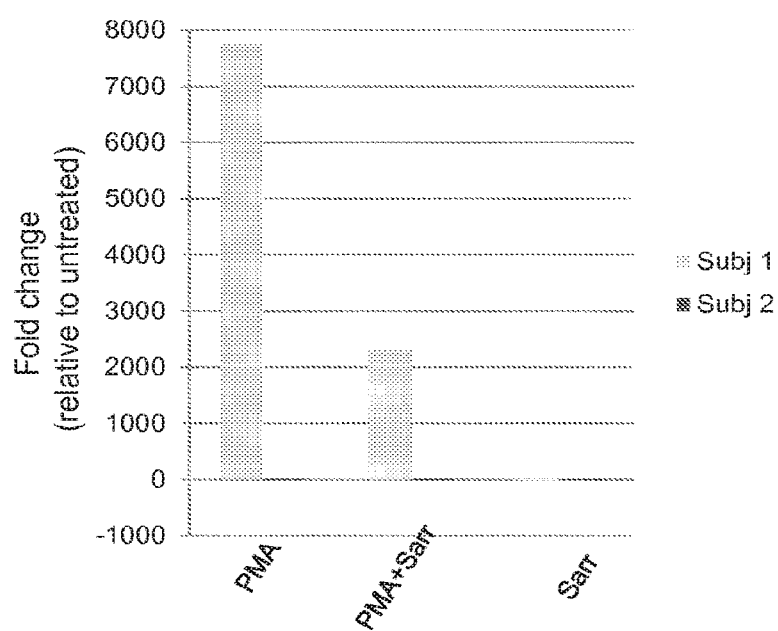
Figure 43I:
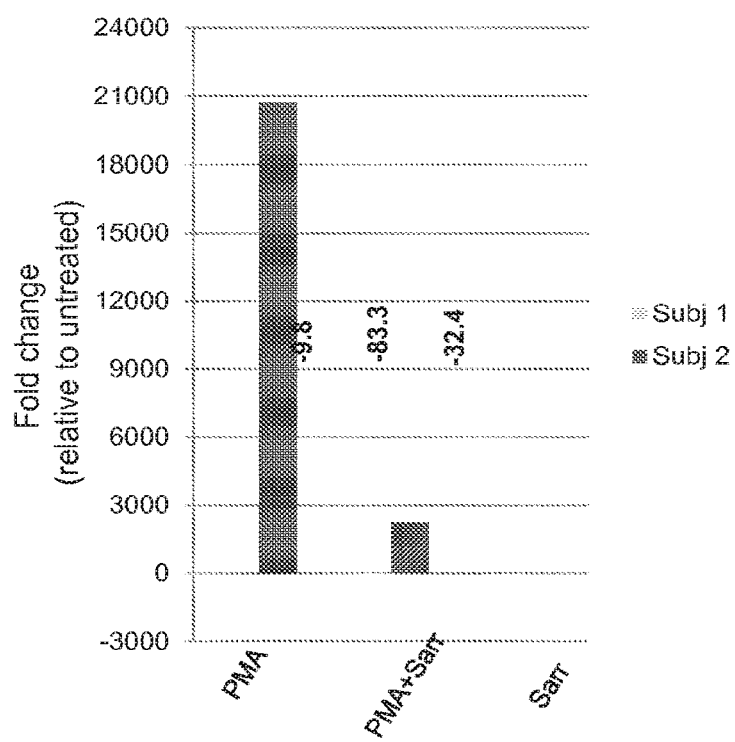
Figure 44A:
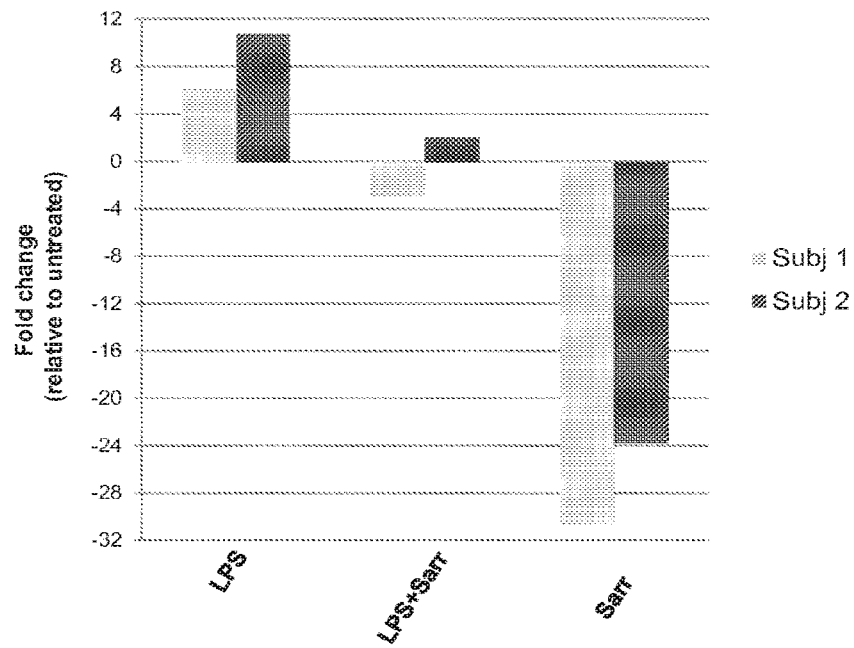
FIGS. 44A-44I illustrate cytokine response of *S. purpurea* treated PBMCs.
Figure 44B:
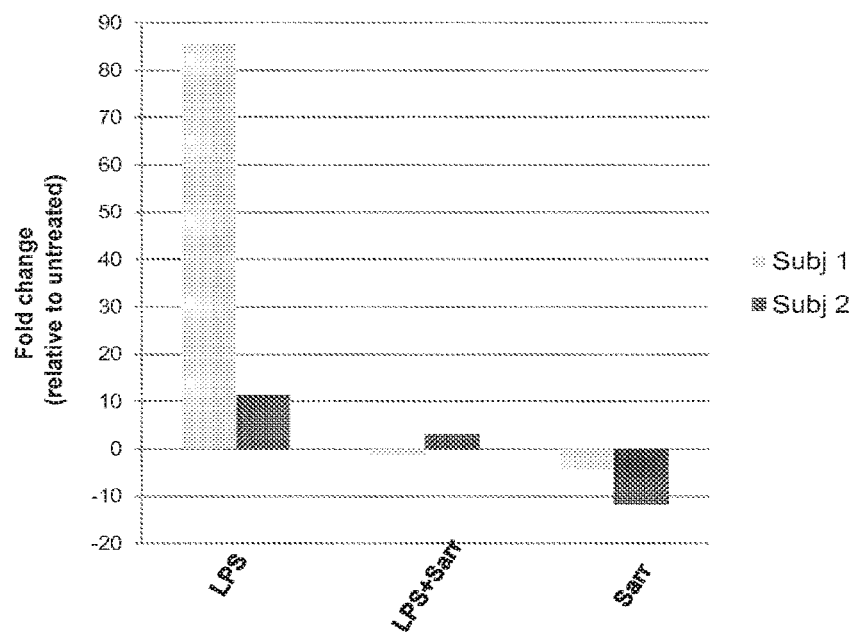
Figure 44C:
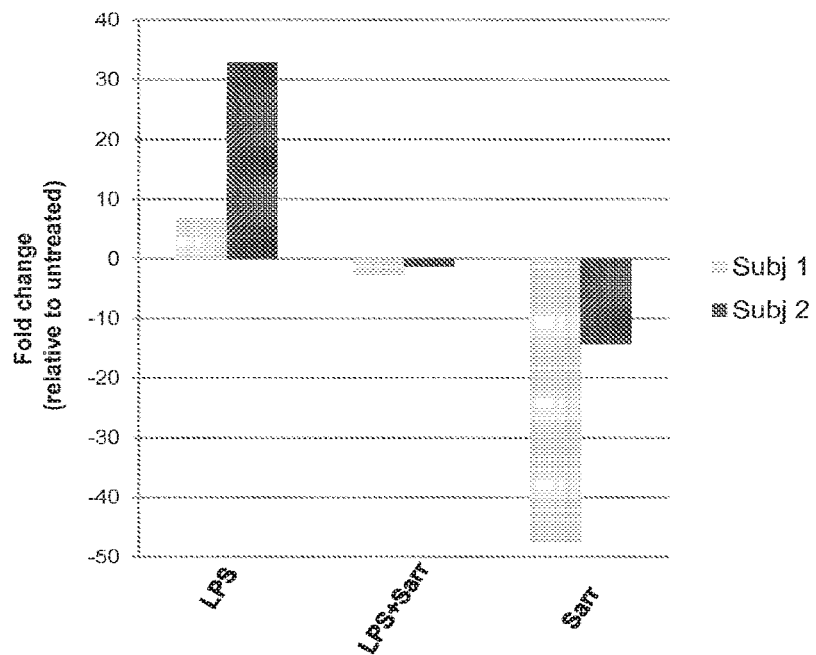
Figure 44D:
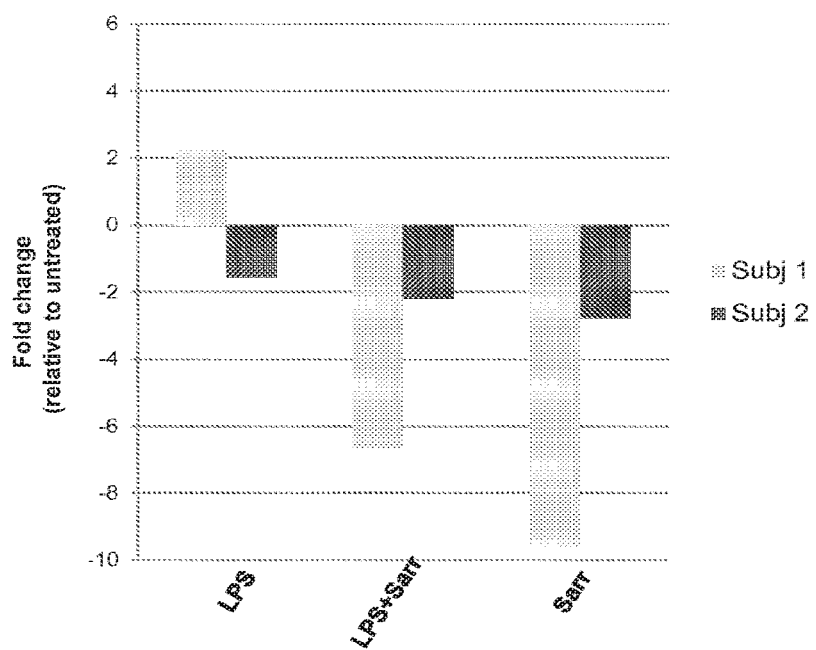
Figure 44E:
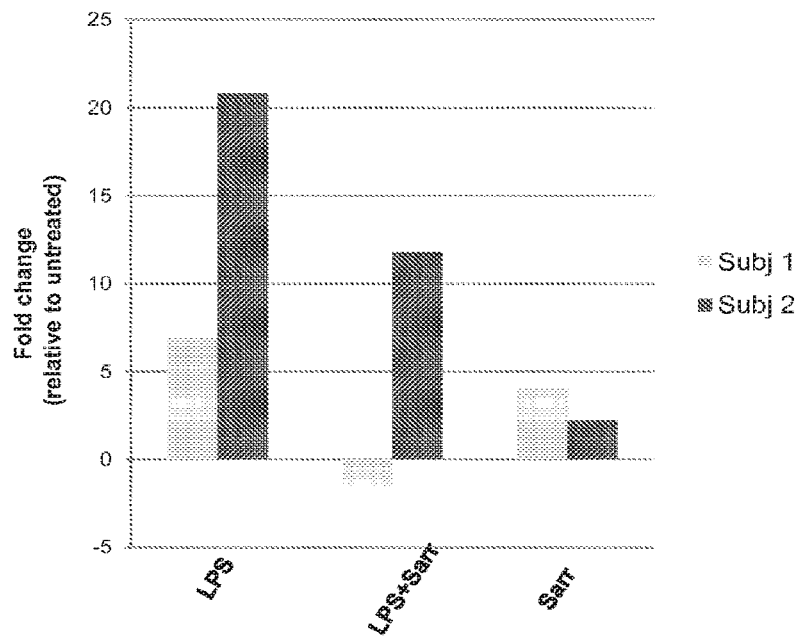
Figure 44F:
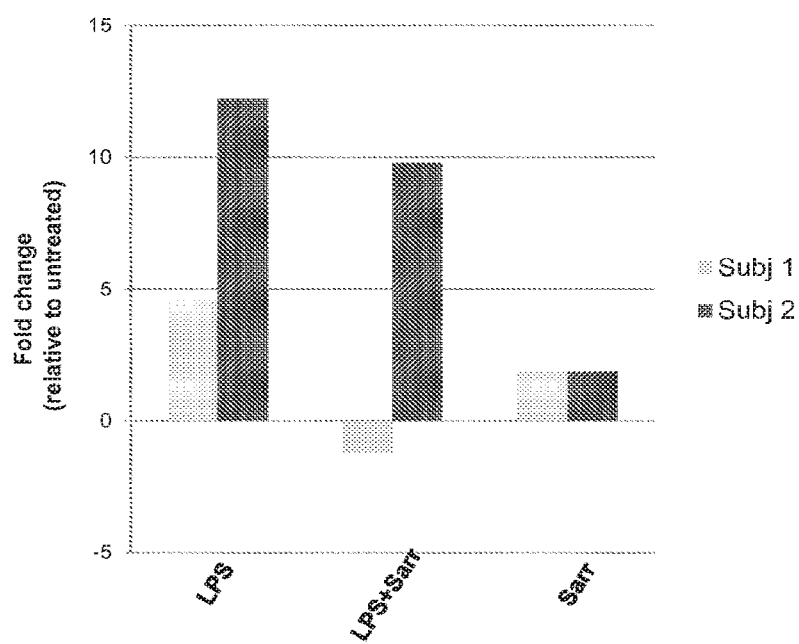
Figure 44G:
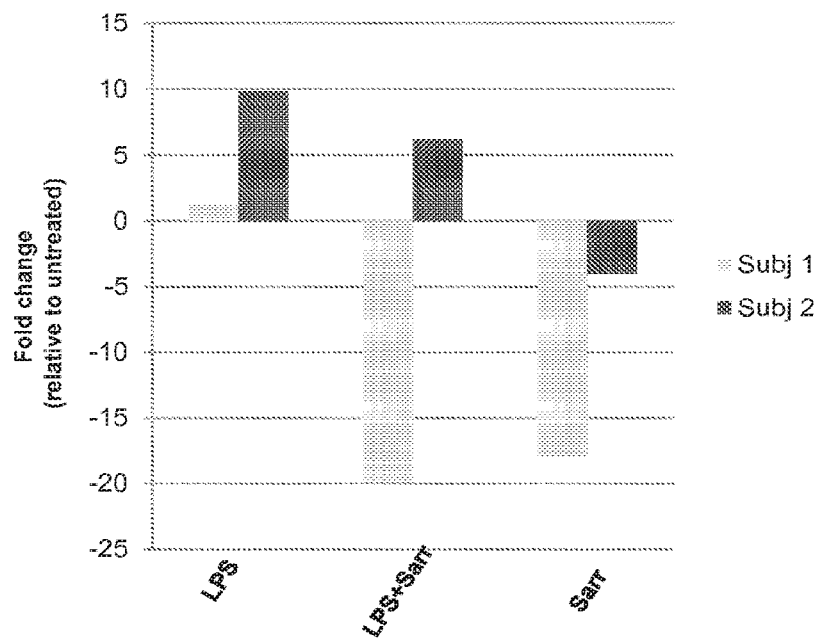
Figure 44H:
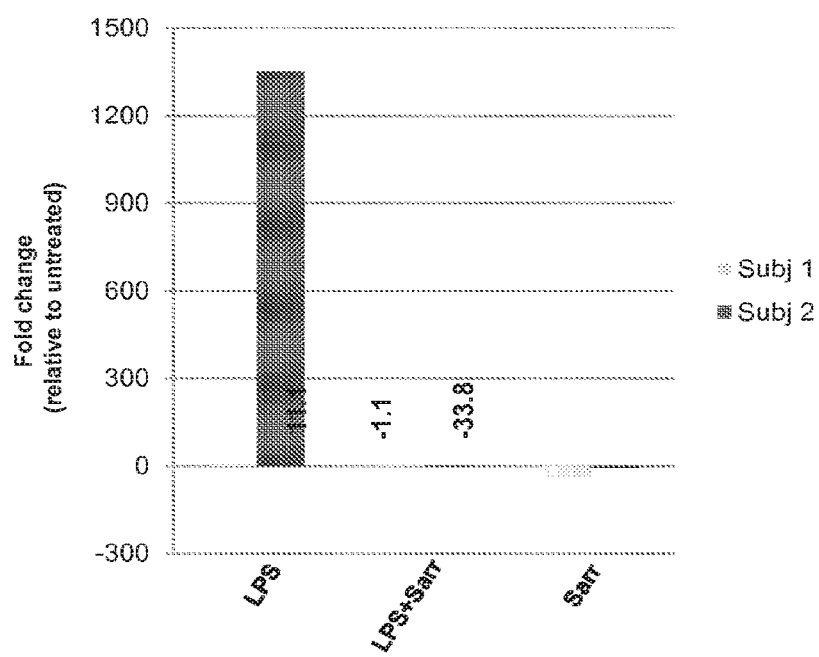
Figure 44I:
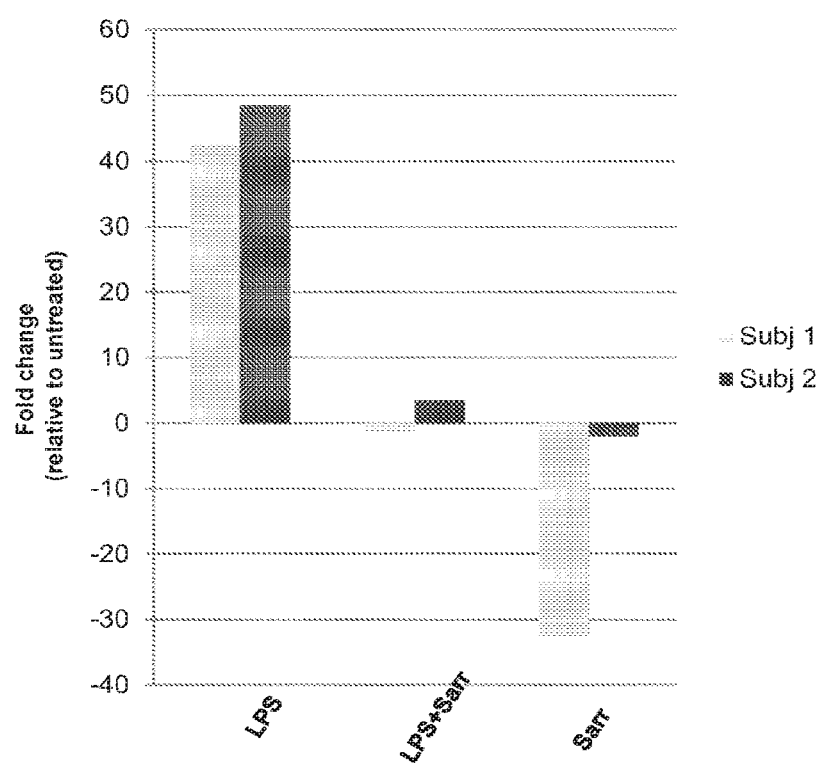
Figure 45A:
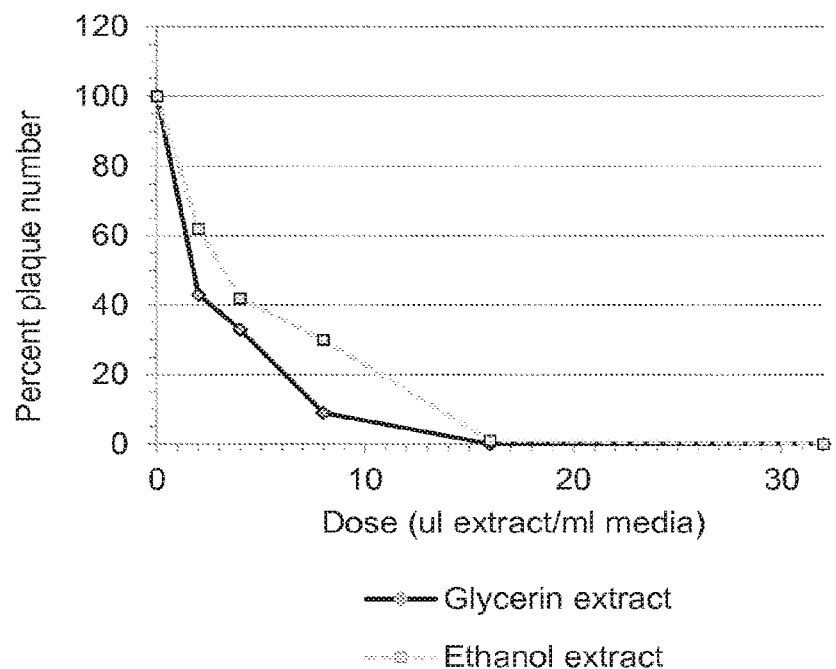
FIGS. 45A-45F illustrate antiviral activity of ethanol and glycerin botanical extracts.
Figure 45B:
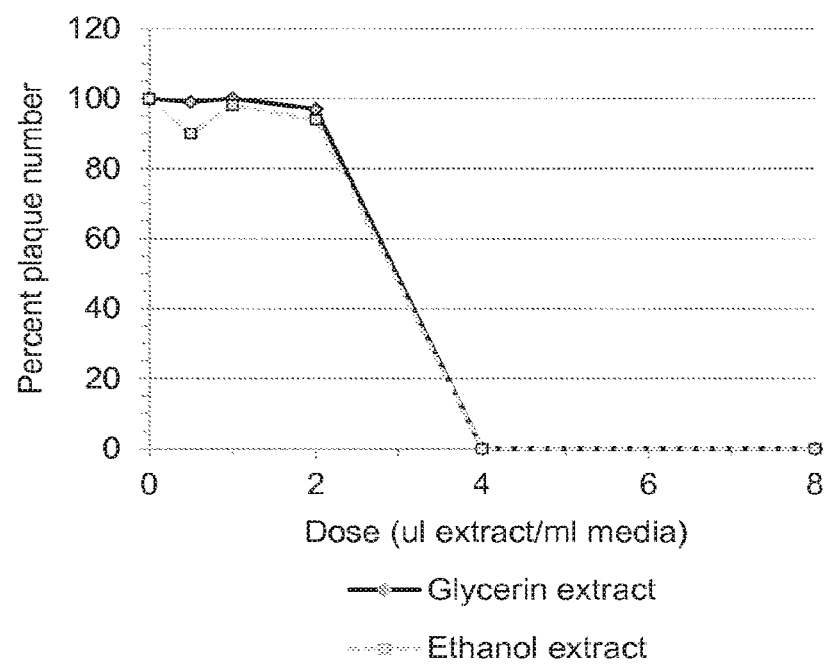
Figure 45C:
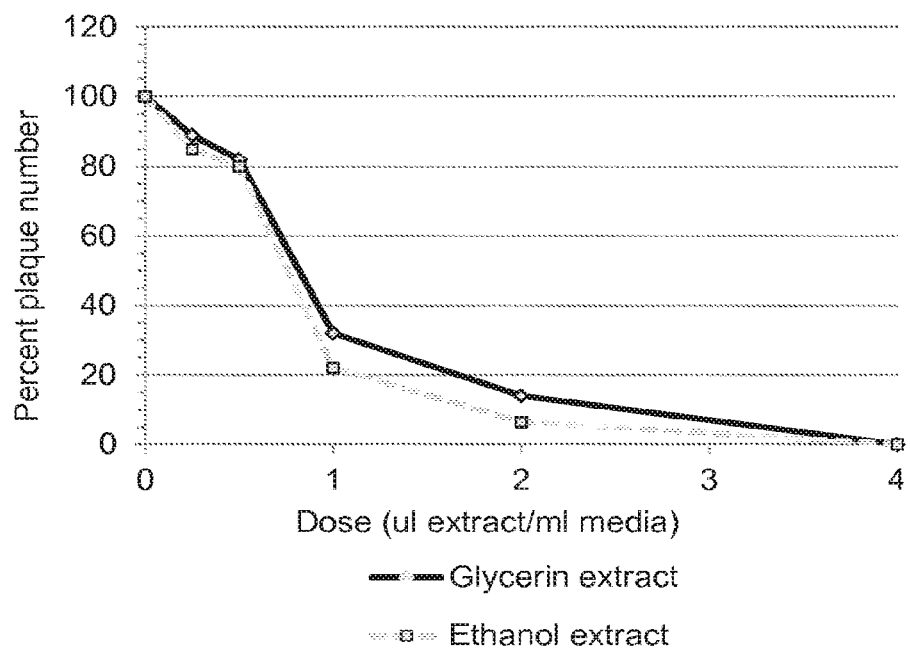
Figure 45D:
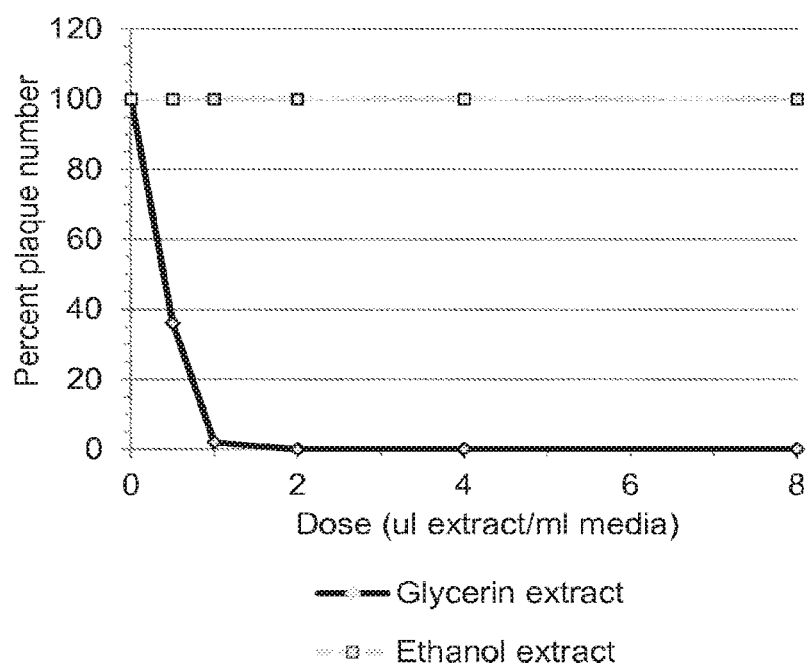
Figure 45E:
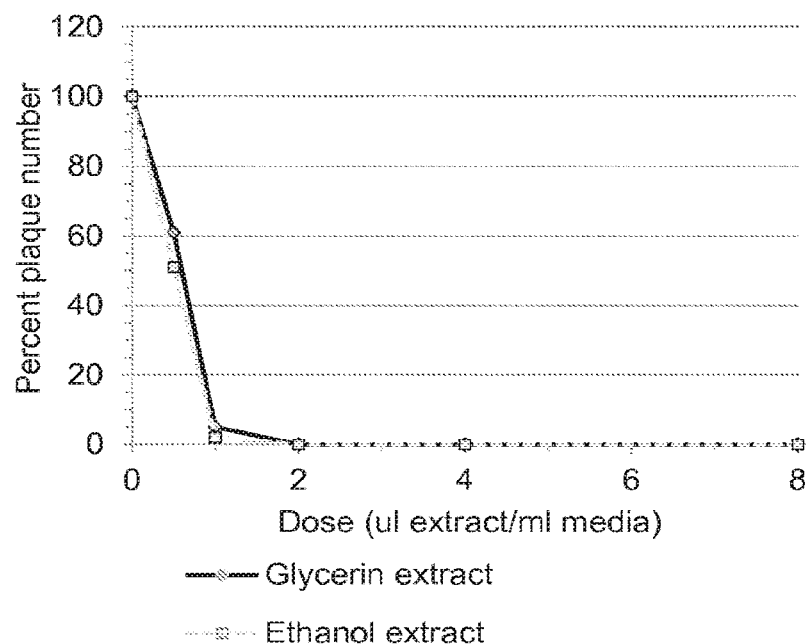
Figure 45F:
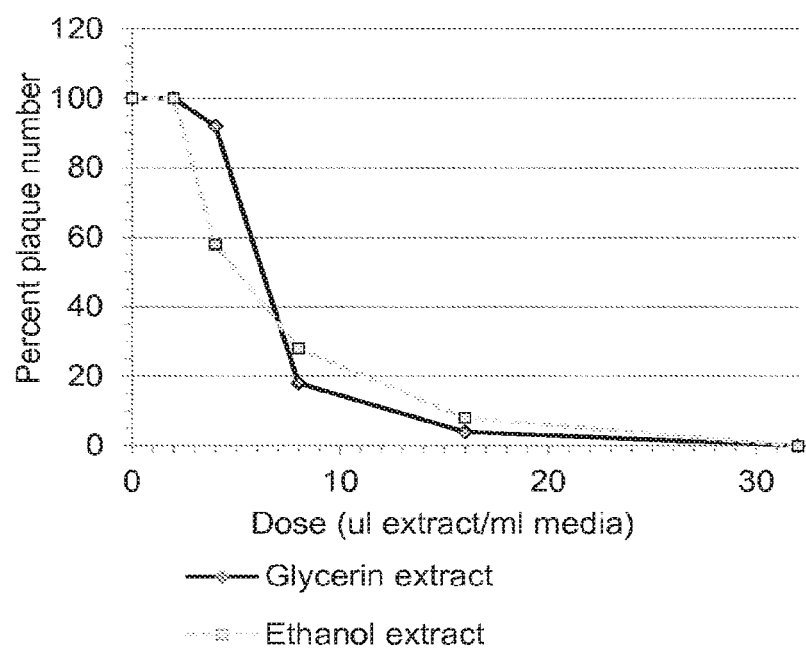

The results of these assays are shown in FIGS. 42A-42R. Cycle threshold (Ct) is the cycle number at which the fluorescence for the reaction crosses the threshold value. In this figure, the ΔCt value represents the change in the Ct value of the experimental group minus the untreated group. As shown, PMA+ionomycin and LPS treatment induced the expression of various cytokines as represented by a decrease in the ΔCt value. This can easily be seen for CCL3 (FIGS. 42A and 42B (subject 1 and subject 2, respectively)), TNF-α (FIGS. 42C and 42D (subject 1 and subject 2, respectively)), IL5 (FIGS. 42K and 42L (subject 1 and subject 2, respectively)), IL-1B (for LPS) (FIGS. 42E and 42F (subject 1 and subject 2, respectively)), IL2. (for PMA+ionomycin) (FIGS. 42G and 42H (subject 1 and subject 2, respectively)), IFN-γ (FIGS. 42O and 42P (subject 1 and subject 2, respectively)), and IL6 (FIGS. 42M and 42N (subject 1 and subject 2, respectively)). Cells which were pre-treated with S. purpurea followed by PMA+ionomycin or LPS, typically showed a decrease in the expression level of these cytokines. This can be observed especially for CCL3, IL5 (for PMA-ionomycin), IL-1 ß, and IL6 (FIGS. 42Q and 42R (subject 1 and subject 2, respectively)). In addition, treatment of cells with S. purpurea extract alone led to a decrease in the endogenous level of expression of various cytokines. This can be observed especially for CCL3, TNF-α, IL8 (FIGS. 42I and 42J (subject 1 and subject 2, respectively)), IL-1 ß, ILK) (FIGS. 42M and 42N (subject 1 and subject 2, respectively)), and IL6.

For the data illustrated in FIGS. 43A-44I, specific time points were graphed showing the fold-change of expression of the cytokine mRNAs relative to untreated cells. As shown in FIGS. 43A-43L S. purpurea treatment led to a block in cytokine induction by PMA+ionomycin for CCL3 (18 HPT, FIG. 43A), TNF-α (12 HPT, FIG. 43B), IL1 ß (12 HPT, FIG. 43C), IL2 (6HPT, FIG. 43D), IL5 (16 HPT, FIG. 43F), IL10 (6HPT, FIG. 43G), IFN-γ (12 HPT, FIG. 43H) and IL6 (12 HPT, FIG. 43I). Notably, no change was observed for IL8 (12 HPT, FIG. 43E). Similar results were observed for the results of the experiment illustrated in FIGS. 44A-44I where S. purpurea treatment led to a block in cytokine induction by LPS for CCL3 (18 HPT, FIG. 44A), TNF-α (12 HPT, FIG. 44B), IL-1 ß (12 HPT, FIG. 44C), IL2 (6HPT, FIG. 44D), ILK), (6HPT, FIG. 44G) IFN-γ (12 HPT, FIG. 44H) and IL6 (12 HPT, FIG. 44I). Notably, only minor changes were observed for IL8 (12 HPT, FIG. 44E) and IL5 (16 HPT, FIG. 44F).

Together, these in vitro results support results observed in human subjects treated with a botanical extract composition in accordance with various embodiments, or S. purpurea extract alone, where a reduction in inflammation was observed. These results support that S. purpurea can reduced the expression of various cytokines involved in a pro-inflammatory response.

Comparison of Ethanol and Glycerin Based Extraction Solvents

FIGS. 45A-45F illustrate the results of comparison of the activity of the six Species II extracts for ethanol versus glycerin based extraction methods. As shown, for five of the six Species II botanical extracts described, extractions can be performed either using ethanol-based solutions or glycerin-based solutions, with the extracts showing similar anti-viral activity. Ethanol-based extractions were performed with ethanol percentages as described in the Extract Preparation section. Glycerin extraction was done using distilled water/glycerol (25%/75%). As shown, anti-viral activity associated with S. purpurea (FIG. 45A), M. officinalis (FIG. 45E), G. glabra (FIG. 45B), E. senticosus (FIG. 45F) and H. perforatum (FIG. 45C) was similar whether extracted using ethanol or glycerin based extraction solutions. Notably, extraction of L. officinalis (FIG. 45D) required extraction using a glycerin based extraction solution. Extraction of this botanical with an ethanol based solution did not produce any detectable antiviral activity. These results suggest that the active constituents) present in Lavandula officinalis requires the presence of glycerin to either release the active molecules from the plant material or to maintain the active constituent(s) in a stable, active form.

Procedure for Extraction of Sarracenia Species Plant Material

Finely ground dried plant material was mixed with extraction solution at a ratio of 1:15 kg plant material:liter extraction solution. Extraction solution was 5:4:1 190 proof ethanol:distilled water:glycerin. The mixture was incubated at room temperature in an amber glass container, with agitation for 1-2 minutes every 6 hours to resuspend solid material. After a 7 day extraction period, the extraction mixture was clarified by centrifugation, and the solid cake discarded. The clarified extraction was then filtered through a 0.2 μm filter into a sterile container.

Procedure for Extraction of Melissa officinalis Species Plant Material

Finely ground dried plant material was mixed with extraction solution at a ratio of 1:8 kg plant material: liter extraction solution. Extraction solution was 3:1 glycerin: distilled water. The mixture was incubated at room temperature in an amber glass container, with agitation for 1-2 minutes every 6 hours to resuspend solid material. After a 7 day extraction period, the extraction mixture was clarified by centrifugation, and the solid cake discarded. The clarified extraction was then filtered through a 0.2 μm filter into a sterile container.

Procedure for Extraction of Lavandula officinalis Species Plant Material

Finely ground dried plant material was mixed with extraction solution at a ratio of 1:8 kg plant material: liter extraction solution. Extraction solution was 3:1 glycerin:

distilled water. The mixture was incubated at room temperature in an amber glass container, with agitation for 1-2 minutes every 6 hours to resuspend solid material. After a 7 day extraction period, the extraction mixture was clarified by centrifugation, and the solid cake discarded. The clarified extraction was then filtered through a 0.2 μm filter into a sterile container.

Procedure for Extraction of *Hypericum perforatum* Species Plant Material

Finely ground dried plant material was mixed with extraction solution at a ratio of 1:4 kg plant material: liter extraction solution. Extraction solution was 58:32:10 ethanol:distilled water:glycerin. The mixture was incubated at room temperature in an amber glass container, with agitation for 1-2 minutes every 6 hours to resuspend solid material. After a 7 day extraction period, the extraction mixture was clarified by centrifugation, and the solid cake discarded. The clarified extraction was then filtered through a 0.2 μm filter into a sterile container.

Procedure for Extraction of *Eleutherococcus senticosus* Species Plant Material

Finely ground dried plant material was mixed with extraction solution at a ratio of 1:6 kg plant material: liter extraction solution. Extraction solution was 42:53:5 ethanol: distilled water:glycerin. The mixture was incubated at room temperature in an amber glass container, with agitation for 1-2 minutes every 6 hours to resuspend solid material After a 7 day extraction period, the extraction mixture was clarified by centrifugation, and the solid cake discarded. The clarified extraction was then filtered through a 0.2 μm filter into a sterile container.

Procedure for Extraction of *Glycyrrhiza glabra* Species Plant Material

Finely ground dried plant material was mixed with extraction solution at a ratio of 1:6 kg plant material: liter extraction solution. Extraction solution was 3:1 glycerin: distilled water. The mixture was incubated at room temperature in an amber glass container, with agitation for 1-2 minutes every 6 hours to resuspend solid material. After a 7 day extraction period, the extraction mixture was clarified by centrifugation, and the solid cake discarded. The clarified extraction was then filtered through a 0.2 μm filter into a sterile container.

Compositions

TABLE 5

Component concentrations of manufactured 100 ml botanical extract composition.

| Ingredient | Percent (Vol/Vol) | VIU/ml botanical extract | VIU/100 ml Batch LIQUID blend |
| --- | --- | --- | --- |
| *Sarracenia purpurea* | 50 | 125 | 3250 |
| *Melissa officinalis* | 12 | 2000 | 24000 |
| *Lavendula officinalis* | 20 | 150 | 3000 |
| *Glycyrrhiza glabra* | 5 | 100 | 500 |
| *Hypericum performatum* | 5 | 2000 | 10000 |
| *Eleutherococcus senticosus* | 8 | 500 | 4000 |
| Total | 100 | N/a | 47750 |

TABLE 6

Therapeutic composition formulation.

| Ingredient | Percent | VIU/100 ml Batcj GEL blend |
| --- | --- | --- |
| Botanical extract composition (from Table 5) | 50 (vol.) | 47750 |
| Versa Base gel | 50 (wt.) | None* |
| Total | 100 | 23875 |

All publications, patents and patent applications are incorporated herein by reference. While in the foregoing specification this invention has been described in relation to various embodiments thereof, and many details have been set forth for purposes of illustration, it will be apparent to those skilled in the art that the invention is susceptible to additional embodiments and that certain of the details described herein may be varied considerably without departing from the basic principles of the present disclosure.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for inhibiting a replication of a poxvirus by exposing the poxvirus to a liquid extract from a plant material selected from *Sarracenia, Nepenthes, Melissa, Lavandula, Glycyrrhiza, Eleutherococcus, Hypericum, Darlingtonia, Heliamphora, Roridula, Drosera, Dionaea, Aldrovanda, Drosophyllum, Triphyophyllum, Catopsis, Brocchinia, Paepalanthus, Utricularia, Genlisea, Pin-*

*guicula, Ibicella, Byblis, Philcoxia, Stylidium* and *Cephalotus* wherein the plant material is prepared by steps comprising:

obtaining fresh plant material less than about ten (10) days following harvest of the plant material;

washing and air drying the plant material;

combining the plant material with a liquid comprising ethanol and glycerol at a ratio of about one (1) gram of the plant material to about fifteen (15) milliliters of the liquid;

allowing the liquid to extract the plant material at room temperature in an amber glass jar for about two (2) to about sixty (60) days or by boiling for between about thirty (30) minutes to about four (4) hours to form the liquid extract; and separating the liquid extract from the plant material.

2. The method of claim 1 wherein the poxvirus is selected from the group consisting of orthopoxvirus, parpoxvirus, avipoxvirus, capripoxvirus, leporipoxvirus, suipoxvirus, molluscipoxvinis molluscipox virus and yatapox virus.

3. The method of claim 1, wherein the pox virus is selected from the group consisting of vaccinia virus, monkeypox virus, variola virus, and molluscum contagiosum virus.

4. The method of claim 1, further comprising steps standardizing a biological activity of the liquid extract comprising:

growing a cell culture to a target cell density for a viral infection;

preparing a dilution of a viral stock to a known plaque forming unit (pfu) concentration;

preparing a serial dilution of the liquid extract to produce a plurality of liquid extract treatment concentrations;

combining the dilution of the viral stock with each of the plurality of liquid extract treatment concentrations;

adding each of the plurality of liquid extract treatment concentration/viral stock combinations to an aliquot of the cell culture to produce a plurality of infected cell cultures;

adding a fresh equivalent liquid extract treatment concentration to each of the plurality of infected cell cultures;

incubating each of the plurality of the infected cell culture/liquid extract combinations;

measuring a viral plaque formation by counting the number of viral plaques and reporting the viral plaque formation as a percentage of plaque formation, wherein the percentage of plaque formation is the observed number of plaques divided by an expected number of plaques based on the viral concentration of the viral stock aliquot; and determining the biological activity of the liquid extract from the percentage of viral plaque formation.

5. The method of claim 4, wherein the liquid extract comprises about 50% of an extract of *Sarracenia purpurea* having biological activity of about fifty (50) viral inhibitory units per milliliter and about 12% of an extract of *Melissa officinalis* having a biological activity of about eighty (80) viral inhibitory units per milliliter.

* * * * *